United States Patent
Gray et al.

(10) Patent No.: US 10,017,477 B2
(45) Date of Patent: *Jul. 10, 2018

(54) JANUS KINASE INHIBITORS AND USES THEREOF

(71) Applicant: Dana-Farber Cancer Institute, Inc., Boston, MA (US)

(72) Inventors: Nathanael S. Gray, Boston, MA (US); Li Tan, Shanghai (CN)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/305,801

(22) PCT Filed: Apr. 23, 2015

(86) PCT No.: PCT/US2015/027312
§ 371 (c)(1),
(2) Date: Oct. 21, 2016

(87) PCT Pub. No.: WO2015/164614
PCT Pub. Date: Oct. 29, 2015

(65) Prior Publication Data
US 2017/0044111 A1  Feb. 16, 2017

Related U.S. Application Data

(60) Provisional application No. 61/983,175, filed on Apr. 23, 2014.

(51) Int. Cl.
| | | |
|---|---|---|
| *C07D 239/48* | (2006.01) | |
| *C07D 403/12* | (2006.01) | |
| *C07D 401/14* | (2006.01) | |
| *C07D 405/14* | (2006.01) | |
| *C07D 401/12* | (2006.01) | |

(Continued)

(52) U.S. Cl.
CPC ......... *C07D 239/48* (2013.01); *C07D 239/47* (2013.01); *C07D 401/12* (2013.01); *C07D 401/14* (2013.01); *C07D 403/12* (2013.01); *C07D 405/12* (2013.01);
(Continued)

(58) Field of Classification Search
CPC .. C07D 239/47; C07D 413/12; C07D 405/14; C07D 401/14
See application file for complete search history.

(56) References Cited

U.S. PATENT DOCUMENTS 4,231,938 A  11/1980 Monaghan et al.
4,270,537 A  6/1981 Romaine et al.
(Continued)

FOREIGN PATENT DOCUMENTS

CA  2486101 A1  11/2003
CA  2503646 A1  5/2004
(Continued)

OTHER PUBLICATIONS

International Preliminary Report on Patentability for PCT/US2016/024345, dated Oct. 12, 2017.
(Continued)

*Primary Examiner* — Alexander R Pagano
*Assistant Examiner* — Ebenezer Sackey
(74) *Attorney, Agent, or Firm* — Wolf, Greenfield & Sacks, P.C.

(57) ABSTRACT

The present invention provides kinase inhibitors, such as compounds of Formula (I) and Formula (II). The compounds may covalently or non-covalently bind a kinase (e.g., Janus kinase 3 (JAK3)). Also provided are pharmaceutical compositions, kits, methods, and uses that involve the compounds for reducing the activity of a kinase and/or treating and/or preventing a condition associated with aberrant activity of a kinase (e.g., a proliferative disease, inflammatory disorder, autoimmune disorder, painful condition, and/or viral infection). (I) (II)

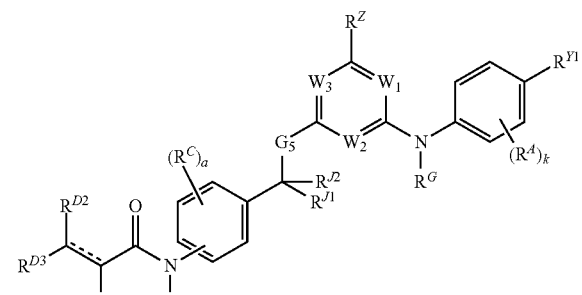

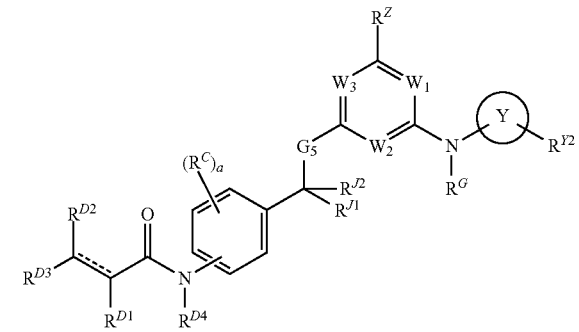

27 Claims, No Drawings

(51) Int. Cl.
    *C07D 405/12*     (2006.01)
    *C07D 239/47*     (2006.01)
    *C07D 413/12*     (2006.01)
    *C07D 487/04*     (2006.01)
    *C07D 495/04*     (2006.01)

(52) U.S. Cl.
    CPC ......... *C07D 405/14* (2013.01); *C07D 413/12* (2013.01); *C07D 487/04* (2013.01); *C07D 495/04* (2013.01)

(56) References Cited

U.S. PATENT DOCUMENTS

| | | | |
|---|---|---|---|
| 4,596,556 A | 6/1986 | Morrow et al. |
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,394,818 B2 | 3/2013 | Gray et al. |
| 8,765,747 B2 | 7/2014 | Choi et al. |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,758,522 B2 | 9/2017 | Gray et al. |
| 9,862,688 B2 * | 1/2018 | Gray ................. C07D 239/48 |
| 2003/0139416 A1 | 7/2003 | Buchanan et al. |
| 2004/0106634 A1 | 6/2004 | Satoh et al. |
| 2005/0026914 A1 | 2/2005 | Buchanan et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0105250 A1 | 4/2009 | Sim et al. |
| 2010/0056524 A1 | 3/2010 | Mciver et al. |
| 2010/0197688 A1 | 8/2010 | Nantermet et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0202809 A1 | 8/2012 | Li et al. |
| 2012/0277248 A1 | 11/2012 | Caruso et al. |
| 2012/0329771 A1* | 12/2012 | Treu ................. C07D 401/14 514/210.2 |
| 2013/0040949 A1 | 2/2013 | Gray et al. |
| 2013/0184264 A1 | 7/2013 | Bradner et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2015/0274728 A1 | 10/2015 | Gray et al. |
| 2016/0046636 A1 | 2/2016 | Gray et al. |
| 2016/0122323 A1 | 5/2016 | Gray et al. |
| 2016/0368910 A1 | 12/2016 | Gray et al. |
| 2017/0044112 A1 | 2/2017 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 1 935 890 A1 | 6/2008 |
| EP | 2 311 842 A2 | 4/2011 |
| GB | 796524 A | 6/1958 |
| JP | 2003-503481 A | 1/2003 |
| JP | 2004-529140 A | 9/2004 |
| JP | 2005-501860 A | 1/2005 |
| JP | 2005-505535 A | 2/2005 |
| JP | 2005-530711 A | 10/2005 |
| JP | 2005-534635 A | 11/2005 |
| JP | 2005-538100 A | 12/2005 |
| JP | 2006-521394 A | 9/2006 |
| JP | 2007-500226 A | 1/2007 |
| JP | 2007-500725 A | 1/2007 |
| JP | 2008-500320 A | 1/2008 |
| JP | 2008-501669 A | 1/2008 |
| JP | 2008-502610 A | 1/2008 |
| JP | 2009-510110 A | 3/2009 |
| JP | 2010-511655 A | 4/2010 |
| JP | 2010-521487 A | 6/2010 |
| JP | 2011-516533 A | 5/2011 |
| JP | 2012-530071 A | 11/2012 |
| JP | 2016-533379 A | 10/2016 |
| JP | 2017-504651 A | 2/2017 |

(56) References Cited

FOREIGN PATENT DOCUMENTS

| | | |
|---|---|---|
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/26412 A1 | 10/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/17861 A1 | 6/1996 |
| WO | WO 96/21456 A1 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 00/44777 A1 | 8/2000 |
| WO | WO 2000/50032 A1 | 8/2000 |
| WO | WO 00/61186 A1 | 10/2000 |
| WO | WO 2001/02369 A2 | 1/2001 |
| WO | WO 2001/019829 A2 | 3/2001 |
| WO | WO 02/076986 A1 | 10/2002 |
| WO | WO 02/079197 A1 | 10/2002 |
| WO | WO 02/080926 A1 | 10/2002 |
| WO | WO 2002/083653 A1 | 10/2002 |
| WO | WO 02/096905 A1 | 12/2002 |
| WO | WO 02/102800 A1 | 12/2002 |
| WO | WO 2003/018021 A1 | 3/2003 |
| WO | WO 2003/018022 A1 | 3/2003 |
| WO | WO 03/026664 A1 | 4/2003 |
| WO | WO 2003/051847 A1 | 6/2003 |
| WO | WO 2003/078403 A2 | 9/2003 |
| WO | WO 2003/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/039796 A1 | 5/2004 |
| WO | WO 2004/078757 A2 | 9/2004 |
| WO | WO 2004/087699 A2 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/048070 A2 | 4/2007 |
| WO | WO 2007/075869 A2 | 7/2007 |
| WO | WO 2007/129195 A2 | 11/2007 |
| WO | WO 2007/138277 A1 | 12/2007 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 A2 | 7/2008 |
| WO | WO 2008/112913 A1 | 9/2008 |
| WO | WO 2008/124393 A1 | 10/2008 |
| WO | WO 2008/144253 A1 | 11/2008 |
| WO | WO 2008/151183 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/145360 A1 | 12/2009 |
| WO | WO 2009/152027 A1 | 12/2009 |
| WO | WO 2009/155017 A2 | 12/2009 |
| WO | WO 2010/008847 A2 | 1/2010 |
| WO | WO 2010/051781 A1 | 5/2010 |
| WO | WO 2010/125799 A1 | 11/2010 |
| WO | WO 2010/144909 A1 | 12/2010 |
| WO | WO 2011/115725 A2 | 9/2011 |
| WO | WO 2013/014162 A1 | 1/2013 |
| WO | WO 2013/040436 A2 | 3/2013 |
| WO | WO 2013/074986 A1 | 5/2013 |
| WO | WO 2013/154778 A1 | 10/2013 |
| WO | WO 2014/063061 A1 | 4/2014 |
| WO | WO 2014/063068 A1 | 4/2014 |
| WO | WO 2015/013635 A2 | 1/2015 |
| WO | WO 2015/058126 A1 | 4/2015 |
| WO | WO 2015/058140 A1 | 4/2015 |
| WO | WO 2015/117087 A1 | 8/2015 |
| WO | WO 2015/154022 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/105528 A2 | 6/2016 |

OTHER PUBLICATIONS

International Preliminary Report on Patentability for PCT/US/2016/037086, dated Dec. 21, 2017.

Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.

Takemori et al., Inactivation of HDAC5 by SIK1 in AICAR-treated C2C12 myoblasts. Endocr J. 2009;56(1):121-30. Epub Oct. 22, 2008.

Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.

International Search Report and Written Opinion for PCT/US2012/065618, dated Mar. 19, 2013.

International Preliminary Report on Patentability for PCT/US2012/065618, dated May 30, 2014.

International Search Report and Written Opinion for PCT/US2013/065708, dated Feb. 4, 2014.

(56) References Cited

OTHER PUBLICATIONS

International Preliminary Report on Patentability for PCT/US2013/065708, dated Apr. 30, 2015.
International Search Report and Written Opinion for PCT/US2013/065689, dated Mar. 4, 2014.
International Preliminary Report on Patentability for PCT/US2013/065689, dated Apr. 30, 2015.
International Search Report and Written Opinion for PCT/US2013/065698, dated Feb. 20, 2014.
International Preliminary Report on Patentability for PCT/US2013/065698, dated Apr. 30, 2015.
International Search Report and Written Opinion for PCT/US2014/061232, dated Dec. 23, 2014.
International Search Report and Written Opinion for PCT/US2015/027312, dated Jul. 10, 2015.
International Preliminary Report on Patentability for PCT/US2015/027312, dated Nov. 3, 2016.
International Search Report and Written Opinion for PCT/US2015/027294, dated Jul. 10, 2015.
Extended European Search Report for EP 10786967.9, dated Oct. 23, 2012.
International Search Report and Written Opinion for PCT/US2010/038518, dated Aug. 6, 2010.
International Preliminary Report on Patentability for PCT/US2010/038518, dated Dec. 22, 2011.
Extended European Search Report for EP 10844280.7, dated Apr. 17, 2013.
Partial European Search Report for EP 15160591.2, dated Jul. 14, 2015.
Extended European Search Report for EP 15160591.2, dated Nov. 2, 2015.
International Search Report and Written Opinion for PCT/US2010/062310, dated Oct. 4, 2011.
International Preliminary Report on Patentability for PCT/US2010/062310, dated Jul. 12, 2012.
International Search Report and Written Opinion for PCT/US2015/000297, dated Mar. 4, 2016.
International Preliminary Report on Patentability PCT/US2015/000297, dated Jul. 6, 2017.
International Search Report and Written Opinion for PCT/US2016/037086, dated Sep. 2, 2016.
Invitation to Pay Additional Fees for PCT/US2016/024345, dated Aug. 9, 2016.
International Search Report and Written Opinion for PCT/US2016/024345, dated Oct. 6, 2016.
Invitation to Pay Additional Fees for PCT/US2016/051118, dated Dec. 1, 2016.
International Search Report and Written Opinion for PCT/US2016/051118, dated Mar. 13, 2017.
Invitation to Pay Additional Fees for PCT/US2011/025423, dated May 31, 2011.
International Search Report and Written Opinion from PCT/US2011/025423, dated Nov. 5, 2012.
International Preliminary Report on Patentability PCT/US2011/025423, dated Nov. 29, 2012.
CAS Registry No. 916173-61-0, STN Entry Date Dec. 21, 2006.
CAS Registry No. 769961-42-4, STN Entry Date Oct. 27, 2004.
CAS Registry No. 769961-59-3, STN Entry Date Oct. 27, 2004.
CAS Registry No. 1334419-59-8, STN Entry Date Dec. 30, 2013.
GenBank Accession No. M80629. Lapidot-Lifson et al., Dec 31, 1994. 2 pages.
GenBank Accession No. NP_001790. Yang et al., Oct 6, 2016. 4 pages.
PubChem-CID-68365059. Available at https://pubchem.ncbi.nlm.nih.gov/compound/68365059. Accessed Jun. 17, 2016.
Uniprot No. Q9NYV4. Last modified Mar. 15, 2017. 14 pages.
Akhtar et al., TFIH kinase places bivalent marks on the carboxy-terminal domain of RNA polymerase II. Mol Cell. May 15, 2009;34(3):387-93. doi: 10.1016/j.molcel.2009.04.016.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13/2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Berge et al., Pharmaceutical salts. J. Pharmaceutical Sciences 1977 66:1-19.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bosken et al., The structure and substrate specificity of human Cdk12/Cyclin K. Nat Commun. Mar. 24, 2014;5:3505. doi: 10.1038/ncomms4505.
Brower et al., Tumor Angiogenesis: New drugs on the block. Nature Biotechnology 1999;17:963-8.
Brunton et al., eds., Chemotherapy of Neoplastic Diseases. In Goodman & Gilman's The Pharmacological Basis of Therapeutics. 2008; 11th edition:853-908.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.
Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chiarugi et al., Cox-2, iNOS and p53 as play-makers of tumor angiogenesis. International Journal of Molecular Medicine 1998;2:715-9.
Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.
Chong et al., Positive and negative regulation of Raf kinase activity and function by phosphorylation EMBO J. Jul. 16, 2001;20(14):3716-27.
Christensen et al., Targeting transcriptional addictions in small cell lung cancer with a covalent CDK7 inhibitor. Cancer Cell. Dec. 8, 2014;26(6):909-22.

(56) References Cited

OTHER PUBLICATIONS

Christian et al., Flavopiridol in chronic lymphocytic leukemia: a concise review. Clin Lymphoma Myeloma. 2009;9 Suppl 3:S179-85. doi: 10.3816/CLM.2009.s.009.
Davies et al., Mutations of the BRAF gene in human cancer Nature. Jun. 27, 2002;417(6892):949-54. Epub Jun. 9, 2002.
Davis et al., Comprehensive analysis of kinase inhibitor selectivity. Nat Biotechnol. Oct. 30, 2011;29(11):1046-51. doi: 10.1038/nbt.1990.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Downward, Targeting RAS signalling pathways in cancer therapy Nat Rev Cancer. Jan. 2003;3(1):11-22.
Drapkin et al., Human cyclin-dependent kinase-activating kinase exists in three distinct complexes. Proc Natl Acad Sci U S A. Jun. 25, 1996;93(13):6488-93.
Ercan et al., Reactivation of ERK signaling causes resistance to EGFR kinase inhibitors. Cancer Discov. Oct. 2012;2(10):934-47.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fernandez et al., Neovascularization produced by angiotensin I.Journal of Laboratory and Clinical Medicine 1985;105(2):141-5.
Filippakopoulos et al., Selective inhibition of BET bromodomains. Nature. Dec. 23, 2010;468(7327):1067-73.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-38.
Garnett et al., Guilty as charged: B-RAF is a human oncogene Cancer Cell. Oct. 2004;6(4):313-9.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.

Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2014.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kantarjian et al., Dasatinib versus imatinib in newly diagnosed chronic-phase chronic myeloid leukemia. N Engl J Med. Jun. 17, 2010;362(24):2260-70.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Lee et al., BRAF mutations in non-Hodgkin's lymphoma. Br J Cancer. Nov. 17, 2003;89(10):1958-60.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl(phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Two cyclin-dependent kinases promote RNA polymerase II transcription and formation of the scaffold complex. Mol Cell Biol. Feb. 2004;24(4):1721-35.

(56) References Cited

OTHER PUBLICATIONS

Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008. 10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Marques et al., A new subfamily of high molecular mass CDC2-related kinases with PITAI/VRE motifs. Biochem Biophys Res Commun. Dec. 29, 2000;279(3):832-7.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10. 007. Epub Oct. 22, 2014.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/ JTO.0b013e31821528d3.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Seed et al., The Inhibition of colon-26 Adenocarcinoma Development and Angiogenesis by Topical Diclofenac in 2.5% Hyaluronan. Cancer Research 1997;57:1625-9.
Serizawa et al., Association of Cdk-activating kinase subunits with transcription factor TFIIH. Nature. Mar. 16, 1995;374(6519):280-2.
Sharma et al., A chromatin-mediated reversible drug-tolerant state in cancer cell subpopulations. Cell. Apr. 2, 2010;141(1):69-80.
Shiekhattar et al., Cdk-activating kinase complex is a component of human transcription factor TFIIH. Nature. Mar. 16, 1995;374(6519):283-7.
Smith et al., Recent advances in the research and development of RAF kinase inhibitors. Curr. Top Med. Chem. 2006; 6(11):1071-89.

Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.
Stanovnik et al., The Tautomerism of Heterocycles: Substituent Tautomerism of Six-Membered Ring Heterocycles. Advances in Heterocyclic Chemistry. 2006;91:1-134.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Terai et al., Activation of the FGF2-FGFR1 autocrine pathway: a novel mechanism of acquired resistance to gefitinib in NSCLC. Mol Cancer Res. Jul. 2013;11(7):759-67.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc. 2014.161. Epub Jun. 9, 2014.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mal Cell Biol. Nov. 2004; 5(11):875-85.
Xin et al., Peroxisome proliferator-activated receptor angiogenesis in vitro and in vivo. Journal of Biological Chemistry 1996;274(13):9116-21.
Yalpani, Cholesterol Lowering Drugs. Chemistry and Industry Feb. 1996;3:85-89.
Zambon et al., Small molecule inhibitors of BRAF in clinical trials. Bioorg Med Chem Lett. Jan. 15, 2012;22(2):789-92. doi: 10.1016/ j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Zebisch et al., Back to the roots: the remarkable RAF oncogene story Cell Mol Life Sci. Jun. 2006:63(11):1314-30.
Zhang et al., Discovery of potent and selective covalent inhibitors of JNK. Chem Biol. Jan. 27, 2012;19(1):140-54. doi: 10.1016/j. chembiol.2011.11.010.
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. Journal of the National Cancer Institute 1982;69(2):475.
U.S. Appl. No. 15/699,948, filed Sep. 8, 2017, Gray et al.
U.S. Appl. No. 15/538,763, filed Jun. 22, 2017, Gray et al.
U.S. Appl. No. 15/561,729, Sep. 26, 2017, Gray et al.
PCT/US2016/024345, Oct. 12, 2017, International Preliminary Report on Patentability.
PCT/US2016/037086, Dec. 21, 2017, International Preliminary Report on Patentability.

* cited by examiner

JANUS KINASE INHIBITORS AND USES THEREOF

RELATED APPLICATIONS

The present application is a national stage filing under 35 U.S.C. § 371 of international PCT application, PCT/US2015/027312, filed Apr. 23, 2015, which claims priority under 35 U.S.C. § 119(e) to U.S. provisional patent application, 61/983,175, filed Apr. 23, 2014, each of which is incorporated herein by reference.

BACKGROUND OF THE INVENTION

Kinase inhibitors are rapidly becoming one of the most validated and pursued class of drug targets. Janus kinases (JAKs) comprise a family of 4 kinases that play multiple roles downstream of cytokine signalling in both immune and non-immune cells. Autoimmunity is driven by an aberrant adaptive immune response to self-antigens and JAK-STAT signalling is known to play a key role in this process. Thus JAK inhibitors have considerable potential for the development of drugs to treat autoimmunity. JAK3 is an especially attractive target as, unlike other JAKs, its expression is restricted to the immune system. Several pharmaceutical companies have considerable efforts underway to develop JAK3 inhibitors. While the FDA recently approved the JAK3 inhibitor Tofacitnib (XELJANZ®), which is actually a pan-JAK inhibitor, it was rejected by CHMP in Europe due to safety concerns. This highlights the fact that while pan-JAK inhibitors are effective in RA, they carry a range of adverse side effects, many of which may relate to the functions of JAKs outside the adaptive immune system. Therefore, development of selective small molecule inhibitors of JAK3 would potentially represent a promising class of novel therapeutics.

SUMMARY OF THE INVENTION

The present invention is based on the development of kinase inhibitors, such as the compounds described herein, e.g., compounds of Formula (I) and (II):

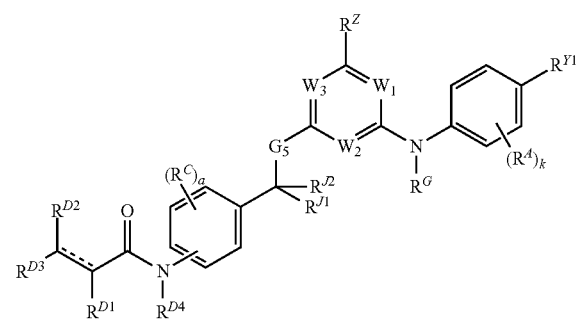
(I)

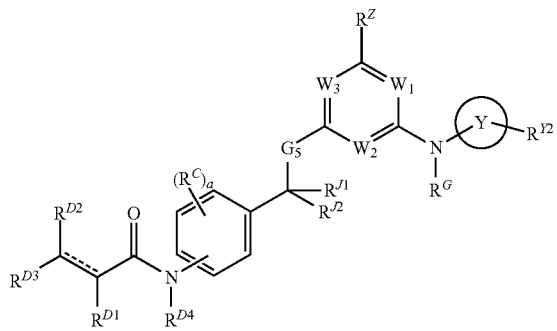
(II)

and pharmaceutically acceptable salts thereof, wherein ====, $R^{D1}$, $R^{D2}$, $R^{D3}$, $R^{D4}$, $G_5$, $R^A$, $R^C R^G$, $R^{J1}$, $R^{J2}$, $R^Z$, $W_1$, $W_2$, $W_3$, $R^{Y1}$, $R^{Y2}$, a, k, y, and x are as described herein.

In certain embodiments, the compounds of Formula (I) and (II) are of Formula:

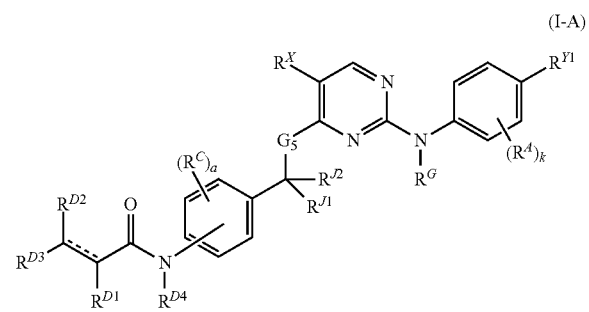
(I-A)

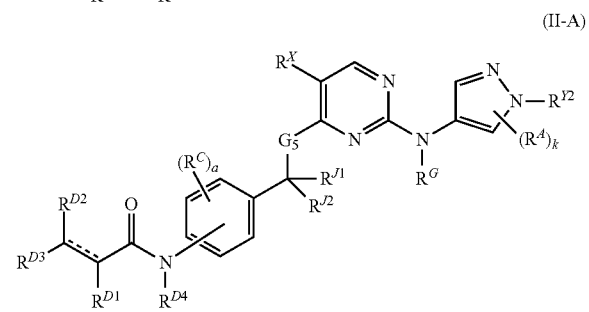
(II-A)

or pharmaceutically acceptable salts thereof.

In certain aspects, the kinase inhibitors of Formula (I) or (II) inhibit JAK, e.g., JAK1, JAK2, JAK3, or TYK2. In certain aspects, the kinase inhibitors of Formula (I) or (II) inhibit JAK3. In certain aspects, the kinase inhibitors of Formula (I) or (II) inhibit JAK3 selectively. In certain aspects, the kinase inhibitors of Formula (I) or (II) inhibit JAK3 up to about 100-fold selectively over JAK1 and/or JAK2, which do not possess an equivalently placed cysteine residue.

In certain aspects, the kinase inhibitors of Formula (I) or (II) inhibit EGFR. In certain aspects, the kinase inhibitors of Formula (I) or (II) inhibit a gatekeeper mutant (T790M) of EGFR.

In certain embodiments, the compounds described herein comprises group of formula

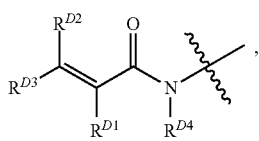

i.e., wherein ═══ provided in a compound of Formula (I) or (II) is a double bond, wherein such group in certain embodiments covalently reacts with and/or binds to the kinase.

Alternatively, in certain embodiments, the compounds describe herein comprises a group of formula:

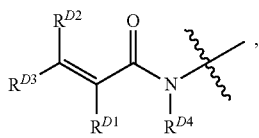

i.e., wherein ═══ provided in a compound of Formula (I) or (II) is a single bond.

In another aspect, provided are pharmaceutical compositions comprising a compound of Formula (I) or (II) and a pharmaceutically acceptable excipient. In certain embodiments, the pharmaceutical composition may be useful for reducing the activity of a kinase in a subject in need thereof, and/or for treating and/or preventing in a subject in need thereof a condition associated with aberrant activity of a kinase (e.g., a proliferative disease, inflammatory disorder, autoimmune disorder, painful condition, or viral infection).

In another aspect, provided are methods for reducing the activity of a kinase in a subject in need thereof. In certain embodiments, the method includes administering to the subject a compound described herein, or a pharmaceutical composition thereof, in an amount sufficient to reduce the activity of the kinase.

In another aspect, provided are methods for treating and/or preventing in a subject in need thereof a condition associated with aberrant activity of a kinase (e.g., a proliferative disease, inflammatory disorder, autoimmune disorder, painful condition, or viral infection).

In certain embodiments, the method includes administering to the subject a compound described herein, or a pharmaceutical composition thereof, in an amount sufficient to treat and/or prevent the condition.

In another aspect, provided are kits comprising a container with a compound described herein, or a pharmaceutical composition thereof. The kits may include a single dose or multiple doses of a compound described herein or a pharmaceutical composition thereof.

The kits may be useful for reducing the activity of a kinase in a subject in need thereof. The kits may also be useful for treating and/or preventing in a subject in need thereof a condition associated with aberrant activity of a kinase. In certain embodiments, the kits further include instructions for using the kit (e.g., for administering a compound described herein, or a pharmaceutical composition thereof).

The details of one or more embodiments of the invention are set forth herein. Other features, objects, and advantages of the invention will be apparent from the Detailed Description, the Examples, and the Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75 Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer, or geometric isomer, or can be in the form of a mixture of stereoisomers, including racemic mixtures and mixtures enriched in one or more stereoisomer. "Racemic" refers to a compound in which the percent by weight of one enantiomer is equal to the percent by weight of the other enantiomer.

The terms "enantiomerically enriched," "enantiomerically pure" and "non-racemic," as used interchangeably herein, refer to a compound in which the percent by weight of one enantiomer is greater than the amount of that one enantiomer compared to a control mixture of the racemic composition (e.g., greater than 1:1 by weight). For example, an enantiomerically enriched enantiomer, means a compound having greater than 50% by weight of one enantiomer relative to the other enantiomer, e.g., at least 75% by weight, or at least 80% by weight. In some embodiments, the enrichment can be much greater than 80% by weight, providing a "substantially enantiomerically enriched," "substantially enantiomerically pure" or a "substantially non-racemic" compound, which refers to a compound with at least 85% by weight of one enantiomer relative to other enantiomer, e.g., at least 90% by weight, or at least 95% by weight.

Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972).

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "haloalkyl" is a substituted alkyl group as described herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1, 2, 3, or 4 heteroatoms within the parent chain ("heteroC$_{1-10}$ alkyl"). In some embodiments, a heteroalkyl group is a saturated group having 1 to 9 carbon atoms and 1, 2, 3, or 4 heteroatoms within the parent chain ("heteroC$_{1-9}$ alkyl"). In some embodiments, a heteroalkyl group is a saturated group having 1 to 8 carbon atoms and 1, 2, 3, or 4 heteroatoms within the parent chain ("heteroC$_{1-8}$ alkyl"). In some embodiments, a heteroalkyl group is a saturated group having 1 to 7 carbon atoms and 1, 2, 3, or 4 heteroatoms within the parent chain ("heteroC$_{1-7}$ alkyl"). In some embodiments, a heteroalkyl group is a saturated group having 1 to 6 carbon atoms and 1, 2, or 3 heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

The term "heteroalkenyl" refers to an alkenyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1, 2, 3, or 4 heteroatoms within the parent chain ("heteroC$_{2-10}$ alkenyl"). In some embodiments, a heteroalkenyl group has 2 to 9 carbon atoms at least one double bond, and 1, 2, 3, or 4 heteroatoms within the parent chain ("heteroC$_{2-9}$ alkenyl"). In some embodiments, a heteroalkenyl group has 2 to 8 carbon atoms, at least one double bond, and 1, 2, 3, or 4 heteroatoms within the parent chain ("heteroC$_{2-8}$ alkenyl"). In some embodiments, a heteroalkenyl group has 2 to 7 carbon atoms, at least one double bond, and 1, 2, 3, or 4 heteroatoms within the parent chain ("heteroC$_{2-7}$ alkenyl"). In some embodiments, a heteroalkenyl group has 2 to 6 carbon atoms, at least one double bond, and 1, 2, or 3 heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more triple bonds (e.g., 1, 2, 3, or 4 triple bonds) and optionally one or more double bonds (e.g., 1, 2, 3, or 4 double bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group as described herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1, 2, 3, or 4 heteroatoms within the parent chain ("heteroC$_{2-10}$ alkynyl"). In some embodiments, a heteroalkynyl group has 2 to 9 carbon atoms, at least one triple bond, and 1, 2, 3, or 4 heteroatoms within the parent chain ("heteroC$_{2-9}$ alkynyl"). In some embodiments, a heteroalkynyl group has 2 to 8 carbon atoms, at least one triple bond, and 1, 2, 3, or 4 heteroatoms within the parent chain ("heteroC$_{2-8}$ alkynyl"). In some embodiments, a heteroalkynyl group has 2 to 7 carbon atoms, at least one triple bond, and 1, 2, 3, or 4 heteroatoms within the parent chain ("heteroC$_{2-7}$ alkynyl"). In some embodiments, a heteroalkynyl group has 2 to 6 carbon atoms, at least one triple bond, and 1, 2, or 3 heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 9 ring carbon atoms ("C$_{3-9}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. In certain embodiments, the carbocyclyl group is either monocyclic ("monocyclic carbocyclyl") or polycyclic (e.g., containing a fused, bridged or spiro-fused ring system such as a bicyclic system ("bicyclic carbocyclyl") or tricyclic system ("tricyclic carbocyclyl")) and can be saturated or can contain one or more carbon-carbon double or triple bonds. Exemplary fused bicyclic systems include, but are not limited to, decalin (cis or trans decalin). Exemplary fused tricyclic systems include, but are not limited to, fluorenyl. Exemplary spiro-fused bicyclic systems include, but are not limited to, spiropentane. Exemplary bridged bicyclic systems include, but are not limited to, norbornane, norbornene, bicyclo[2.2.2]octane, bicyclo[2.2.2]oct-2-ene, bicyclo[3.2.1]octane, and bicyclo[2.2.1]heptan-2-one. Exemplary bridged tricyclic systems include, but are not limited to adamantane. "Carbocyclyl" includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

"Carbocyclylalkyl" is a subset of "alkyl" and refers to an alkyl group, as described herein, substituted by an carbocyclyl group, as described herein, wherein the point of attachment is on the alkyl moiety.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. In certain embodiments, the heterocyclyl group is either monocyclic ("monocyclic heterocyclyl") or polycyclic (e.g., containing a fused, bridged or spiro-fused ring system such as a bicyclic system ("bicyclic heterocyclyl") or tricyclic system ("tricyclic heterocyclyl")) and can be saturated or can contain one or more carbon-carbon double or triple bonds. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl, and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Heterocyclylalkyl" is a subset of "alkyl" and refers to an alkyl group, as described herein, substituted by one or more heterocyclyl groups, as described herein, wherein the point of attachment is on the alkyl moiety.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracenyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" or "arylalkyl" is a subset of "alkyl" and refers to an alkyl group, as described herein, substituted by one or more aryl groups, as described herein, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" or "heteroarylalkyl" is a subset of "alkyl" and refers to an alkyl group, as described herein, substituted by one or more heteroaryl groups, as described herein, wherein the point of attachment is on the alkyl moiety.

The term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

The term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as described herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction.

Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$+X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{cc}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl; C$_{2-10}$ heteroalkynyl, C$_{3-14}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{1-14}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$+X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$heteroalkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl) X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(═O)(C$_{1-6}$ alkyl), —CO$_2$H, —CO$_2$(C$_{1-6}$ alkyl), —OC(═O)(C$_{1-6}$ alkyl), —OCO$_2$(C$_{1-6}$ alkyl), —C(═O)NH$_2$, —C(═O)N(C$_{1-6}$ alkyl)$_2$, —OC(═O)NH(C$_{1-6}$ alkyl), —NHC(═O)(C$_{1-6}$ alkyl), —N(C$_{1-6}$ alkyl)C(═O)(C$_{1-6}$ alkyl), —NHCO$_2$(C$_{1-6}$ alkyl), —NHC(═O)N(C$_{1-6}$ alkyl)$_2$, —NHC(═O)NH(C$_{1-6}$ alkyl), —NHC(═O)NH$_2$, —C(═NH)O(C$_{1-6}$ alkyl), —OC(═NH)(C$_{1-6}$ alkyl), —OC(═NH)OC$_{1-6}$ alkyl, —C(═NH)N(C$_{1-6}$ alkyl)$_2$, —C(═NH)NH(C$_{1-6}$ alkyl), —C(═NH)NH$_2$, —OC(═NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(═NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(═S)N(C$_{1-6}$ alkyl)$_2$, C(═S)NH(C$_{1-6}$ alkyl), C(═S)NH$_2$, —C(═O)S(C$_{1-6}$ alkyl), —C(═S)SC$_{1-6}$ alkyl, —SC(═S)SC$_{1-6}$ alkyl, —P(═O)$_2$(C$_{1-6}$ alkyl), —P(═O)(C$_{1-6}$ alkyl)$_2$, —OP(═O)(C$_{1-6}$ alkyl)$_2$, —OP(═O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{1-6}$heteroalkyl, C$_{2-6}$ heteroalkenyl, C$_{2-4}$heteroalkynyl, C$_{3-10}$ carbocyclyl, C$_{6-10}$ aryl, 3-10 membered heterocyclyl, 5-10 membered heteroaryl; or two geminal $R^{gg}$ substituents can be joined to form ═O or ═S; wherein X$^-$ is a counterion.

In certain embodiments, one or more carbon atom substituents are selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —C(═O)R$^{aa}$, —CO$_2$H, —CHO, —CO$_2$R$^{aa}$, —OC(═O)R$^{aa}$, —OCO$_2$R$^{aa}$, —C(═O)N(R$^{bb}$)$_2$, —OC(═O)N(R$^{bb}$)$_2$, —NR$^{bb}$C(═O)R$^{aa}$, —NR$^{bb}$CO$_2$R$^{aa}$, —NR$^{bb}$C(═O)N(R$^{bb}$)$_2$, —C(═O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —S(═O)R$^{aa}$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups.

The term "halo" or "halogen" refers to fluorine (fluoro, —F), chlorine (chloro, —Cl), bromine (bromo, —Br), or iodine (iodo, —I).

The term "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

The term "hydroxyl" or "hydroxy" refers to the group —OH. The term "substituted hydroxyl" or "substituted hydroxy," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(═O)SR$^{aa}$, —OC(═O)R$^{aa}$, —OCO$_2$R$^{aa}$, —OC(═O)N(R$^{bb}$)$_2$, —OC(═NR$^{bb}$)R$^{aa}$, —OC(═NR$^{bb}$)OR$^{aa}$, —OC(═NR$^{bb}$)N(R$^{bb}$)$_2$, —OS(═O)R$^{aa}$, —OSO$_2$R$^{aa}$, —OSi(R$^{aa}$)$_3$, —OP(R$^{cc}$)$_2$, —OP(R$^{cc}$)$_3$, —OP(═O)$_2$R$^{aa}$, —OP(═O)(R$^{aa}$)$_2$, —OP(═O)(OR$^{cc}$)$_2$, —OP(═O)$_2$N(R$^{bb}$)$_2$, and —OP(═O)(NR$^{bb}$)$_2$, wherein R$^{aa}$, R$^{bb}$, and R$^{cc}$ are as described herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S═SR$^{cc}$, —SC(═S)SR$^{aa}$, —SC(═O)SR$^{aa}$, —SC(═O)OR$^{aa}$, and —SC(═O)R$^{aa}$, wherein R$^{aa}$ and R$^{cc}$ are as described herein.

The term "amino" refers to the group —NH$_2$. The term "substituted amino," by extension, refers to a monosubstituted amino, a disubstituted amino, or a trisubstituted amino, as described herein. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(═O)R$^{aa}$, —NHCO$_2$R$^{aa}$, —NHC(═O)N(R$^{bb}$)$_2$, —NHC(═NR$^{bb}$)N(R$^{bb}$)$_2$, —NHSO$_2$R$^{aa}$, —NHP(═O)(OR$^{cc}$)$_2$, and —NHP(═O)(NR$^{bb}$)$_2$, wherein R$^{aa}$, R$^{bb}$ and R$^{cc}$ are as described herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(═O)R$^{aa}$, —NR$^{bb}$CO$_2$R$^{aa}$, —NR$^{bb}$C(═O)N(R$^{bb}$)$_2$, —NR$^{bb}$C(═NR$^{bb}$)N(R$^{bb}$)$_2$, —NR$^{bb}$SO$_2$R$^{aa}$, —NR$^{bb}$P(═O)(OR$^{cc}$)$_2$, and —NR$^{bb}$P(═O)(NR$^{bb}$)$_2$, wherein R$^{aa}$, R$^{bb}$, and R$^{cc}$ are as described herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as described herein.

The term "oxo" refers to the group ═O, and the term "thiooxo" refers to the group ═S.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(═O)R$^{aa}$, —C(═O)N(R$^{cc}$)$_2$, —CO$_2$R$^{aa}$, —SO$_2$R$^{aa}$, —C(═NR$^{bb}$)R$^{aa}$, —C(═NR$^{cc}$)OR$^{aa}$, —C(═NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(═S)N(R$^{cc}$)$_2$, —C(═O)SR$^{cc}$, —C(═S)SR$^{cc}$, —P(═O)$_2$R$^{aa}$, —P(═O)(R$^{aa}$)$_2$, —P(═O)$_2$N(R$^{cc}$)$_2$, —P(═O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ to alkyl (e.g., alkyl, aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as described herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., —$C(=O)R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —$C(=O)OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)] methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate. Nitrogen protecting groups such as sulfonamide groups (e.g., —$S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as described herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as described herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

It understood that divalent moieties depicted herein are interpreted to be read left ("a") to right ("b"), e.g., as provided below, and that the attachment of the divalent moiety into the reference Formula is also interpreted to be attached left to right:

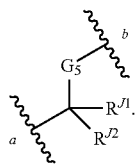

Other Definitions

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

A "condition," "disease," and "disorder" are used interchangeably herein.

The term "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound described herein may vary depending on such factors as the desired biological endpoint, the pharmacokinetics of the compound, the disease being treated, the mode of administration, and the age, health, and condition of the subject. An effective amount encompasses therapeutic and prophylactic treatment.

The term "therapeutically effective amount" of a compound refers to an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent. In certain embodiments, the condition is associated with aberrant activity of a kinase (e.g., JAK3). In certain embodiments, a therapeutically effective amount is an amount sufficient to reduce the activity or expression of a kinase (e.g., JAK3) and/or inhibit cell proliferation.

A "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

The term "inhibitor" refers to the ability of a compound to reduce (e.g., slow, halt) or prevent activity of a particular biological process (kinase activity) in a cell relative to vehicle.

Use of the phrase "at least one" instance refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKR$^{D3}$, ANPa, ANPb, ARAF, ARAFps, ARG, AurA, AurAps, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIKi, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRKIA, DYRKIB, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps, Erk3ps2, Erk3ps3, Erk3ps4, Erk4, Erk5, Erk7, FAK, FER, FERps, FES, FGFR1, FGFR2, FGFR3, FGFR4, FGR, FLT1, FLTlps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB 1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFR$^{aa}$, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKHIps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgKO50ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK, skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK. In certain embodiments, the kinase is a JAK kinase, e.g., a JAK1, JAK2, JAK3, or TYK2 kinase. In certain embodiments, the kinase is JAK3 kinase.

DETAILED DESCRIPTION OF CERTAIN EMBODIMENTS OF THE INVENTION

Previous efforts have led to the development of an ATP-site directed library of acrylamide modified kinase inhibitors that have the potential to form covalent bonds with cysteine residues situated in and around the ATP binding site. These libraries have been used successfully to develop covalent inhibitors of numerous kinases, including EGFR, BTK, BMX, JNK and FGFR. Current estimates suggest 180 kinases may represent attractive targets for the development of new therapeutics. To-date, there exist only 11 kinases that are targeted by FDA approved kinase inhibitors, suggesting that there exists considerable opportunity for new covalent inhibitor drugs. The advantage of covalent inhibitors from a therapeutic standpoint is the potential to achieve durable target suppression without the necessity of maintaining high continuous drug exposure. Given the potential advantages of these agents and the considerable interest in developing inhibitors of JAK3 in the pharmaceutical field, inhibitors possessing the ability to covalently modify JAK3 were developed. In addition to the covalent inhibitors, non-covalent analogs were also discovered (e.g., reduced acrylamide moiety) that could serve as complementary therapeutics that exhibit alternate modes of inhibition and pharmacokinetic/pharmacodynamic profiles.

As generally described herein, provided are compounds of Formula (I) and (II) designed as kinase inhibitors, e.g., JAK inhibitors, e.g., which may inhibit JAK (e.g., JAK3) selectively:

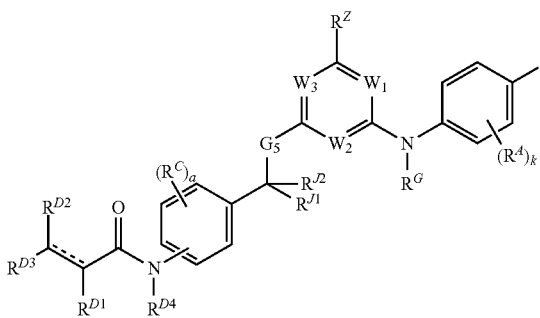

(I)

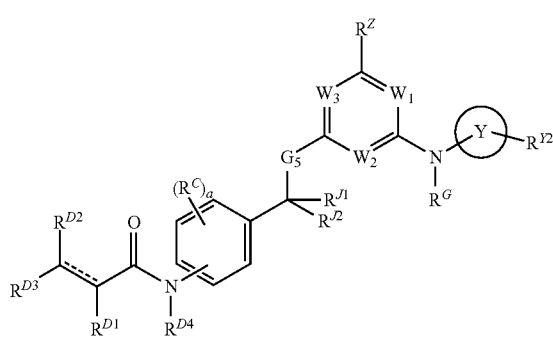

(II)

and pharmaceutically acceptable salts thereof,
wherein:

$W_1$ is N, $W_2$ is N and $W_3$ is $CR^X$, or $W_1$ is N, $W_2$ is CH, and $W_3$ is N;

$R^{Y1}$ is a group of formula

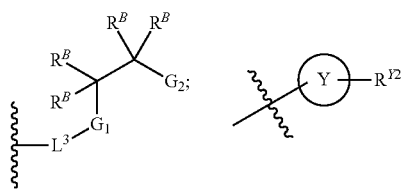

is selected from the group consisting of:

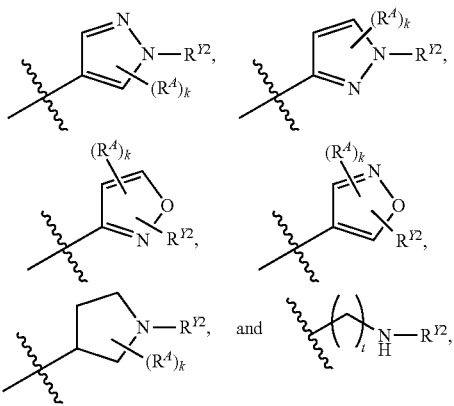

wherein t is 2, 3, 4, 5, or 6;

$R^{Y2}$ is hydrogen, substituted or unsubstituted alkyl, —C(=O)$R^{A2}$, a nitrogen protecting group if attached to a nitrogen atom, or a group of formula

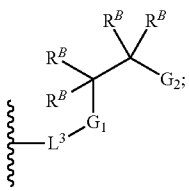

$R^{A2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$L^3$ is a bond or a linker selected from the group consisting of substituted and unsubstituted $C_{1-6}$alkylene, substituted and unsubstituted $C_{2-6}$alkenylene, substituted and unsubstituted $C_{2-6}$alkynylene, substituted and unsubstituted heteroC$_{1-6}$alkylene, substituted and unsubstituted hetero $C_{2-6}$alkenylene, and substituted and unsubstituted hetero $C_{2-6}$alkynylene;

$G_1$ is $NR^{G1a}$ and $G_2$ is $N(R^{G2a})_2$, $OR^{G2a}$, or $C(R^{G2a})_2$; or $G_1$ is $CHR^{G1a}$ and $G_2$ is $N(R^{G2a})_2$, $OR^{G2a}$;

each instance of $R^{G1a}$ and $R^{G2a}$ is independently hydrogen, substituted or unsubstituted alkyl, substituted or unsubstituted hydroxyl, a nitrogen protecting group when attached to a nitrogen atom, or an oxygen protecting group when attached to an oxygen atom, or $R^{G1a}$ and one instance of $R^{G2a}$ are joined to form the group —C(R$^B$)$_2$—C(R$^B$)$_2$—;

═══ represents a single or double bond;

each instance of $R^{D1}$, $R^{D2}$, and $R^{D3}$ is independently hydrogen or substituted or unsubstituted alkyl;

$R^{D4}$ is hydrogen, substituted or unsubstituted alkyl, or a nitrogen protecting group;

$G_5$ is O, S, or $NR^E$;

each instance of $R^E$ and $R^G$ is independently hydrogen, substituted or unsubstituted alkyl, or a nitrogen protecting group;

each instance of $R^{J1}$ and $R^{J2}$ is independently hydrogen, halogen, or substituted or unsubstituted alkyl;

each instance of $R^A$ and $R^C$ is independently halogen, substituted or unsubstituted alkyl, substituted or unsubstituted alkenyl, substituted or unsubstituted alkynyl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$;

each instance of $R^B$ is independently hydrogen, halogen, substituted or unsubstituted alkyl, substituted or unsubstituted alkenyl, substituted or unsubstituted alkynyl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$; or two $R^B$ groups attached to the same carbon atom are joined to form an oxo (=O) group;

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic or substituted or unsubstituted heteroaryl ring;

a and k are each independently 0, 1, or 2, provided when k is 0 then $R^A$ is absent, and when a is 0 then $R^C$ is absent; and each instance of $R^X$ and $R^Z$ is independently hydrogen, halogen, substituted or unsubstituted alkyl, cyclopropyl, —CN, —OR$^{X1}$, or —NHR$^{X1}$, wherein $R^{X1}$ is hydrogen, substituted or unsubstituted alkyl, an oxygen protecting group when attached to an oxygen, or a nitrogen protecting group when attached to a nitrogen, or $R^X$ and $R^Z$ are joined to form a substituted or unsubstituted 5-membered heterocyclic ring;

or $R^X$ and $R^E$ are joined to form a substituted or unsubstituted 5- to 6-membered heterocyclic ring.

As generally described herein, compounds of Formula (I) and (II), and pharmaceutically acceptable salts thereof, are contemplated useful as kinase inhibitors (e.g., JAK inhibitors, e.g., JAK3 inhibitors). Also provided are pharmaceutical compositions and kits comprising such compounds, and methods of their use and treatment, e.g., for reducing the activity of a kinase. and/or treating and/or preventing a condition associated with aberrant activity of a kinase (e.g., a proliferative disease, inflammatory disorder, autoimmune disorder, painful condition, or viral infection), in a subject in need thereof.

Core Ring System comprising $W_1$, $W_2$, $W_3$, $R^X$, and $R^Z$

As generally described herein, $W_1$ is N, $W_2$ is N and $W_3$ is $CR^X$, or $W_1$ is N, $W_2$ is CH, and $W_3$ is N. Thus, the following two core ring systems corresponding to the group:

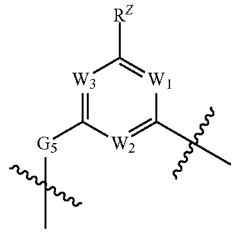

are contemplated herein:

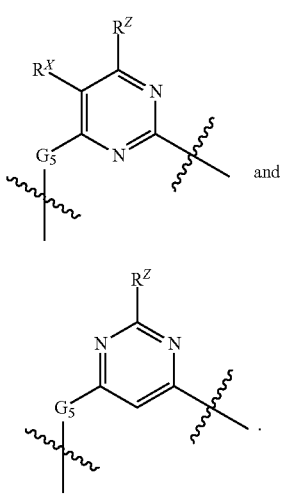

wherein:

$G_5$ is O, S, or $NR^E$;

each instance of $R^E$ is independently hydrogen, substituted or unsubstituted alkyl, or a nitrogen protecting group;

each instance of $R^X$ and $R^Z$ is independently hydrogen, halogen, substituted or unsubstituted alkyl, cyclopropyl, —CN, —OR$^{X1}$, or —NHR$^{X1}$, wherein $R^{X1}$ is hydrogen, substituted or unsubstituted alkyl, an oxygen protecting group when attached to an oxygen, or a nitrogen protecting group when attached to a nitrogen, or $R^X$ and $R^Z$ are joined to form a substituted or unsubstituted 5-membered heterocyclic ring;

or $R^X$ and $R^E$ are joined to form a substituted or unsubstituted 5- to 6-membered heterocyclic ring.

In certain embodiments, $R^Z$ is hydrogen or —NHR$^{X1}$ (e.g., —NH$_2$).

In certain embodiments, $R^Z$ is hydrogen to provide a ring system of formula:

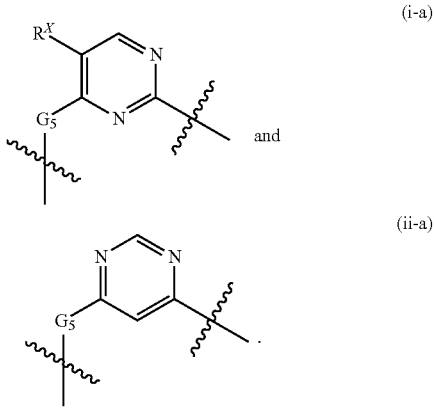

In certain embodiments, various bicyclic ring systems are contemplated.

For example, in certain embodiments, $R^X$ and $R^Z$ are joined to form a substituted or unsubstituted 5-membered heterocyclic ring. For example, in certain embodiments, wherein $R^X$ and $R^Z$ are joined to form a substituted or unsubstituted 5-membered heterocyclic ring, provided is a group of formula:

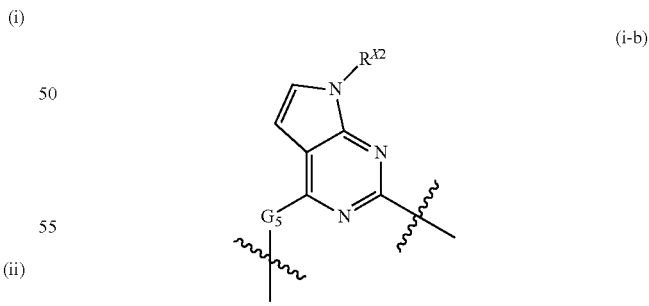

wherein $R^{X2}$ is hydrogen, substituted or unsubstituted alkyl, or a nitrogen protecting group.

Alternatively, in certain embodiments, $R^X$ and $R^E$ are joined to form a substituted or unsubstituted 5- to 6-membered heterocyclic ring. For example, in certain embodiments, wherein $R^X$ and $R^E$ are joined to form a substituted or unsubstituted 5- to 6-membered heterocyclic ring, provided is a group of formula:

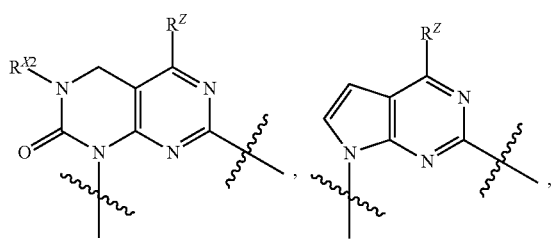

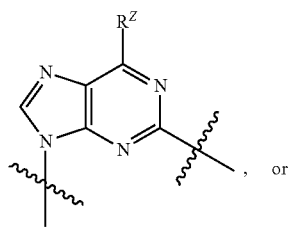, or

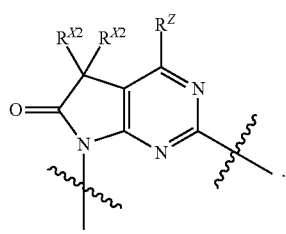.

wherein $R^{X2}$ is hydrogen, substituted or unsubstituted alkyl, or a nitrogen protecting group when attached to a nitrogen atom.

Furthermore, alternatively, $R^X$ is not joined to form a ring with either $R^Z$ or $R^E$. In certain embodiments, $R^X$ is hydrogen, halogen, substituted or unsubstituted alkyl, cyclopropyl, —CN, —OR$^{X1}$, or —NHR$^{X1}$, wherein R$^{X1}$ is hydrogen, substituted or unsubstituted alkyl, an oxygen protecting group when attached to an oxygen, or a nitrogen protecting group when attached to a nitrogen.

In certain embodiments of Formula (I) or Formula (II), $R^X$ is hydrogen. In certain embodiments, both $R^X$ and $R^Z$ are hydrogen, e.g., to provide a ring system of formula:

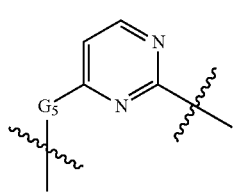

(i-c)

In certain embodiments of Formula (I) or Formula (II), $R^X$ is halogen. In certain embodiments of Formula (I) or Formula (II), $R^X$ is F. In certain embodiments of Formula (I) or Formula (II), $R^X$ is Cl. In certain embodiments of Formula (I) or Formula (II), $R^X$ is Br. In certain embodiments of Formula (I) or Formula (II), $R^X$ is I (iodine). In certain embodiments, $R^X$ is halogen ("Hal") and $R^Z$ is hydrogen, e.g., to provide a ring system of formula:

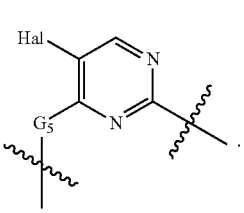

(i-d)

In certain embodiments of Formula (I) or Formula (II), $R^X$ is cyclopropyl. In certain embodiments of Formula (I) or Formula (II), $R^X$ is substituted alkyl. In certain embodiments of Formula (I) or Formula (II), $R^X$ is unsubstituted alkyl. In certain embodiments of Formula (I) or Formula (II), $R^X$ is unsubstituted $C_{1-6}$ alkyl. In certain embodiments of Formula (I) or Formula (II), $R^X$ is substituted $C_{1-6}$ alkyl. In certain embodiments of Formula (I) or Formula (II), $R^X$ is $C_{1-6}$ alkyl substituted with at least one halogen. In certain embodiments of Formula (I) or Formula (II), $R^X$ is —CH$_3$. In certain embodiments of Formula (I) or Formula (II), $R^X$ is substituted methyl. In certain embodiments of Formula (I) or Formula (II), $R^X$ is —CH$_2$F. In certain embodiments of Formula (I) or Formula (II), $R^X$ is —CHF$_2$. In certain embodiments of Formula (I) or Formula (II), $R^X$ is —CF$_3$. In certain embodiments of Formula (I) or Formula (II), $R^X$ is substituted or unsubstituted ethyl. In certain embodiments of Formula (I) or Formula (II), $R^X$ is substituted or unsubstituted propyl. In certain embodiments of Formula (I) or Formula (II), $R^X$ is substituted or unsubstituted butyl. In certain embodiments of Formula (I) or Formula (II), $R^X$ is substituted or unsubstituted pentyl. In certain embodiments of Formula (I) or Formula (II), $R^X$ is substituted or unsubstituted hexyl. In certain embodiments, $R^X$ is alkyl or cyclopropyl ("Alk") and $R^Z$ is hydrogen, e.g., to provide a ring system of formula:

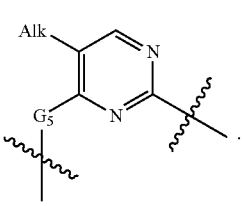

(i-e)

In certain embodiments of Formula (I) or Formula (II), $R^X$ is —CN. In certain embodiments, $R^X$ is —CN and $R^Z$ is hydrogen, e.g., to provide a ring system of formula:

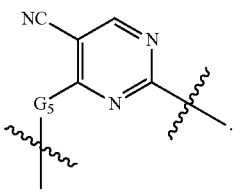

(i-f)

In certain embodiments of Formula (I) or Formula (II), $R^X$ is —OR$^{X1}$. In certain embodiments, $R^X$ is —OR$^{X1}$ and $R^Z$ is hydrogen, e.g., to provide a ring system of formula:

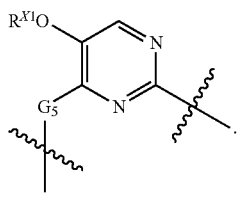

(i-g)

In certain embodiments of Formula (I) or Formula (II), $R^X$ is —$OR^{X1}$ wherein $R^{X1}$ is hydrogen (i.e., to provide —OH).

In certain embodiments of Formula (I) or Formula (II), $R^X$ is —$OR^{X1}$, wherein $R^{X1}$ is substituted alkyl. In certain embodiments of Formula (I) or Formula (II), $R^{X1}$ is unsubstituted alkyl. In certain embodiments of Formula (I) or Formula (II), $R^{X1}$ is unsubstituted $C_{1-6}$ alkyl.

In certain embodiments of Formula (I) or Formula (II), $R^{X1}$ is substituted $C_{1-6}$ alkyl. In certain embodiments of Formula (I) or Formula (II), $R^{X1}$ is $C_{1-6}$ alkyl substituted with at least one halogen. In certain embodiments of Formula (I) or Formula (II), $R^{X1}$ is —$CH_3$. In certain embodiments of Formula (I) or Formula (II), $R^{X1}$ is substituted methyl. In certain embodiments of Formula (I) or Formula (II), $R^{X1}$ is —$CH_2F$. In certain embodiments of Formula (I) or Formula (II), $R^{X1}$ is —$CHF_2$. In certain embodiments of Formula (I) or Formula (II), $R^{X1}$ is —$CF_3$. In certain embodiments of Formula (I) or Formula (II), $R^{X1}$ is substituted or unsubstituted ethyl. In certain embodiments of Formula (I) or Formula (II), $R^{X1}$ is substituted or unsubstituted propyl. In certain embodiments of Formula (I) or Formula (II), $R^{X1}$ is substituted or unsubstituted butyl. In certain embodiments of Formula (I) or Formula (II), $R^{X1}$ is substituted or unsubstituted pentyl. In certain embodiments of Formula (I) or Formula (II), $R^{X1}$ is substituted or unsubstituted hexyl.

In certain embodiments of Formula (I) or Formula (II), $R^X$ is —$OR^{X1}$, wherein $R^{X1}$ is an oxygen protecting group. In certain embodiments of Formula (I) or Formula (II), $R^{X1}$ is silyl, TBDPS, TBDMS, TIPS, TES, TMS, MOM, THP, t-Bu, Bn, allyl, acetyl, pivaloyl, or benzoyl.

In certain embodiments of Formula (I) or Formula (II), $R^X$ is —$NHR^{X1}$.

Group Y

As generally described herein, Formula (II) comprises a group of formula:

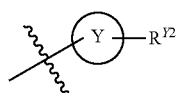

selected from the group consisting of:

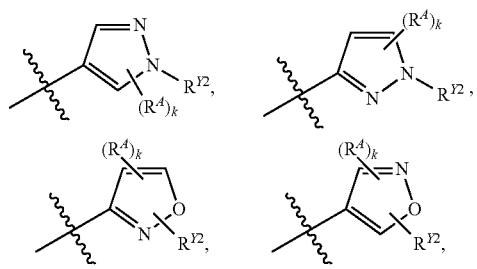

-continued

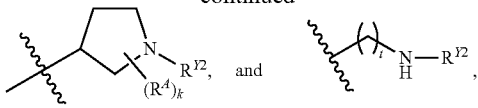

wherein t is 2, 3, 4, 5, or 6.

In certain embodiments of Formula (II), the group is

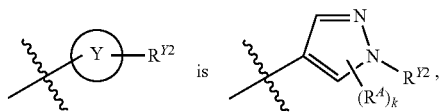

to provide a compound of Formula:

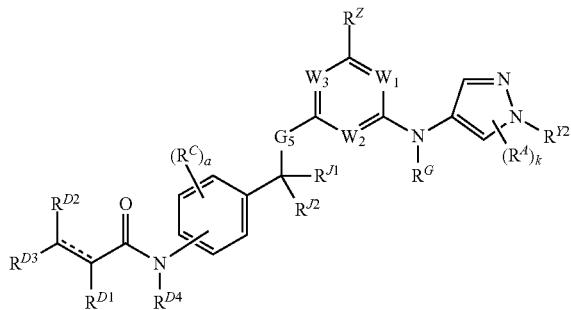

(II-C)

or a pharmaceutically acceptable salt thereof. In certain embodiments, $W_1$ is N, $W_2$ is N and $W_3$ is $CR^X$. In certain embodiments, $G_5$ is $NR^E$. In certain embodiments, $R^Z$ is hydrogen.

In certain embodiments of Formula (II), the group is

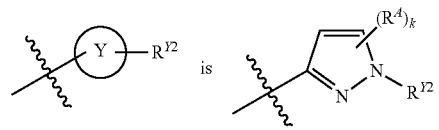

to provide a compound of Formula:

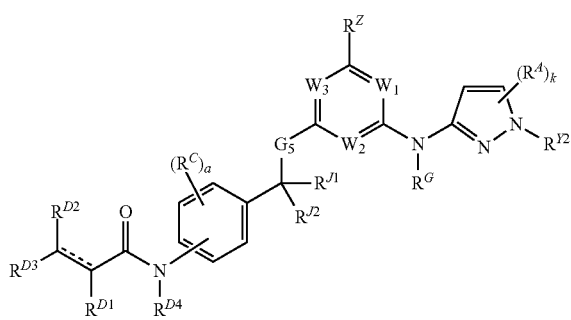

(II-D)

or a pharmaceutically acceptable salt thereof. In certain embodiments, $W_1$ is N, $W_2$ is N and $W_3$ is $CR^X$. In certain embodiments, $G_5$ is $NR^E$. In certain embodiments, $R^Z$ is hydrogen.

In certain embodiments of Formula (II), the group

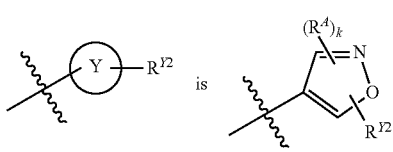

is to provide a compound of Formula:

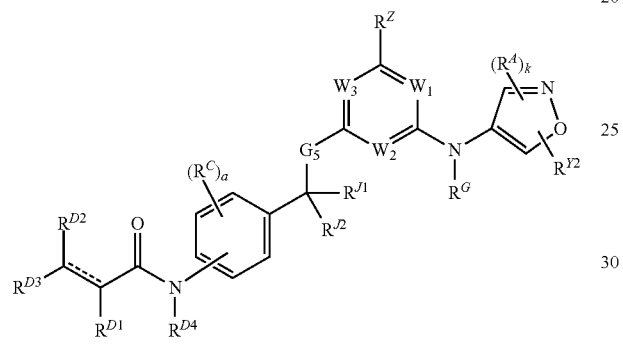
(II-E)

or a pharmaceutically acceptable salt thereof. In certain embodiments, $W_1$ is N, $W_2$ is N and $W_3$ is $CR^X$. In certain embodiments, $G_5$ is $NR^E$. In certain embodiments, $R^Z$ is hydrogen.

In certain embodiments of Formula (II), the group

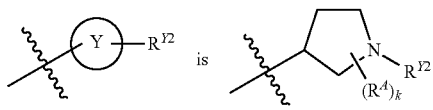

is to provide a compound of Formula:

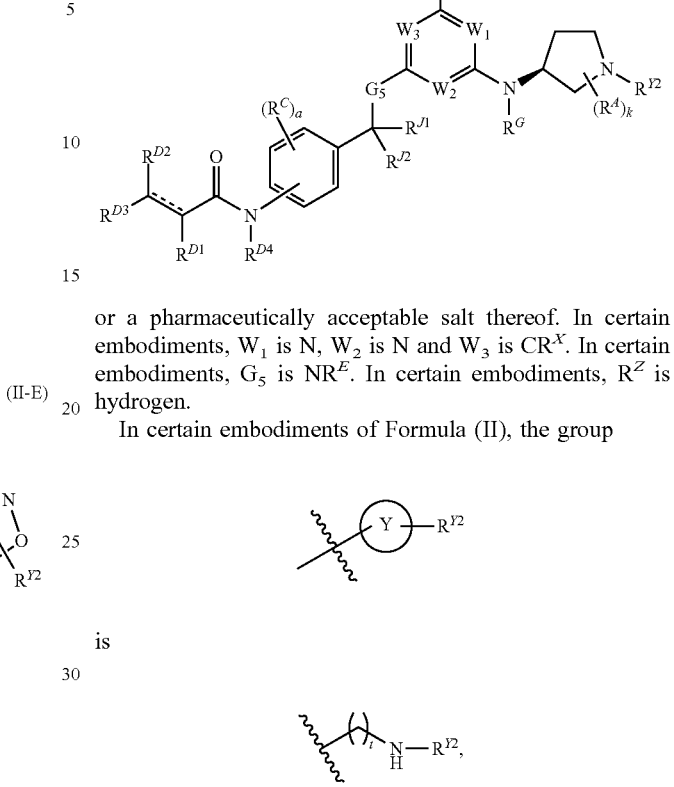
(II-F)

or

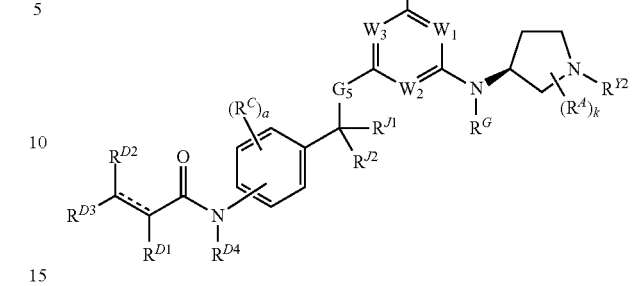
(II-G)

or a pharmaceutically acceptable salt thereof. In certain embodiments, $W_1$ is N, $W_2$ is N and $W_3$ is $CR^X$. In certain embodiments, $G_5$ is $NR^E$. In certain embodiments, $R^Z$ is hydrogen.

In certain embodiments of Formula (II), the group is wherein t is 2, 3, 4, 5, or 6, to provide a compound of formula:

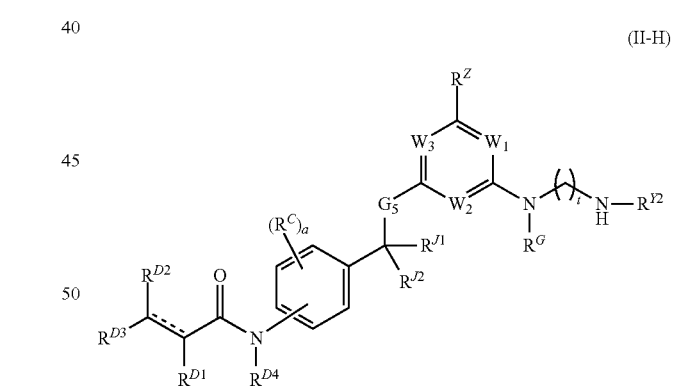
(II-H)

or a pharmaceutically acceptable salt thereof. In certain embodiments, $W_1$ is N, $W_2$ is N and $W_3$ is $CR^X$. In certain embodiments, $G_5$ is $NR^E$. In certain embodiments, $R^Z$ is hydrogen. In certain embodiments, t is 4.

Group $R^A$ and k

As generally described herein, each instance of $R^A$ of Formula (I) and (II) is independently halogen, substituted or unsubstituted alkyl, substituted or unsubstituted alkenyl, substituted or unsubstituted alkynyl, —$OR^{A1}$, —$N(R^{A1})_2$, —$SR^{A1}$, —CN, —SCN, —C(=$NR^{A1}$)$R^{A1}$, —C(=$NR^{A1}$)$OR^{A1}$, —C(=$NR^{A1}$)$N(R^{A1})_2$, —C(=O)$R^{A1}$, —C(=O)$OR^{A1}$, —C(=O)$N(R^{A1})_2$, —$NO_2$, —$NR^{A1}$C(=O)$R^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$, and k is 0, 1, or 2, provided when k is 0 then R$^A$ is absent.

In certain embodiments of Formula (I) or (II), k is 0 and R$^A$ is absent.

In certain embodiments of Formula (I) or (II), k is 1. In certain embodiments of Formula (I), k is 1 and R$^A$ is a group as described herein attached ortho to the point of attachment to —N(R$^G$)—. In certain embodiments of Formula (I), k is 1 and R$^A$ is a group as described herein attached meta to the point of attachment to —N(R$^G$)—.

In certain embodiments of Formula (I) or (II), k is 2. In certain embodiments of Formula (I), k is 2, and each R$^A$ is independently a group as described herein, wherein one R$^A$ is attached ortho and one R$^A$ is attached meta to the point of attachment to —N(R$^G$)—. In certain embodiments of Formula (I), k is 2, and each R$^A$ is independently a group as described herein, both R$^A$ groups are attached ortho to the point of attachment to —N(R$^G$)—. In certain embodiments of Formula (I), k is 2, and each R$^A$ is independently a group as described herein, both R$^A$ groups are attached meta to the point of attachment to —N(R$^G$)—.

In certain embodiments of Formula (I) or (II), k is 1 or 2 and at least one instance of R$^A$ is halogen. In certain embodiments of Formula (I) or (II), k is 1 or 2 and at least one instance of R$^A$ is F. In certain embodiments of Formula (I) or (II), k is 1 or 2 and at least one instance of R$^A$ is Cl. In certain embodiments of Formula (I) or (II), k is 1 or 2 and at least one instance of R$^A$ is Br. In certain embodiments of Formula (I) or (II), k is 1 or 2 and at least one instance of R$^A$ is I (iodine). In certain embodiments of Formula (I) or (II), k is 2 and both instances of R$^A$ are independently halogen. In certain embodiments of Formula (I) or (II), k is 2 and both instances of R$^A$ are F. In certain embodiments of Formula (I) or (II), k is 2 and both instances of R$^A$ are Cl.

In certain embodiments of Formula (I) or (II), k is 1 or 2 and at least one instance of R$^A$ is substituted alkyl. In certain embodiments of Formula (I) or (II), k is 1 or 2 and at least one instance of R$^A$ is unsubstituted alkyl. In certain embodiments of Formula (I) or (II), k is 1 or 2 and at least one instance of R$^A$ is unsubstituted C$_{1-6}$ alkyl. In certain embodiments of Formula (I) or (II), k is 1 or 2 and at least one instance of R$^A$ is substituted C$_{1-6}$ alkyl. In certain embodiments of Formula (I) or (II), k is 1 or 2 and at least one instance of R$^A$ is C$_{1-6}$ alkyl substituted with at least one halogen. In certain embodiments of Formula (I) or (II), k is 1 or 2 and at least one instance of R$^A$ is —CH$_3$. In certain embodiments of Formula (I) or (II), k is 1 or 2 and at least one instance of R$^A$ is substituted methyl. In certain embodiments of Formula (I) or (II), k is 1 or 2 and at least one instance of R$^A$ is —CH$_2$F. In certain embodiments of Formula (I) or (II), k is 1 or 2 and at least one instance of R$^A$ is —CHF$_2$. In certain embodiments of Formula (I) or (II), k is 1 or 2 and at least one instance of R$^A$ is —CF$_3$. In certain embodiments of Formula (I) or (II), k is 1 or 2 and at least one instance of R$^A$ is substituted or unsubstituted ethyl. In certain embodiments of Formula (I) or (II), k is 1 or 2 and at least one instance of R$^A$ is substituted or unsubstituted propyl. In certain embodiments of Formula (I) or (II), k is 1 or 2 and at least one instance of R$^A$ is substituted or unsubstituted butyl. In certain embodiments of Formula (I) or (II), k is 1 or 2 and at least one instance of R$^A$ is substituted or unsubstituted pentyl. In certain embodiments of Formula (I) or (II), k is 1 or 2 and at least one instance of R$^A$ is substituted or unsubstituted hexyl.

In certain embodiments of Formula (I) or (II), k is 1 or 2 and at least one instance of R$^A$ is substituted or unsubstituted alkenyl, e.g., substituted or unsubstituted C$_{2-6}$alkenyl, substituted or unsubstituted C$_{2-5}$alkenyl, substituted or unsubstituted C$_{2-4}$alkenyl, or substituted or unsubstituted C$_{2-3}$alkenyl. In certain embodiments of Formula (I) or (II), k is 1 or 2 and at least one instance of R$^A$ is unsubstituted alkenyl.

In certain embodiments of Formula (I) or (II), k is 1 or 2 and at least one instance of R$^A$ is substituted alkynyl, e.g., substituted or unsubstituted C$_{2-6}$alkynyl, substituted or unsubstituted C$_{2-5}$alkynyl, substituted or unsubstituted C$_{2-4}$alkynyl, or substituted or unsubstituted C$_{2-3}$alkynyl. In certain embodiments of Formula (I) or (II), k is 1 or 2 and at least one instance of R$^A$ is unsubstituted alkynyl.

In certain embodiments of Formula (I) or (II), k is 1 or 2 and at least one instance of R$^A$ is —OR$^{A1}$, wherein R$^{A1}$ is hydrogen (i.e., to provide —OH), or a non-hydrogen group.

In certain embodiments of Formula (I) or (II), k is 1 or 2 and at least one instance of R$^A$ is —SR$^{A1}$, wherein R$^{A1}$ is hydrogen (i.e., to provide —SH), or a non-hydrogen group.

In certain embodiments of Formula (I) or (II), k is 1 or 2 and at least one instance of R$^A$ is —N(R$^{A1}$)$_2$, wherein at least one R$^{A1}$ is hydrogen (e.g., to provide —NH$_2$ or NHR$^{A1}$), each R$^{A1}$ is a non-hydrogen group, or wherein two R$^{A1}$ groups are joined to form a substituted or unsubstituted heterocyclic or heteroaryl ring.

In certain embodiments of Formula (I) or (II), k is 1 or 2 and at least one instance of R$^A$ is —CN. In certain embodiments of Formula (I) or (II), k is 1 or 2 and at least one instance of R$^A$ is —NO$_2$.

In certain embodiments of Formula (I) or (II), k is 1 or 2 and at least one instance of R$^A$ is —C(=NR$^{A1}$)R$^{A1}$, wherein R$^{A1}$ is hydrogen (i.e., to provide —C(=NH)H), or a non-hydrogen group.

In certain embodiments of Formula (I) or (II), k is 1 or 2 and at least one instance of R$^A$ is —C(=NR$^{A1}$)OR$^{A1}$, wherein R$^{A1}$ is hydrogen (i.e., to provide —C(=NH)OH), or a non-hydrogen group.

In certain embodiments of Formula (I) or (II), k is 1 or 2 and at least one instance of R$^A$ is —C(=NR$^{A1}$)N(R$^{A1}$)$_2$, wherein R$^{A1}$ is hydrogen (i.e., to provide —C(=NH)NH$_2$), or a non-hydrogen group.

In certain embodiments of Formula (I) or (II), k is 1 or 2 and at least one instance of R$^A$ is —C(=O)R$^{A1}$, wherein R$^{A1}$ is hydrogen (i.e., to provide —C(=O)H), or a non-hydrogen group.

In certain embodiments of Formula (I) or (II), k is 1 or 2 and at least one instance of R$^A$ is —C(=O)OR$^{A1}$, wherein R$^{A1}$ is hydrogen (i.e., to provide —C(=O)OH), or a non-hydrogen group.

In certain embodiments of Formula (I) or (II), k is 1 or 2 and at least one instance of R$^A$ is —C(=O)N(R$^{A1}$)$_2$, wherein R$^{A1}$ is hydrogen (i.e., to provide —C(=O)NH$_2$), or a non-hydrogen group.

In certain embodiments of Formula (I) or (II), k is 1 or 2 and at least one instance of R$^A$ is —C(=O)N(R$^{A1}$)$_2$, wherein R$^{A1}$ is hydrogen (i.e., to provide —C(=O)NH$_2$), or a non-hydrogen group. In certain embodiments of Formula (I) or (II), k is 1 or 2 and at least one instance of R$^A$ is —C(=O)NMe$_2$, or —C(=O)NHMe.

In certain embodiments of Formula (I) or (II), k is 1 or 2 and at least one instance of R$^A$ is —NR$^{A1}$C(=O)R$^{A1}$, wherein R$^{A1}$ is hydrogen (i.e., to provide —NHC(=O)H), or a non-hydrogen group.

In certain embodiments of Formula (I) or (II), k is 1 or 2 and at least one instance of R$^A$ is —NR$^{A1}$C(=O)OR$^{A1}$, wherein R$^{A1}$ is hydrogen (i.e., to provide —NHC(=O)OH), or a non-hydrogen group.

In certain embodiments of Formula (I) or (II), k is 1 or 2 and at least one instance of $R^A$ is —$NR^{A1}C(=O)N(R^{A1})_2$, wherein $R^{A1}$ is hydrogen (i.e., to provide —NHC(=O)NH$_2$), or a non-hydrogen group.

In certain embodiments of Formula (I) or (II), k is 1 or 2 and at least one instance of $R^A$ is —$OC(=O)R^{A1}$, wherein $R^{A1}$ is hydrogen (i.e., to provide —OC(=O)H), or a non-hydrogen group.

In certain embodiments of Formula (1) or (II), k is 1 or 2 and at least one instance of $R^A$ is —$OC(=O)OR^{A1}$, wherein $R^{A1}$ is hydrogen (i.e., to provide —OC(=O)OH), or a non-hydrogen group.

In certain embodiments of Formula (I) or (II), k is 1 or 2 and at least one instance of $R^A$ is —$OC(=O)N(R^{A1})_2$, wherein $R^{A1}$ is hydrogen (i.e., to provide —OC(=O)NH$_2$), or a non-hydrogen group.

Furthermore, as generally described herein, in any of the above described embodiments of group $R^A$ comprising a group $R^{A1}$, each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic or substituted or unsubstituted heteroaryl ring.

For example, in any of the above described embodiments of $R^A$ comprising a group $R^{A1}$, at least one instance of $R^{A1}$ is hydrogen.

In any of the above described embodiments of $R^A$ comprising a group $R^{A1}$, at least one instance of $R^{A1}$ is substituted or unsubstituted alkyl, e.g., substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl.

In any of the above described embodiments of $R^A$ comprising a group $R^{A1}$, at least one instance of $R^{A1}$ is substituted or unsubstituted $C_{2-6}$alkenyl, e.g., substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl.

In any of the above described embodiments of $R^A$ comprising a group $R^{A1}$, at least one instance of $R^{A1}$ is substituted or unsubstituted $C_{2-6}$alkynyl, e.g., substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments of Formula (I) or Formula (II), at least one instance of $R^{A1}$ is substituted or unsubstituted carbocyclyl. In certain embodiments of Formula (I) or Formula (II), at least one instance of $R^{A1}$ is saturated carbocyclyl. In certain embodiments of Formula (I) or Formula (II), at least one instance of $R^{A1}$ is unsaturated carbocyclyl. In certain embodiments of Formula (I) or Formula (II), at least one instance of $R^{A1}$ is monocyclic $C_{3-7}$ carbocyclyl.

In certain embodiments of Formula (I) or Formula (II), at least one instance of $R^{A1}$ is substituted or unsubstituted heterocyclyl. In certain embodiments of Formula (I) or Formula (II), at least one instance of $R^{A1}$ is saturated heterocyclyl. In certain embodiments of Formula (I) or Formula (II), at least one instance of $R^{A1}$ is unsaturated heterocyclyl. In certain embodiments of Formula (I) or Formula (II), at least one instance of $R^{A1}$ is heterocyclyl, wherein one, two, or three atoms in the heterocyclic ring system are independently selected from the group consisting of nitrogen, oxygen, and sulfur. In certain embodiments of Formula (I) or Formula (II), at least one instance of $R^{A1}$ is 3- to 7-membered, monocyclic heterocyclyl.

In certain embodiments of Formula (I) or Formula (II), at least one instance of $R^{A1}$ is substituted or unsubstituted aryl. In certain embodiments of Formula (I) or Formula (II), at least one instance of $R^{A1}$ is $C_{6-10}$ aryl. In certain embodiments of Formula (I) or Formula (II), at least one instance of $R^{A1}$ is monocyclic aryl. In certain embodiments of Formula (I) or Formula (II), at least one instance of $R^{A1}$ is substituted phenyl. In certain embodiments of Formula (I) or Formula (II), at least one instance of $R^{A1}$ is unsubstituted phenyl. In certain embodiments of Formula (I) or Formula (II), at least one instance of $R^{A1}$ is bicyclic aryl.

In certain embodiments of Formula (I) or Formula (II), at least one instance of $R^{A1}$ is substituted or unsubstituted heteroaryl. In certain embodiments of Formula (I) or Formula (II), at least one instance of $R^{A1}$ is heteroaryl, wherein one, two, three, or four atoms in the heteroaryl ring system are independently selected from the group consisting of nitrogen, oxygen, and sulfur. In certain embodiments of Formula (I) or Formula (II), at least one instance of $R^{A1}$ is monocyclic heteroaryl. In certain embodiments of Formula (I) or Formula (II), at least one instance of $R^{A1}$ is 5- or 6-membered, monocyclic heteroaryl. In certain embodiments of Formula (I) or Formula (II), at least one instance of $R^{A1}$ is bicyclic heteroaryl, wherein the point of attachment may be on any atom of the bicyclic heteroaryl ring system, as valency permits.

In certain embodiments of Formula (I) or Formula (II), at least one instance of $R^{A1}$ is a nitrogen protecting group when attached to a nitrogen atom. In certain embodiments of Formula (I) or Formula (II), at least one instance of $R^{A1}$ is Bn, Boc, Cbz, Fmoc, trifluoroacetyl, triphenylmethyl, acetyl, or Ts when attached to a nitrogen atom.

In certain embodiments of Formula (I) or Formula (II), $R^{A1}$ is an oxygen protecting group when attached to an oxygen atom. In certain embodiments of Formula (I) or Formula (II), $R^{A1}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments of Formula (I) or Formula (II), $R^{A1}$ is a sulfur protecting group when attached to a sulfur atom. In certain embodiments of Formula (I) or Formula (II), $R^{A1}$ is acetamidomethyl, t-Bu, 3-nitro-2-pyridine sulfenyl, 2-pyridine-sulfenyl, or triphenylmethyl when attached to a sulfur atom.

In certain embodiments of Formula (I) or Formula (II), e.g., wherein $R^A$ is —$N(R^{A1})_2$, —$C(=NR^{A1})N(R^{A1})_2$, —$C(=O)N(R^{A1})_2$, —$NR^{A1}C(=O)N(R^{A1})_2$, or —$OC(=O)N(R^{A1})_2$, two instances of $R^{A1}$, e.g., attached to the same nitrogen (N) atom, are joined to form a substituted or unsubstituted heterocyclic ring. In certain embodiments of Formula (I) or Formula (II), two instances of $R^{A1}$ are joined to form a saturated heterocyclic ring. In certain embodiments of Formula (I) or Formula (II), two instances of $R^{A1}$ are joined to form an unsaturated heterocyclic ring. In certain embodiments of Formula (I) or Formula (II), two instances of $R^{A1}$ are joined to form a heterocyclic ring, wherein one, two, or three atoms in the heterocyclic ring system are independently selected from the group consisting of nitrogen, oxygen, and sulfur. In certain embodiments of Formula (I) or Formula (II), two instances of $R^{A1}$ are joined to form a 3- to 7-membered, monocyclic heterocyclic ring.

In certain embodiments of Formula (I) or Formula (II), e.g., wherein $R^A$ is $-N(R^{A1})_2$, $-C(=NR^{A1})N(R^{A1})_2$, $-C(=O)N(R^{A1})_2$, $-NR^{A1}C(=O)N(R^{A1})_2$, or $-OC(=O)N(R^{A1})_2$, two instances of $R^{A1}$, e.g., attached to the same nitrogen (N) atom, are joined to form a substituted or unsubstituted heteroaryl ring. In certain embodiments of Formula (I) or Formula (II), two instances of $R^{A1}$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I) or Formula (II), two instances of $R^{A1}$ are joined to form a substituted or unsubstituted, 9- to 10-membered, monocyclic heteroaryl ring, wherein one, two, three, or four atoms in the heteroaryl ring system are independently nitrogen, oxygen, or sulfur.

In certain embodiments of Formula (I) or Formula (II), each instance of $R^A$ is independently hydrogen, halogen, substituted or unsubstituted $C_{1-6}$ alkyl, or $-OR^{A1}$, wherein $R^{A1}$ is substituted or unsubstituted $C_{1-6}$ alkyl. In certain embodiments of Formula (I) or Formula (II), each instance of $R^A$ is independently hydrogen, halogen, unsubstituted $C_{1-6}$ alkyl, $C_{1-6}$ alkyl substituted with at least one halogen, or $-OR^{A1}$, wherein $R^{A1}$ is unsubstituted $C_{1-6}$ alkyl.

In certain embodiments of Formula (I), k is 1; and the group:

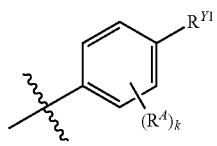

corresponds to any one of formula:

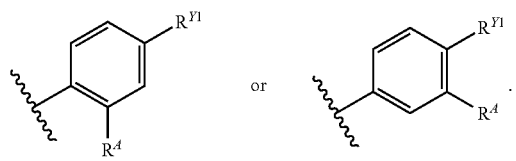

In certain embodiments of Formula (I), k is 2 and the group:

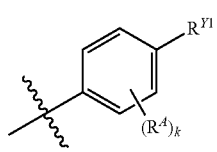

corresponds to any one of formula:

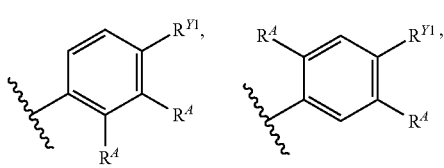

In certain embodiments of Formula (I), at least one instance of $R^A$ is $-OR^{A1}$, and and the group:

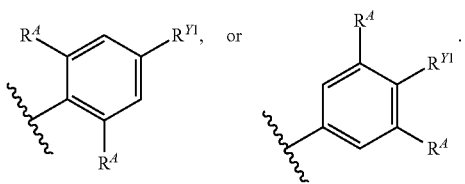

corresponds to any one of formula:

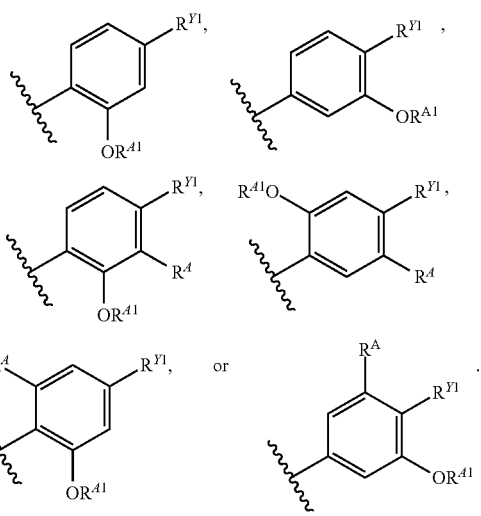

In certain embodiments of Formula (I), at least one instance of $R^A$ is halogen, and and the group:

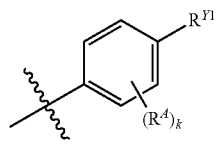

corresponds to any one of formula:

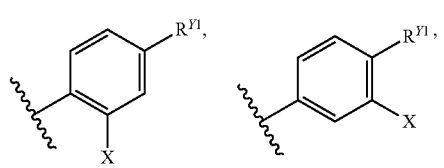

-continued

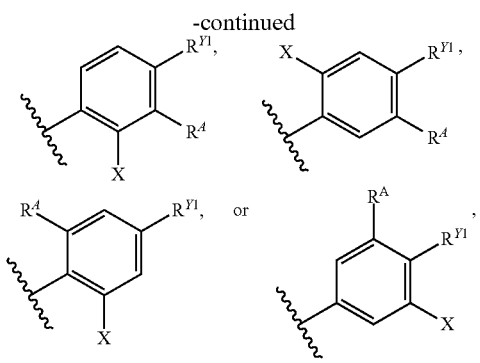

wherein X is halogen.

Linker $L^3$ and Groups $R^{Y1}$, $R^{Y2}$, $G_1$, $G_2$, $R^{G1a}$, $R^{G2a}$, $R^{A2}$, and $R^B$ As generally described herein, $R^{Y1}$, which is attached to a compound of Formula (I), is a group of formula:

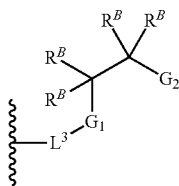

wherein $G_1$, $G_2$, $L^3$, and $R^B$ are as defined herein.

Furthermore, as generally described herein, $R^{Y2}$, attached to a compound of Formula (II), is hydrogen, substituted or unsubstituted alkyl, —C(=O)$R^{A2}$, a nitrogen protecting group, or a group of formula:

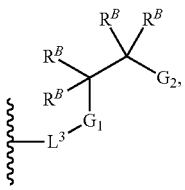

wherein $G_1$, $G_2$, $L^3$, and $R^B$ are as defined herein, and $R^A$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments of Formula (II), $R^{Y2}$ is hydrogen. In certain embodiments of Formula (II), $R^{Y2}$ is not hydrogen.

In certain embodiments of Formula (II), $R^{Y2}$ is substituted or unsubstituted alkyl. In certain embodiments of Formula (II), $R^{Y2}$ is substituted alkyl. In certain embodiments of Formula (II), $R^{Y2}$ is unsubstituted alkyl. In certain embodiments of Formula (II), $R^{Y2}$ is unsubstituted $C_{1-6}$ alkyl. In certain embodiments of Formula (II), $R^{Y2}$ is substituted $C_{1-6}$ alkyl. In certain embodiments of Formula (II), $R^{Y2}$ is $C_{1-6}$ alkyl substituted with at least one halogen, —OR$^{Y3}$, —N(R$^{Y3}$)$_2$, —C(=O)OR$^{Y3}$, —C(=O)N(R$^{Y3}$)$_2$, wherein $R^{Y3}$ is independently hydrogen, substituted or unsubstituted alkyl, or two $R^{Y3}$ groups attached to a N atom are joined to form a substituted or unsubstituted 5- to 6-membered heterocyclic ring. In certain embodiments of Formula (II), $R^{Y2}$ is —CH$_3$. In certain embodiments of Formula (II), $R^{Y2}$ is substituted methyl. In certain embodiments of Formula (II), $R^{Y2}$ is —CH$_2$F, —CHF$_2$, —CF$_3$, —CH$_2$OR$^{Y3}$, —CH$_2$N(R$^3$)$_2$, —CH$_2$C(=O)OR$^{Y3}$, or —CH$_2$C(=O)N(R$^{Y3}$)$_2$. In certain embodiments of Formula (II), $R^{Y2}$ is substituted or unsubstituted ethyl. In certain embodiments of Formula (II), $R^{Y2}$ is —CH$_2$CH$_3$, —CH$_2$CH$_2$F, —CH$_2$CHF$_2$, —CH$_2$CF$_3$, —CH$_2$CH$_2$OR$^{Y3}$, —CH$_2$CH$_2$N(R$^{Y3}$)$_2$, —CH$_2$CH$_2$C(=O)OR$^{Y3}$, —CH$_2$CH$_2$C(=O)N(R$^{Y3}$)$_2$. In certain embodiments of Formula (II), $R^{Y2}$ is substituted or unsubstituted propyl. In certain embodiments of Formula (II), $R^{Y2}$ is substituted or unsubstituted isopropyl. In certain embodiments of Formula (II), $R^{Y2}$ is substituted or unsubstituted butyl. In certain embodiments of Formula (II), $R^{Y2}$ is substituted or unsubstituted isobutyl. In certain embodiments of Formula (II), $R^{Y2}$ is substituted or unsubstituted secbutyl. In certain embodiments of Formula (II), $R^{Y2}$ is substituted or unsubstituted pentyl. In certain embodiments of Formula (II), $R^{Y2}$ is substituted or unsubstituted neopentyl. In certain embodiments of Formula (II), $R^{Y2}$ is substituted or unsubstituted hexyl.

In certain embodiments of Formula (II), $R^{Y2}$ is —C(=O)$R^{A2}$, wherein $R^{A2}$ is as defined herein.

In certain embodiments of Formula (II), $R^{A2}$ is substituted alkyl. In certain embodiments of Formula (II), $R^{A2}$ is unsubstituted alkyl. In certain embodiments of Formula (II), $R^{A2}$ is unsubstituted $C_{1-6}$ alkyl. In certain embodiments of Formula (II), $R^{A2}$ is substituted or unsubstituted methyl. In certain embodiments of Formula (II), $R^{A2}$ is substituted or unsubstituted ethyl. In certain embodiments of Formula (II), $R^{A2}$ is substituted or unsubstituted propyl. In certain embodiments of Formula (II), $R^{A2}$ is substituted or unsubstituted butyl. In certain embodiments of Formula (II), $R^{A2}$ is substituted or unsubstituted pentyl. In certain embodiments of Formula (II), $R^{A2}$ is substituted or unsubstituted hexyl.

In certain embodiments of Formula (II), $R^{A2}$ is substituted alkenyl. In certain embodiments of Formula (II), $R^{A2}$ is unsubstituted alkenyl.

In certain embodiments of Formula (II), $R^{A2}$ is substituted alkynyl. In certain embodiments of Formula (II), $R^{A2}$ is unsubstituted alkynyl.

In certain embodiments of Formula (II), $R^{A2}$ is substituted or unsubstituted carbocyclyl. In certain embodiments of Formula (II), $R^{A2}$ is saturated carbocyclyl. In certain embodiments of Formula (II), $R^{A2}$ is unsaturated carbocyclyl. In certain embodiments of Formula (II), $R^{A2}$ is monocyclic $C_{3-7}$ carbocyclyl.

In certain embodiments of Formula (II), $R^{A2}$ is substituted or unsubstituted heterocyclyl. In certain embodiments of Formula (II), $R^2$ is saturated heterocyclyl. In certain embodiments of Formula (II), $R^2$ is unsaturated heterocyclyl. In certain embodiments of Formula (II), $R^{A2}$ is heterocyclyl, wherein one, two, or three atoms in the heterocyclic ring system are independently selected from the group consisting of nitrogen, oxygen, and sulfur. In certain embodiments of Formula (II), $R^{A2}$ is 3- to 7-membered, monocyclic heterocyclyl.

In certain embodiments of Formula (II), $R^{A2}$ is substituted or unsubstituted aryl. In certain embodiments of Formula (II), $R^{A2}$ is $C_{6-10}$ aryl. In certain embodiments of Formula (II), $R^{A2}$ is monocyclic aryl. In certain embodiments of Formula (II), $R^{A2}$ is substituted phenyl. In certain embodiments of Formula (II), $R^{A2}$ is unsubstituted phenyl. In certain embodiments of Formula (II), $R^{A2}$ is bicyclic aryl.

In certain embodiments of Formula (II), $R^{A2}$ is substituted or unsubstituted heteroaryl. In certain embodiments of Formula (II), $R^{A2}$ is heteroaryl, wherein one, two, three, or four atoms in the heteroaryl ring system are independently selected from the group consisting of nitrogen, oxygen, and sulfur. In certain embodiments of Formula (II), $R^{A2}$ is monocyclic heteroaryl. In certain embodiments of Formula (II), $R^{A2}$ is 5- or 6-membered, monocyclic heteroaryl. In certain embodiments of Formula (II), $R^{A2}$ is bicyclic heteroaryl, wherein the point of attachment may be on any atom of the bicyclic heteroaryl ring system, as valency permits.

In certain embodiments of Formula (II), $R^{Y2}$ is a nitrogen protecting group. In certain embodiments of Formula (II), $R^{Y2}$ is Bn, Boc, Cbz, Fmoc, trifluoroacetyl, triphenylmethyl, acetyl, or Ts.

As generally described herein, each instance of $R^B$, provided in Formula (I) or (II), is independently hydrogen, halogen, substituted or unsubstituted alkyl, substituted or unsubstituted alkenyl, substituted or unsubstituted alkynyl, —$OR^{A1}$, —$N(R^{A1})_2$, —$SR^{A1}$, —CN, —SCN, —$C(=NR^{A1})R^{A1}$, —$C(=NR^{A1})OR^{A1}$, —$C(=NR^{A1})N(R^{A1})_2$, —$C(=O)R^{A1}$, —$C(=O)OR^{A1}$, —$C(=O)N(R^{A1})_2$, —$NO_2$, —$NR^{A1}C(=O)R^{A1}$, —$NR^{A1}C(=O)OR^{A1}$, —$NR^{A1}C(=O)N(R^{A1})_2$, —$OC(=O)R^{A1}$, —$OC(=O)OR^{A1}$, or —$OC(=O)N(R^{A1})_2$; or two $R^B$ groups attached to the same carbon atom are joined to form a =O group.

In certain embodiments of Formula (I) or Formula (II), at least one instance of $R^B$ is hydrogen. In certain embodiments of Formula (I) or Formula (II), at least two instances of $R^B$ are hydrogen. In certain embodiments of Formula (I) or Formula (II), at least three instances of $R^B$ are hydrogen. In certain embodiments of Formula (I) or Formula (II), at least four instances of $R^B$ are hydrogen. In certain embodiments of Formula (I) or Formula (II), at least five instances of $R^B$ are hydrogen. In certain embodiments of Formula (I) or Formula (II), at least six instances of $R^B$ are hydrogen. In certain embodiments of Formula (I) or Formula (II), at least seven instances of $R^B$ are hydrogen. In certain embodiments of Formula (I) or Formula (II), all instances of $R^B$ are hydrogen.

In certain embodiments of Formula (I) or Formula (II), at least one instance of $R^B$ is halogen. In certain embodiments of Formula (I) or Formula (II), at least one instance of $R^B$ is F. In certain embodiments of Formula (I) or Formula (II), at least one instance of $R^B$ is Cl. In certain embodiments of Formula (I) or Formula (II), at least one instance of $R^B$ is Br. In certain embodiments of Formula (I) or Formula (II), at least one instance of $R^B$ is I (iodine). In certain embodiments of Formula (I) or Formula (II), at least two instances of $R^B$ are independently halogen. In certain embodiments of Formula (I) or Formula (II), at least two instances of $R^B$ are F. In certain embodiments of Formula (I) or Formula (II), at least two instances of $R^B$ are Cl.

In certain embodiments of Formula (I) or Formula (II), at least one instance of $R^B$ is substituted alkyl. In certain embodiments of Formula (I) or Formula (II), at least one instance of $R^B$ is unsubstituted alkyl. In certain embodiments of Formula (I) or Formula (II), at least one instance of $R^B$ is unsubstituted $C_{1-6}$ alkyl. In certain embodiments of Formula (I) or Formula (II), at least one instance of $R^B$ is substituted $C_{1-6}$ alkyl. In certain embodiments of Formula (I) or Formula (II), at least one instance of $R^B$ is $C_{1-6}$ alkyl substituted with at least one halogen. In certain embodiments of Formula (I) or Formula (II), at least one instance of $R^B$ is —$CH_3$. In certain embodiments of Formula (I) or Formula (II), at least one instance of $R^B$ is substituted methyl. In certain embodiments of Formula (I) or Formula (II), at least one instance of $R^B$ is —$CH_2F$. In certain embodiments of Formula (I) or Formula (II), at least one instance of $R^B$ is —$CHF_2$. In certain embodiments of Formula (I) or Formula (II), at least one instance of $R^B$ is —$CF_3$. In certain embodiments of Formula (I) or Formula (II), at least one instance of $R^B$ is substituted or unsubstituted ethyl. In certain embodiments of Formula (I) or Formula (II), at least one instance of $R^B$ is substituted or unsubstituted propyl. In certain embodiments of Formula (I) or Formula (II), at least one instance of $R^B$ is substituted or unsubstituted butyl. In certain embodiments of Formula (I) or Formula (II), at least one instance of $R^B$ is substituted or unsubstituted pentyl. In certain embodiments of Formula (I) or Formula (II), at least one instance of $R^B$ is substituted or unsubstituted hexyl.

In certain embodiments of Formula (I) or Formula (II), at least one instance of $R^B$ is substituted alkenyl. In certain embodiments of Formula (I) or Formula (II), at least one instance of $R^B$ is unsubstituted alkenyl.

In certain embodiments of Formula (I) or Formula (II), at least one instance of $R^B$ is substituted alkynyl. In certain embodiments of Formula (I) or Formula (II), at least one instance of $R^B$ is unsubstituted alkynyl.

In certain embodiments of Formula (I) or (II), at least one instance of $R^B$ is —$OR^{A1}$, wherein $R^{A1}$ is hydrogen (i.e., to provide —OH), or a non-hydrogen group.

In certain embodiments of Formula (I) or (II), at least one instance of $R^B$ is —$SR^{A1}$, wherein $R^{A1}$ is hydrogen (i.e., to provide —SH), or a non-hydrogen group.

In certain embodiments of Formula (I) or (II), at least one instance of $R^B$ is —$N(R^{A1})_2$, wherein at least one $R^{A1}$ is hydrogen (e.g., to provide —$NH_2$ or $NHR^{A1}$), each $R^{A1}$ is a non-hydrogen group, or wherein two $R^{A1}$ groups are joined to form a substituted or unsubstituted heterocyclic or heteroaryl ring.

In certain embodiments of Formula (I) or (II), at least one instance of $R^B$ is —CN. In certain embodiments of Formula (I) or (II), at least one instance of $R^B$—$NO_2$.

In certain embodiments of Formula (I) or (II), at least one instance of $R^B$ is —$C(=NR^{A1})R^{A1}$, wherein $R^{A1}$ is hydrogen (i.e., to provide —C(=NH)H), or a non-hydrogen group.

In certain embodiments of Formula (I) or (II), at least one instance of $R^B$ is —$C(=NR^{A1})OR^{A1}$, wherein $R^{A1}$ is hydrogen (i.e., to provide —C(=NH)OH), or a non-hydrogen group.

In certain embodiments of Formula (I) or (II), at least one instance of $R^B$ is —$C(=NR^{A1})N(R^{A1})_2$, wherein $R^{A1}$ is hydrogen (i.e., to provide —$C(=NH)NH_2$), or a non-hydrogen group.

In certain embodiments of Formula (I) or (II), at least one instance of $R^B$ is —$C(=O)R^{A1}$, wherein $R^{A1}$ is hydrogen (i.e., to provide —C(=O)H), or a non-hydrogen group.

In certain embodiments of Formula (I) or (II), at least one instance of $R^B$ is —$C(=O)OR^{A1}$, wherein $R^A$ is hydrogen (i.e., to provide —C(=O)OH), or a non-hydrogen group.

In certain embodiments of Formula (I) or (II), at least one instance of $R^B$ is —$C(=O)N(R^{A1})_2$, wherein $R^{A1}$ is hydrogen (i.e., to provide —$C(=O)NH_2$), or a non-hydrogen group.

In certain embodiments of Formula (I) or (II), at least one instance of $R^B$ is —$C(=O)N(R^{A1})_2$, wherein $R^{A1}$ is hydrogen (i.e., to provide —$C(=O)NH_2$), or a non-hydrogen group. In certain embodiments of Formula (I) or (II), at least one instance of $R^B$ is —$C(=O)NMe_2$, or —C(=O)NHMe.

In certain embodiments of Formula (I) or (II), at least one instance of $R^B$ is —$NR^{A1}C(=O)R^{A1}$, wherein $R^{A1}$ is hydrogen (i.e., to provide —NHC(=O)H), or a non-hydrogen group.

In certain embodiments of Formula (I) or (II), at least one instance of $R^B$ is —$NR^{A1}C(=O)OR^{A1}$, wherein $R^{A1}$ is hydrogen (i.e., to provide —NHC(=O)OH), or a non-hydrogen group.

In certain embodiments of Formula (I) or (II), at least one instance of $R^B$ is —$NR^{A1}C(=O)N(R^{A1})_2$, wherein $R^{A1}$ is hydrogen (i.e., to provide —NHC(=O)NH$_2$), or a non-hydrogen group.

In certain embodiments of Formula (I) or (II), at least one instance of $R^B$ is —$OC(=O)R^{A1}$, wherein $R^{A1}$ is hydrogen (i.e., to provide —OC(=O)H), or a non-hydrogen group.

In certain embodiments of Formula (I) or (II), at least one instance of $R^B$ is —$OC(=O)OR^{A1}$, wherein $R^{A1}$ is hydrogen (i.e., to provide —OC(=O)OH), or a non-hydrogen group.

In certain embodiments of Formula (I) or (II), at least one instance of $R^B$ is —$OC(=O)N(R^{A1})_2$, wherein $R^{A1}$ is hydrogen (i.e., to provide —OC(=O)NH$_2$), or a non-hydrogen group.

Furthermore, as generally described herein, in any of the above described embodiments of group $R^B$ comprising a group $R^{A1}$, each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic or substituted or unsubstituted heteroaryl ring.

For example, in any of the above described embodiments of $R^B$ comprising a group $R^{A1}$, at least one instance of $R^{A1}$ is hydrogen.

In any of the above described embodiments of $R^B$ comprising a group $R^{A1}$, at least one instance of $R^{A1}$ is substituted or unsubstituted alkyl, e.g., substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl.

In any of the above described embodiments of $R^B$ comprising a group $R^{A1}$, at least one instance of $R^{A1}$ is substituted or unsubstituted $C_{2-6}$alkenyl, e.g., substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl In any of the above described embodiments of $R^B$ comprising a group $R^{A1}$, at least one instance of $R^{A1}$ is substituted or unsubstituted $C_{2-6}$alkynyl, e.g., substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments of Formula (I) or Formula (II), e.g., wherein $R^B$ is —$N(R^{A1})_2$, —$C(=NR^{A1})N(R^{A1})_2$, —$C(=O)N(R^{A1})_2$, —NR AC(=O)N(R^{A1})_2, or —$OC(=O)N(R^{A1})_2$, two instances of $R^{A1}$, e.g., attached to the same nitrogen (N) atom, are joined to form a substituted or unsubstituted heterocyclic ring. In certain embodiments of Formula (I) or Formula (II), two instances of $R^{A1}$ are joined to form a saturated heterocyclic ring. In certain embodiments of Formula (I) or Formula (II), two instances of $R^{A1}$ are joined to form an unsaturated heterocyclic ring. In certain embodiments of Formula (I) or Formula (II), two instances of $R^{A1}$ are joined to form a heterocyclic ring, wherein one, two, or three atoms in the heterocyclic ring system are independently selected from the group consisting of nitrogen, oxygen, and sulfur. In certain embodiments of Formula (I) or Formula (II), two instances of $R^{A1}$ are joined to form a 3- to 7-membered, monocyclic heterocyclic ring.

In certain embodiments of Formula (I) or Formula (II), e.g., wherein $R^B$ is —$N(R^{A1})_2$, —$C(=NR^{A1})N(R^{A1})_2$, —$C(=O)N(R^{A1})_2$, —$NR^{A1}C(=O)N(R^{A1})_2$, or —$OC(=O)N(R^{A1})_2$, two instances of $R^{A1}$, e.g., attached to the same nitrogen (N) atom, are joined to form a substituted or unsubstituted heteroaryl ring. In certain embodiments of Formula (I) or Formula (II), two instances of $R^{A1}$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I) or Formula (II), two instances of $R^{A1}$ are joined to form a substituted or unsubstituted, 9- to 10-membered, monocyclic heteroaryl ring, wherein one, two, three, or four atoms in the heteroaryl ring system are independently nitrogen, oxygen, or sulfur.

In certain embodiments of Formula (I) or Formula (II), each instance of $R^B$ is independently hydrogen, halogen, substituted or unsubstituted $C_{1-6}$ alkyl, or —$OR^{A1}$, wherein $R^{A1}$ is substituted or unsubstituted $C_{1-6}$ alkyl. In certain embodiments of Formula (I) or Formula (II), each instance of $R^B$ is independently hydrogen, halogen, unsubstituted $C_{1-6}$ alkyl, $C_{1-6}$ alkyl substituted with at least one halogen, or —$OR^{A1}$, wherein $R^{A1}$ is unsubstituted $C_{1-6}$ alkyl.

Furthermore, in certain embodiments of Formula (I) or Formula (II), two $R^B$ groups attached to the same carbon atom are joined to form a =O group.

As generally described herein, $L^3$, provided in a compound of Formula (I) or (II), is a bond or a linker selected from the group consisting of substituted and unsubstituted $C_{1-6}$alkylene, substituted and unsubstituted $C_{2-6}$alkenylene, substituted and unsubstituted $C_{2-6}$alkynylene, substituted and unsubstituted hetero$C_{1-6}$alkylene, substituted and unsubstituted hetero$C_{2-6}$alkenylene, and substituted and unsubstituted hetero$C_{2-6}$alkynylene.

In certain embodiments of Formula (I) or (II), $L^3$ is a bond, i.e., a direct, covalent single bond.

In certain embodiments of Formula (I) or (II), $L^3$ is a substituted or unsubstituted $C_{1-6}$alkylene, e.g., substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^3$ is unsubstituted $C_{1-6}$ alkylene.

In certain embodiments of Formula (I) or Formula (II), $L^3$ is a substituted or unsubstituted $C_{2-6}$alkenylene, e.g., substituted or unsubstituted $C_{3-6}$alkenylene, substituted or unsubstituted $C_{4-6}$alkenylene, substituted or unsubstituted $C_{5-6}$alkenylene, substituted or unsubstituted $C_{2-5}$alkenylene, substituted or unsubstituted $C_{2-4}$alkenylene, substituted or unsubstituted $C_{2-3}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene. In certain embodiments of Formula (I) or Formula (II), $L^3$ is unsubstituted $C_{2-6}$alkenylene.

In certain embodiments of Formula (I) or Formula (II), $L^3$ is a substituted or unsubstituted $C_{2-6}$alkynylene, e.g., substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene. In certain embodiments of Formula (I) or Formula (II), $L^3$ is unsubstituted $C_{2-6}$alkynylene.

In certain embodiments of Formula (I) or Formula (II), $L^3$ is a substituted or unsubstituted hetero$C_{1-6}$alkylene, e.g., substituted or unsubstituted hetero$C_{2-6}$alkylene, substituted or unsubstituted hetero$C_{3-6}$alkylene, substituted or unsubstituted hetero$C_{4-6}$alkylene, substituted or unsubstituted hetero$C_{5-6}$alkylene, substituted or unsubstituted hetero$C_{2-5}$alkylene, substituted or unsubstituted hetero$C_{2-4}$alkylene, substituted or unsubstituted hetero$C_{2-3}$alkylene, substituted or unsubstituted hetero$C_1$alkylene, substituted or unsubstituted hetero$C_2$alkylene, substituted or unsubstituted hetero$C_3$alkylene, substituted or unsubstituted hetero$C_4$alkylene, substituted or unsubstituted hetero$C_5$alkylene, or substituted or unsubstituted hetero$C_6$alkylene. In certain embodiments of Formula (I) or Formula (II), $L^3$ is unsubstituted hetero$C_{1-6}$alkylene. In certain embodiments of Formula (I) or Formula (II), wherein $L^3$ is a substituted or unsubstituted hetero$C_{1-6}$alkylene, the hetero$C_{2-6}$alkylene comprises includes one, two, or three heteroatoms in the heteroalkylene chain, wherein the heteroatoms are independently nitrogen, oxygen, or sulfur.

In certain embodiments of Formula (I) or Formula (II), $L^3$ is a substituted or unsubstituted hetero$C_{2-6}$alkenylene, e.g., substituted or unsubstituted hetero$C_{3-6}$alkenylene, substituted or unsubstituted hetero$C_{4-6}$alkenylene, substituted or unsubstituted hetero$C_{5-6}$alkenylene, substituted or unsubstituted hetero$C_{2-5}$alkenylene, substituted or unsubstituted hetero$C_{2-4}$alkenylene, substituted or unsubstituted hetero$C_{2-3}$alkenylene, substituted or unsubstituted hetero$C_2$alkenylene, substituted or unsubstituted hetero$C_3$alkenylene, substituted or unsubstituted hetero$C_4$alkenylene, or substituted or unsubstituted hetero$C_5$alkenylene, or substituted or unsubstituted hetero$C_6$alkenylene. In certain embodiments of Formula (I) or Formula (II), $L^3$ is unsubstituted hetero$C_{2-6}$alkenylene. In certain embodiments of Formula (I) or Formula (II), wherein $L^3$ is a substituted or unsubstituted hetero$C_{2-6}$alkenylene, the hetero$C_{2-6}$alkenylene comprises one, two, or three heteroatoms in the heteroalkenylene chain, wherein the heteroatoms are independently nitrogen, oxygen, or sulfur.

In certain embodiments of Formula (I) or Formula (II), $L^3$ is a substituted or unsubstituted hetero$C_{2-6}$alkynylene, e.g., substituted or unsubstituted hetero$C_{2-6}$alkynylene, substituted or unsubstituted hetero$C_{3-6}$alkynylene, substituted or unsubstituted hetero$C_{4-6}$alkynylene, substituted or unsubstituted hetero$C_{5-6}$alkynylene, substituted or unsubstituted hetero$C_{2-5}$alkynylene, substituted or unsubstituted hetero$C_{2-4}$alkynylene, substituted or unsubstituted hetero$C_{2-3}$alkynylene, substituted or unsubstituted hetero$C_2$alkynylene, substituted or unsubstituted hetero$C_3$alkynylene, substituted or unsubstituted hetero$C_4$alkynylene, substituted or unsubstituted hetero$C_5$alkynylene, or substituted or unsubstituted hetero$C_6$alkynylene. In certain embodiments of Formula (I) or Formula (II), $L^3$ is unsubstituted heteroalkynylene. In certain embodiments of Formula (I) or Formula (II), wherein $L^3$ is a substituted or unsubstituted hetero$C_{2-6}$alkynylene, $L^3$ includes one, two, or three heteroatoms in the heteroalkynylene chain, wherein the heteroatoms are independently nitrogen, oxygen, or sulfur.

As generally described herein, as provided in a compound of Formula (I) or (II), $G_1$ is $NR^{G1a}$ and $G_2$ is $N(R^{G2a})_2$, $OR^{G2a}$, or $C(R^{G2a})_2$; or $G_1$ is $CHR^{G1a}$ and $G_2$ is $N(R^{G2a})_2$, $OR^{G2a}$; each instance of $R^{G1a}$ and $R^{G2a}$ is independently hydrogen, substituted or unsubstituted alkyl, substituted or unsubstituted hydroxyl, a nitrogen protecting group when attached to a nitrogen atom, or an oxygen protecting group when attached to an oxygen atom, or $R^{G1a}$ and one instance of $R^{G2a}$ are joined to form the group —$C(R^B)_2$—$C(R^B)_2$—.

In certain embodiments of Formula (I) or Formula (II), $G_1$ is $NR^{G1a}$. In certain embodiments of Formula (I) or Formula (II), $G_1$ is $CHR^{G1a}$.

In certain embodiments of Formula (I) or Formula (II), $G_2$ is $N(R^{G2a})_2$. In certain embodiments of Formula (I) or Formula (II), $G_2$ is $OR^{G2a}N(R^{G2a})$.

In certain embodiments of Formula (I) or Formula (II), wherein $G_1$ is $NR^{G1a}$ or $CHR^{G1a}$, $R^{G1a}$ is hydrogen.

In certain embodiments of Formula (I) or Formula (II), wherein $G_1$ is $NR^{G1a}$ or $CHR^{G1a}$, $R^{G1a}$ is substituted or unsubstituted alkyl. In certain embodiments of Formula (I) or Formula (II), $R^{G1a}$ is substituted alkyl. In certain embodiments of Formula (I) or Formula (II), $R^{G1a}$ is unsubstituted alkyl. In certain embodiments of Formula (I) or Formula (II), $R^{G1a}$ is unsubstituted $C_{1-6}$ alkyl. In certain embodiments of Formula (I) or Formula (II), $R^{G1a}$ is substituted $C_{1-6}$ alkyl. In certain embodiments of Formula (I) or Formula (II), $R^{G1a}$ is $C_{1-6}$ alkyl substituted with at least one halogen. In certain embodiments of Formula (I) or Formula (II), $R^{G1a}$ is —$CH_3$. In certain embodiments of Formula (I) or Formula (II), $R^{G1a}$ is substituted methyl. In certain embodiments of Formula (I) or Formula (II), $R^{G1a}$ is —$CH_2F$. In certain embodiments of Formula (I) or Formula (II), $R^{G1a}$ is —$CHF_2$. In certain embodiments of Formula (I) or Formula (II), $R^{G1a}$ is —$CF_3$. In certain embodiments of Formula (I) or Formula (II), $R^{G1a}$ is substituted or unsubstituted ethyl. In certain embodiments of Formula (I) or Formula (II), $R^{G1a}$ is substituted or unsubstituted propyl. In certain embodiments of Formula (I) or Formula (II), $R^{G1a}$ is substituted or unsubstituted butyl. In certain embodiments of Formula (I) or Formula (II), $R^{G1a}$ is substituted or unsubstituted pentyl. In certain embodiments of Formula (I) or Formula (II), $R^{G1a}$ is substituted or unsubstituted hexyl.

In certain embodiments of Formula (I) or Formula (II), wherein $G_1$ is $NR^{G1a}R^{G1a}$ is a nitrogen protecting group. In certain embodiments of Formula (I) or Formula (II), wherein $G_1$ is $NR^{G1a}$, $R^{G1a}$ is Bn, Boc, Chz, Fmoc, trifluoroacetyl, triphenylmethyl, acetyl, or Ts.

In certain embodiments of Formula (I) or Formula (II), wherein $G_2$ is $N(R^{G2a})_2$ or $G_2$ is $OR^{G2a}$, at least one instance of $R^{G2a}$ is hydrogen.

In certain embodiments of Formula (I) or Formula (II), wherein $G_2$ is $N(R^{G2a})_2$ or $G_2$ is $OR^{G2a}$, at least one instance of $R^{G2a}$ is substituted or unsubstituted alkyl. In certain embodiments of Formula (I) or Formula (II), at least one instance of $R^{G2a}$ is substituted alkyl. In certain embodiments of Formula (I) or Formula (II), at least one instance of $R^{G2a}$ is unsubstituted alkyl. In certain embodiments of Formula (I) or Formula (II), at least one instance of $R^{G2a}$ is unsubstituted $C_{1-6}$ alkyl. In certain embodiments of Formula (I) or Formula (II), at least one instance of $R^{G2a}$ is substituted $C_{1-6}$ alkyl. In certain embodiments of Formula (I) or Formula (II), at least one instance of $R^{G2a}$ is $C_{1-6}$ alkyl substituted with at least one halogen. In certain embodiments of Formula (I) or Formula (II), at least one instance of $R^{G2a}$ is —CH$_3$. In certain embodiments of Formula (I) or Formula (II), at least one instance of $R^{G2a}$ is substituted methyl. In certain embodiments of Formula (I) or Formula (II), at least one instance of $R^{G2a}$ is —CH$_2$F. In certain embodiments of Formula (I) or Formula (II), at least one instance of $R^{G2a}$ is —CHF$_2$. In certain embodiments of Formula (I) or Formula (II), at least one instance of $R^{G2a}$ is —CF$_3$. In certain embodiments of Formula (I) or Formula (II), at least one instance of $R^{G2a}$ is substituted or unsubstituted ethyl. In certain embodiments of Formula (I) or Formula (II), at least one instance of $R^{G2a}$ is substituted or unsubstituted propyl. In certain embodiments of Formula (I) or Formula (II), at least one instance of $R^{G2a}$ is substituted or unsubstituted butyl. In certain embodiments of Formula (I) or Formula (II), at least one instance of $R^{G2a}$ is substituted or unsubstituted pentyl. In certain embodiments of Formula (I) or Formula (II), at least one instance of $R^{G2a}$ is substituted or unsubstituted hexyl.

In certain embodiments of Formula (I) or Formula (II), wherein $G_2$ is $N(R^{G2a})_2$, at least one instance of $R^{G2a}$ is a nitrogen protecting group. In certain embodiments of Formula (I) or Formula (II), wherein $G_2$ is $N(R^{G2a})_2$, at least one instance of $R^{G2a}$ is Bn, Boc, Cbz, Fmoc, trifluoroacetyl, triphenylmethyl, acetyl, or Ts.

In certain embodiments of Formula (I) or Formula (II), wherein $G_2$ is $OR^{G2a}$ at least one instance of $R^{G2a}$ is an oxygen protecting group. In certain embodiments of Formula (I) or Formula (II), wherein $G_2$ is $OR^{G2a}$, at least one instance of $R^{G2a}$ is silyl, TBDPS, TBDMS, TIPS, TES, TMS, MOM, THP, t-Bu, Bn, allyl, acetyl, pivaloyl, or benzoyl.

In certain embodiments of Formula (I) or Formula (II), wherein $G_1$ is $CHR^{G1a}$ and $G_2$ is $OR^{G2a}$, $R^{G1a}$ and one instance of $R^{G2a}$ are joined to form the group —C(R$^B$)$_2$—C(R$^B$)$_2$—, i.e., to provide a group of formula:

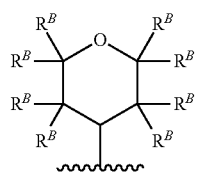

wherein $R^B$ is as defined herein. In certain embodiments, each instance of $R^B$ is hydrogen.

In certain embodiments of Formula (I) or Formula (II), wherein $G_1$ is $NR^{G1a}$ and $G_2$ is $OR^{G2a}$, $R^{G1a}$ and one instance of $R^{G2a}$ are joined to form the group —C(R$^B$)$_2$—C(R$^B$)$_2$—, i.e., to provide a group of the formula:

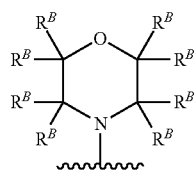

wherein $R^B$ is as defined herein. In certain embodiments, each instance of $R^B$ is hydrogen.

In certain embodiments of Formula (I) or Formula (II), wherein $G_1$ is $CHR^{G1a}$ and $G_2$ is $N(R^{G2a})_2$, $R^{G1a}$ and one instance of $R^{G2a}$ are joined to form the group —C(R$^B$)$_2$—C(R$^B$)$_2$—, i.e., to provide a group of the formula:

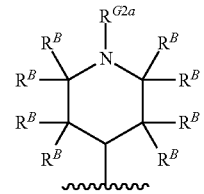

wherein $R^{G2a}$ and $R^B$ are as defined herein. In certain embodiments, each instance of $R^B$ is hydrogen. In certain embodiments, $R^{G2a}$ is substituted or unsubstituted alkyl, e.g., —CH$_3$.

In certain embodiments of Formula (I) or Formula (II), wherein $G_1$ is $NR^{G1a}$ and $G_2$ is $N(R^{G2a})_2$, $R^{G1a}$ and one instance of $R^{G2a}$ are joined to form the group —C(R$^B$)$_2$—C(R$^B$)$_2$—, i.e., to provide a group of the formula:

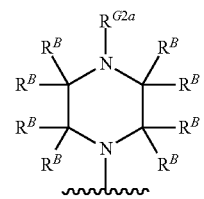

wherein $R^{G2a}$ and $R^B$ are as defined herein. In certain embodiments, each instance of $R^B$ is hydrogen. In certain embodiments, $R^{G2a}$ is substituted or unsubstituted alkyl, e.g., —CH$_3$.

In certain embodiments of Formula (I) or Formula (II), wherein $G_1$ is $NR^{G1a}$ and $G_2$ is $C(R^{G2a})_2$, $R^{G1a}$ and one instance of $R^{G2a}$ are joined to form the group —C(R$^B$)$_2$—C(R$^B$)$_2$—, i.e., to provide a group of the formula:

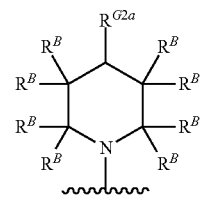

wherein $R^{G2a}$ and $R^B$ are as defined herein. In certain embodiments, each instance of $R^B$ is hydrogen. In certain embodiments, $R^{G2a}$ is substituted or unsubstituted alkyl, e.g., —CH$_3$, or substituted or unsubstituted hydroxyl, e.g., —OH or —OCH$_3$.

Group $R^C$ and a

As generally described herein, each instance of $R^C$ is independently halogen, substituted or unsubstituted alkyl, substituted or unsubstituted alkenyl, substituted or unsubstituted alkynyl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$, and a is 0, 1, or 2, provided when a is 0 then $R^C$ is absent.

In certain embodiments of Formula (I) or (II), a is 1. In certain embodiments of Formula (I) or (II), a is 1 and $R^C$ is a group as described herein attached ortho to the point of attachment to

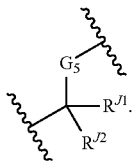

In certain embodiments of Formula (I) or (II), a is 1 and $R^C$ is a group as described herein attached meta to the point of attachment to

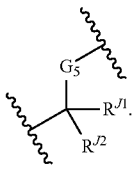

In certain embodiments of Formula (I) or (II), a is 2. In certain embodiments of Formula (I) or (II), a is 2, and each $R^C$ is independently a group as described herein, wherein one $R^C$ is attached ortho and one $R^C$ is attached meta to the point of attachment to

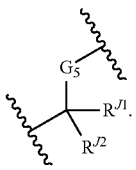

In certain embodiments of Formula (I) or (II), a is 2, and each $R^C$ is independently a group as described herein, both $R^C$ groups are attached ortho to the point of attachment to

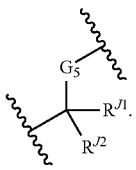

In certain embodiments of Formula (I) or (II), a is 2, and each $R^C$ is independently a group as described herein, both $R^C$ groups are attached meta to the point of attachment to

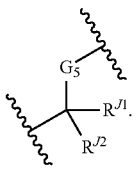

In certain embodiments of Formula (I) or (II), a is 1 or 2 and at least one instance of $R^C$ is halogen. In certain embodiments of Formula (I) or (II), a is 1 or 2 and at least one instance of $R^C$ is F. In certain embodiments of Formula (I) or (II), a is 1 or 2 and at least one instance of $R^C$ is Cl. In certain embodiments of Formula (I) or (II), a is 1 or 2 and at least one instance of $R^C$ is Br. In certain embodiments of Formula (I) or (II), a is 1 or 2 and at least one instance of $R^C$ is I (iodine). In certain embodiments of Formula (I) or (II), a is 2 and both instances of $R^C$ are independently halogen. In certain embodiments of Formula (I) or (II), a is 2 and both instances of $R^C$ are F. In certain embodiments of Formula (I) or (II), a is 2 and both instances of $R^C$ are Cl.

In certain embodiments of Formula (I) or (II), a is 1 or 2 and at least one instance of $R^C$ is substituted alkyl. In certain embodiments of Formula (I) or (II), a is 1 or 2 and at least one instance of $R^C$ is unsubstituted alkyl. In certain embodiments of Formula (I) or (II), a is 1 or 2 and at least one instance of $R^C$ is unsubstituted $C_{1-6}$ alkyl. In certain embodiments of Formula (I) or (II), a is 1 or 2 and at least one instance of $R^C$ is substituted $C_{1-6}$ alkyl. In certain embodiments of Formula (I) or (II), a is 1 or 2 and at least one instance of $R^C$ is $C_{1-6}$ alkyl substituted with at least one halogen. In certain embodiments of Formula (I) or (II), a is 1 or 2 and at least one instance of $R^C$ is —$CH_3$. In certain embodiments of Formula (I) or (II), a is 1 or 2 and at least one instance of $R^C$ is substituted methyl. In certain embodiments of Formula (I) or (II), a is 1 or 2 and at least one instance of $R^C$ is —$CH_2F$. In certain embodiments of Formula (I) or (II), a is 1 or 2 and at least one instance of $R^C$ is —$CHF_2$. In certain embodiments of Formula (I) or (II), a is 1 or 2 and at least one instance of $R^C$ is —$CF_3$. In certain embodiments of Formula (I) or (II), a is 1 or 2 and at least one instance of $R^C$ is substituted or unsubstituted ethyl. In certain embodiments of Formula (I) or (II), a is 1 or 2 and at least one instance of $R^C$ is substituted or unsubstituted propyl. In certain embodiments of Formula (I) or (II), a is 1 or 2 and at least one instance of $R^C$ is substituted or unsubstituted butyl. In certain embodiments of Formula (I) or (II), a is 1 or 2 and at least one instance of $R^C$ is substituted or unsubstituted pentyl. In certain embodiments of Formula (I) or (II), a is 1 or 2 and at least one instance of $R^C$ is substituted or unsubstituted hexyl.

In certain embodiments of Formula (I) or (II), a is 1 or 2 and at least one instance of $R^C$ is substituted or unsubstituted alkenyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl.

In certain embodiments of Formula (I) or (II), a is 1 or 2 and at least one instance of $R^C$ is substituted or unsubstituted alkynyl, e.g., substituted or unsubstituted $C_{2-6}$alkenyl, substituted or unsubstituted $C_{2-5}$alkenyl, substituted or unsubstituted $C_{2-4}$alkenyl, or substituted or unsubstituted $C_{2-3}$alkenyl.

In certain embodiments of Formula (I) or (II), a is 1 or 2 and at least one instance of $R^C$ is —$OR^{41}$, wherein $R^{41}$ is hydrogen (i.e., to provide —OH), or a non-hydrogen group.

In certain embodiments of Formula (I) or (II), a is 1 or 2 and at least one instance of $R^C$ is —$SR^{41}$, wherein $R^{41}$ is hydrogen (i.e., to provide —SH), or a non-hydrogen group.

In certain embodiments of Formula (I) or (II), a is 1 or 2 and at least one instance of $R^C$ is —$N(R^{41})_2$, wherein at least one $R^{41}$ is hydrogen (e.g., to provide —$NH_2$ or $NHR^{41}$), each $R^{41}$ is a non-hydrogen group, or wherein two $R^{41}$ groups are joined to form a substituted or unsubstituted heterocyclic or heteroaryl ring.

In certain embodiments of Formula (I) or (II), a is 1 or 2 and at least one instance of $R^C$ is —CN. In certain embodiments of Formula (I) or (II), a is 1 or 2 and at least one instance of $R^C$ is —NO$_2$.

In certain embodiments of Formula (I) or (II), a is 1 or 2 and at least one instance of $R^C$ is —C(=NR$^{A1}$)R$^{A1}$, wherein R$^{A1}$ is hydrogen (i.e., to provide —C(=NH)H), or a non-hydrogen group.

In certain embodiments of Formula (I) or (II), a is 1 or 2 and at least one instance of $R^C$ is —C(=NR$^{A1}$)OR$^{A1}$, wherein R$^{A1}$ is hydrogen (i.e., to provide —C(=NH)OH), or a non-hydrogen group.

In certain embodiments of Formula (I) or (II), a is 1 or 2 and at least one instance of $R^C$ is —C(=NR$^{A1}$)N(R$^{A1}$)$_2$, wherein R$^{A1}$ is hydrogen (i.e., to provide —C(=NH)NH$_2$), or a non-hydrogen group.

In certain embodiments of Formula (I) or (II), a is 1 or 2 and at least one instance of $R^C$ is —C(=O)R$^{A1}$, wherein R$^{A1}$ is hydrogen (i.e., to provide —C(=O)H), or a non-hydrogen group.

In certain embodiments of Formula (I) or (II), a is 1 or 2 and at least one instance of $R^C$ is —C(=O)OR$^{A1}$, wherein R$^{A1}$ is hydrogen (i.e., to provide —C(=O)OH), or a non-hydrogen group.

In certain embodiments of Formula (I) or (II), a is 1 or 2 and at least one instance of $R^C$ is —C(=O)N(R$^{A1}$)$_2$, wherein R$^{A1}$ is hydrogen (i.e., to provide —C(=O)NH$_2$), or a non-hydrogen group.

In certain embodiments of Formula (I) or (II), a is 1 or 2 and at least one instance of $R^C$ is —C(=O)N(R$^{A1}$)$_2$, wherein R$^{A1}$ is hydrogen (i.e., to provide —C(=O)NH$_2$), or a non-hydrogen group. In certain embodiments of Formula (I) or (II), a is 1 or 2 and at least one instance of $R^C$ is —C(=O)NMe$_2$, or —C(=O)NHMe.

In certain embodiments of Formula (I) or (II), a is 1 or 2 and at least one instance of $R^C$ is —NR$^{A1}$C(=O)R$^{A1}$, wherein R$^{A1}$ is hydrogen (i.e., to provide —NHC(=O)H), or a non-hydrogen group.

In certain embodiments of Formula (I) or (II), a is 1 or 2 and at least one instance of $R^C$ is —NR$^{A1}$C(=O)OR$^{A1}$, wherein R$^{A1}$ is hydrogen (i.e., to provide —NHC(=O)OH), or a non-hydrogen group.

In certain embodiments of Formula (I) or (II), a is 1 or 2 and at least one instance of $R^C$ is —NR$^{A1}$C(=O)N(R$^{A1}$)$_2$, wherein R$^{A1}$ is hydrogen (i.e., to provide —NHC(=O)NH$_2$), or a non-hydrogen group.

In certain embodiments of Formula (I) or (II), a is 1 or 2 and at least one instance of $R^C$ is —OC(=O)R$^{A1}$, wherein R$^{A1}$ is hydrogen (i.e., to provide —OC(=O)H), or a non-hydrogen group.

In certain embodiments of Formula (I) or (II), a is 1 or 2 and at least one instance of $R^C$ is —OC(=O)OR$^{A1}$, wherein R$^{A1}$ is hydrogen (i.e., to provide —OC(=O)OH), or a non-hydrogen group.

In certain embodiments of Formula (I) or (II), a is 1 or 2 and at least one instance of $R^C$ is —OC(=O)N(R$^{A1}$)$_2$, wherein R$^{A1}$ is hydrogen (i.e., to provide —OC(=O)NH$_2$), or a non-hydrogen group.

Furthermore, as generally described herein, in any of the above described embodiments of group $R^C$ comprising a group R$^{A1}$, each instance of R$^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1}$ groups are joined to form a substituted or unsubstituted heterocyclic or substituted or unsubstituted heteroaryl ring.

For example, in any of the above described embodiments of $R^C$ comprising a group R$^{A1}$, at least one instance of R$^{A1}$ is hydrogen.

In any of the above described embodiments of $R^C$ comprising a group R$^{A1}$, at least one instance of R$^{A1}$ is substituted or unsubstituted alkyl, e.g., substituted or unsubstituted C$_{1-6}$ alkyl, e.g., substituted or unsubstituted C$_1$alkyl, substituted or unsubstituted C$_2$alkyl, substituted or unsubstituted C$_3$alkyl, substituted or unsubstituted C$_4$alkyl, substituted or unsubstituted C$_5$alkyl, or substituted or unsubstituted C$_6$alkyl.

In any of the above described embodiments of $R^C$ comprising a group R$^{A1}$, at least one instance of R$^{A1}$ is substituted or unsubstituted C$_{2-6}$alkenyl, e.g., substituted or unsubstituted C$_2$alkenyl, substituted or unsubstituted C$_3$alkenyl, substituted or unsubstituted C$_4$alkenyl, substituted or unsubstituted C$_5$alkenyl, or substituted or unsubstituted C$_6$alkenyl In any of the above described embodiments of $R^C$ comprising a group R$^{A1}$, at least one instance of R$^{A1}$ is substituted or unsubstituted C$_{2-6}$alkynyl, e.g., substituted or unsubstituted C$_2$alkynyl, substituted or unsubstituted C$_3$alkynyl, substituted or unsubstituted C$_4$alkynyl, substituted or unsubstituted C$_5$alkynyl, or substituted or unsubstituted C$_6$alkynyl.

In certain embodiments of Formula (I) or Formula (II), e.g., wherein $R^C$ is —N(R$^{A1}$)$_2$, —C(=NR$^{A1}$)N(R$^{A1}$)$_2$, —C(=O)N(R$^{A1}$)$_2$, —NR$^{A1}$C(=O)N(R$^{A1}$)$_2$, or —OC(=O)N(R$^{A1}$)$_2$, two instances of R$^{A1}$, e.g., attached to the same nitrogen (N) atom, are joined to form a substituted or unsubstituted heterocyclic ring. In certain embodiments of Formula (I) or Formula (II), two instances of R$^{A1}$ are joined to form a saturated heterocyclic ring. In certain embodiments of Formula (I) or Formula (II), two instances of R$^{A1}$ are joined to form an unsaturated heterocyclic ring. In certain embodiments of Formula (I) or Formula (II), two instances of R$^{A1}$ are joined to form a heterocyclic ring, wherein one, two, or three atoms in the heterocyclic ring system are independently selected from the group consisting of nitrogen, oxygen, and sulfur. In certain embodiments of Formula (I) or Formula (II), two instances of R$^{A1}$ are joined to form a 3- to 7-membered, monocyclic heterocyclic ring.

In certain embodiments of Formula (I) or Formula (II), e.g., wherein $R^C$ is —N(R$^{A1}$)$_2$, —C(=NR$^{A1}$)N(R$^{A1}$)$_2$, —C(=O)N(R$^{A1}$)$_2$, —NR$^{A1}$C(=O)N(R$^{A1}$)$_2$, or —OC(=O)N(R$^{A1}$)$_2$, two instances of R$^{A1}$, e.g., attached to the same nitrogen (N) atom, are joined to form a substituted or unsubstituted heteroaryl ring. In certain embodiments of Formula (I) or Formula (II), two instances of R$^{A1}$ are joined to form a substituted or unsubstituted, 5- to 6-membered, monocyclic heteroaryl ring, wherein one, two, three, or four atoms in the heteroaryl ring system are independently nitrogen, oxygen, or sulfur. In certain embodiments of Formula (I) or Formula (II), two instances of R$^{A1}$ are joined to form a substituted or unsubstituted, 9- to 10-membered, monocyclic heteroaryl ring, wherein one, two, three, or four atoms in the heteroaryl ring system are independently nitrogen, oxygen, or sulfur.

In certain embodiments of Formula (I) or Formula (II), each instance of $R^C$ is independently hydrogen, halogen, substituted or unsubstituted C$_{1-6}$ alkyl, or —OR$^{A1}$, wherein R$^{A1}$ is substituted or unsubstituted C$_{1-6}$ alkyl. In certain embodiments of Formula (I) or Formula (II), each instance of $R^C$ is independently hydrogen, halogen, unsubstituted $C_{1-6}$ alkyl, $C_{1-6}$ alkyl substituted with at least one halogen, or $-OR^{41}$, wherein $R^{41}$ is unsubstituted $C_{1-6}$ alkyl.

Group $G^5$ and $R^E$

As generally described herein, $G_5$ is O, S, or $NR^E$.

As generally described herein, $R^E$ is hydrogen, substituted or unsubstituted alkyl, or a nitrogen protecting group.

In certain embodiments of Formula (I) or Formula (II), $G_5$ is O. In certain embodiments of Formula (I) or Formula (II), $G_5$ is S. In certain embodiments of Formula (I) or Formula (II), $G_5$ is $NR^E$.

In certain embodiments of Formula (I) or Formula (II), $R^E$ is hydrogen.

In certain embodiments of Formula (I) or Formula (II), $R^E$ is substituted or unsubstituted $C_{1-6}$ alkyl, e.g., substituted or unsubstituted $C_{1-2}$ alkyl, substituted or unsubstituted $C_{1-3}$ alkyl, substituted or unsubstituted $C_{1-4}$ alkyl, or substituted or unsubstituted $C_{1-5}$ alkyl. In certain embodiments of Formula (I) or Formula (II), $R^E$ is substituted or unsubstituted methyl. In certain embodiments of Formula (I) or Formula (II), $R^E$ is substituted or unsubstituted ethyl. In certain embodiments of Formula (I) or Formula (II), $R^E$ is substituted or unsubstituted propyl. In certain embodiments of Formula (I) or Formula (II), $R^E$ is substituted or unsubstituted butyl. In certain embodiments of Formula (I) or Formula (II), $R^E$ is a nitrogen protecting group. In certain embodiments of Formula (I) or Formula (II), $R^E$ is a nitrogen protecting group selected from the group consisting of Bn, BOC, Cbz, Fmoc, trifluoroacetyl, triphenylmethyl, acetyl, and Ts.

In certain embodiments of Formula (I) or Formula (II), $G_5$ is $NR^E$ and $R^E$ is hydrogen or substituted or unsubstituted $C_{1-2}$ alkyl (e.g., $-CH_3$, $-CF_3$).

Group $R^G$

As generally described herein, $R^G$ is hydrogen, substituted or unsubstituted alkyl, or a nitrogen protecting group.

In certain embodiments of Formula (I) or Formula (II), $R^G$ is hydrogen. In certain embodiments of Formula (I) or Formula (II), $R^G$ is substituted or unsubstituted $C_{1-6}$ alkyl, e.g., substituted or unsubstituted $C_{1-2}$ alkyl, substituted or unsubstituted $C_{1-3}$ alkyl, substituted or unsubstituted $C_{1-4}$ alkyl, or substituted or unsubstituted $C_{1-5}$ alkyl. In certain embodiments of Formula (I) or Formula (II), $R^G$ is substituted or unsubstituted methyl. In certain embodiments of Formula (I) or Formula (II), $R^G$ is substituted or unsubstituted ethyl.

In certain embodiments of Formula (I) or Formula (II), $R^G$ is substituted or unsubstituted propyl. In certain embodiments of Formula (I) or Formula (II), $R^G$ is substituted or unsubstituted butyl. In certain embodiments of Formula (I) or Formula (II), $R^G$ is a nitrogen protecting group. In certain embodiments of Formula (I) or Formula (II), $R^G$ is a nitrogen protecting group selected from the group consisting of Bn, BOC, Cbz, Fmoc, trifluoroacetyl, triphenylmethyl, acetyl, or Ts.

In certain embodiments of Formula (I) or Formula (II), $R^G$ is hydrogen or substituted or unsubstituted $C_{1-2}$ alkyl (e.g., $-CH_3$, $-CF_3$).

Groups $R^{J1}$ and $R^{J2}$

As generally described herein, each instance of $R^{J1}$ and $R^{J2}$ is independently hydrogen, halogen, or substituted or unsubstituted alkyl.

In certain embodiments of Formula (I) or Formula (II), $R^{J1}$ is hydrogen. In certain embodiments of Formula (I) or Formula (II), $R^{J2}$ is hydrogen. In certain embodiments of Formula (I) or Formula (II), both $R^{J1}$ and $R^{J2}$ are hydrogen.

In certain embodiments of Formula (I) or Formula (II), neither $R^{J1}$ nor $R^{J2}$ are hydrogen.

In certain embodiments of Formula (I) or Formula (II), $R^{J1}$ is halogen. In certain embodiments of Formula (I) or Formula (II), $R^{J2}$ is halogen. In certain embodiments of Formula (I) or Formula (II), $R^{J1}$ is F. In certain embodiments of Formula (I) or Formula (II), $R^{J2}$ is F. In certain embodiments of Formula (I) or Formula (II), both $R^{J1}$ and $R^{J2}$ are F.

In certain embodiments of Formula (I) or Formula (II), $R^{J1}$ is Cl. In certain embodiments of Formula (I) or Formula (II), $R^{J2}$ is Cl. In certain embodiments of Formula (I) or Formula (II), both $R^{J}1$ and $R^{J2}$ are Cl.

In certain embodiments of Formula (I) or Formula (II), at least one of $R^{J1}$ and $R^{J2}$ is substituted alkyl. In certain embodiments of Formula (I) or Formula (II), at least one of $R^{J1}$ and $R^{J2}$ is unsubstituted alkyl. In certain embodiments of Formula (I) or Formula (II), at least one of $R^{J1}$ and $R^{J2}$ is unsubstituted $C_{1-6}$ alkyl. In certain embodiments of Formula (I) or Formula (II), at least one of $R^{J1}$ and $R^{J2}$ is substituted $C_{1-6}$ alkyl. In certain embodiments of Formula (I) or Formula (II), at least one of $R^{J1}$ and $R^{J2}$ is $C_{1-6}$ alkyl substituted with at least one halogen. In certain embodiments of Formula (I) or Formula (II), at least one of $R^{J1}$ and $R^{J2}$ is $-CH_3$. In certain embodiments of Formula (I) or Formula (II), at least one of $R^{J1}$ and $R^{J2}$ is substituted methyl. In certain embodiments of Formula (I) or Formula (II), at least one of $R^{J1}$ and $R^{J2}$ is $-CH_2F$. In certain embodiments of Formula (I) or Formula (II), at least one of $R^{J1}$ and $R^{J2}$ is $-CHF_2$. In certain embodiments of Formula (I) or Formula (II), at least one of $R^{J1}$ and $R^{J2}$ is $-CF_3$. In certain embodiments of Formula (I) or Formula (II), at least one of $R^{J1}$ and $R^{J2}$ is substituted or unsubstituted ethyl. In certain embodiments of Formula (I) or Formula (II), at least one of $R^{J1}$ and $R^{J2}$ is substituted or unsubstituted propyl. In certain embodiments of Formula (I) or Formula (II), at least one of $R^{J1}$ and $R^{J2}$ is substituted or unsubstituted butyl. In certain embodiments of Formula (I) or Formula (II), at least one of $R^{J1}$ and $R^{J2}$ is substituted or unsubstituted pentyl. In certain embodiments of Formula (I) or Formula (II), at least one of $R^{J1}$ and $R^{J2}$ is substituted or unsubstituted hexyl.

$R^{D1}$, $R^{D2}$, $R^{D3}$, and $R^{D4}$

As generally described herein, for the group as provided in Formula (I) and (II) having the structure:

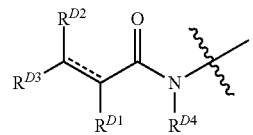

each instance of $R^{D1}$, $R^{D2}$, and $R^{D3}$ is independently hydrogen or substituted or unsubstituted alkyl, and $R^{D4}$ is hydrogen, substituted or unsubstituted alkyl, or a nitrogen protecting group, and ==== represents a single bond or a double bond.

In certain embodiments of Formula (I) or Formula (II), ==== represents a double bond. In certain embodiments of Formula (I) or Formula (II), ==== represents a single bond.

In certain embodiments, the group of formula

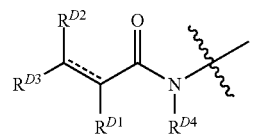

is attached meta or para to the point of attachment

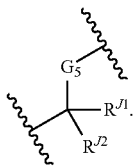

In certain embodiments, the group is attached meta to the point of attachment. In certain embodiments, the group is attached para to the point of attachment.

In certain embodiments of Formula (I) or Formula (II), each of $R^{D1}$, $R^{D2}$, and $R^{D3}$ is hydrogen. In certain embodiments of Formula (I) or Formula (II), each of $R^{D2}$ and $R^{D3}$ is hydrogen, and $R^{D1}$ is —CH$_3$. In certain embodiments of Formula (I) or Formula (II), each of $R^D$ and $R^{D2}$ is hydrogen, and $R^{D3}$ is —CH$_2$N(R$^{D1a}$)$_2$. In certain embodiments of Formula (I) or Formula (II), each of $R^{D1}$ and $R^{D2}$ is hydrogen, and $R^{D3}$ is —CH$_2$OR$^{D1a}$. In certain embodiments of Formula (I) or Formula (II), each of $R^{D1}$ and $R^{D2}$ is hydrogen, $R^{D3}$ is —CH$_2$N(R$^{D1a}$)$_2$, and $R^{D1a}$ is hydrogen. In certain embodiments of Formula (I) or Formula (II), each of $R^{D1}$ and $R^{D2}$ is hydrogen, $R^{D3}$ is —CH$_2$N(R$^{D1a}$)$_2$, and $R^{D1a}$ is methyl. In certain embodiments of Formula (I) or Formula (II), each of $R^{D1}$ and $R^{D2}$ is hydrogen, $R^{D3}$ is —CH$_2$OR$^{D1a}$, and $R^{D1a}$ is hydrogen. In certain embodiments of Formula (I) or Formula (II), each of $R^{D1}$ and $R^{D2}$ is hydrogen, $R^{D3}$ is —CH$_2$OR$^{D1a}$, and $R^{D1a}$ is methyl.

In certain embodiments of Formula (I) or Formula (II), $R^{D4}$ is hydrogen. In certain embodiments of Formula (I) or Formula (II), $R^{D4}$ is substituted or unsubstituted alkyl.

In certain embodiments of Formula (I) or Formula (II), $R^{D4}$ is a nitrogen protecting group.

Exemplary compounds of Formula (I)

Various combinations of certain embodiments of Formula (I) are further contemplated herein.

For example, in certain embodiments, a compound described herein is a compound of Formula (Ia):

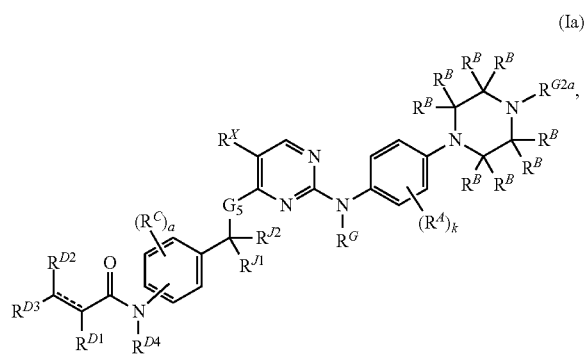

(Ia)

or a pharmaceutically acceptable salt thereof. In certain embodiments, $R^{G2a}$ is hydrogen. In certain embodiments, $R^{G2a}$ is unsubstituted C$_{1-6}$ alkyl. In certain embodiments, $R^{G2a}$ is substituted C$_{1-6}$ alkyl. In certain embodiments, $R^{G2a}$ is —CH$_3$. In certain, $R^{G2a}$ is substituted methyl. In certain embodiments, $R^{G2a}$ is a nitrogen protecting group. In certain embodiments, all instances of $R^B$ are hydrogen. In certain embodiments, k is 0. In certain embodiments, k is 1. In certain embodiments, k is 2. In certain embodiments, at least one instance of $R^A$ is halogen. In certain embodiments, at least one instance of $R^A$ is F. In certain embodiments, at least one instance of $R^A$ is Cl. In certain embodiments, at least two instances of $R^A$ are independently halogen. In certain embodiments, at least two instances of $R^A$ are F. In certain embodiments, at least two instances of $R^A$ are Cl. In certain embodiments, at least one instance of $R^A$ is unsubstituted C$_{1-6}$ alkyl. In certain embodiments, at least one instance of $R^A$ is substituted C$_{1-6}$ alkyl. In certain embodiments, at least one instance of $R^A$ is —CH$_3$. In certain embodiments, at least one instance of $R^A$ is —CF$_3$. In certain embodiments, $R^G$ is hydrogen. In certain embodiments, $R^G$ is —CH$_3$. In certain embodiments, $R^X$ is hydrogen. In certain embodiments, $R^X$ is —CN. In certain embodiments, $R^X$ is —OR$^{X1}$. In certain embodiments, $R^X$ is —OR$^{X1}$; and $R^{X1}$ is —CH$_3$. In certain embodiments, $R^X$ is —OR$^{X1}$; and $R^{X1}$ is an oxygen protecting group. In certain embodiments, $R^X$ is F. In certain embodiments, $R^{X1}$ is Cl. In certain embodiments, $R^X$ is Br. In certain embodiments, $R^X$ is I (iodine). In certain embodiments, $R^X$ is unsubstituted C$_{1-6}$ alkyl. In certain embodiments, $R^X$ is substituted C$_{1-6}$ alkyl. In certain embodiments, $R^X$ is C$_{1-6}$ alkyl substituted with at least one halogen. In certain embodiments, $R^X$ is —CH$_3$. In certain embodiments, $R^X$ is —CF$_3$. In certain embodiments, G$_5$ is S. In certain embodiments, G$_5$ is NR$^E$; and $R^E$ is hydrogen. In certain embodiments, G$_5$ is NR$^E$; and $R^E$ is —CH$_3$. In certain embodiments, both $R^{J1}$ and $R^{J2}$ are hydrogen. In certain embodiments, $R^{J1}$ is hydrogen; and $R^{J2}$ is substituted or unsubstituted C$_{1-6}$alkyl. In certain embodiments, $R^{J1}$ is hydrogen; and $R^{J2}$ is —CH$_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, ==== represents a single bond. In certain embodiments, ═ represents a double bond. In certain embodiments, each of $R^{D1}$, $R^{D2}$, and $R^{D3}$ is hydrogen. In certain embodiments, each of $R^{D2}$ and $R^D$ is hydrogen, and $R^{D1}$ is —CH$_3$. In certain embodiments, each of $R^{D1}$ and $R^{D2}$ is hydrogen, and $R^{D3}$ is —CH$_2$N(R$^{D1a}$)$_2$. In certain embodiments, each of $R^{D1}$ and $R^{D2}$ is hydrogen, and $R^{D3}$ is —CH$_2$OR$^{D1a}$. In certain embodiments, each of $R^{D1}$ and $R^{D2}$ is hydrogen, $R^{D3}$ is —CH$_2$N(R$^{D1a}$)$_2$, and $R^{D1a}$ is hydrogen. In certain embodiments, each of $R^{D1}$ and $R^{D2}$ is hydrogen, $R^{D3}$ is —CH$_2$N(R$^{D1a}$)$_2$, and $R^{D1a}$ is methyl. In certain embodiments, each of $R^{D1}$ and $R^{D2}$ is hydrogen, $R^{D3}$ is —CH$_2$OR$^{D1a}$, and $R^{D1a}$ is hydrogen. In certain embodiments, each of $R^{D1}$ and $R^{D2}$ is hydrogen, $R^{D3}$ is —CH$_2$OR$^{D1a}$, and $R^{D1a}$ is methyl. In certain embodiments, $R^{D4}$ is hydrogen. In certain embodiments, $R^{D4}$ is substituted or unsubstituted alkyl. In certain embodiments, $R^{D4}$ is a nitrogen protecting group. In certain embodiments, the group

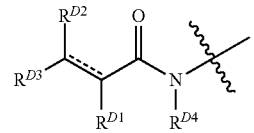

is attached meta to the point of attachment

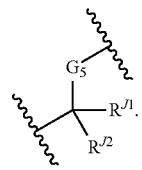

In certain embodiments, the group

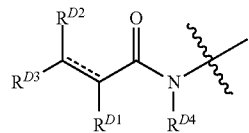

is attached para to the point of attachment

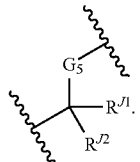

In certain embodiments, a compound of Formula (Ia) is a compound of Formula (Ia-1):

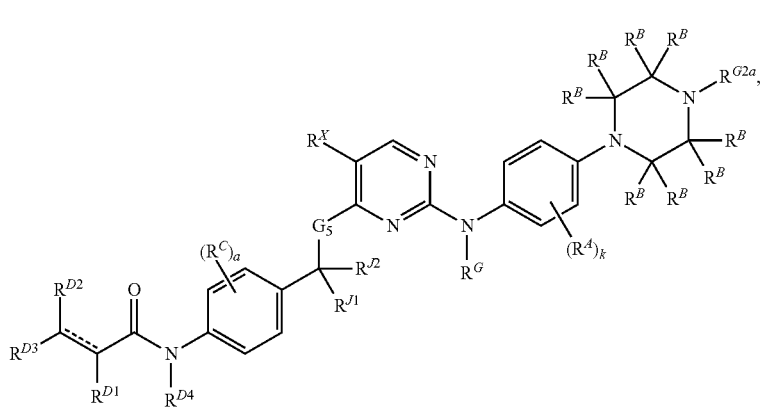

(Ia-1)

or a pharmaceutically acceptable salt thereof.

In certain embodiments, a compound of Formula (Ia) is a compound of Formula (Ia-2):

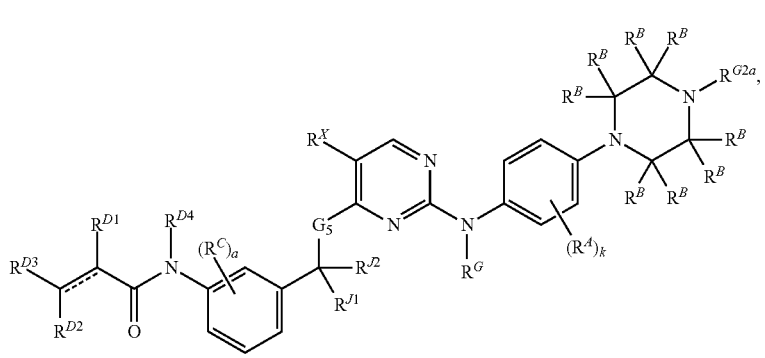

(Ia-2)

or a pharmaceutically acceptable salt thereof.

In certain embodiments, a compound of Formula (Ia) wherein $R^A$ is a non-hydrogen group is a compound of Formula (Ia-3):

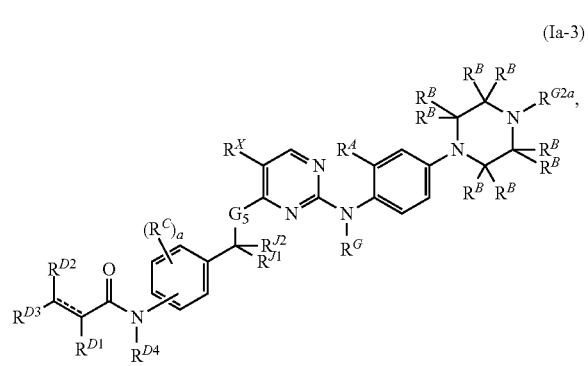

(Ia-3)

or a pharmaceutically acceptable salt thereof. In certain embodiments, the group

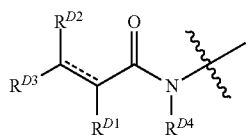

is attached meta to the point of attachment

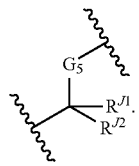

In certain embodiments, the group

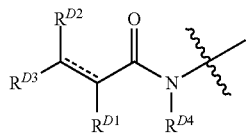

is attached para to the point of attachment

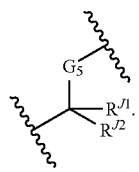

In certain embodiments, a compound of Formula (Ia) wherein $R^A$ is a non-hydrogen group is a compound of Formula (Ia-4):

(Ia-4)

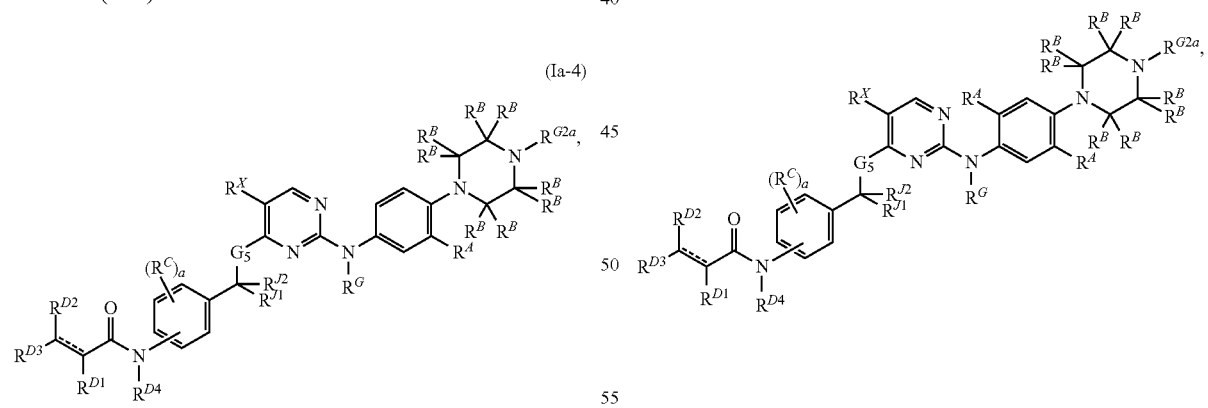

or a pharmaceutically acceptable salt thereof. In certain embodiments, the group

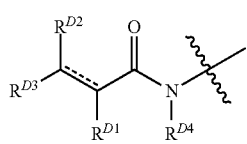

is attached meta to the point of attachment

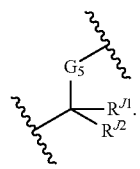

In certain embodiments, the group

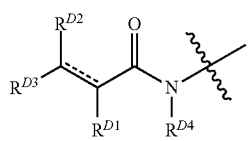

is attached para to the point of attachment

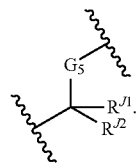

In certain embodiments, a compound of Formula (Ia) wherein $R^A$ is a non-hydrogen group is a compound of Formula (Ia-5):

(Ia-5)

or a pharmaceutically acceptable salt thereof. In certain embodiments, the group

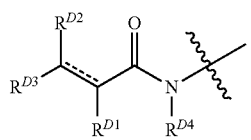

is attached meta to the point of attachment

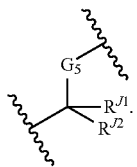

In certain embodiments, the group

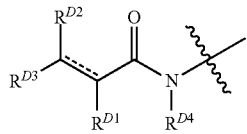

is attached para to the point of attachment

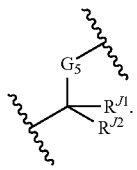

In certain embodiments, a compound of Formula (Ia) wherein $R^A$ is a non-hydrogen group is a compound of Formula (Ia-6):

(Ia-6)

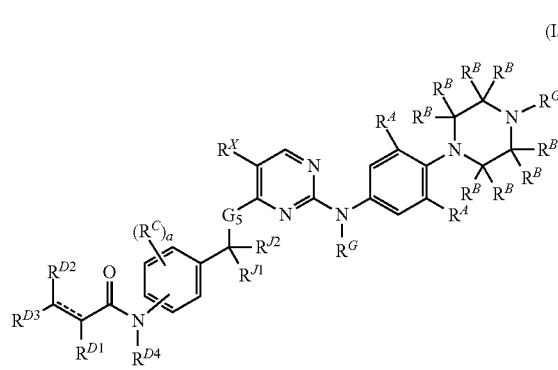

or a pharmaceutically acceptable salt thereof.
In certain embodiments, the group

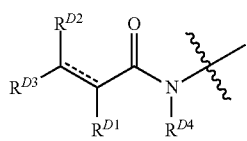

is attached meta to the point of attachment

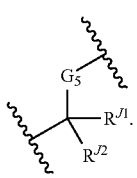

In certain embodiments, the group

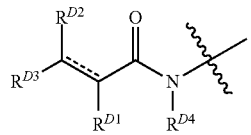

is attached para to the point of attachment

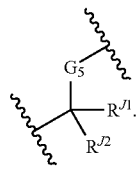

In certain embodiments, a compound of Formula (Ia) is a compound of Formula (Ia-7):

(Ia-7)

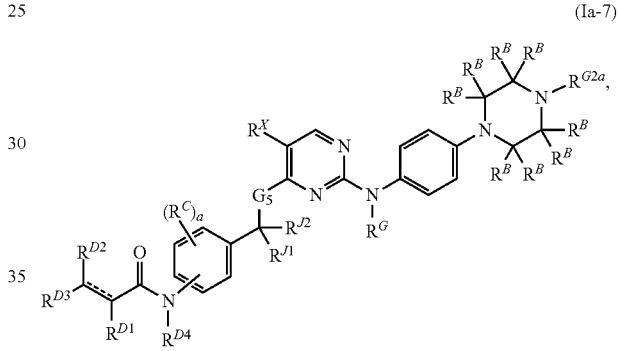

or a pharmaceutically acceptable salt thereof. In certain embodiments, the group

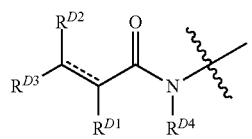

is attached meta to the point of attachment

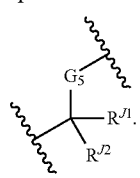

In certain embodiments, the group

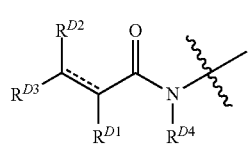

is attached para to the point of attachment

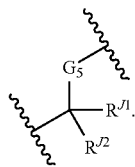

In certain embodiments, a compound described herein is a compound of Formula (Ib):

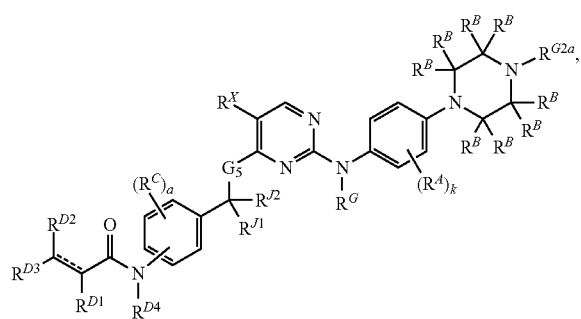

or a pharmaceutically acceptable salt thereof. In certain embodiments, $R^{G1a}$ is hydrogen. In certain embodiments, $R^{G2a}$ is unsubstituted $C_{1-6}$ alkyl. In certain embodiments, $R^{G2a}$ is substituted $C_{1-6}$ alkyl. In certain embodiments, $R^{G2a}$ is —$CH_3$. In certain, $R^{G2a}$ is substituted methyl. In certain embodiments, $R^{G2a}$ is a nitrogen protecting group. In certain embodiments, all instances of $R^B$ are hydrogen. In certain embodiments, k is 0. In certain embodiments, k is 1. In certain embodiments, k is 2. In certain embodiments, at least one instance of $R^A$ is halogen. In certain embodiments, at least one instance of $R^A$ is F. In certain embodiments, at least one instance of $R^A$ is Cl. In certain embodiments, at least two instances of $R^A$ are independently halogen. In certain embodiments, at least two instances of $R^A$ are F. In certain embodiments, at least two instances of $R^A$ are Cl. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is —$CH_3$. In certain embodiments, at least one instance of $R^A$ is —$CF_3$. In certain embodiments, $R^G$ is hydrogen. In certain embodiments, $R^G$ is —$CH_3$. In certain embodiments, $R^X$ is hydrogen. In certain embodiments, $R^X$ is —CN. In certain embodiments, $R^X$ is —$OR^{X1}$. In certain embodiments, $R^X$ is —$OR^{X1}$; and $R^{X1}$ is —$CH_3$. In certain embodiments, $R^X$ is —$OR^{X1}$; and $R^{X1}$ is an oxygen protecting group. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —$CH_3$. In certain embodiments, $R^X$ is —$CF_3$. In certain embodiments, $G_5$ is S. In certain embodiments, $G_5$ is $NR^E$; and $R^E$ is hydrogen. In certain embodiments, $G_5$ is $NR^E$; and $R^E$ is —$CH_3$. In certain embodiments, both $R^{J1}$ and $R^{J2}$ are hydrogen. In certain embodiments, $R^{J1}$ is hydrogen; and $R^{J2}$ is substituted or unsubstituted $C_{1-6}$ alkyl. In certain embodiments, $R^{J1}$ is hydrogen; and $R^{J2}$ is —$CH_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, ==== represents a single bond. In certain embodiments, ==== represents a double bond. In certain embodiments, each of $R^{D1}$, $R^{D2}$, and $R^{D3}$ is hydrogen. In certain embodiments, each of $R^{D2}$ and $R^{D3}$ is hydrogen, and $R^{D1}$ is —$CH_3$. In certain embodiments, each of $R^{D1}$ and $R^{D2}$ is hydrogen, and $R^{D3}$ is —$CH_2N(R^{D1a})_2$. In certain embodiments, each of $R^{D1}$ and $R^{D2}$ is hydrogen, and $R^{D3}$ is —$CH_2OR^{D1a}$. In certain embodiments, each of $R^{D1}$ and $R^{D2}$ is hydrogen, $R^{D3}$ is —$CH_2N(R^Da)_2$, and $R^{D1a}$ is hydrogen. In certain embodiments, each of $R^{D1}$ and $R^{D2}$ is hydrogen, $R^{D3}$ is —$CH_2N(R^{D1})_2$, and $R^{D1a}$ is methyl. In certain embodiments, each of $R^{D1}$ and $R^{D2}$ is hydrogen, $R^{D3}$ is —$CH_2OR^{D1a}$, and $R^{D1a}$ is hydrogen. In certain embodiments, each of $R^{D1}$ and $R^{D2}$ is hydrogen, $R^{D3}$ is —$CH_2OR^{D1a}$, and $R^{D1a}$ is methyl. In certain embodiments, $R^{D4}$ is hydrogen. In certain embodiments, $R^{D4}$ is substituted or unsubstituted alkyl. In certain embodiments, $R^{D4}$ is a nitrogen protecting group. In certain embodiments, the group

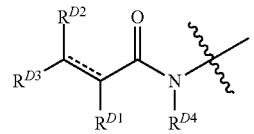

is attached meta to the point of attachment

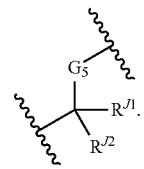

In certain embodiments, the group

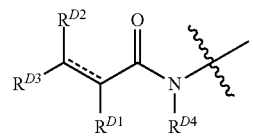

is attached para to the point of attachment

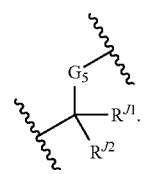

In certain embodiments, a compound of Formula (Ib) is a compound of Formula (Ib-1):

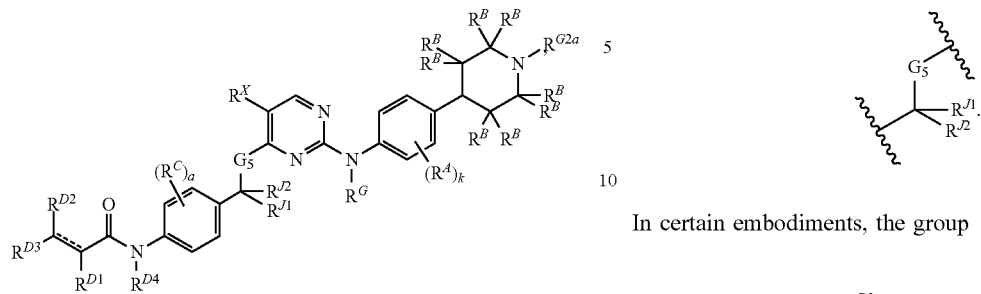

or a pharmaceutically acceptable salt thereof.

In certain embodiments, a compound of Formula (Ib) is a compound of Formula (Ib-2):

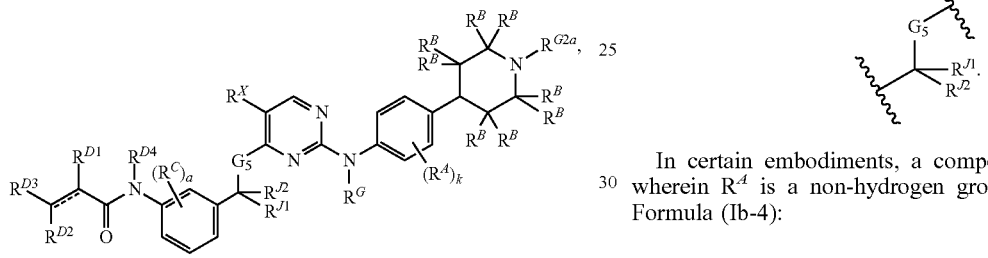

or a pharmaceutically acceptable salt thereof.

In certain embodiments, a compound of Formula (Ib) wherein $R^A$ is a non-hydrogen group is a compound of Formula (Ib-3):

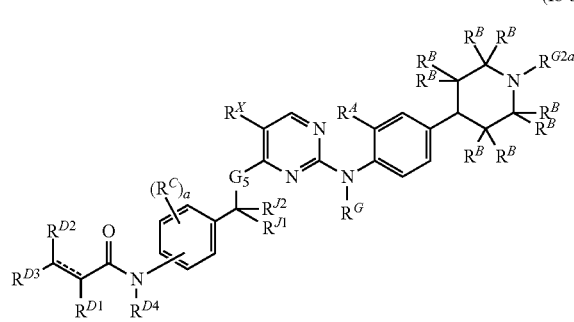

or a pharmaceutically acceptable salt thereof. In certain embodiments, the group

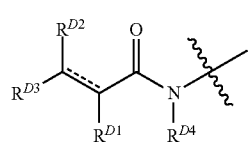

is attached meta to the point of attachment

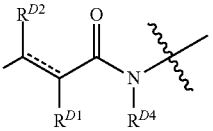

In certain embodiments, the group

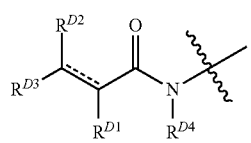

is attached para to the point of attachment

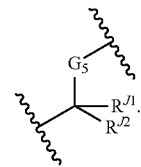

In certain embodiments, a compound of Formula (Ib) wherein $R^A$ is a non-hydrogen group is a compound of Formula (Ib-4):

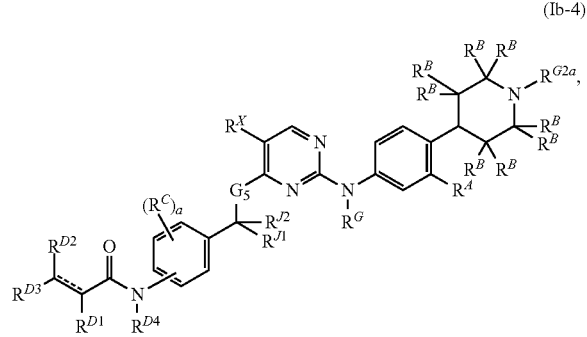

or a pharmaceutically acceptable salt thereof. In certain embodiments, the group is attached meta to the point of attachment In certain embodiments, the group

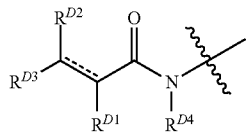

is attached para to the point of attachment

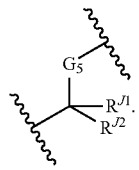

In certain embodiments, a compound of Formula (Ib) wherein $R^A$ is a non-hydrogen group is a compound of Formula (Ib-5):

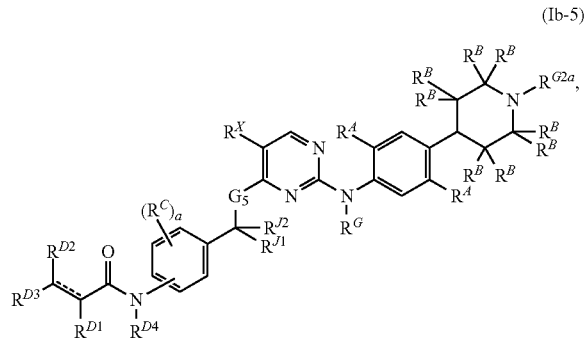

(Ib-5)

or a pharmaceutically acceptable salt thereof. In certain embodiments, the group

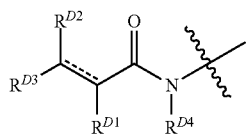

is attached meta to the point of attachment

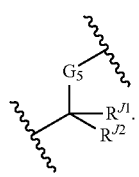

In certain embodiments, the group

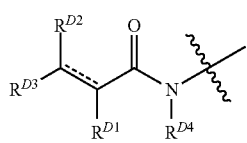

is attached para to the point of attachment

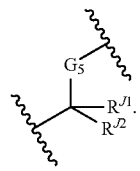

In certain embodiments, a compound of Formula (Ib) wherein $R^A$ is a non-hydrogen group is a compound of Formula (Ib-6):

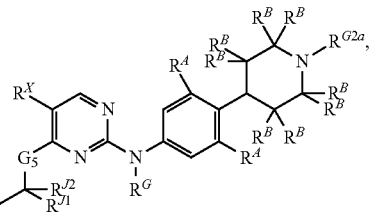

(Ib-6)

or a pharmaceutically acceptable salt thereof. In certain embodiments, the group

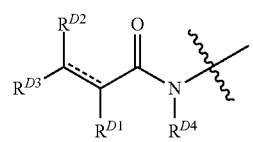

is attached meta to the point of attachment

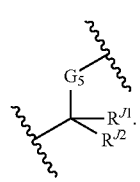

In certain embodiments, the group

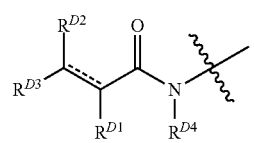

is attached para to the point of attachment

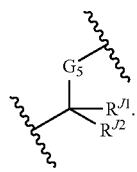

In certain embodiments, a compound of Formula (Ib) is a compound of Formula (Ib-7):

(Ib-7)

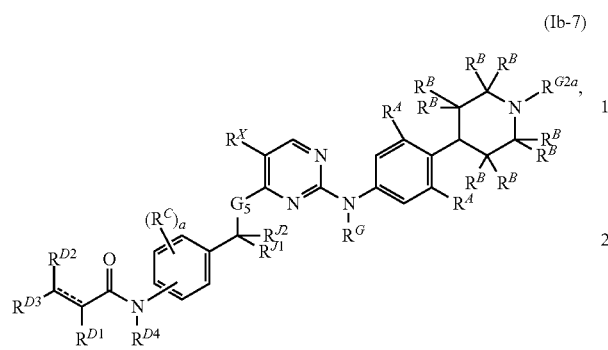

or a pharmaceutically acceptable salt thereof. In certain embodiments, the group

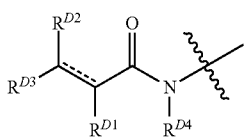

is attached meta to the point of attachment

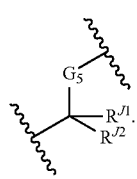

In certain embodiments, the group

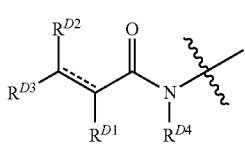

is attached para to the point of attachment

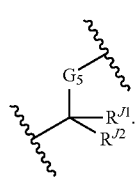

In certain embodiments, a compound described herein is a compound of Formula (Ic):

(Ic)

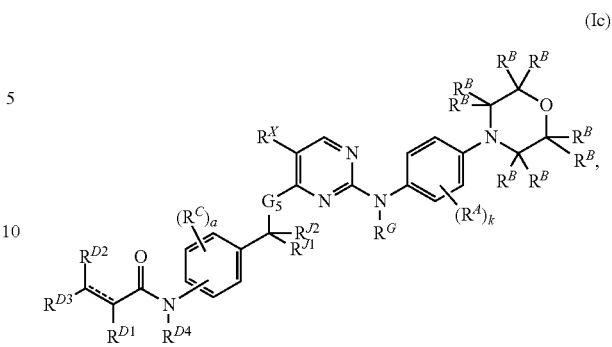

or a pharmaceutically acceptable salt thereof. In certain embodiments, all instances of $R^B$ are hydrogen. In certain embodiments, k is 0. In certain embodiments, k is 1. In certain embodiments, k is 2. In certain embodiments, at least one instance of $R^A$ is halogen. In certain embodiments, at least one instance of $R^A$ is F. In certain embodiments, at least one instance of $R^A$ is Cl. In certain embodiments, at least two instances of $R^A$ are independently halogen. In certain embodiments, at least two instances of $R^A$ are F. In certain embodiments, at least two instances of $R^A$ are Cl. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is —$CH_3$. In certain embodiments, at least one instance of $R^A$ is —$CF_3$. In certain embodiments, $R^G$ is hydrogen. In certain embodiments, $R^G$ is —$CH_3$. In certain embodiments, $R^X$ is hydrogen. In certain embodiments, $R^X$ is —CN. In certain embodiments, $R^X$ is —$OR^{X1}$. In certain embodiments, $R^X$ is —$OR^{X1}$; and $R^{X1}$ is —$CH_3$. In certain embodiments, $R^X$ is —$OR^{X1}$; and $R^{X1}$ is an oxygen protecting group. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —$CH_3$. In certain embodiments, $R^X$ is —$CF_3$. In certain embodiments, $G_5$ is S. In certain embodiments, $G_5$ is $NR^E$; and $R^E$ is hydrogen. In certain embodiments, $G_5$ is $NR^E$; and $R^E$ is —$CH_3$. In certain embodiments, both $R^{J1}$ and $R^{J2}$ are hydrogen. In certain embodiments, $R^{J1}$ is hydrogen; and $R^{J2}$ is substituted or unsubstituted $C_{1-6}$alkyl. In certain embodiments, $R^{n1}$ is hydrogen; and $R^{J2}$ is —$CH_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, ==== represents a single bond. In certain embodiments, ==== represents a double bond. In certain embodiments, each of $R^{D1}$, $R^{D2}$, and $R^{D3}$ is hydrogen. In certain embodiments, each of $R^{D2}$ and $R^{D3}$ is hydrogen, and $R^{D1}$ is —$CH_3$. In certain embodiments, each of $R^{D1}$ and $R^{D2}$ is hydrogen, and $R^{D3}$ is —$CH_2N(R^{D1a})_2$. In certain embodiments, each of $R^{D1}$ and $R^{D2}$ is hydrogen, and $R^{D3}$ is —$CH_2OR^{D1a}$. In certain embodiments, each of $R^{D1}$ and $R^{D2}$ is hydrogen, $R^{D3}$ is —$CH_2N(R^{D1a})_2$, and $R^{D1a}$ is hydrogen. In certain embodiments, each of $R^{D1}$ and $R^{D2}$ is hydrogen, $R^{D3}$ is —$CH_2N(R^{D1a})_2$, and $R^{D1a}$ is methyl. In certain embodiments, each of $R^{D1}$ and $R^{D2}$ is hydrogen, $R^{D3}$ is —$CH_2OR^{D1a}$, and $R^{D1a}$ is hydrogen. In certain embodiments, each of $R^{D1}$ and $R^{D2}$ is hydrogen, $R^{D3}$ is —CH$_2$OR$^{D1a}$, and $R^{D1a}$ is methyl. In certain embodiments, $R^{D4}$ is hydrogen. In certain embodiments, $R^{D4}$ is substituted or unsubstituted alkyl. In certain embodiments, the group

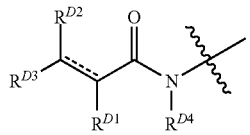

is attached meta to the point of attachment

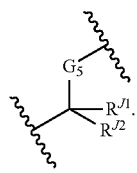

In certain embodiments, the group

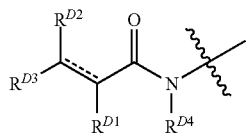

is attached para to the point of attachment

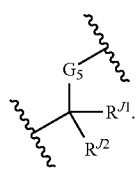

In certain embodiments, a compound of Formula (Ic) is a compound of Formula (Ic-1):

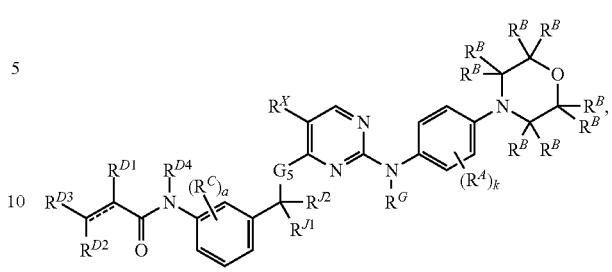

(Ic-1)

or a pharmaceutically acceptable salt thereof.

In certain embodiments, a compound of Formula (Ic) is a compound of Formula (Ic-2):

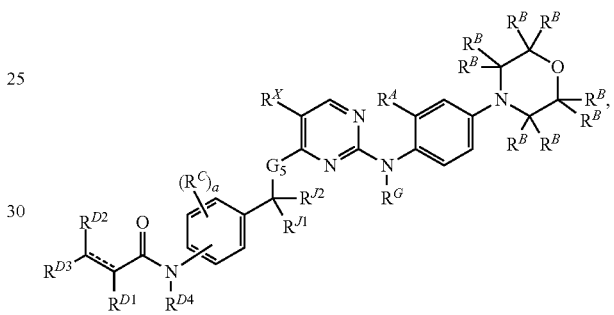

(Ic-2)

or a pharmaceutically acceptable salt thereof.

In certain embodiments, a compound of Formula (Ic) wherein $R^A$ is a non-hydrogen group is a compound of Formula (Ic-3):

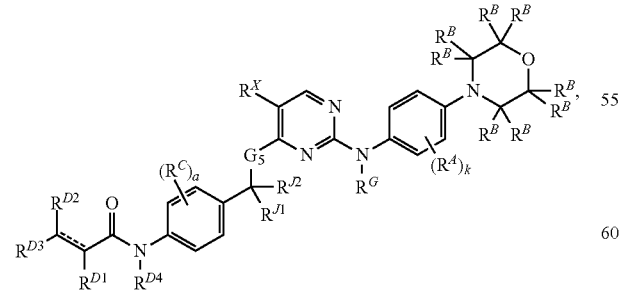

(Ic-3)

or a pharmaceutically acceptable salt thereof.

In certain embodiments, the group

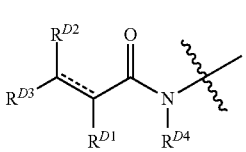

is attached meta to the point of attachment

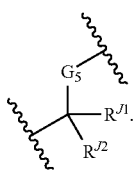

In certain embodiments, the group is attached para to the point of attachment

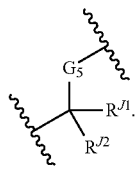

In certain embodiments, a compound of Formula (Ic) wherein $R^A$ is a non-hydrogen group is a compound of Formula (Ic-4):

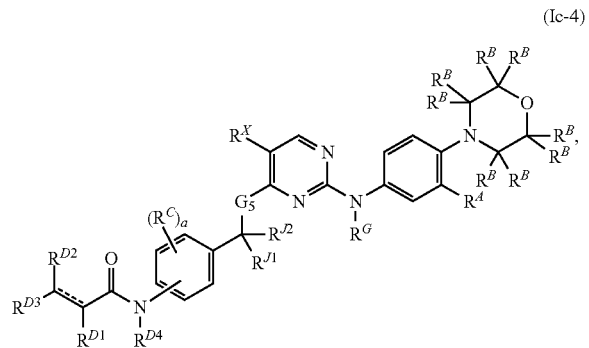

(Ic-4)

or a pharmaceutically acceptable salt thereof. In certain embodiments, the group

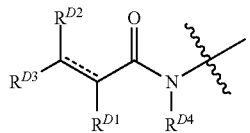

is attached meta to the point of attachment

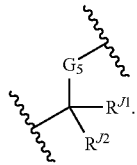

In certain embodiments, the group

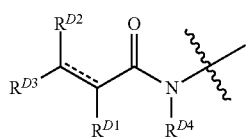

is attached para to the point of attachment

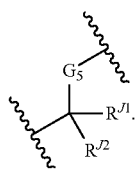

In certain embodiments, a compound of Formula (Ic) wherein $R^A$ is a non-hydrogen group is a compound of Formula (Ic-5):

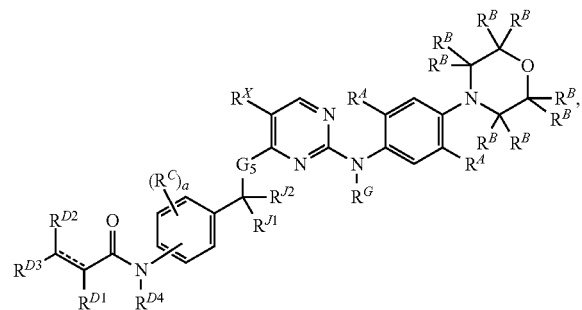

(Ic-5)

or a pharmaceutically acceptable salt thereof. In certain embodiments, the group

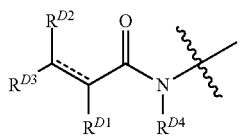

is attached meta to the point of attachment

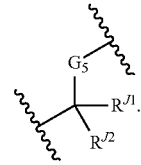

In certain embodiments, the group

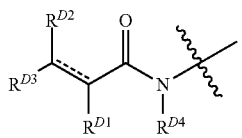

is attached para to the point of attachment

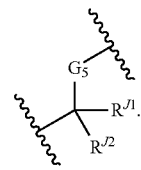

In certain embodiments, a compound of Formula (Ic) wherein $R^A$ is a non-hydrogen group is a compound of Formula (Ic-6):

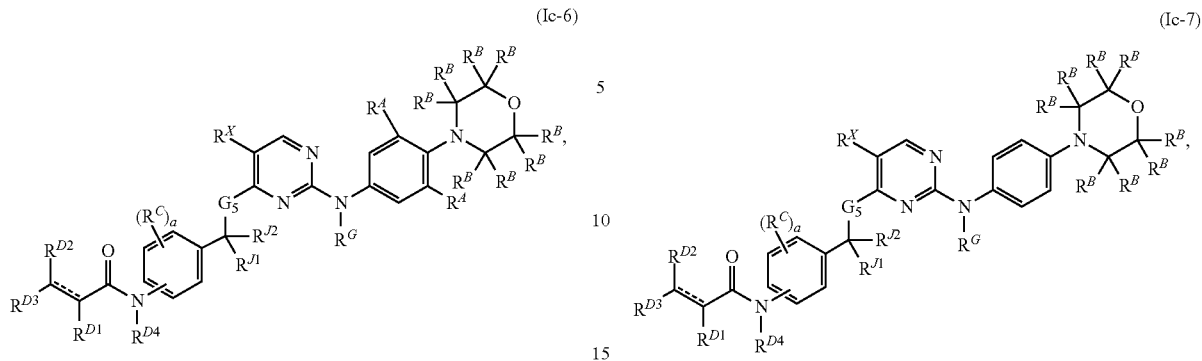

or a pharmaceutically acceptable salt thereof. In certain embodiments, the group

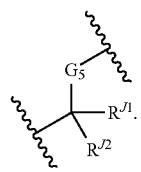

is attached meta to the point of attachment

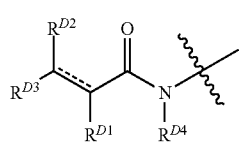

In certain embodiments, the group

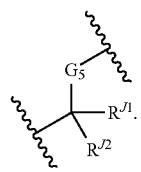

is attached para to the point of attachment

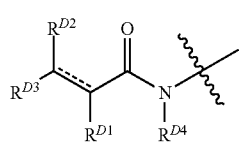

In certain embodiments, a compound of Formula (Ic) is a compound of Formula (Ic-7):

or a pharmaceutically acceptable salt thereof. In certain embodiments, the group

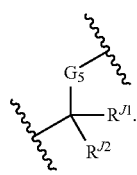

is attached meta to the point of attachment

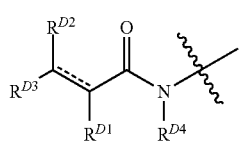

In certain embodiments, the group

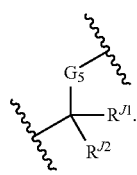

is attached para to the point of attachment

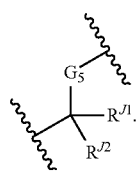

In certain embodiments, a compound described herein is a compound of Formula (Id):

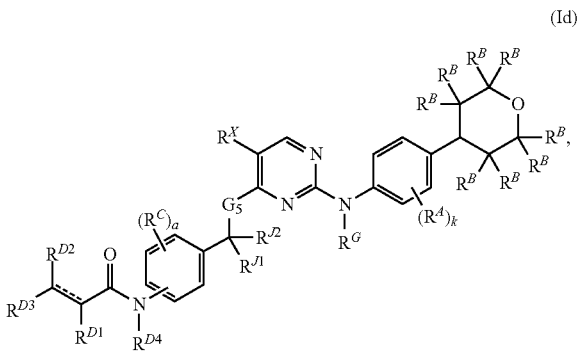

(Id)

or a pharmaceutically acceptable salt thereof. In certain embodiments, all instances of $R^B$ are hydrogen. In certain embodiments, k is 0. In certain embodiments, k is 1. In certain embodiments, k is 2. In certain embodiments, at least one instance of $R^A$ is halogen. In certain embodiments, at least one instance of $R^A$ is F. In certain embodiments, at least one instance of $R^A$ is Cl. In certain embodiments, at least two instances of $R^A$ are independently halogen. In certain embodiments, at least two instances of $R^A$ are F. In certain embodiments, at least two instances of $R^A$ are Cl. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is —$CH_3$. In certain embodiments, at least one instance of $R^A$ is —$CF_3$. In certain embodiments, $R^G$ is hydrogen. In certain embodiments, $R^G$ is —$CH_3$. In certain embodiments, $R^X$ is hydrogen. In certain embodiments, $R^X$ is —CN. In certain embodiments, $R^X$ is —$OR^{X1}$. In certain embodiments, $R^X$ is —$OR^{X1}$; and $R^{X1}$ is —$CH_3$. In certain embodiments, $R^X$ is —$OR^{X1}$; and $R^{X1}$ is an oxygen protecting group. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —$CH_3$. In certain embodiments, $R^X$ is —$CF_3$. In certain embodiments, $G_5$ is S. In certain embodiments, $G_5$ is $NR^E$; and $R^E$ is hydrogen. In certain embodiments, $G_5$ is $NR^E$; and $R^E$ is —$CH_3$. In certain embodiments, both $R^{J1}$ and $R^{J2}$ are hydrogen. In certain embodiments, $R^{J1}$ is hydrogen; and $R^{J2}$ is substituted or unsubstituted $C_{1-6}$alkyl. In certain embodiments, $R^{J1}$ is hydrogen; and $R^{J2}$ is —$CH_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, === represents a single bond. In certain embodiments, === represents a double bond. In certain embodiments, each of $R^{D1}$, $R^{D2}$, and $R^{D3}$ is hydrogen. In certain embodiments, each of $R^{D2}$ and $R^{D3}$ is hydrogen, and $R^{D1}$ is —$CH_3$. In certain embodiments, each of $R^{D1}$ and $R^{D2}$ is hydrogen, and $R^{D3}$ is —$CH_2N(R^{D1a})_2$. In certain embodiments, each of $R^{D1}$ and $R^{D2}$ is hydrogen, and $R^{D3}$ is —$CH_2OR^{D1a}$. In certain embodiments, each of $R^{D1}$ and $R^{D2}$ is hydrogen, $R^{D3}$ is —$CH_2N(R^{D1a})_2$, and $R^{D1a}$ is hydrogen. In certain embodiments, each of $R^{D1}$ and $R^{D2}$ is hydrogen, $R^{D3}$ is —$CH_2N(R^Da)_2$, and $R^{D1a}$ is methyl. In certain embodiments, each of $R^{D1}$ and $R^{D2}$ is hydrogen, $R^{D3}$ is —$CH_2OR^{D1a}$, and $R^{D1a}$ is hydrogen. In certain embodi-ments, each of $R^{D1}$ and $R^{D2}$ is hydrogen, $R^{D3}$ is —$CH_2OR^{D1a}$, and $R^{D1a}$ is methyl. In certain embodiments, $R^{D4}$ is hydrogen. In certain embodiments, $R^{D4}$ is substituted or unsubstituted alkyl. In certain embodiments, $R^{D4}$ is a nitrogen protecting group. In certain embodiments, the group

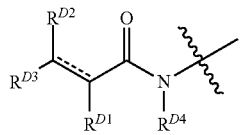

is attached meta to the point of attachment

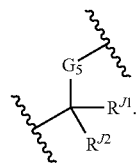

In certain embodiments, the group

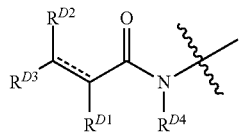

is attached para to the point of attachment

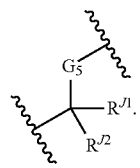

In certain embodiments, a compound of Formula (Id) is a compound of Formula (Id-1):

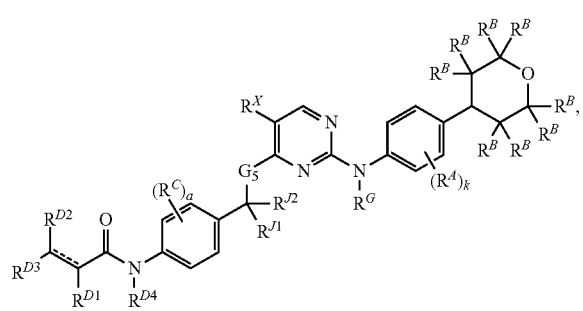

(Id-1)

or a pharmaceutically acceptable salt thereof.

In certain embodiments, a compound of Formula (Id) is a compound of Formula (Id-2):

(Id-2)

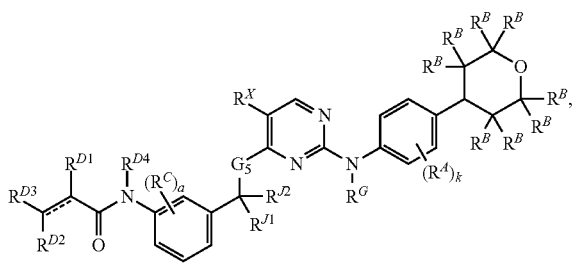

or a pharmaceutically acceptable salt thereof.

In certain embodiments, a compound of Formula (Id) wherein $R^A$ is a non-hydrogen group is a compound of Formula (Id-3):

(Id-3)

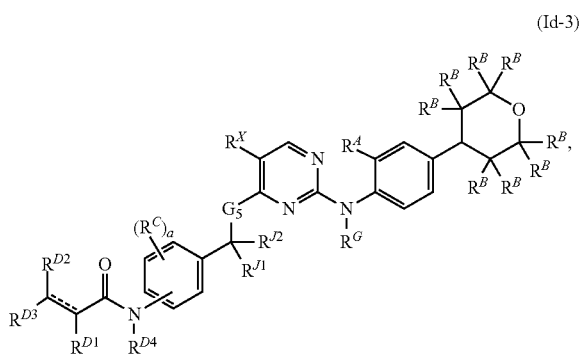

or a pharmaceutically acceptable salt thereof.

In certain embodiments, the group

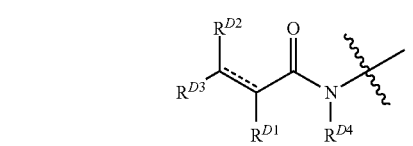

is attached meta to the point of attachment

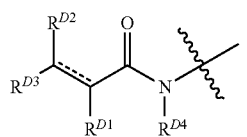

In certain embodiments, the group is attached para to the point of attachment

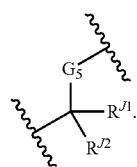

In certain embodiments, a compound of Formula (Id) wherein $R^A$ is a non-hydrogen group is a compound of Formula (Id-4):

(Id-4)

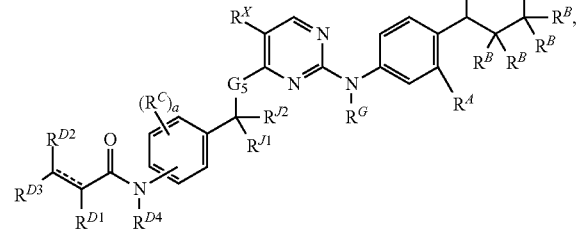

or a pharmaceutically acceptable salt thereof. In certain embodiments, the group

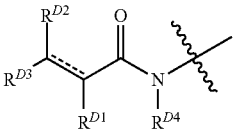

is attached meta to the point of attachment

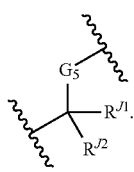

In certain embodiments, the group

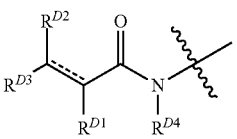

is attached para to the point of attachment

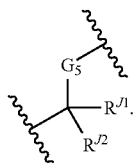

In certain embodiments, a compound of Formula (Id) wherein R^A is a non-hydrogen group is a compound of Formula (Id-5):

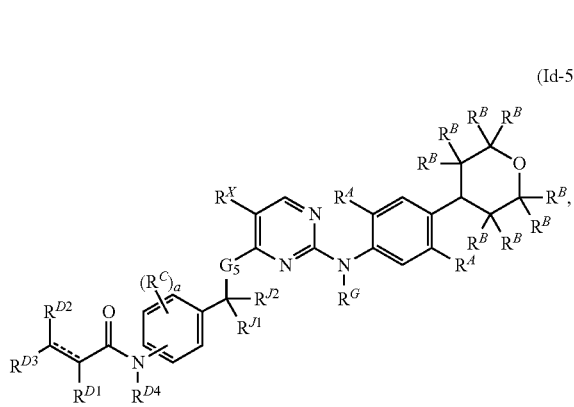

(Id-5)

or a pharmaceutically acceptable salt thereof. In certain embodiments, the group

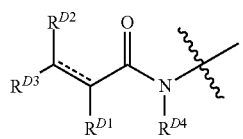

is attached meta to the point of attachment

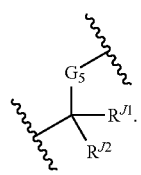

In certain embodiments, the group

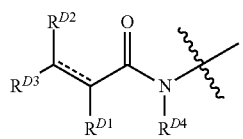

is attached para to the point of attachment

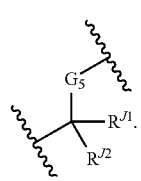

In certain embodiments, a compound of Formula (Id) wherein R^A is a non-hydrogen group is a compound of Formula (Id-6):

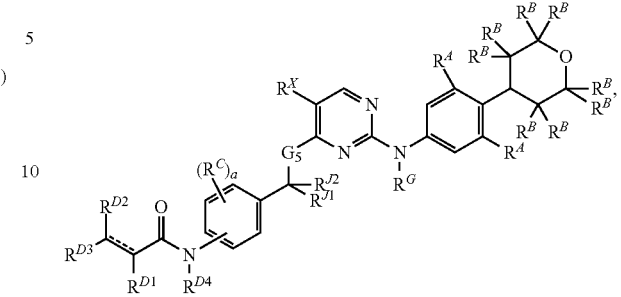

(Id-6)

or a pharmaceutically acceptable salt thereof. In certain embodiments, the group

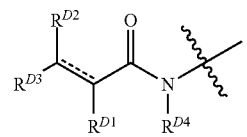

is attached meta to the point of attachment

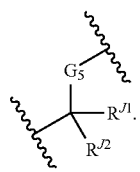

In certain embodiments, the group

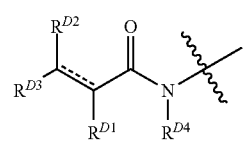

is attached para to the point of attachment

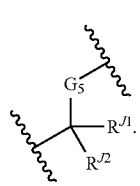

In certain embodiments, a compound of Formula (Id) is a compound of Formula (Id-7):

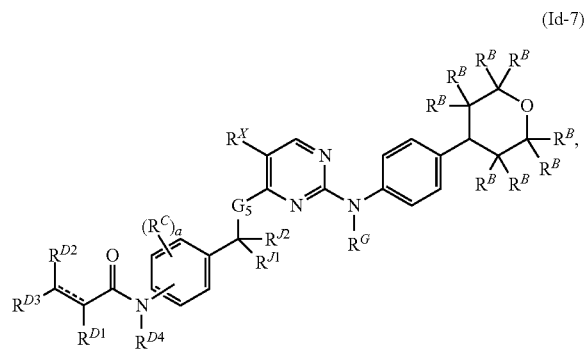
(Id-7)
or a pharmaceutically acceptable salt thereof. In certain embodiments, the group
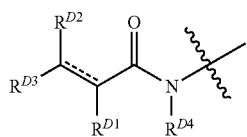
is attached meta to the point of attachment
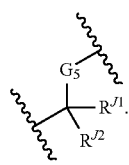
In certain embodiments, the group
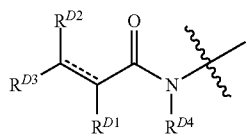
is attached para to the point of attachment
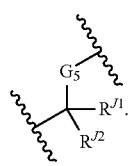
In certain embodiments, a compound described herein is a compound of the formula:
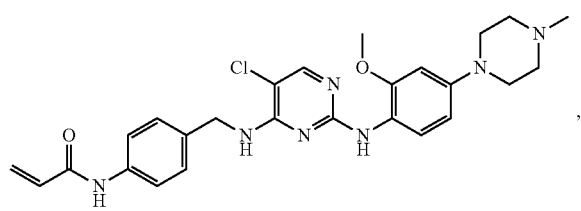
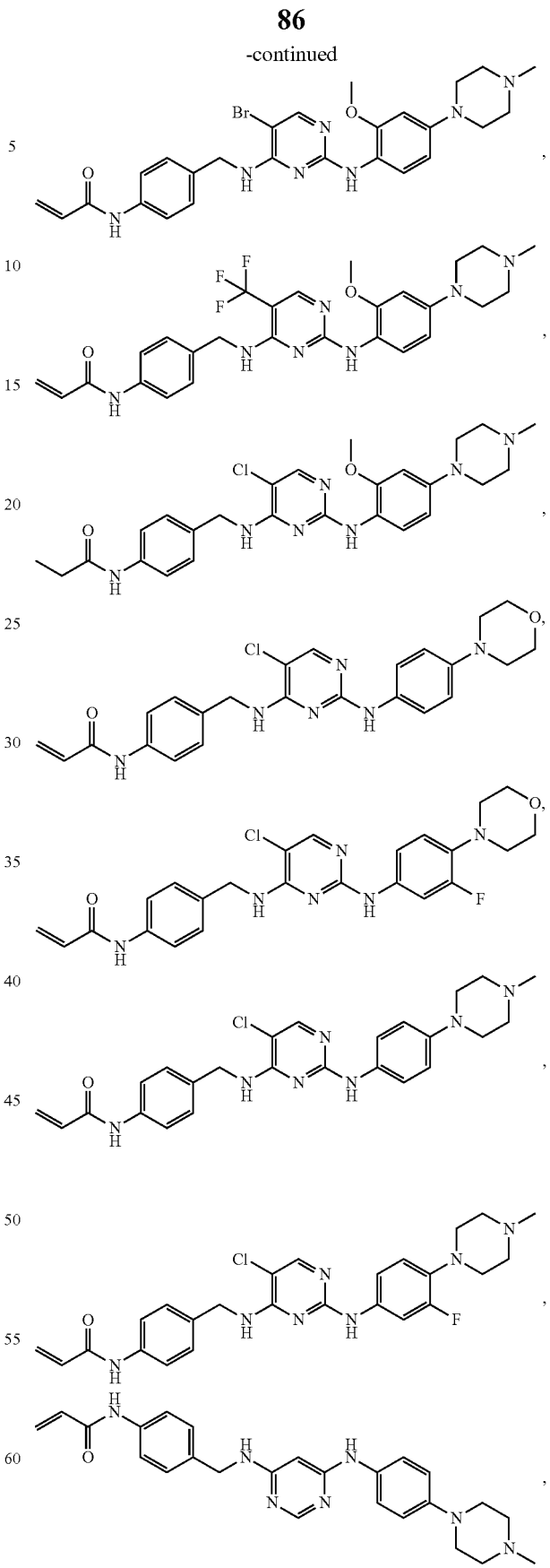
or a pharmaceutically acceptable salt thereof.

In certain embodiments, a compound described herein is a compound of the formula:
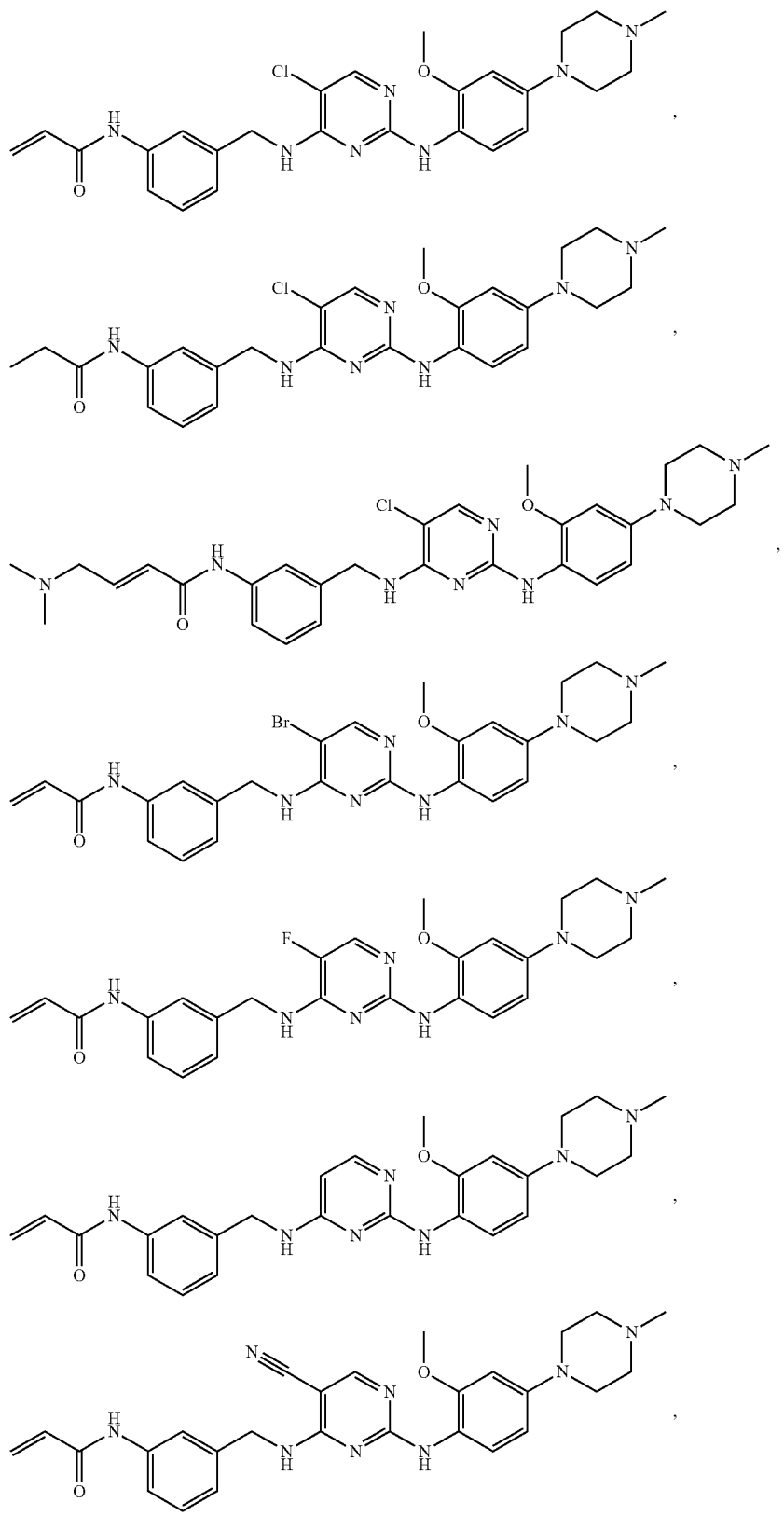

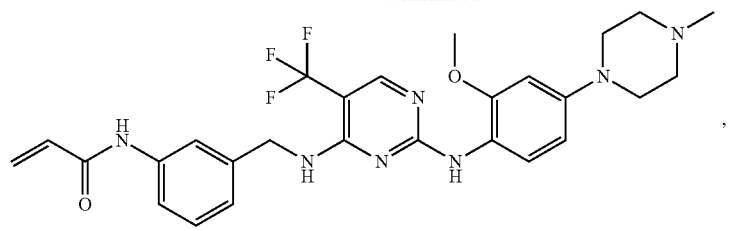,
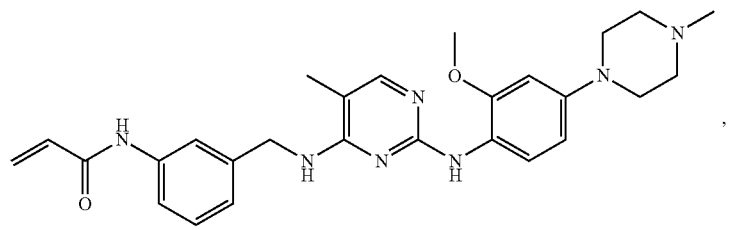,
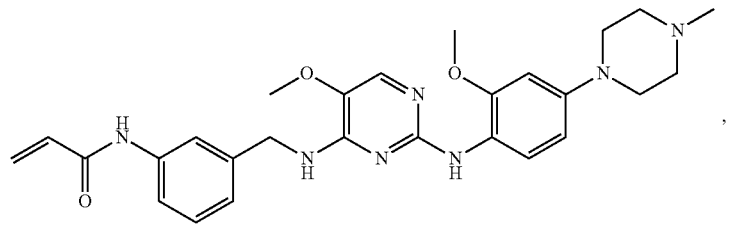,
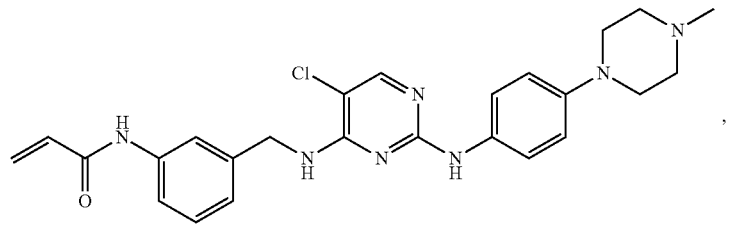,
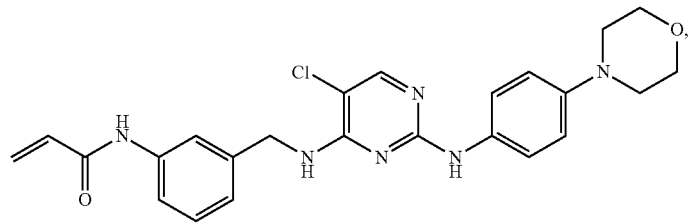,
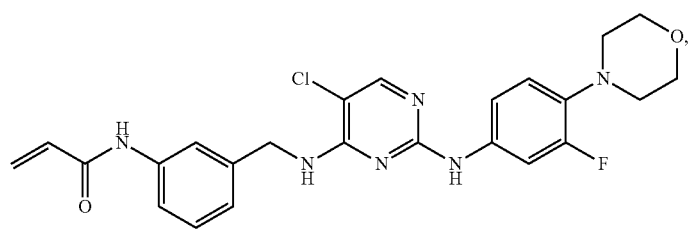,
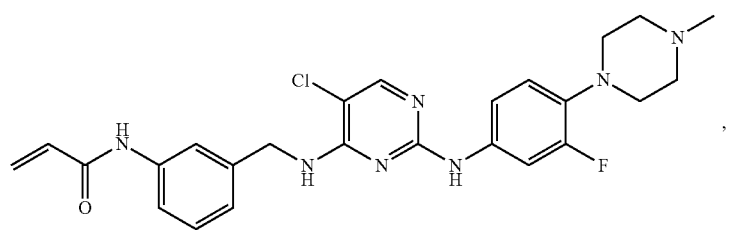,

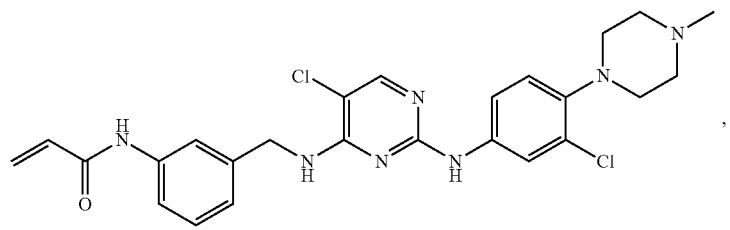
,
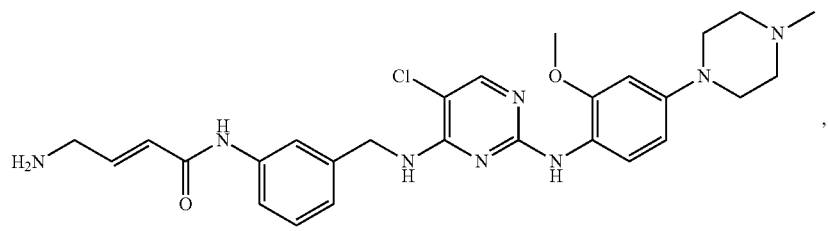
,
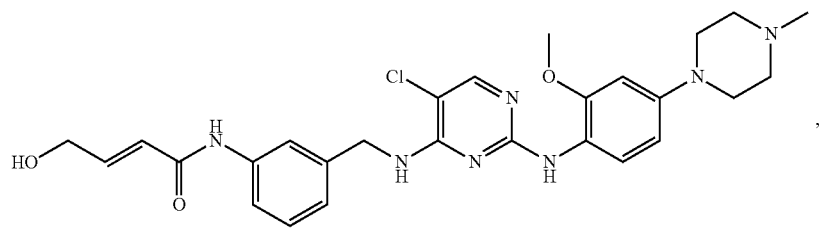
,
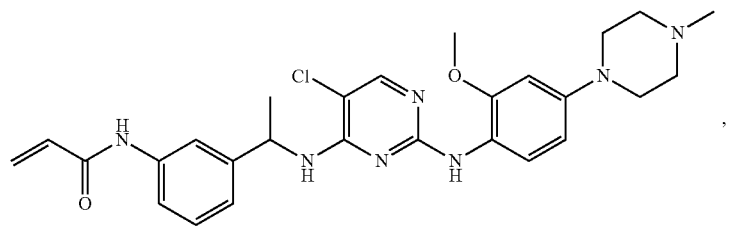
,
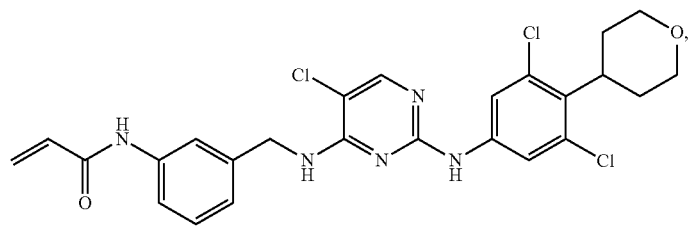
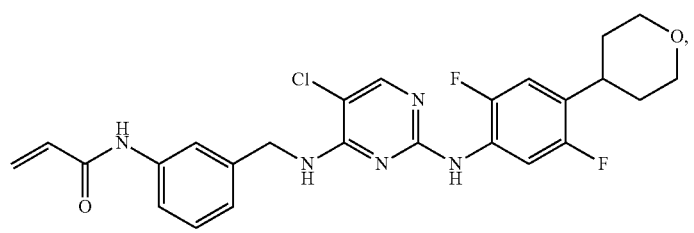
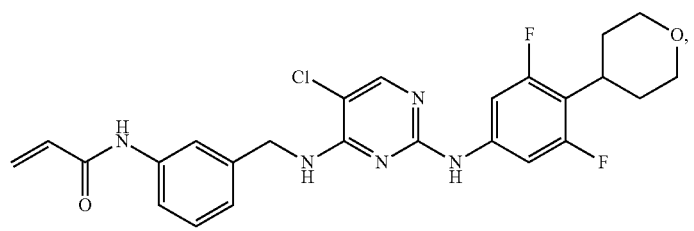

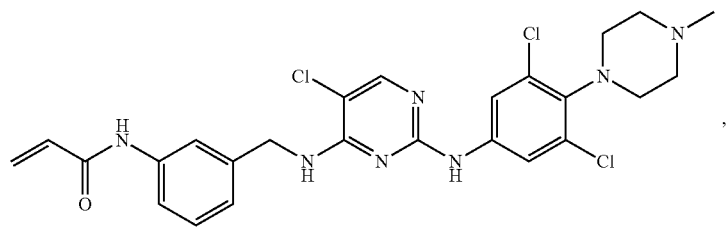,
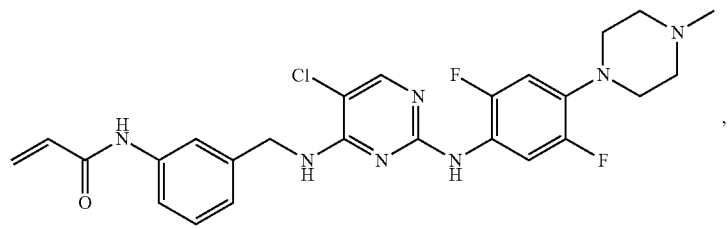,
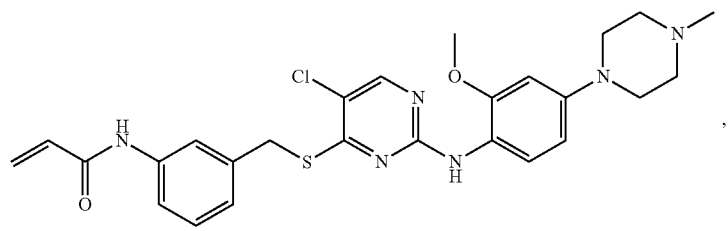,
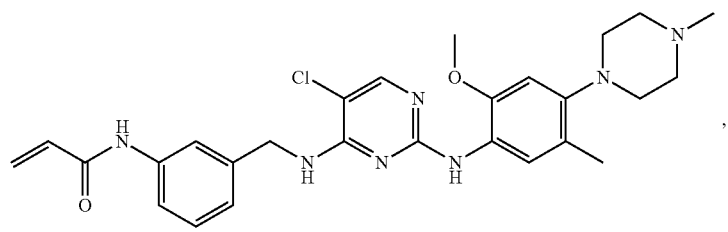,
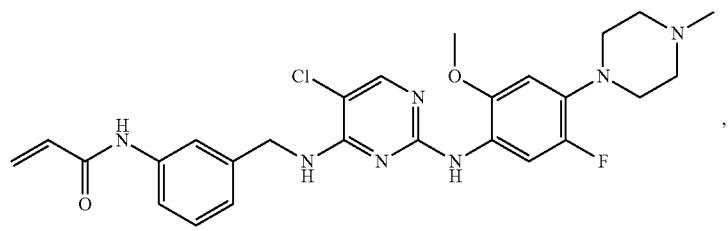,
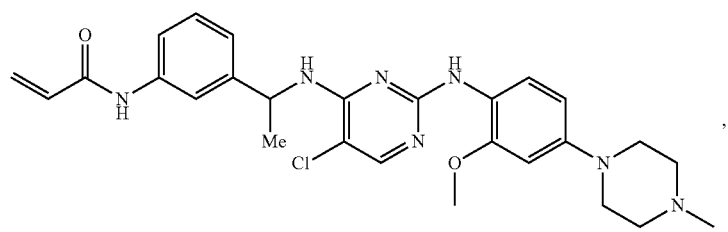,
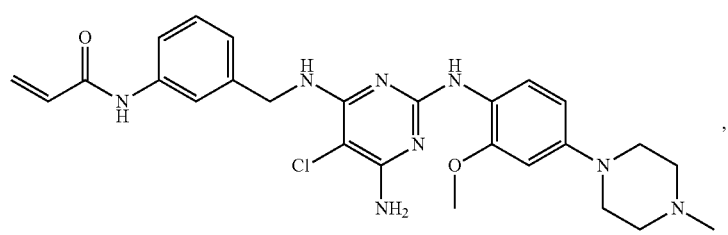,

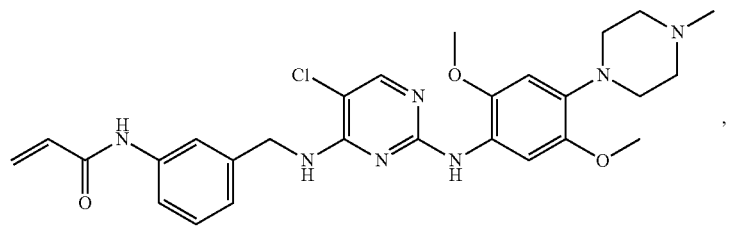
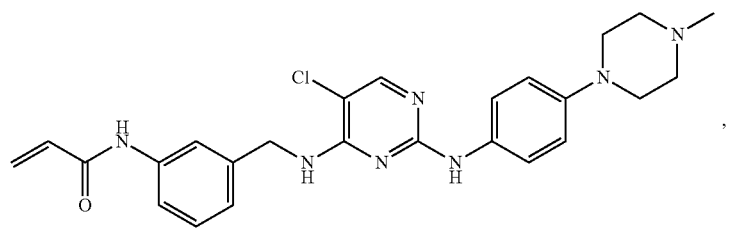
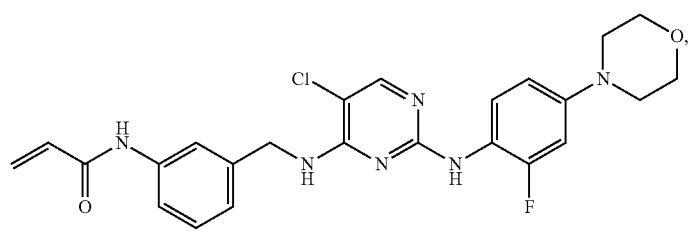
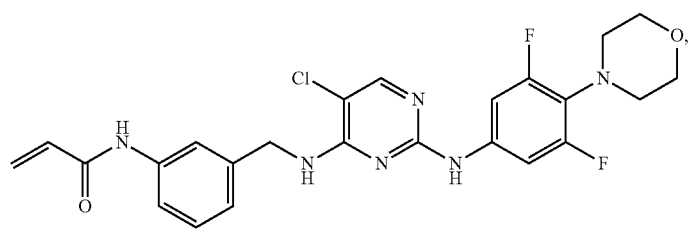
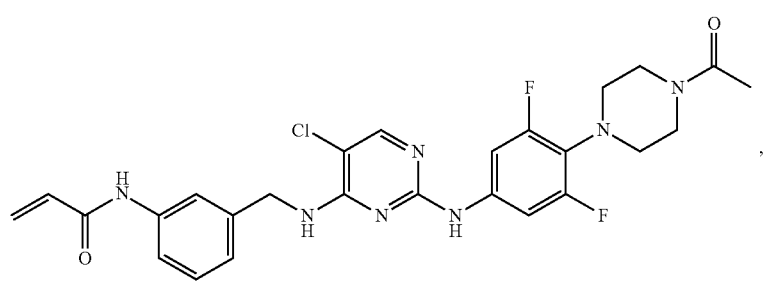
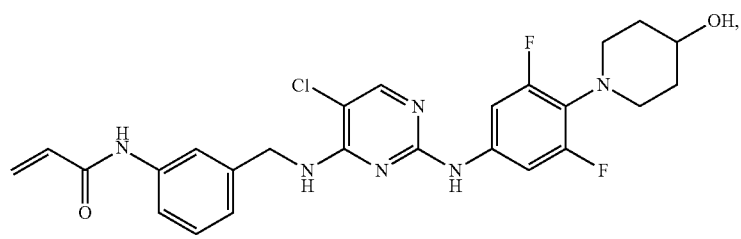
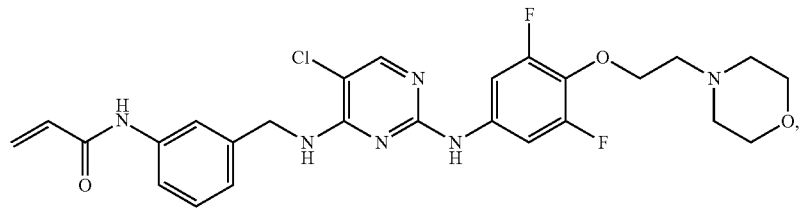

-continued

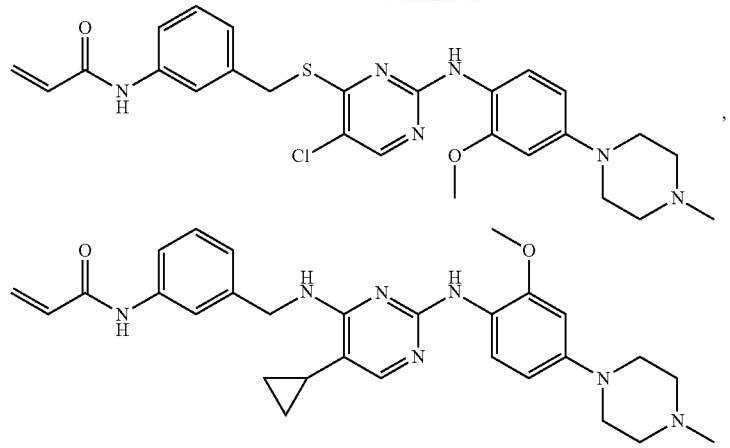

or a pharmaceutically acceptable salt thereof.

In certain embodiments, a compound described herein is a compound of the formula:

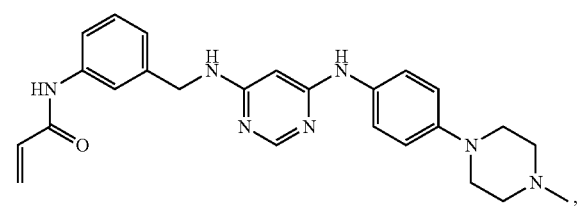

or a pharmaceutically acceptable salt thereof.

In certain embodiments, a compound described herein is a compound of the formula:

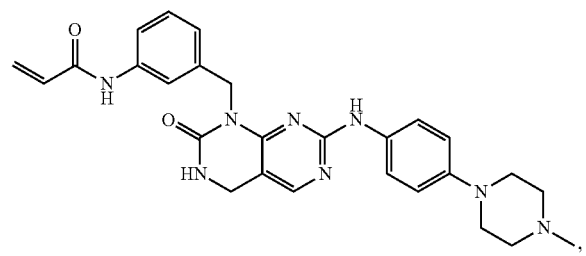

-continued

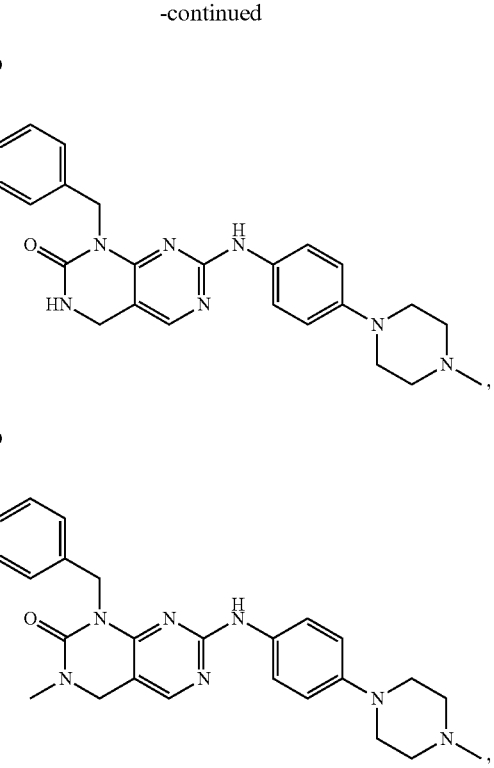

or a pharmaceutically acceptable salt thereof.

In certain embodiments, a compound described herein is a compound of the formula:

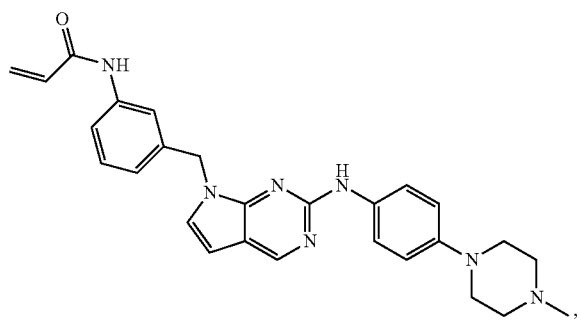

-continued

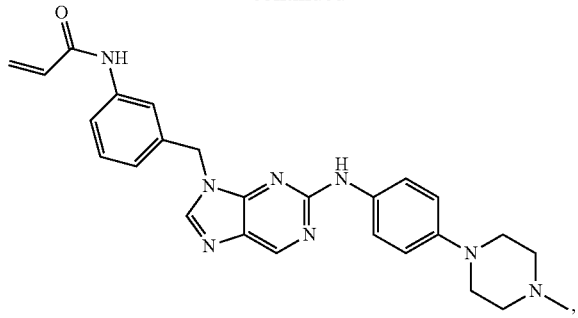

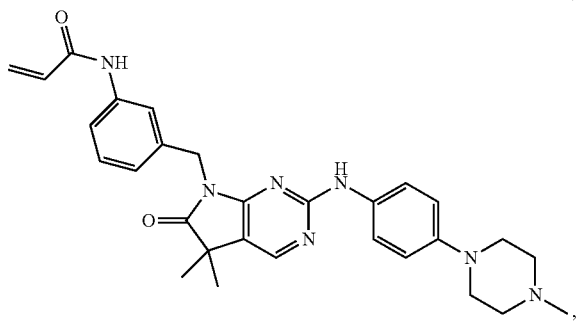

or a pharmaceutically acceptable salt thereof.

In certain embodiments, a compound described herein is a compound of the formula:

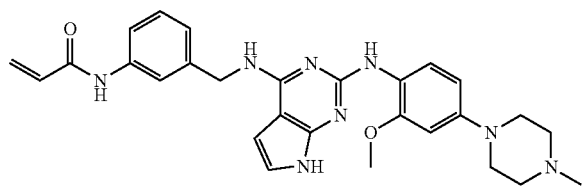 [SMILES: C=CC(=O)Nc1cccc(CNc2nc(Nc3ccc(N4CCN(C)CC4)cc3OC)nc3[nH]ccc23)c1]

or a pharmaceutically acceptable salt thereof.

Exemplary Compounds of Formula (II)

Various combinations of certain embodiments of Formula (II) are further contemplated herein.

For example, in certain embodiments, a compound described herein is a compound of Formula (IIa):

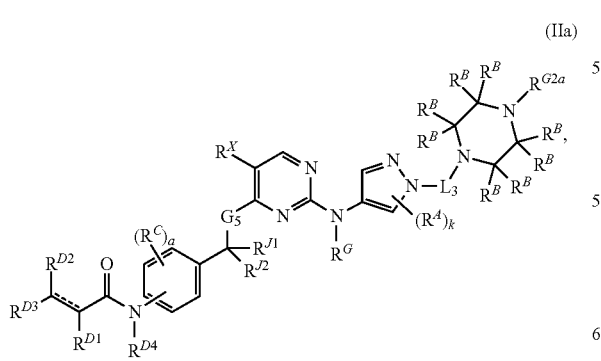

(IIa)

or a pharmaceutically acceptable salt thereof. In certain embodiments, $R^{G2a}$ is hydrogen. In certain embodiments, $R^{G2a}$ is unsubstituted $C_{1-6}$ alkyl. In certain embodiments, $R^{G2a}$ is substituted $C_{1-6}$ alkyl. In certain embodiments, $R^{G2a}$ is —CH$_3$. In certain, $R^{G2a}$ is substituted methyl. In certain embodiments, $R^{G2a}$ is a nitrogen protecting group. In certain embodiments, $R^{G2a}$ is acetyl. In certain embodiments, all instances of $R^B$ are hydrogen. In certain embodiments, $L^3$ is an unsubstituted $C_{1-3}$alkylene. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is —CH$_3$. In certain embodiments, at least one instance of $R^A$ is —CF$_3$. In certain embodiments, $R^G$ is hydrogen. In certain embodiments, $R^G$ is —CH$_3$. In certain embodiments, $R^X$ is hydrogen. In certain embodiments, $R^X$ is —CN. In certain embodiments, $R^X$ is —OR$^{X1}$. In certain embodiments, $R^X$ is —OR$^{X1}$; and $R^{X1}$ is —CH$_3$. In certain embodiments, $R^X$ is —OR$^{X1}$; and $R^{X1}$ is an oxygen protecting group. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —CH$_3$. In certain embodiments, $R^X$ is —CF$_3$. In certain embodiments, $G_5$ is S. In certain embodiments, $G_5$ is NR$^E$; and $R^E$ is hydrogen. In certain embodiments, $G_5$ is NR$^E$; and $R^E$ is —CH$_3$. In certain embodiments, both $R^{J1}$ and $R^{J2}$ are hydrogen. In certain embodiments, $R^{J1}$ is hydrogen; and $R^{J2}$ is substituted or unsubstituted $C_{1-6}$alkyl. In certain embodiments, $R^{J1}$ is hydrogen; and $R^{J2}$ is —CH$_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, ═══ represents a single bond. In certain embodiments, ═══ represents a double bond. In certain embodiments, each of $R^{D1}$, $R^{D2}$, and $R^{D3}$ is hydrogen. In certain embodiments, each of $R^{D2}$ and $R^{D3}$ is hydrogen, and $R^{D1}$ is —CH$_3$. In certain embodiments, each of $R^{D1}$ and $R^{D2}$ is hydrogen, and $R^{D3}$ is —CH$_2$N($R^{D1a}$)$_2$. In certain embodiments, each of $R^{D1}$ and $R^{D2}$ is hydrogen, and $R^{D3}$ is —CH$_2$OR$^{D1a}$. In certain embodiments, each of $R^{D1}$ and $R^{D2}$ is hydrogen, $R^{D3}$ is —CH$_2$N($R^{D1a}$)$_2$, and $R^{D1a}$ is hydrogen. In certain embodiments, each of $R^{D1}$ and $R^{D2}$ is hydrogen, $R^{D3}$ is —CH$_2$N($R^{D1a}$)$_2$, and $R^{D1a}$ is methyl. In certain embodiments, each of $R^{D1}$ and $R^{D2}$ is hydrogen, $R^{D3}$ is —CH$_2$OR$^{D1a}$, and $R^{D1a}$ is hydrogen. In certain embodiments, each of $R^{D1}$ and $R^{D2}$ is hydrogen, $R^{D3}$ is —CH$_2$OR$^{D1a}$, and $R^{D1a}$ is methyl. In certain embodiments, $R^{D4}$ is hydrogen. In certain embodiments, $R^{D4}$ is substituted or unsubstituted alkyl. In certain embodiments, $R^{D4}$ is a nitrogen protecting group. In certain embodiments, the group

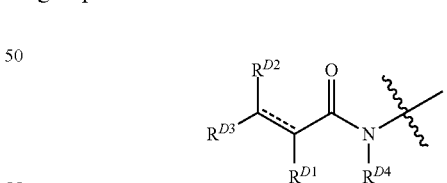

is attached meta to the point of attachment

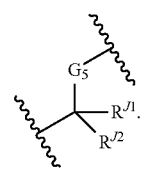

101

In certain embodiments, the group

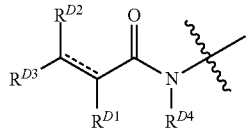

is attached para to the point of attachment

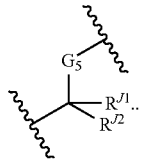

In certain embodiments, a compound of Formula (IIa) is a compound of Formula (IIa-1):

(IIa-1)

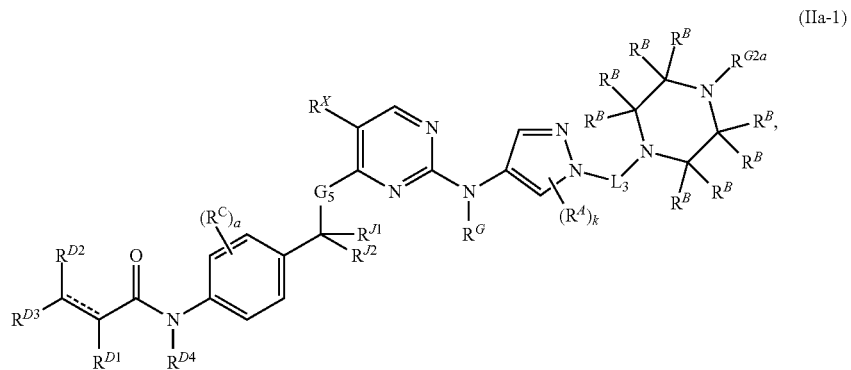

or a pharmaceutically acceptable salt thereof.

In certain embodiments, a compound of Formula (IIa) is a compound of Formula (IIa-2):

(IIa-2)

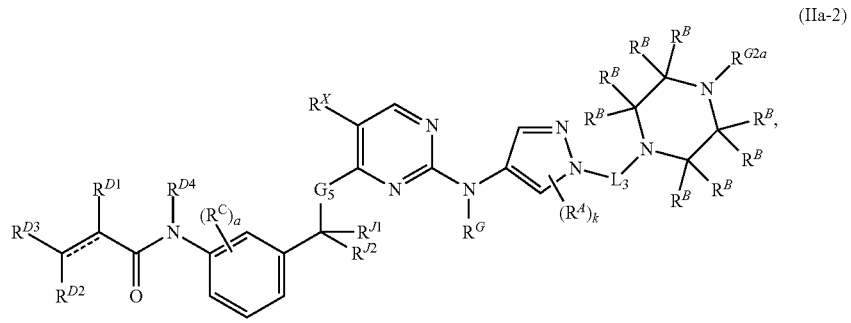

or a pharmaceutically acceptable salt thereof.

In certain embodiments, a compound of Formula (IIa) is a compound of Formula (IIa-3):

(IIa-3)

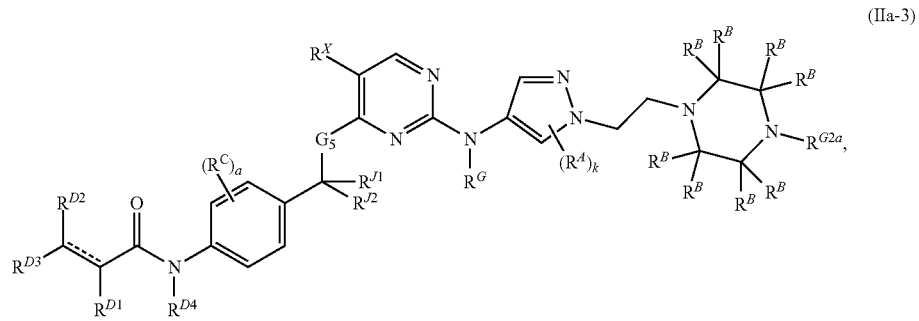

or a pharmaceutically acceptable salt thereof.

In certain embodiments, a compound of Formula (IIa) is a compound of Formula (IIa-4):

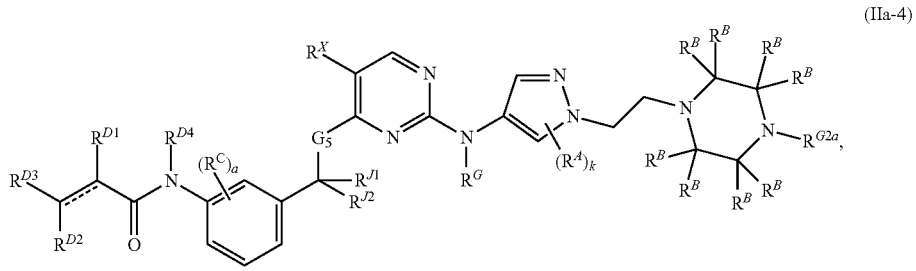

(IIa-4)

or a pharmaceutically acceptable salt thereof.

In certain embodiments, a compound of Formula (IIa) is a compound of Formula (IIa-5):

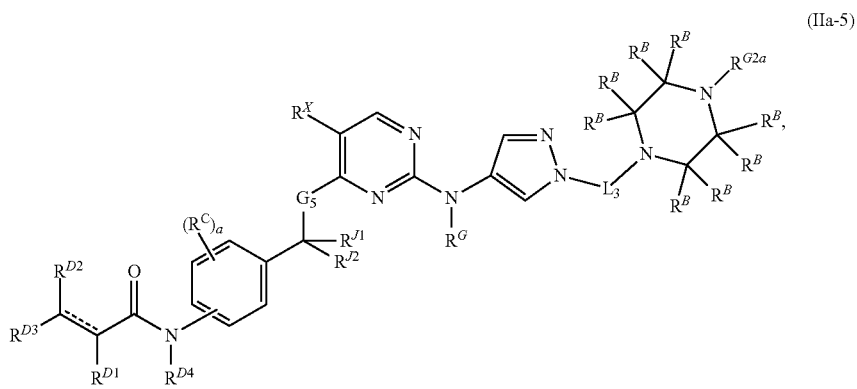

(IIa-5)

or a pharmaceutically acceptable salt thereof. In certain embodiments, the group

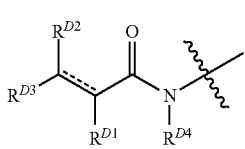

is attached meta to the point of attachment

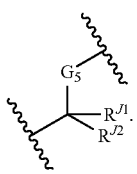

In certain embodiments, the group

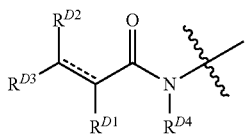

is attached para to the point of attachment

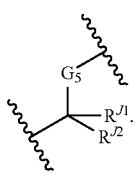

In certain embodiments, a compound of Formula (IIa) is a compound of Formula (IIa-6):

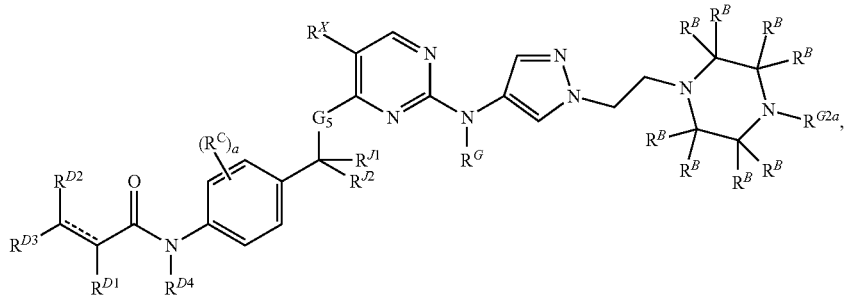

(IIa-6)

or a pharmaceutically acceptable salt thereof.

In certain embodiments, a compound of Formula (IIa) is a compound of Formula (IIa-7):

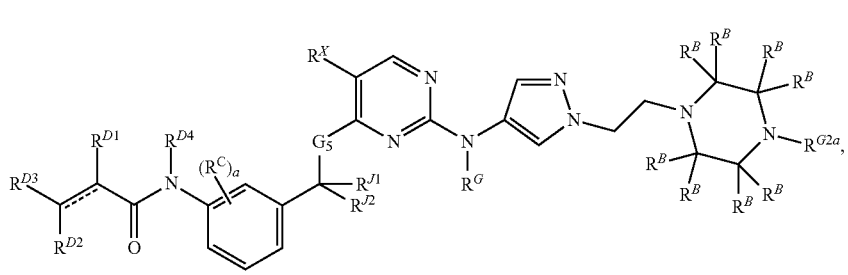

(IIa-7)

or a pharmaceutically acceptable salt thereof.

In certain embodiments, a compound described herein is a compound of Formula (IIb):

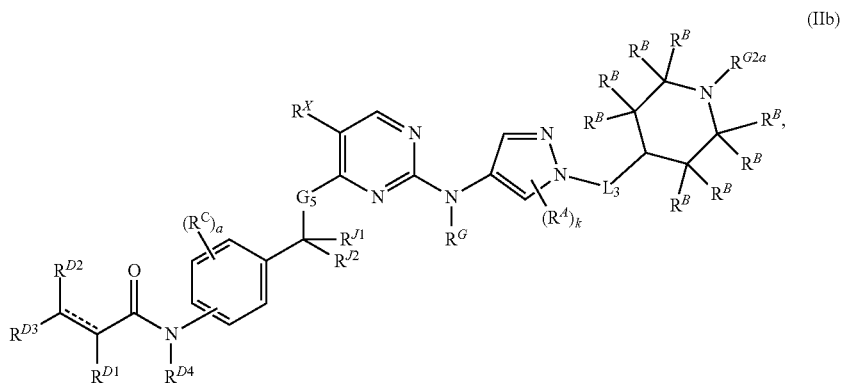

(IIb)

or a pharmaceutically acceptable salt thereof. In certain embodiments, $R^{G2a}$ is hydrogen. In certain embodiments, $R^{G2a}$ is unsubstituted $C_{1-6}$ alkyl. In certain embodiments, $R^{G2a}$ is substituted $C_{1-6}$ alkyl. In certain embodiments, $R^{G2a}$ is —$CH_3$. In certain, $R^{G2a}$ is substituted methyl. In certain embodiments, $R^{G2a}$ is a nitrogen protecting group. In certain embodiments, $R^{G2a}$ is acetyl. In certain embodiments, all instances of $R^B$ are hydrogen. In certain embodiments, $L^3$ is a bond. In certain embodiments, $L^3$ is an unsubstituted $C_{1-3}$alkylene linker. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is —$CH_3$. In certain embodiments, at least one instance of $R^A$ is —$CF_3$. In certain embodiments, $R^G$ is hydrogen. In certain embodiments, $R^G$ is —$CH_3$. In certain embodiments, $R^X$ is hydrogen. In certain embodiments, $R^X$ is —CN. In certain embodiments, $R^X$ is —$OR^{X1}$. In certain embodiments, $R^X$ is —$OR^{X1}$; and $R^{X1}$ is —$CH_3$. In certain embodiments, $R^X$ is —$OR^{X1}$; and $R^{X1}$ is an oxygen protecting group. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —$CH_3$. In certain embodiments, $R^X$ is —$CF_3$. In certain embodiments, $G_5$ is S. In certain embodiments, $G_5$ is $NR^E$; and $R^E$ is hydrogen. In certain embodiments, $G_5$ is $NR^E$; and $R^E$ is —$CH_3$. In certain embodiments, $G_5$ is $NR^E$; and $R^E$ is a nitrogen protecting group. In certain embodiments, both $R^{J1}$ and $R^{J2}$ are hydrogen. In certain embodiments, $R^{J1}$ is hydrogen; and $R^{J2}$ is substituted or unsubstituted $C_{1-6}$alkyl. In certain embodiments, $R^{J1}$ is hydrogen; and $R^{J2}$ is —$CH_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, ═══ represents a single bond. In certain embodiments, ═══ represents a double bond. In certain embodiments, each of $R^{D1}$, $R^{D2}$, and $R^{D3}$ is hydrogen. In certain embodiments, each of $R^{D2}$ and $R^{D3}$ is hydrogen, and $R^{D1}$ is —$CH_3$. In certain embodiments, each of $R^{D1}$ and $R^{D2}$ is hydrogen, and $R^{D3}$ is —$CH_2N(R^{D1a})_2$. In certain embodiments, each of $R^{D1}$ and $R^{D4}$ is hydrogen, and $R^{D3}$ is —$CH_2OR^{D1a}$. In certain embodiments, each of $R^{D1}$ and $R^{D2}$ is hydrogen, $R^{D3}$ is —$CH_2N(R^{D1a})_2$, and $R^{D1a}$ is hydrogen. In certain embodiments, each of $R^{D1}$ and $R^{D2}$ is hydrogen, $R^{D3}$ is —$CH_2N(R^{D1a})_2$, and $R^{D1a}$ is methyl. In certain embodiments, each of $R^{D1}$ and $R^{D2}$ is hydrogen, $R^{D3}$ is —$CH_2OR^{D1}a$, and $R^{D1a}$ is hydrogen. In certain embodiments, each of $R^{D1}$ and $R^{D2}$ is hydrogen, $R^{D3}$ is —$CH_2OR^{D1a}$, and $R^{D1a}$ is methyl. In certain embodiments, $R^{D4}$ is hydrogen. In certain embodiments, $R^{D4}$ is substituted or unsubstituted alkyl. In certain embodiments, $R^{D4}$ is a nitrogen protecting group. In certain embodiments, the group

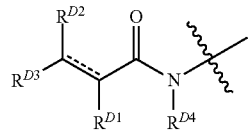

is attached meta to the point of attachment

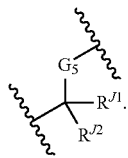

In certain embodiments, the group

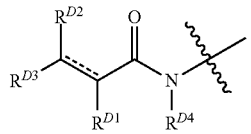

is attached para to the point of attachment

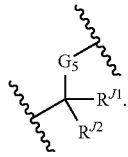

In certain embodiments, a compound of Formula (IIb) is a compound of Formula (IIb-1):

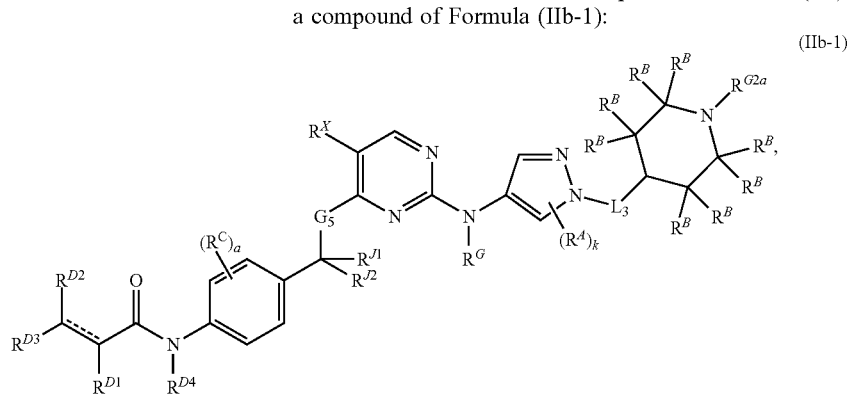

(IIb-1)

or a pharmaceutically acceptable salt thereof.

In certain embodiments, a compound of Formula (IIb) is a compound of Formula (IIb-2):

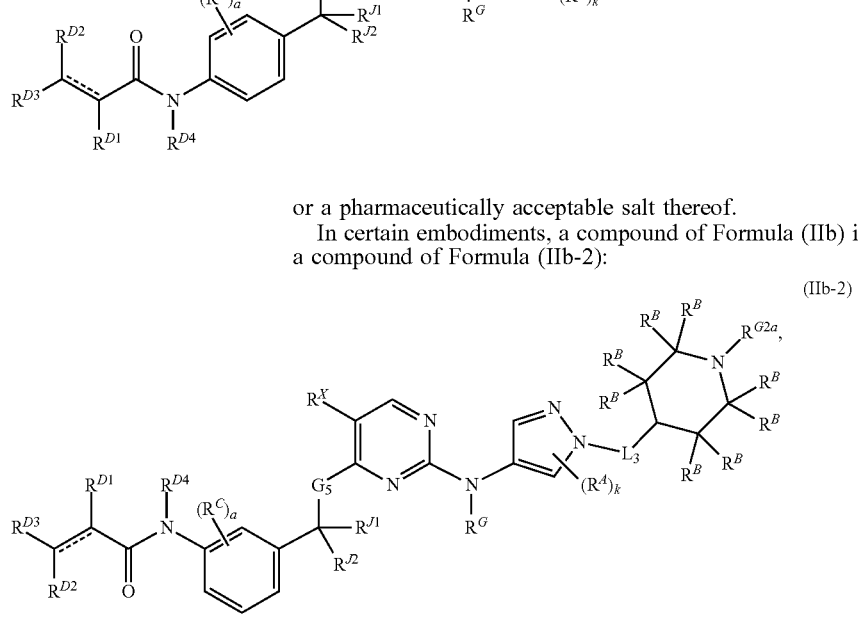

(IIb-2)

or a pharmaceutically acceptable salt thereof.

In certain embodiments, a compound of Formula (IIb) is a compound of Formula (IIb-3):

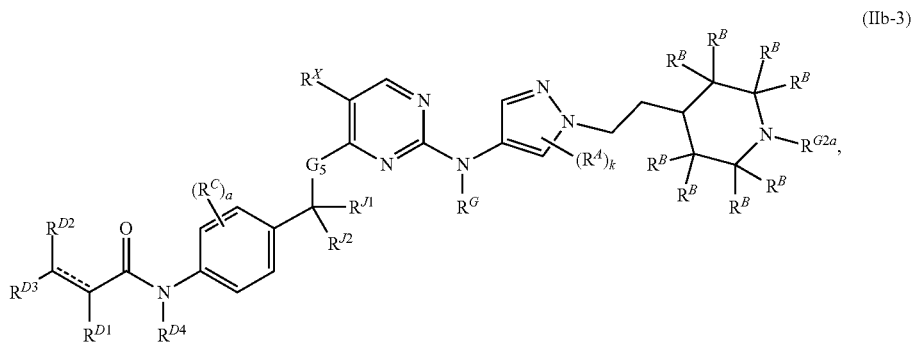

(IIb-3)

or a pharmaceutically acceptable salt thereof.

In certain embodiments, a compound of Formula (IIb) is a compound of Formula (IIb-4):

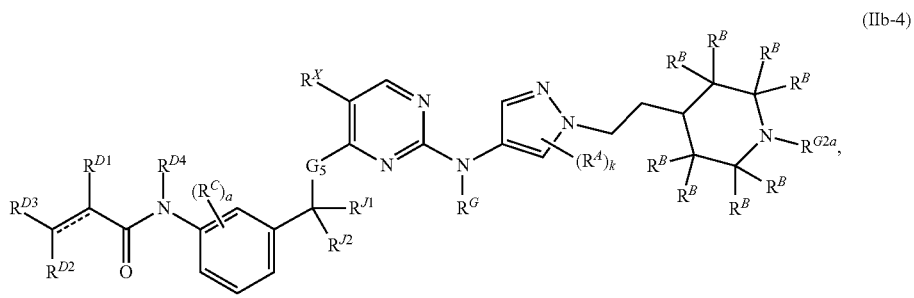

(IIb-4)

or a pharmaceutically acceptable salt thereof.

In certain embodiments, a compound of Formula (IIb) is a compound of Formula (IIb-5):

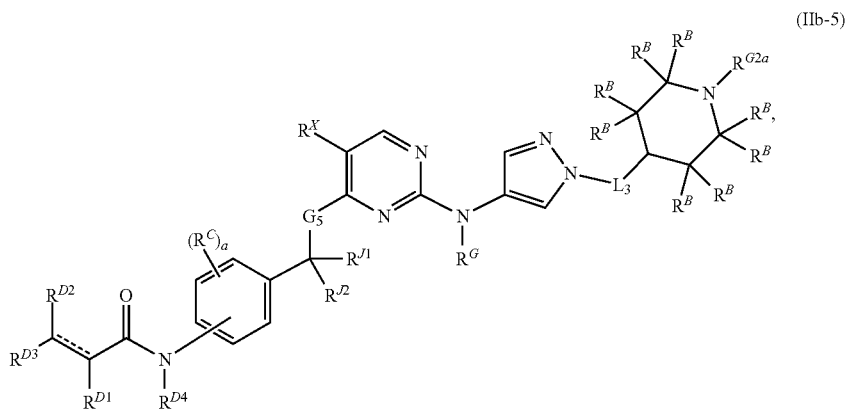

(IIb-5)

or a pharmaceutically acceptable salt thereof. In certain embodiments, the group

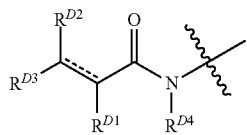

is attached meta to the point of attachment

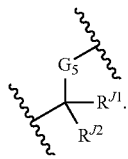

In certain embodiments, the group

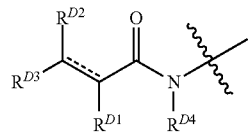

is attached para to the point of attachment

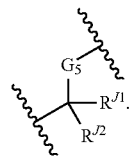

In certain embodiments, a compound of Formula (IIb) is a compound of Formula (IIb-6):

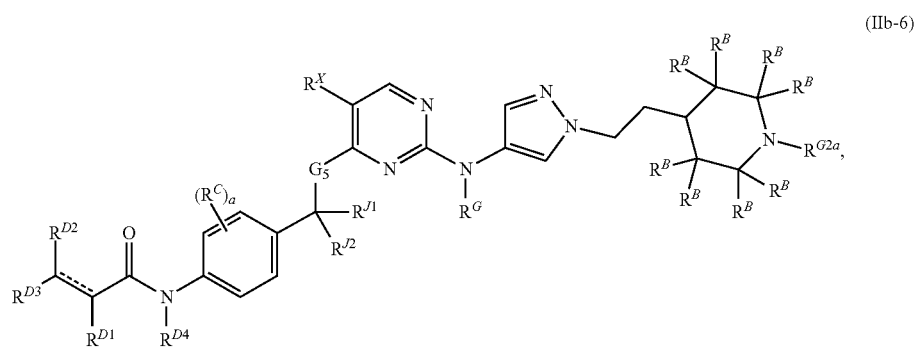

(IIb-6)

or a pharmaceutically acceptable salt thereof.

In certain embodiments, a compound of Formula (IIb) is a compound of Formula (IIb-7):

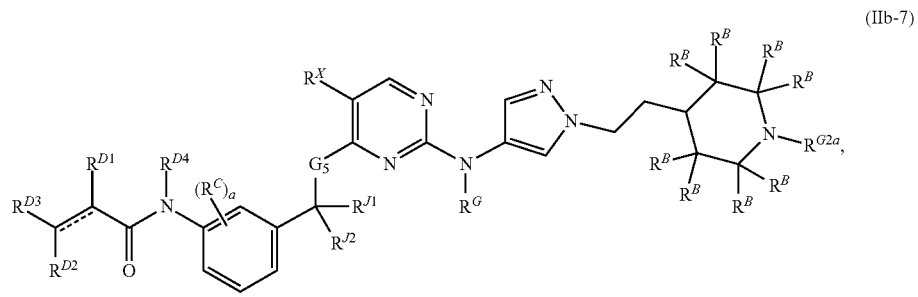

(IIb-7)

or a pharmaceutically acceptable salt thereof.

In certain embodiments, a compound of Formula (IIb) is a compound of Formula (IIb-8):

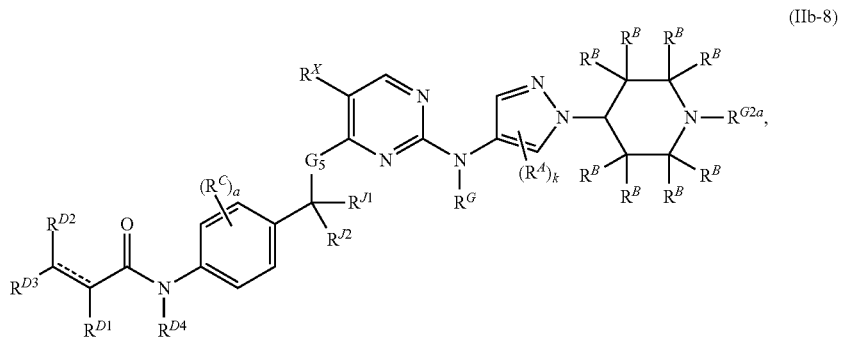

(IIb-8)

or a pharmaceutically acceptable salt thereof.

In certain embodiments, a compound of Formula (IIb) is a compound of Formula (IIb-9):

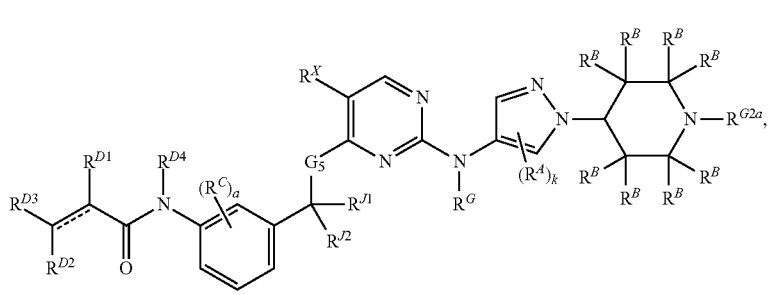

(IIb-9)

or a pharmaceutically acceptable salt thereof.

In certain embodiments, a compound of Formula (IIb) is a compound of Formula (IIb-10):

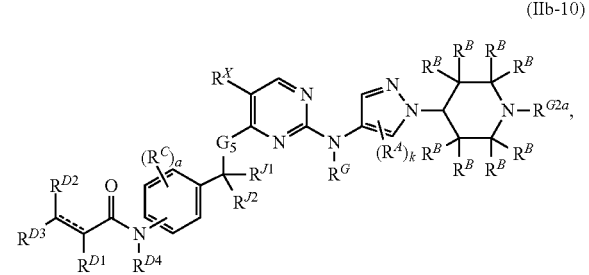

(IIb-10)

or a pharmaceutically acceptable salt thereof. In certain embodiments, the group

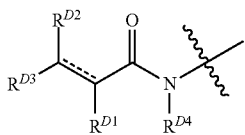

is attached meta to the point of attachment

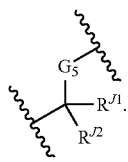

In certain embodiments, the group

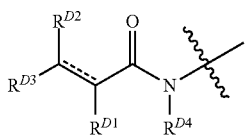

is attached para to the point of attachment

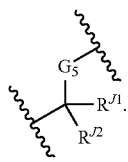

In certain embodiments, a compound of Formula (IIb) is a compound of Formula (IIb-11):

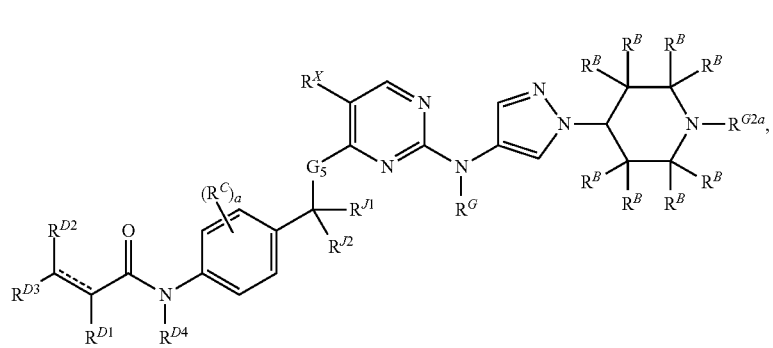

(IIb-11)

or a pharmaceutically acceptable salt thereof.

In certain embodiments, a compound of Formula (IIb) is a compound of Formula (IIb-12):

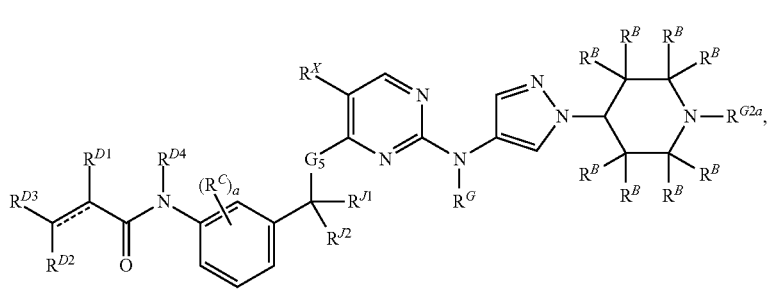

(IIb-12)

or a pharmaceutically acceptable salt thereof.

In certain embodiments, a compound described herein is a compound of Formula (IIc):

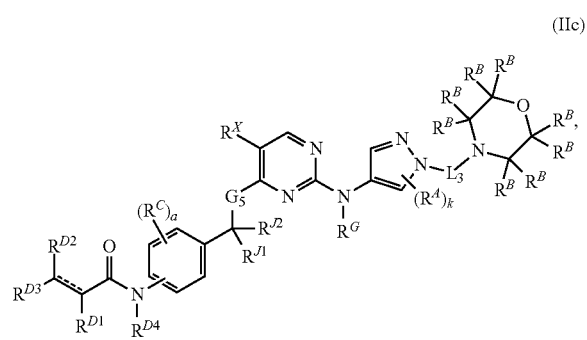

(IIc)

or a pharmaceutically acceptable salt thereof. In certain embodiments, all instances of $R^B$ are hydrogen. In certain embodiments, $L^3$ is an unsubstituted $C_{1-3}$alkylene. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is —$CH_3$. In certain embodiments, at least one instance of $R^A$ is —$CF_3$. In certain embodiments, $R^G$ is hydrogen. In certain embodiments, $R^G$ is —$CH_3$. In certain embodiments, $R^X$ is hydrogen. In certain embodiments, $R^X$ is —CN. In certain embodiments, $R^X$ is —$OR^{X1}$. In certain embodiments, $R^X$ is —$OR^{X1}$; and $R^{X1}$ is —$CH_3$. In certain embodiments, $R^X$ is —$OR^{X1}$; and $R^{X1}$ is an oxygen protecting group. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —$CH_3$. In certain embodiments, $G_5$ is S. In certain embodiments, $G_5$ is $NR^E$; and $R^E$ is hydrogen. In certain embodiments, $G_5$ is $NR^E$; and $R^E$ is —$CH_3$. In certain embodiments, $G_5$ is $NR^E$; and $R^E$ is a nitrogen protecting group. In certain embodiments, both $R^{J1}$ and $R^{J2}$ are hydrogen. In certain embodiments, $R^{J1}$ is hydrogen; and $R^{J2}$ is substituted or unsubstituted $C_{1-6}$alkyl. In certain embodiments, $R^{J1}$ is hydrogen; and $R^{J2}$ is —$CH_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, ═══ represents a single bond. In certain embodiments, ═══ represents a double bond. In certain embodiments, each of $R^{D1}$, $R^{D2}$, and $R^{D3}$ is hydrogen. In certain embodiments, each of $R^{D2}$ and $R^{D3}$ is hydrogen, and $R^{D1}$ is —$CH_3$. In certain embodiments, each of $R^{D1}$ and $R^{D2}$ is hydrogen, and $R^{D3}$ is —$CH_2N(R^{D1a})_2$. In certain embodiments, each of $R^{D1}$ and $R^{D2}$ is hydrogen, and $R^{D3}$ is —$CH_2OR^{D1a}$. In certain embodiments, each of $R^{D1}$ and $R^{D2}$ is hydrogen, $R^{D3}$ is —$CH_2N(R^{D1a})_2$, and $R^{D1}$ is hydrogen. In certain embodiments, each of $R^{D1}$ and $R^{D2}$ is hydrogen, $R^{D3}$ is —$CH_2N(R^{D1a})_2$, and $R^{D1a}$ is methyl. In certain embodiments, each of $R^{D1}$ and $R^{D2}$ is hydrogen, $R^{D3}$ is —$CH_2OR^{D1a}$, and $R^{D1a}$ is hydrogen. In certain embodiments, each of $R^{D1}$ and $R^{D2}$ is hydrogen, $R^{D3}$ is —$CH_2OR^{D1a}$, and $R^{D1a}$ is methyl. In certain embodiments, $R^{D4}$ is hydrogen. In certain embodiments, $R^{D4}$ is substituted or unsubstituted alkyl. In certain embodiments, $R^{D4}$ is a nitrogen protecting group. In certain embodiments, the group

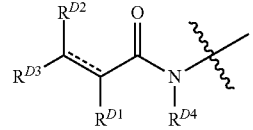

is attached meta to the point of attachment

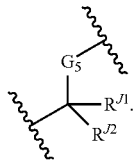

In certain embodiments, the group

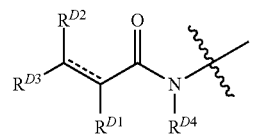

is attached para to the point of attachment

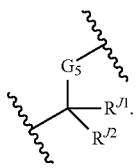

In certain embodiments, a compound of Formula (IIc) is a compound of Formula (IIc-1):

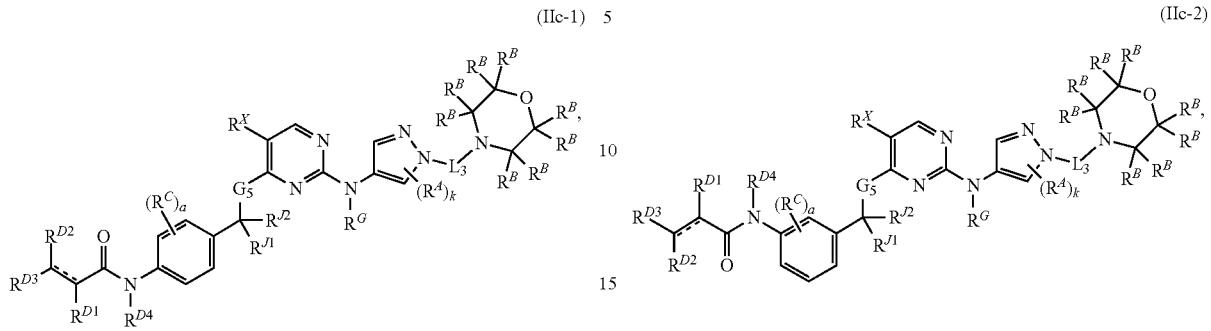

(IIc-1)

or a pharmaceutically acceptable salt thereof.

In certain embodiments, a compound of Formula (IIc) is a compound of Formula (IIc-2):

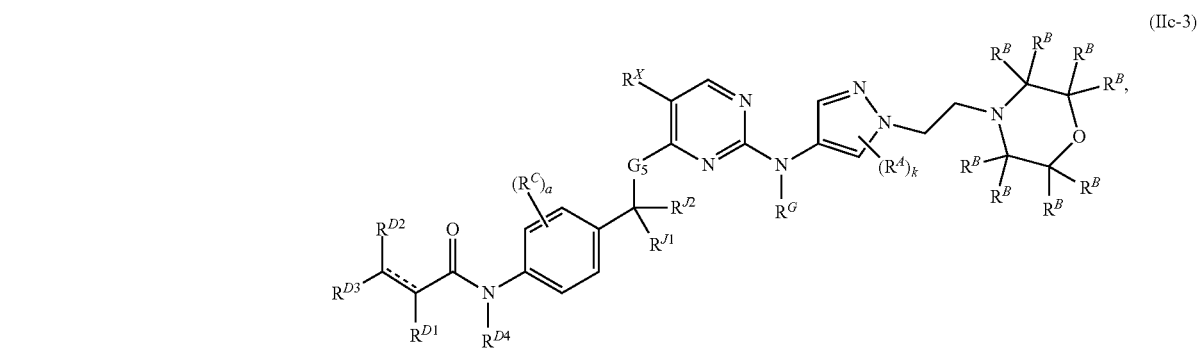

(IIc-2)

or a pharmaceutically acceptable salt thereof.

In certain embodiments, a compound of Formula (IIc) is a compound of Formula (IIc-3):

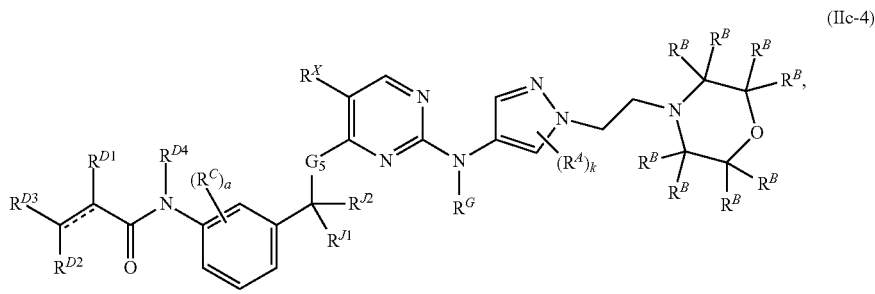

(IIc-3)

or a pharmaceutically acceptable salt thereof.

In certain embodiments, a compound of Formula (IIc) is a compound of Formula (IIc-4):

(IIc-4)

or a pharmaceutically acceptable salt thereof.

In certain embodiments, a compound of Formula (IIc) is a compound of Formula (IIc-5):

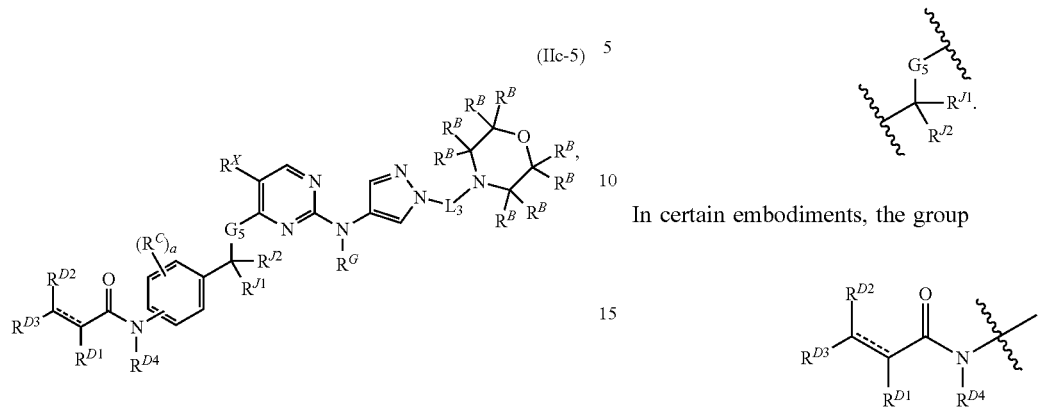

(IIc-5)

or a pharmaceutically acceptable salt thereof. In certain embodiments, the group

is attached meta to the point of attachment

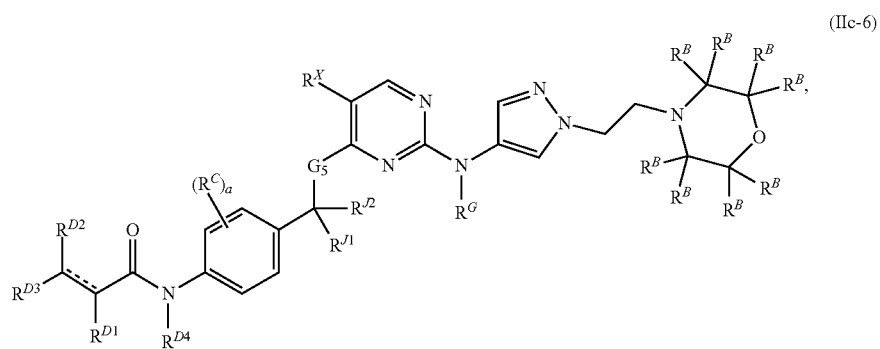

In certain embodiments, the group

is attached para to the point of attachment

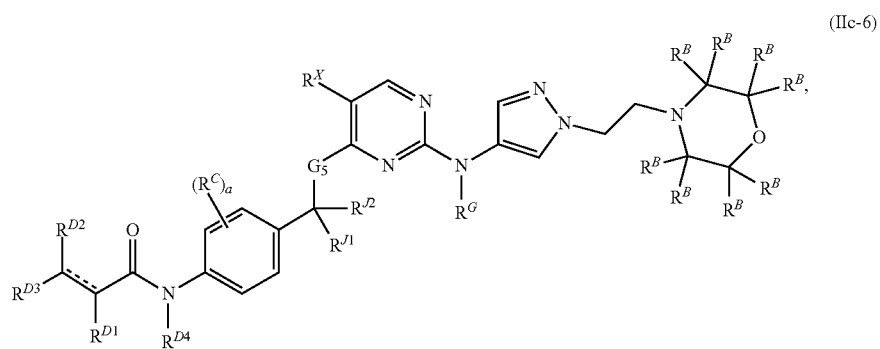

In certain embodiments, a compound of Formula (IIc) is a compound of Formula (IIc-6):

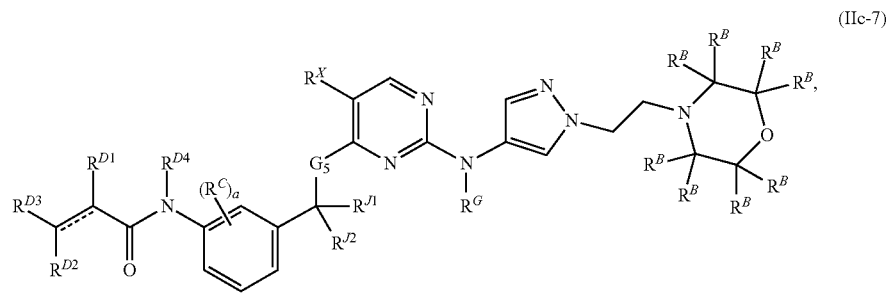

(IIc-6)

or a pharmaceutically acceptable salt thereof.

In certain embodiments, a compound of Formula (IIc) is a compound of Formula (IIc-7):

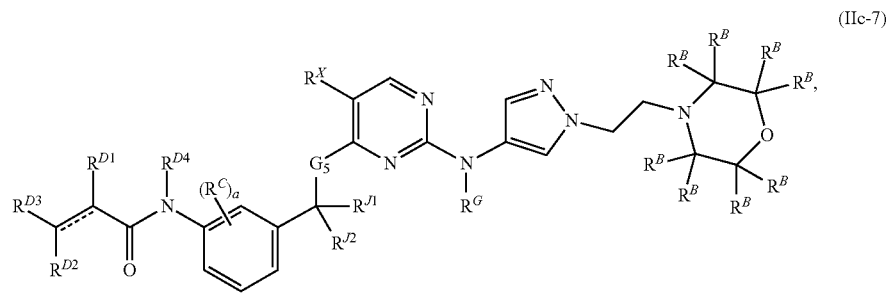

(IIc-7)

or a pharmaceutically acceptable salt thereof.

In certain embodiments, a compound described herein is a compound of Formula (IId):

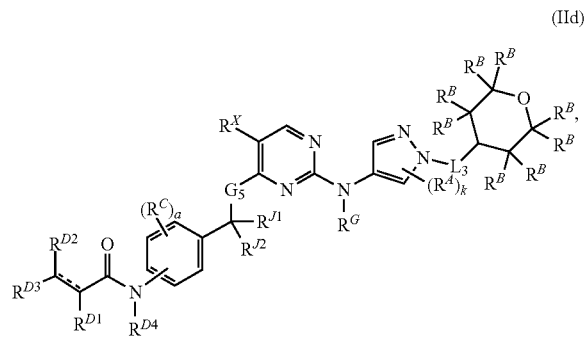

(IId)

or a pharmaceutically acceptable salt thereof. In certain embodiments, all instances of $R^B$ are hydrogen. In certain embodiments, $L^3$ is a bond. In certain embodiments, $L^3$ is an unsubstituted $C_{1-3}$alkylene. In certain embodiments, at least one instance of $R^A$ is unsubstituted $C_{1-6}$ alkyl. In certain embodiments, at least one instance of $R^A$ is substituted $C_{1-6}$ alkyl. In certain embodiments, at least one instance of $R^A$ is —$CH_3$. In certain embodiments, at least one instance of $R^A$ is —$CF_3$. In certain embodiments, $R^G$ is hydrogen. In certain embodiments, $R^G$ is —$CH_3$. In certain embodiments, $R^X$ is hydrogen. In certain embodiments, $R^X$ is —CN. In certain embodiments, $R^X$ is —$OR^{X1}$. In certain embodiments, $R^X$ is —$OR^{X1}$; and $R^{X1}$ is —$CH_3$. In certain embodiments, $R^X$ is —$OR^{X1}$; and $R^{X1}$ is an oxygen protecting group. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —$CH_3$. In certain embodiments, $R^X$ is —$CF_3$. In certain embodiments, $G_5$ is S. In certain embodiments, $G_5$ is $NR^E$; and $R^E$ is hydrogen. In certain embodiments, $G_5$ is $NR^E$; and $R^E$ is —$CH_3$. In certain embodiments, $G_5$ is $NR^E$; and $R^E$ is a nitrogen protecting group. In certain embodiments, both $R^{J1}$ and $R^{J2}$ are hydrogen. In certain embodiments, $R^{J1}$ is hydrogen; and $R^{J2}$ is substituted or unsubstituted $C_{1-6}$alkyl. In certain embodiments, $R^{J1}$ is hydrogen; and $R^{J2}$ is —$CH_3$. In certain embodiments, a is 0. In certain embodiments, a is 1. In certain embodiments, a is 2. In certain embodiments, In certain embodiments, at least one instance of $R^C$ is halogen. In certain embodiments, at least one instance of $R^C$ is F. In certain embodiments, ═══ represents a single bond. In certain embodiments, ═══ represents a double bond. In certain embodiments, each of $R^{D1}$, $R^{D2}$, and $R^{D3}$ is hydrogen. In certain embodiments, each of $R^{D2}$ and $R^{D3}$ is hydrogen, and $R^{D1}$ is —$CH_3$. In certain embodiments, each of $R^{D1}$ and $R^{D2}$ is hydrogen, and $R^{D3}$ is —$CH_2N(R^{D1a})_2$. In certain embodiments, each of $R^{D1}$ and $R^{D2}$ is hydrogen, and $R^{D3}$ is —$CH_2OR^{D1a}$. In certain embodiments, each of $R^{D1}$ and $R^{D2}$ is hydrogen, $R^{D3}$ is —$CH_2N(R^{D1a})_2$, and $R^{D1a}$ is hydrogen. In certain embodiments, each of $R^{D1}$ and $R^{D2}$ is hydrogen, $R^{D3}$ is —$CH_2N(R^{D1a})_2$, and $R^{D1a}$ is methyl. In certain embodiments, each of $R^{D1}$ and $R^{D2}$ is hydrogen, $R^{D3}$ is —$CH_2OR^{D1a}$, and $R^{D1a}$ is hydrogen. In certain embodiments, each of $R^{D1}$ and $R^{D2}$ is hydrogen, $R^{D3}$ is —$CH_2OR^{D1a}$, and $R^{D1a}$ is methyl. In certain embodiments, $R^{D4}$ is hydrogen. In certain embodiments, $R^{D4}$ is substituted or unsubstituted alkyl. In certain embodiments, the group

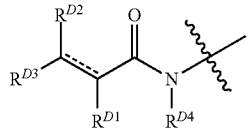

is attached meta to the point of attachment

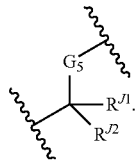

In certain embodiments, the group

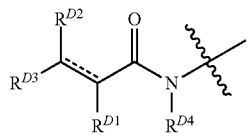

is attached para to the point of attachment

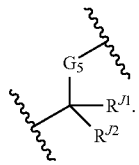

In certain embodiments, a compound of Formula (IId) is a compound of Formula (IId-1):

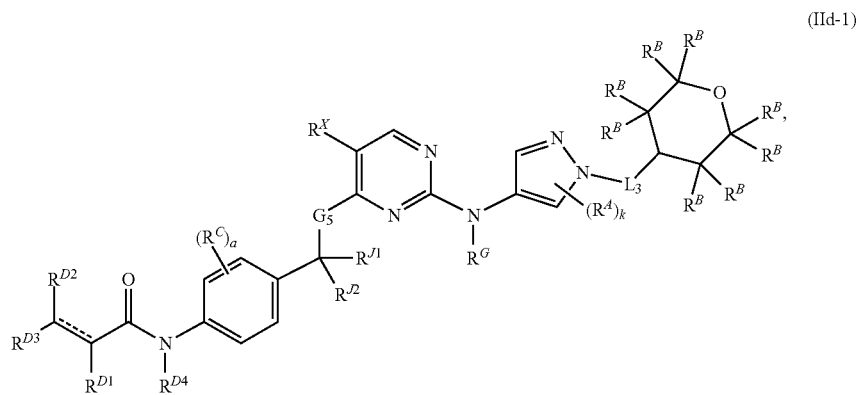

(IId-1)

or a pharmaceutically acceptable salt thereof.

In certain embodiments, a compound of Formula (IId) is a compound of Formula (IId-2):

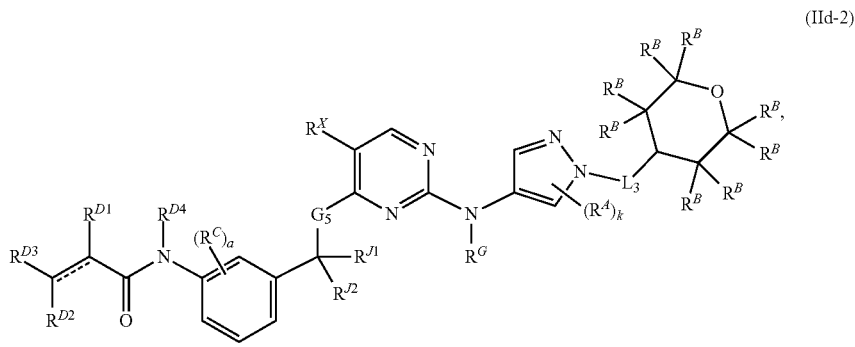

or a pharmaceutically acceptable salt thereof.

In certain embodiments, a compound of Formula (IId) is a compound of Formula (IId-3):

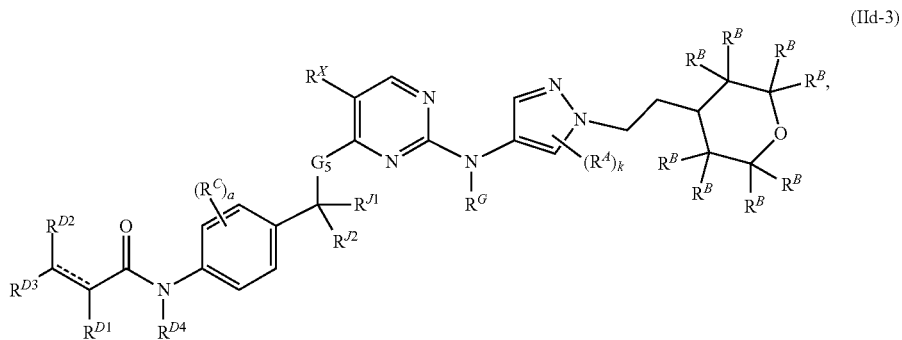

or a pharmaceutically acceptable salt thereof.

In certain embodiments, a compound of Formula (IId) is a compound of Formula (IId-4):

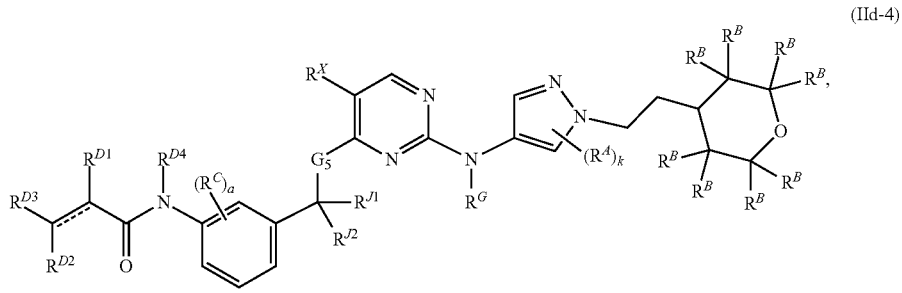

or a pharmaceutically acceptable salt thereof.

In certain embodiments, a compound of Formula (IId) is a compound of Formula (IId-5):

(IId-5)

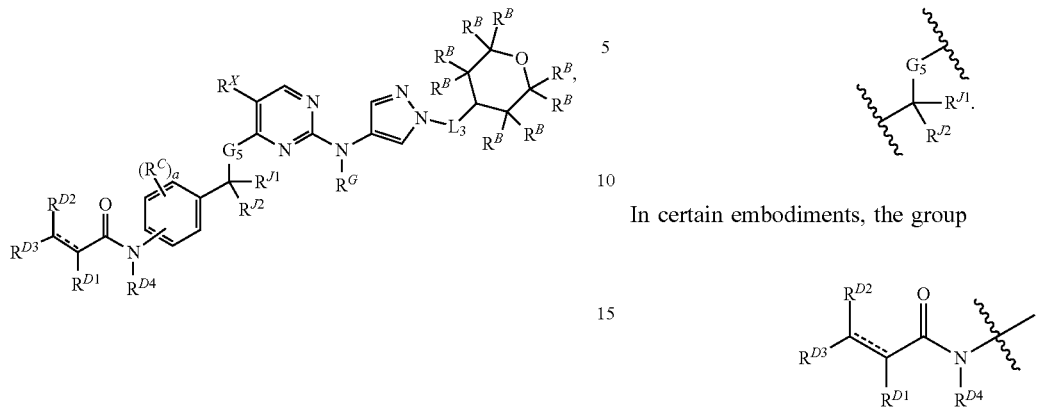

is attached meta to the point of attachment

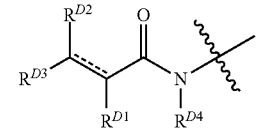

In certain embodiments, the group

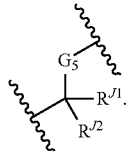

is attached para to the point of attachment or a pharmaceutically acceptable salt thereof. In certain embodiments, the group In certain embodiments, a compound of Formula (IId) is a compound of Formula (IId-6):

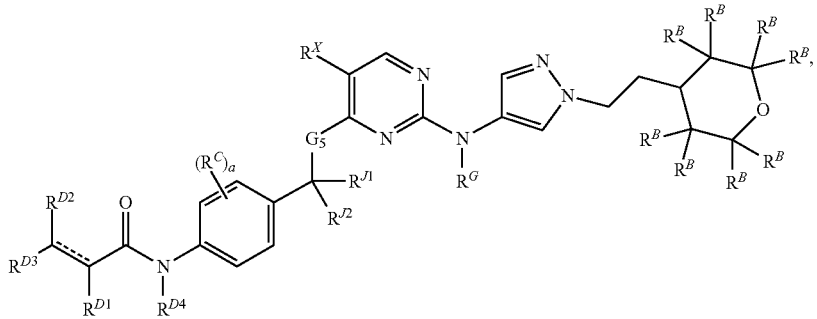

(IId-6)

or a pharmaceutically acceptable salt thereof.

In certain embodiments, a compound of Formula (IId) is a compound of Formula (IId-7):

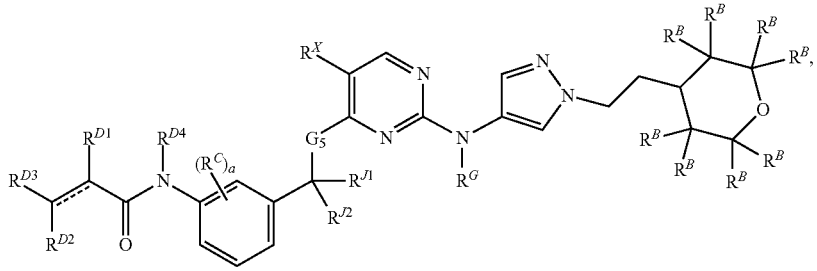

(IId-7)

or a pharmaceutically acceptable salt thereof.

In certain embodiments, a compound of Formula (IId) is a compound of Formula (IId-8):

(IId-8)

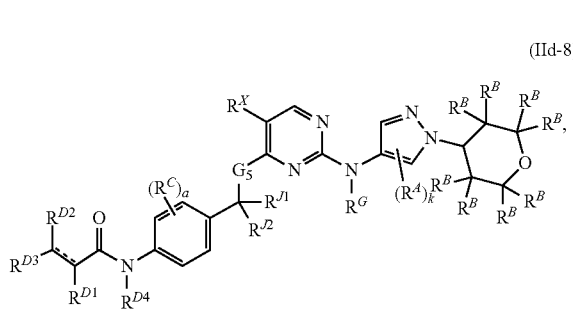

or a pharmaceutically acceptable salt thereof.

In certain embodiments, a compound of Formula (IId) is a compound of Formula (IId-9):

(IId-9)

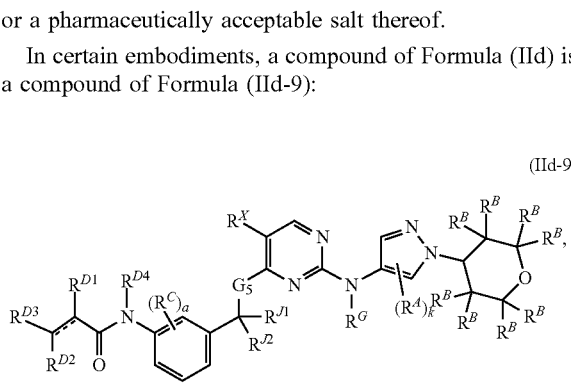

or a pharmaceutically acceptable salt thereof.

In certain embodiments, a compound of Formula (IId) is a compound of Formula (IId-10):

(IId-10)

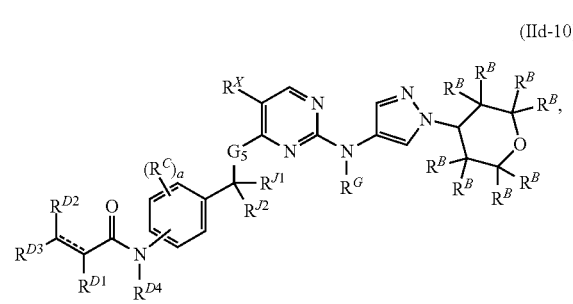

or a pharmaceutically acceptable salt thereof. In certain embodiments, the group

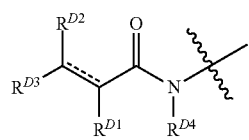

is attached meta or para to the point of attachment to the parent molecule.

In certain embodiments, a compound of Formula (IId) is a compound of Formula (IId-11):

(IId-11)

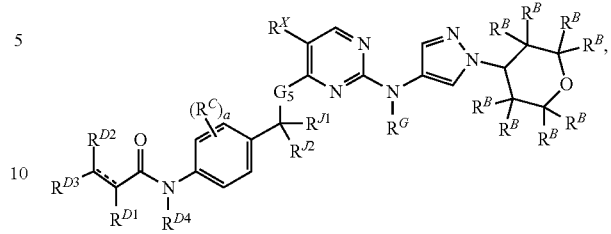

or a pharmaceutically acceptable salt thereof.

In certain embodiments, a compound of Formula (IId) is a compound of Formula (IId-12):

(IId-12)

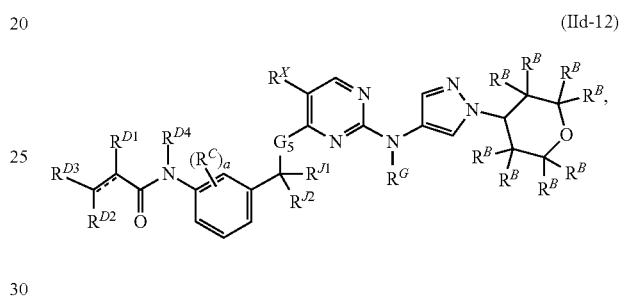

or a pharmaceutically acceptable salt thereof.

In certain embodiments, wherein $R^{Y2}$ is a substituted methyl, a compound described herein is a compound of Formula (IIe):

(IIe)

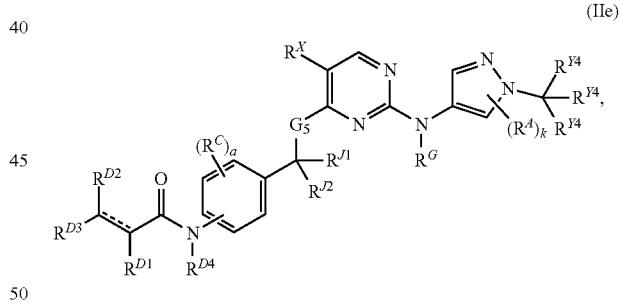

or a pharmaceutically acceptable salt thereof, wherein:

each instance of $R^{Y4}$ is independently hydrogen, halogen, —$OR^{Y3}$, —$N(R^{Y3})_2$, —$C(=O)OR^{Y3}$, —$C(=O)N(R^{Y3})_2$, provided at least one $R^{Y4}$ group is not hydrogen; and $R^{Y3}$ is independently hydrogen, substituted or unsubstituted alkyl, or two $R^{Y3}$ groups attached to a N atom are joined to form a substituted or unsubstituted 5- to 6-membered heterocyclic ring.

In certain embodiments, wherein $R^{Y2}$ is a substituted ethyl, a compound described herein is a compound of Formula (IIf):

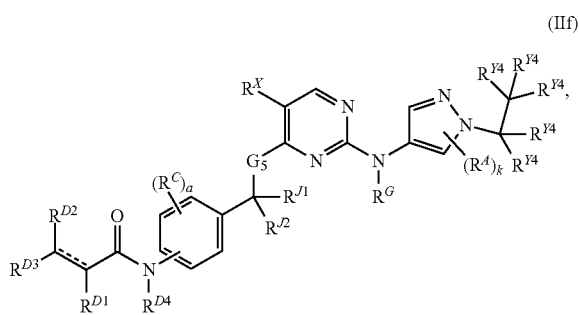

(IIf)

or a pharmaceutically acceptable salt thereof, wherein:

each instance of $R^{Y4}$ is independently hydrogen, halogen, —$OR^{Y3}$, —$N(R^{Y3})_2$, —$C(=O)OR^{Y3}$, —$C(=O)N(R^{Y3})_2$, provided at least one $R^{Y4}$ group is not hydrogen;

$R^{Y3}$ is independently hydrogen, substituted or unsubstituted alkyl, or two $R^{Y3}$ groups attached to a N atom are joined to form a substituted or unsubstituted 5- to 6-membered heterocyclic ring. In certain embodiments, one $R^{Y4}$ is halogen, —$OR^{Y3}$, —$N(R^{Y3})_2$, —$C(=O)OR^{Y3}$, —$C(=O)N(R^{Y3})_2$, and the other two $R^{Y4}$ groups are hydrogen; and each instance of $R^{Y5}$ is independently hydrogen or —$CH_3$.

In certain embodiments, a compound described herein is a compound of the formula:

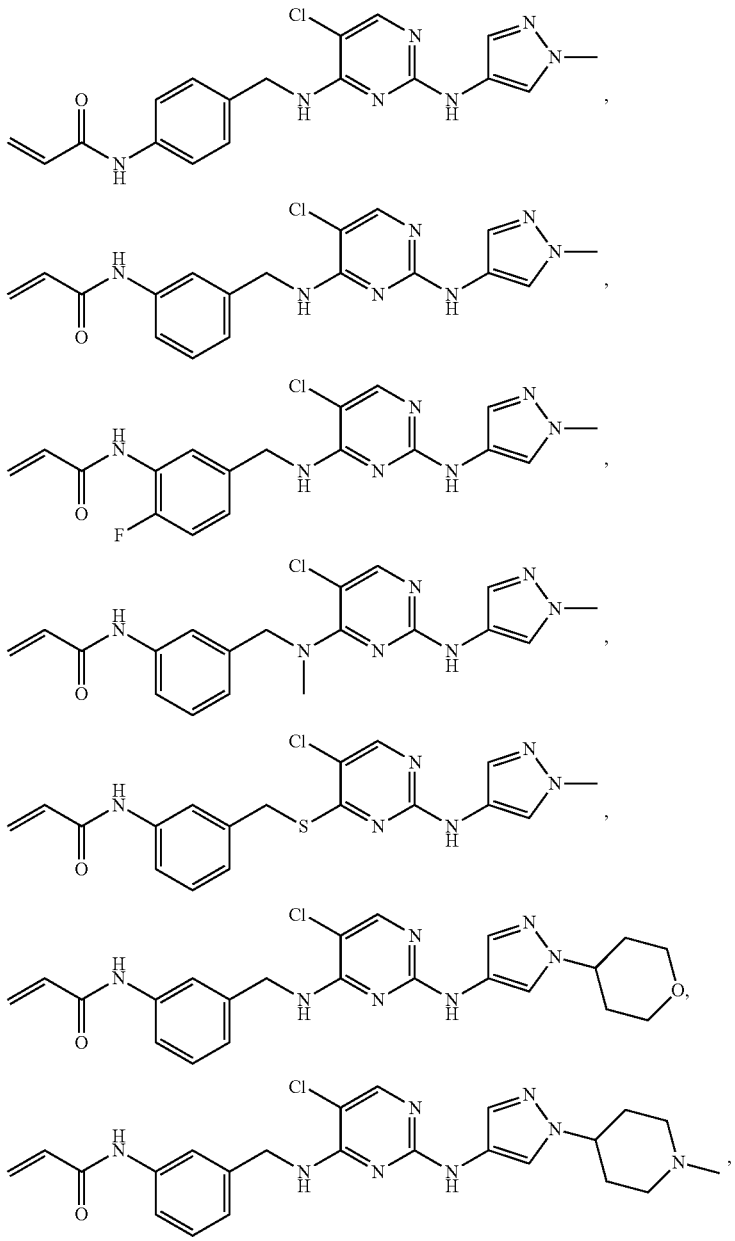

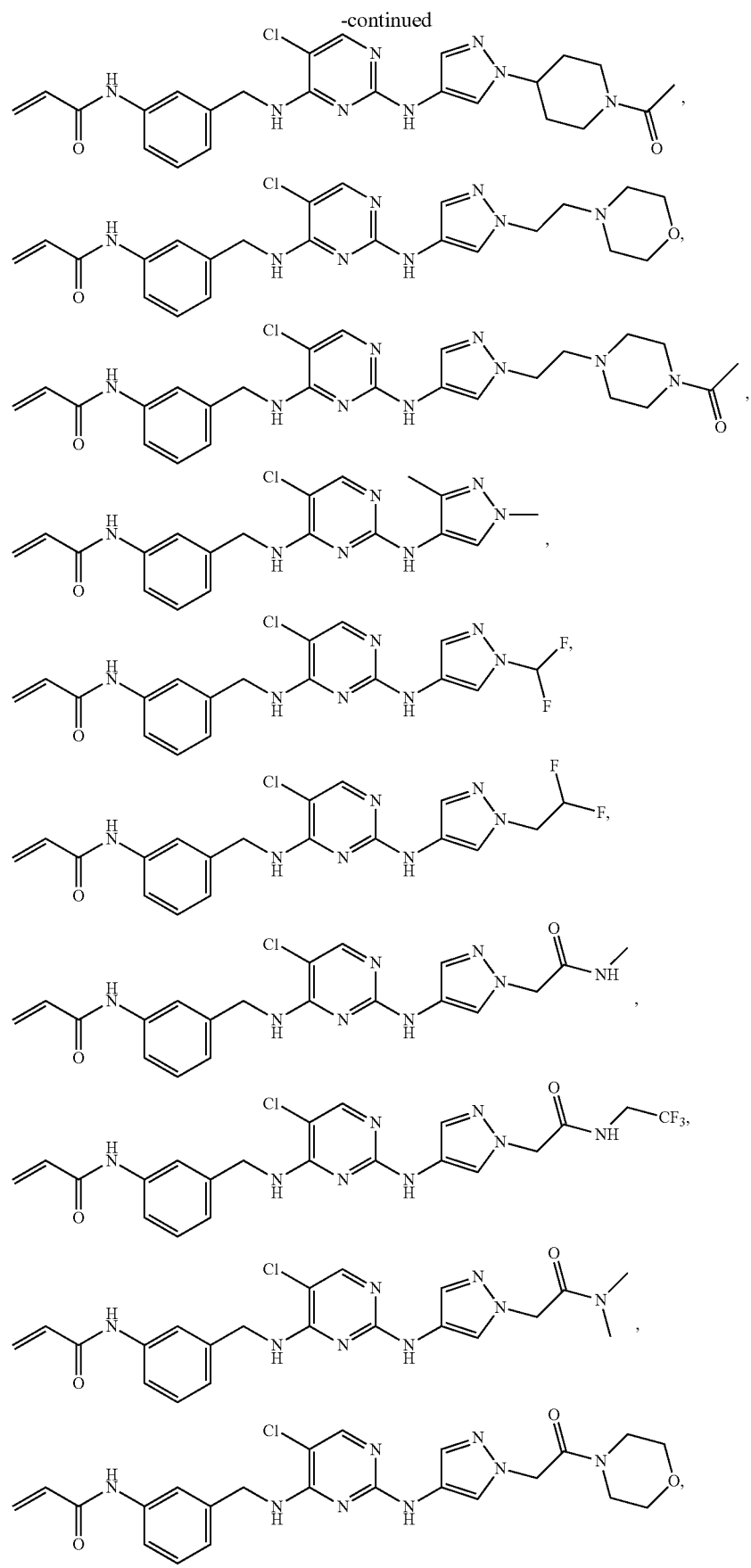

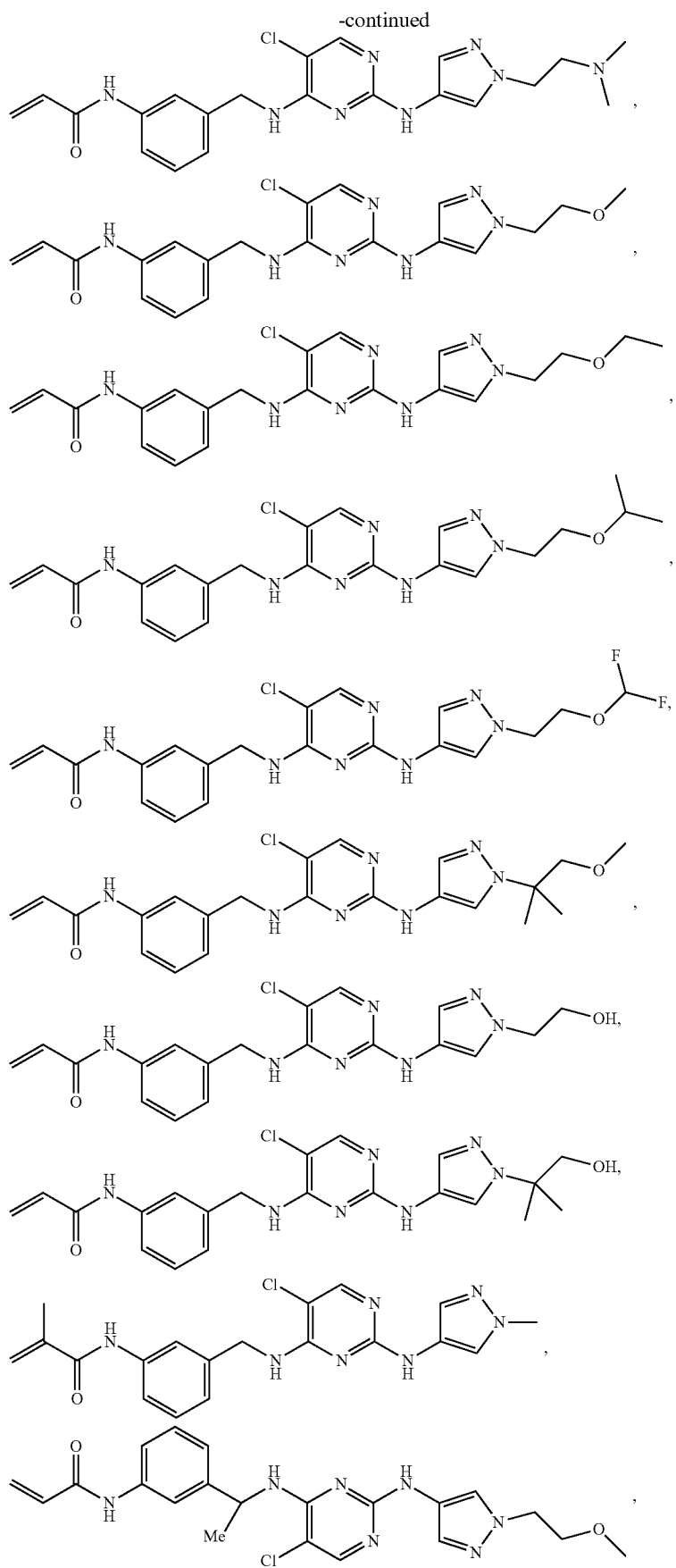

-continued

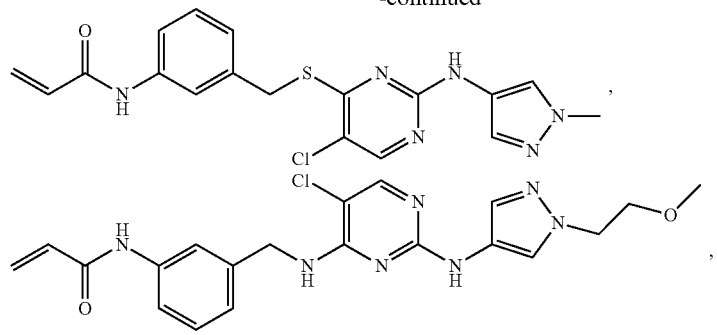

or a pharmaceutically acceptable salt thereof.

In certain embodiments, a compound described herein is a compound of the formula:

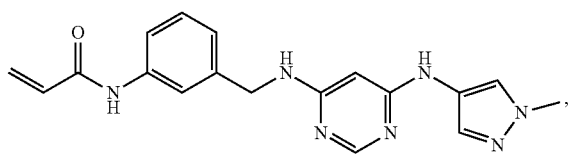 [SMILES: C=CC(=O)Nc1cccc(CNc2cc(Nc3cnn(C)c3)ncn2)c1]

or a pharmaceutically acceptable salt thereof.

In certain embodiments, a compound described herein is a compound of the formula:

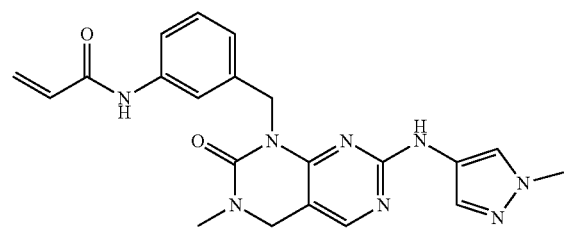 [SMILES: C=CC(=O)Nc1cccc(CN2C(=O)N(C)Cc3cnc(Nc4cnn(C)c4)nc32)c1]

or a pharmaceutically acceptable salt thereof.

In certain embodiments, a compound described herein is a compound of the formula:

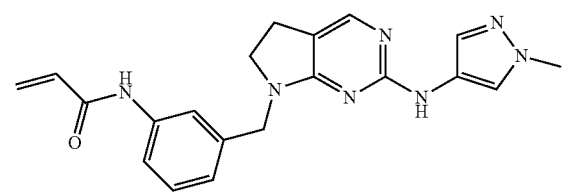 [SMILES: C=CC(=O)Nc1cccc(CN2CCc3cnc(Nc4cnn(C)c4)nc32)c1]

or a pharmaceutically acceptable salt thereof.

In certain embodiments, a compound described herein is a compound of the formula:

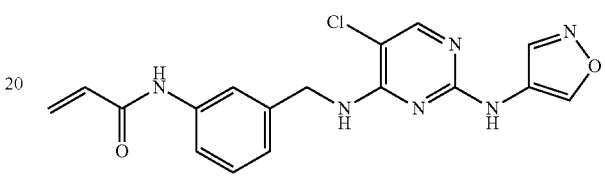

or a pharmaceutically acceptable salt thereof.

In certain embodiments, a compound described herein is a compound of the formula:

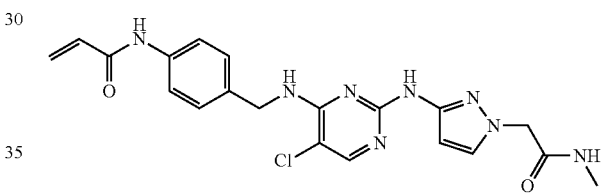

or a pharmaceutically acceptable salt thereof.

In certain embodiments, a compound described herein is a compound of the formula:

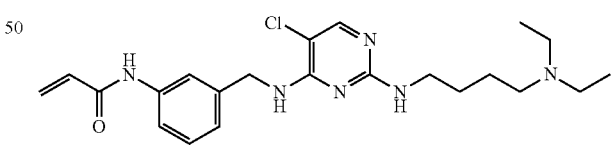

or a pharmaceutically acceptable salt thereof.

In certain embodiments, a compound described herein is a compound of the formula:

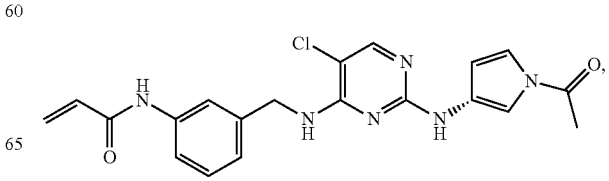

-continued

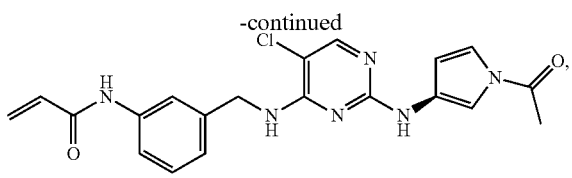

or a pharmaceutically acceptable salt thereof.

Labeling of Compounds

Further contemplated herein are compounds of Formula (I) and (II), wherein $R^{Y1}$ and $R^{Y2}$ are, alternatively, a linking group ("$L^1$") attaching a label ("B") to the core parent structure, e.g., of formula:

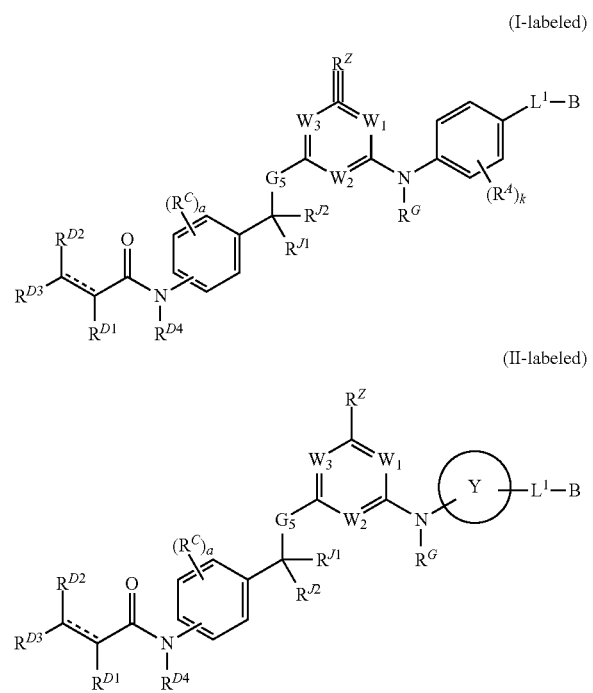

wherein:
Group

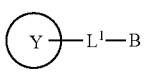

is selected from the group consisting of:

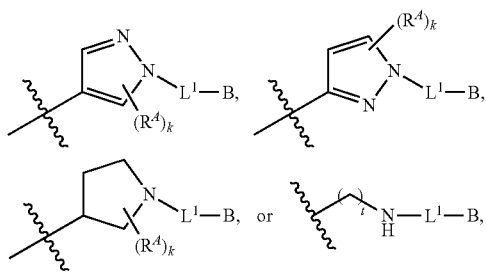

wherein t is 2, 3, 4, 5, or 6;

$L^1$ is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof; and B is a label.

A "label," as used herein, refers to a detectable moiety, i.e., a moiety which provides a detectable (e.g., visually detectable) analytical signal. Various detectable moieties are contemplated herein, and include, but are not limited to, (a) a molecule which contains isotopic moieties, e.g., for use in radioimmunoassays, which may be radioactive and/or isotopic and include, but not limited to, $^2H$, $^3H$, $^{13}C$, $^{14}C$, $^{15}N$ $^{31}P$, $^{32}P$, $^{35}S$, $^{67}Ga$, $^{99}mTc$ (Tc-$^{99}$m), $^{111}In$, $^{123}I$, $^{125}I$, $^{169}Yb$, and $^{186}Re$), (b) an enzyme or coenzyme; (c) a molecule which is colored (chromophore), fluorescent, phosphorescent, or chemiluminescent dyes; (d) a molecule which has one or more photo affinity moieties; (e) a molecule which has a ligand moiety with one or more known binding partners (haptens such as biotin, dinitrophenol (DNP), and digoxigenin); (f) latex and magnetic particles; (g) gold, silver, and selenium colloidal particles; (h) metal chelates; and (i) oligonucleotides. A wide variety of detectable moieties can be used, with the choice of label depending on the sensitivity required, stability requirements, and available instrumentation and disposal provisions. All of above can be used as label, and by attaching to the compound, they can be located with different detection method, e.g., for example, using Halo tag.

In certain embodiments, the label is biotin. The biotin moiety allows the compound of Formula (I) or (II) to bind to certain surfaces such as, for example, a bead, glass, or metal surface.

In certain embodiments, the label is a fluorescent moiety. A "fluorescent moiety" or label as used herein refer to a moiety that absorbs light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2', 7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, *Diversa* Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP, green fluorescent protein (GFP), phycoerythrin, hydroxycoumarin, aminocoumarin, methoxycoumarin, cascade blue, pacific blue, pacific orange, Lucifer yellow, NBD, R-Phycoerythrin (PE), PE-Cy5, PE-Cy7, Red 613, PerCP, TruRed, FluorX, fluorescein, fluorescein isothiocyanate (FITC), X-Rhodamine, Lissamine Rhodamine B, Texas red, tetrarhodamine isothiocynate (TRITC), BODIPY-FL, Cy2, Cy3, Cy3B, Cy3.5, Cy5, Cy5.5, Cy7, Allophycocyanin (APC), APC-Cy7, ATT0655, Alexa Fluor 405, Alexa Fluor 568, and Alexa Fluor 647. See also Lavis et al., *ACS Chem. Biol.* (2008) 142-155 disclosing various florescent labels. In certain embodiments, the label is fluorescein isothiocyanate (FITC).

In certain embodiments, $L^1$ is a linking group comprising at least one instance of substituted or unsubstituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene.

In certain embodiments, $L^1$ is a linking group comprising at least one instance of substituted or unsubstituted heteroalkylene, e.g., substituted or unsubstituted hetero$C_{1-6}$alkylene, substituted or unsubstituted hetero$C_{2-6}$alkylene, substituted or unsubstituted hetero$C_{3-6}$alkylene, substituted or unsubstituted hetero$C_{4-6}$alkylene, substituted or unsubstituted hetero$C_{5-6}$alkylene, substituted or unsubstituted hetero$C_{2-5}$alkylene, substituted or unsubstituted hetero$C_{2-4}$alkylene, substituted or unsubstituted hetero$C_{2-3}$alkylene, substituted or unsubstituted hetero$C_1$alkylene, substituted or unsubstituted hetero$C_2$alkylene, substituted or unsubstituted hetero$C_3$alkylene, substituted or unsubstituted hetero$C_4$alkylene, substituted or unsubstituted hetero$C_5$alkylene, or substituted or unsubstituted hetero$C_6$alkylene.

In certain embodiments, the linking group $L^1$ comprises between 2 to 50 atoms linked in a chain, e.g., between 2 to 45, 2 to 40, 2 to 35, 2 to 30, 2 to 25, 2 to 20, 2 to 15, 2 to 10, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 atoms in length.

In certain embodiments, $L^1$ is a linker group comprising a combination of one or more groups of the formula:

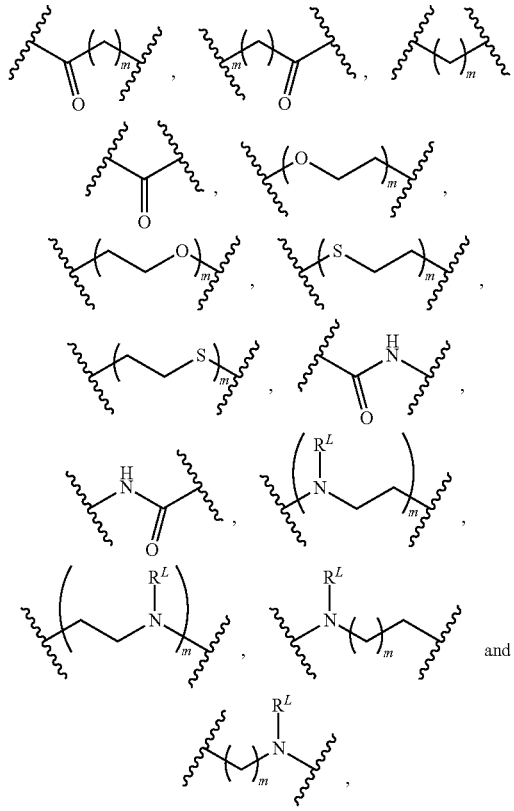

wherein $R^L$ is hydrogen or substituted or unsubstituted alkyl, m is 0 or an integer between 1 to 10, inclusive, e.g., 1, 2, 3, 4, 5, 6, 7, 8, 9, or 10. In certain embodiments, m is 3 or 4.

An exemplary labeled compound is the biotin-labeled compound:

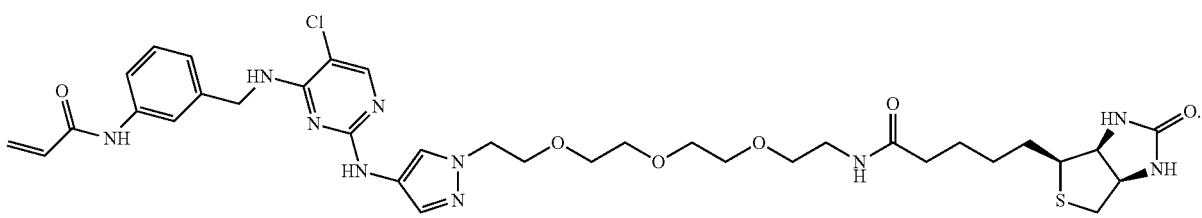 [SMILES: C=CC(=O)Nc1cccc(CNc2nc(Nc3cnn(CCOCCOCCOCCNC(=O)CCCC[C@@H]4SC[C@@H]5NC(=O)N[C@@H]54)c3)ncc2Cl)c1]

Pharmaceutical Compositions and Kits

In certain embodiments, the present invention provides a pharmaceutical composition comprising a compound of Formula (I) or (II) or pharmaceutically acceptable salt thereof and a pharmaceutically acceptable excipient. In certain embodiments, the compound is present in an effective amount, e.g., a therapeutically effective amount or a prophylactically effective amount.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutical compositions described herein can be prepared by any method known in the art of pharmacology. In general, such preparatory methods include the steps of bringing the compound of Formula (I) or (II) or pharmaceutically acceptable salt thereof (the "active ingredient") into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound described herein may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered, by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or atomized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21$^{st}$ ed., Lippincott Williams & Wilkins, 2005.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits described herein. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Treatment, Uses, and, Administration

The present invention also provides methods of using a compound of Formula (I) or (II) or pharmaceutically acceptable salt thereof, e.g., by treating or preventing a condition associated with aberrant activity of a kinase in a subject in need thereof, or by reducing the activity of a kinase (e.g., in vivo or in vitro), comprising administering to the subject a compound of Formula (I) or (II) or pharmaceutically acceptable salt thereof, or a pharmaceutical composition thereof, in an amount sufficient to treat or prevent the condition or reduce the activity of the kinase. Reducing activity of a kinase refers to any undesired abherrant activity, and includes, but is not limited to, over-activity and/or over-expression of the kinase compared to a normal cell.

In certain embodiments, provided is an in vitro method of reducing the activity of a kinase in a tissue, organ, cell, or cell culture, comprising contacting the tissue, organ, cell, or cell culture with a compound of Formula (I) or (II) or pharmaceutically acceptable salt thereof, or a pharmaceutical composition thereof, in an amount sufficient to reduce the activity of the kinase.

In certain embodiments, provided is an in vivo method of reducing the activity of a kinase in a subject in need thereof, comprising administering to the subject a compound of Formula (I) or (II) or pharmaceutically acceptable salt thereof, or a pharmaceutical composition thereof, in an amount sufficient to reduce the activity of the kinase.

In certain embodiments, provided is a method of treating a condition associated with aberrant activity of a kinase in a subject in need thereof, the method comprising administering to the subject a compound of Formula (I) or (II) or pharmaceutically acceptable salt thereof, or a pharmaceutical composition thereof, in an amount sufficient to treat the condition (e.g., a therapeutically effective amount).

In certain embodiments, provided is a method of preventing a condition associated with aberrant activity of a kinase in a subject in need thereof, the method comprising administering to the subject a compound of Formula (I) or (II) or pharmaceutically acceptable salt thereof, or a pharmaceutical composition thereof, in an amount sufficient to prevent the condition (e.g., a prophylactically effective amount).

In certain embodiments, the subject described herein is an animal. In certain embodiments, the subject is a mammal. In certain embodiments, the subject is a human. In certain embodiments, the subject is a non-human animal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the kinase described herein is a protein kinase. In certain embodiments, the protein kinase is tyrosine kinase. In certain embodiments, the tyrosine kinase is a non-receptor tyrosine kinase. In certain embodiments, the non-receptor tyrosine kinase is a Janus kinase (JAK). In certain embodiments, the Janus kinase is Janus kinase 1 (JAK1). In certain embodiments, the Janus kinase is Janus kinase 2 (JAK2). In certain embodiments, the Janus kinase is Janus kinase 3 (JAK3). In certain embodiments, the activity of a kinase (e.g., JAK3) is selectively reduced by a compound described herein, compared to a different kinase (e.g., a kinase other than JAK3, e.g., JAK1, JAK2, or TYK2). In certain embodiments, the activity of a kinase (e.g., JAK3) is selectively reduced by at least 2-fold, at least 5-fold, at least 10-fold, at least 20-fold, at least 30-fold, at least 40-fold, at least 50-fold, at least 60-fold, at least 70-fold, at least 80-fold, at least 90-fold, or at least 100-fold over the activity of JAK1 and/or JAK2 by a compound of Formula (I) or (II) as described herein. In certain embodiments, the compound of Formula (I) or (II) inhibits JAK3 up to about 100-fold selectively over JAK1 and/or JAK2, which do not possess an equivalently placed cysteine residue. In certain embodiments, the tyrosine kinase is a receptor tyrosine kinase (RTK). In certain embodiments, the receptor tyrosine kinase is an epidermal growth factor receptor (EGFR) tyrosine kinase.

In certain embodiments, the compound reduces kinase activity by covalently binding to a kinase (e.g., JAK3). In certain embodiments, a compound described herein covalently binds to Cys909 of JAK3. The compounds described herein may alternatively reduce kinase activity by binding to a kinase (e.g., JAK3) non-covalently (e.g., through electrostatic interactions, Van der Waals interactions, n-interactions, and/or hydrophobic interactions).

Exemplary conditions associated with aberrant activity of a kinase includes, but are not limited to, proliferative diseases, inflammatory disorders, autoimmune disorders, painful conditions, and viral infections.

In certain embodiments, the condition associated with aberrant activity of a kinase is a proliferative disease. Exemplary proliferative diseases include, but are not limited to, tumors, begnin neoplasms, pre-malignant neoplasms (carcinoma in situ), and malignanat neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematological malignancy (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described herein; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva). In certain embodiments, the cancer is a hematological malignancy. In certain embodiments, the cancer is lymphoma. In certain embodiments, the cancer is leukemia.

In certain embodiments, the condition associated with aberrant activity of a kinase is an inflammatory disorder. The term "inflammatory disorder" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is inflammation associated with a proliferative disease, e.g., inflammation associated with cancer.

Janus kinases (JAKs) play multiple roles downstream of cytokine signaling in both immune and non-immune cells. Autoimmunity is driven by an aberrant adaptive immune response to self-antigens and JAK-STAT (signal transducer and activator of transcription) signaling is known to play a key role in this process. Thus, JAK inhibitors may have considerable potential for the development of drugs to treat autoimmunity. JAK3 is an especially attractive target as, unlike other JAKs, its expression is restricted to the immune system. Thus, in certain embodiments, the condition associated with aberrant activity of a kinase is an autoimmune disorder. Exemplary autoimmune disorders include, but are not limited to, arthritis (e.g., rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as nonulcerative dyspepsia (NUD) and non-cardiac chest pain (NCCP, including costo-chondritis)). In certain embodiments, the autoimmune disorder is rheumatoid arthritis. In certain embodiments, the autoimmune disorder is psoriasis.

In certain embodiments, the autoimmune disorder is associated with inflammation or a painful condition.

In certain embodiments, the condition associated with aberrant activity of a kinase is a painful condition. A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition. In certain embodiments, the painful condition is inflammatory pain. In certain embodiments, the painful condition (e.g., inflammatory pain) is associated with an inflammatory disorder and/or an autoimmune disorder.

In certain embodiments, the condition associated with aberrant activity of a kinase is a viral infection. In certain embodiments, the viral infection is Dengue fever, Dengue hemorrhagic fever (DHF), Dengue shock syndrome (DSS), hepatitis A, hepatitis B, hepatitis C, hepatitis D, hepatitis E, hepatitis F, Coxsackie A virus infection, Coxsackie B virus infection, fulminant viral hepatitis, severe acute respiratory syndrome (SARS), viral myocarditis, influenza virus infection (e.g., influenza A virus infection (e.g., an H1N1, H1N2, H2N1, H2N2, H2N3, H3N1, H3N2, H3N8, H5N1, H7N7, H1N2, H9N2, H7N2, H7N3, H7N9, H5N2, H10N7 virus infection), influenza B virus infection, influenza C virus infection), parainfluenza virus infection, an RS virus (RSV) infection (e.g., RSV bronchiolitis, RSV pneumonia, especially an infant and childhood RSV infection and RSV pneumonia in the patients with cardiopulmonary disorders), measles virus infection, vesicular stomatitis virus infection, rabies virus infection, Ebola virus infection, Japanese encephalitis, Junin virus infection, human cytomegalovirus infection, herpes virus infection (e.g., iltovirus infection, mardivirus infection, simplexvirus infection (herpes simplex virus 1 infection), varicellovirus infection, cytomegalovirus infection, muromegalovirus infection, proboscivirus infection, roseolovirus infection, lymphocryptovirus infection, macavirus infection, percavirus infection, rhadinovirus infection), poliovirus infection, Marburg virus infection, Lassa fever virus infection, Venezuelan equine encephalitis, Rift Valley Fever virus infection, Korean hemorrhagic fever virus infection, Crimean-Congo hemorrhagic fever virus infection, HIV infection, acquired immunodeficiency syndrome (AIDS), encephalitis, Saint Louise encephalitis, Kyasanur Forest disease, Murray Valley encephalitis, tick-borne encephalitis, West Nile encephalitis, yellow fever, or a viral infection in subjects with immune disorders. In certain embodiments, the viral infection is an influenza virus infection. In certain embodiments, the viral infection is an influenza A virus infection. In certain embodiments, the viral infection is human flu (e.g., H1N1, H2N2, H3N2, H5N1, H7N7, H1N2, H9N2, H7N2, H7N3, or H10N7 virus infection). In certain embodiments, the viral infection is bird flu (e.g., H5N1 or H7N9 virus infection). In certain embodiments, the viral infection is swine influenza (e.g., H1N1, H1N2, H2N1, H3N1, H3N2, or H2N3 virus infection, or influenza C virus infection). In certain embodiments, the viral infection is equine influenza (e.g., H7N7 or H3N8 virus infection). In certain embodiments, the viral infection is canine influenza (e.g., H3N8 virus infection). In certain embodiments, the viral infection is an influenza B virus infection. In certain embodiments, the viral infection is an influenza C virus infection. In certain embodiments, the viral infection is HIV infection or AIDS. In certain embodiments, the viral infection is hepatitis C.

In still another aspect, the present invention provides methods of reducing cytokine signaling in a subject in need thereof, the method comprising administering to the subject a compound of Formula (I) or (II) or pharmaceutically acceptable salt thereof, or a pharmaceutical composition thereof, in an amount sufficient to reduce the cytokine signaling (e.g., a therapeutically effective amount). In certain embodiments, the cytokine is a tumor necrosis factor (TNF), colony stimulating factor (CSF), interferon (INF), interleukin (IL-1, IL-2, IL-3, IL-4, IL-5, IL-6, IL-7, IL-8, IL-9, IL-10, IL-11, IL-12, IL-13, IL-14, or IL-15), transforming growth factor (TGF), oncostatin M (OSM), leukemia inhibiting factor (LIF), platelet activating factor (PAF), or other soluble immunoregulatory peptide that mediates host defense responses, cell regulation, or cell differentiation. In certain embodiments, the cytokine is an interleukin (e.g., IL-4).

Compounds of Formula (I) or (II), or pharmaceutically acceptable salts thereof may be formulated in dosage unit form for ease of administration and uniformity of dosage. It will be understood, however, that the total daily usage of the compositions comprising a compound described herein will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-inflammatory agent, anti-cancer agent, etc.), and/or it may achieve different effects (e.g., control of adverse side-effects, e.g., emesis controlled by an anti-emetic).

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the compound described herein with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Additional therapeutically active agents include, but are not limited to, small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In certain embodiments, the additional therapeutically agent is a cancer agent (e.g., a biotherapeutic or chemotherapeutic cancer agent). In other embodiments, the additional therapeutically active agent is an anti-inflammatory agent.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Synthesis of the Compounds

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

General Methods and Materials

All reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager and Waters 2767 Sample Manager) using SunFire™ $C_{18}$ column (4.6×50 mm, 5 µm particle size): solvent gradient=100% A at 0 min, 1% A at 5 min; solvent A=0.035% TFA in Water; solvent B=0.035% TFA in MeOH; flow rate: 2.5 mL/min. Purification of reaction products was carried out by flash chromatography using CombiFlash®Rf with Teledyne Isco Redisep®Rf High Performance Gold or Silicycle SiliaSep™ High Performance columns (4 g, 12 g, 24 g, 40 g, or 80 g) and Waters LCMS system using SunFire™ Prep C$_{18}$ column (19×50 mm, 5 μm particle size): solvent gradient=80% A at 0 min, 10% A at 8 min; solvent A=0.035% TFA in Water; solvent B=0.035% TFA in MeOH; flow rate: 25 mL/min. The purity of all compounds was over 95% and was analyzed with Waters LCMS system. $^{1H\ NMR}$ and $^{13}$C NMR spectra were obtained using a Varian INOVA-600 (600 MHz for $^1$H, and 125 MHz for $^{13}$C) spectrometer. Chemical shifts are reported relative to chloroform (δ=7.24) for $^{1H\ NMR}$ or dimethyl sulfoxide (δ=2.50) for $^{1H\ NMR}$ and dimethyl sulfoxide (δ=39.51) for $^{13}$C NMR. Data are reported as (br=broad, s=singlet, d=doublet, t=triplet, q=quartet, m=multiplet).

Example 1. Preparation of N-(3-(((5-chloro-2-((2-methoxy-4-(4-methylpiperazin-1-yl)phenyl)amino)pyrimidin-4-yl)amino)methyl)phenyl)acrylamide (Compound 2)

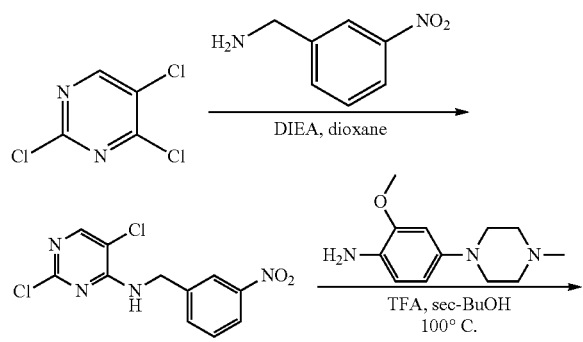

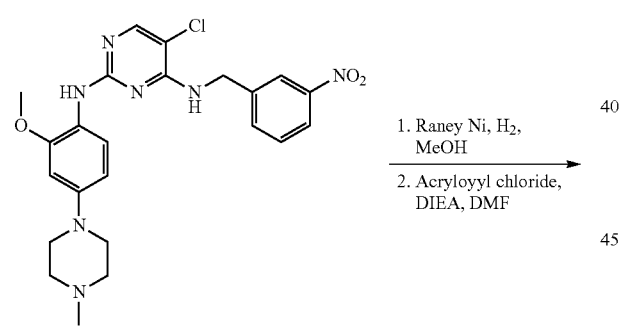

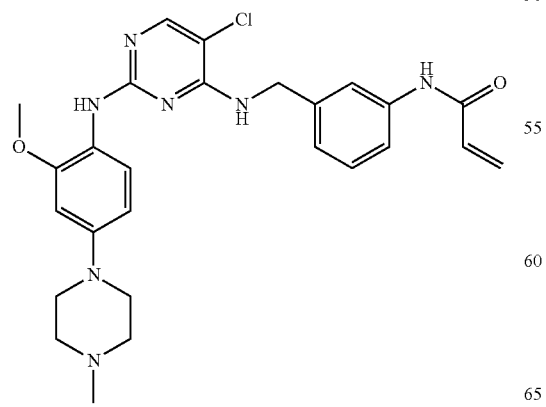

Step 1:
2,5-Dichloro-N-(3-nitrobenzyl)pyrimidin-4-amine

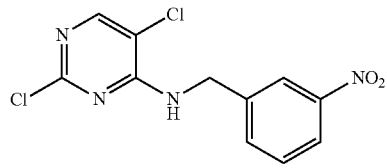 [SMILES: O=[N+]([O-])c1cccc(CNc2nc(Cl)ncc2Cl)c1]

2,4,5-Trichloropyrimidine (112 μL, 1.0 mmol), (3-nitrophenyl)methanamine hydrochloride salt (227 mg, 1.2 mmol), and N,N-diisopropylethylamine (DIEA, 530 μL, 3.0 mmol) were combined in dioxane (5 mL) and stirred overnight. The mixture was then diluted with ethyl acetate and washed with water and brine, dried over Na$_2$SO$_4$, filtered and concentrated. The crude product was purified by column chromatography (hexane:ethyl acetate=1:1) to yield 270 mg (80%) of the title product as a white solid. MS (ESI) m/z 299 (M+H)$^+$.

Step 2: 5-Chloro-N$^2$-(2-methoxy-4-(4-methylpiperazin-1-yl)phenyl)-N$^4$-(3-nitrobenzyl)pyrimidine-2,4-diamine 2,5-Dichloro-N-(3-nitrobenzyl)pyrimidin-4-amine (150 mg, 0.5 mmol), 2-methoxy-4-(4-methylpiperazin-1-yl)aniline (166 mg, 0.75 mmol), and trifluoroacetic acid (57 μL, 0.75 mmol) was combined in sec-butanol (5 mL) and stirred overnight at 100° C. The mixture was then concentrated and purified by column chromatography (dichloromethane:methanol=10:1) to yield 184 mg (76%) of the title product as a pale-yellow solid. MS (ESI) m/z 484 (M+H)$^+$.

Step 3: N-(3-(((5-chloro-2-((2-methoxy-4-(4-methylpiperazin-1-yl)phenyl)amino)pyrimidin-4-yl)amino)methyl)phenyl)acrylamide

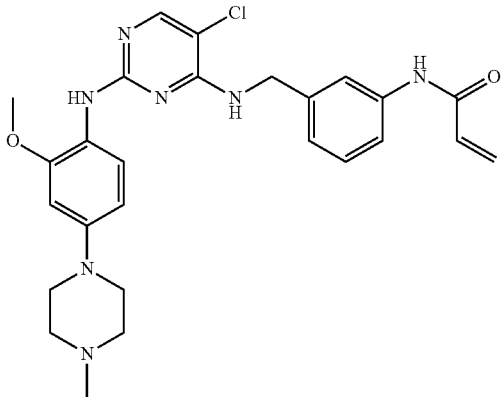 [SMILES: C=CC(=O)Nc1cccc(CNc2nc(Nc3ccc(N4CCN(C)CC4)cc3OC)ncc2Cl)c1]

To 5-chloro-N²-(2-methoxy-4-(4-methylpiperazin-1-yl)phenyl)-N⁴-(3-nitrobenzyl)pyrimidine-2,4-diamine (97 mg, 0.2 mmol) in MeOH (20 mL) was added 1 mL Raney nickel suspension in MeOH. The reaction mixture was stirred for 3 hr under 1 atm of hydrogen. The mixture was then filtered with Celite, and the filtrate was concentrated and dried under vacuum to give a crude product as a white solid. To the obtained white solid in DMF (2 mL) was added N,N-diisopropylethylamine (53 μL, 0.3 mmol), the stirred mixture was then cooled to −60° C., and acryloyl chloride (17.8 μL, 0.22 mmol) was added dropwise. The reaction mixture was stirred at −60° C. for 10 min, allowed to recover to RT (room temperature) gradually in 30 min, and purified by reverse phase HPLC to give 88 mg (TFA salt, 71% for 2 steps) of title compound as a white solid. ¹H NMR (600 MHz, DMSO-d₆) δ 10.07 (s, 1H), 7.82 (s, 1H), 7.73 (m, 1H), 7.59 (s, 1H), 7.52 (d, J=8.4 Hz, 1H), 7.47 (d, J=7.8 Hz, 1H), 7.29 (s, 1H), 7.18 (dd, J=7.8, 7.8 Hz, 1H), 6.90 (d, J=7.2 Hz, 1H), 6.48 (s, 1H), 6.44 (dd, J=16.8, 10.2 Hz, 1H), 6.31 (d, J=8.4 Hz, 1H), 6.25 (d, J=16.8 Hz, 1H), 5.75 (d, J=10.2 Hz, 1H), 4.56 (d, J=6.0 Hz, 2H), 3.78 (s, 3H), 3.04 (m, 4H), 3.01 (m, 4H), 2.22 (s, 3H). MS (ESI) m/z 508 (M+H)⁺.

tert-butyl 4-(4-((5-chloro-4-((3-nitrobenzyl)amino)pyrimidin-2-yl)amino)-3-methoxyphenyl)piperazine-1-carboxylate

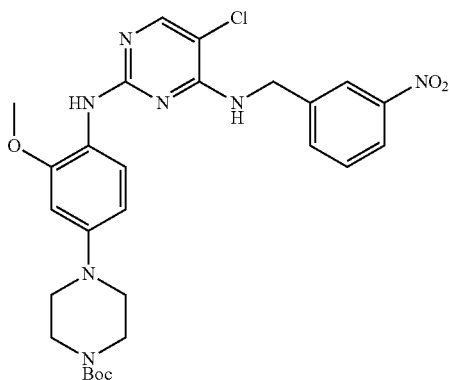 [SMILES: COc1cc(N2CCN(C(=O)OC(C)(C)C)CC2)ccc1Nc1ncc(Cl)c(NCc2cccc([N+](=O)[O-])c2)n1]

2,5-Dichloro-N-(3-nitrobenzyl)pyrimidin-4-amine (150 mg, 0.5 mmol), tert-butyl 4-(4-amino-3-methoxyphenyl)piperazine-1-carboxylate (230 mg, 0.75 mmol), and trifluoroacetic acid (57 μL, 0.75 mmol) was combined in sec-butanol (5 mL) and stirred overnight at 100° C. The mixture was then concentrated and purified by column chromatography (dichloromethane:methanol=10:1) to yield 205 mg (72%) of the title product as a pale-yellow solid. MS (ESI) m/z 570 (M+H)⁺.

Analytical Data of Additional Exemplary Compounds

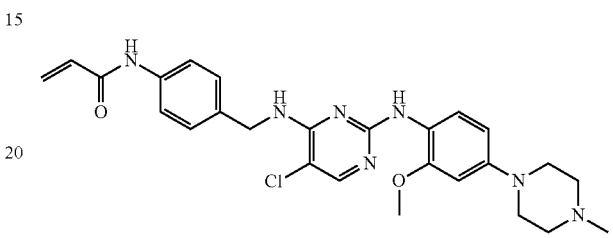

¹H NMR (600 MHz, TFA salt, DMSO-d₆) δ 10.14 (s, 1H), 9.93 (br, 1H), 8.60 (br, 1H), 8.03 (s, 1H), 7.59 (s, 1H), 7.57 (s, 1H), 7.49 (br, 1H), 7.18 (d, J=7.2 Hz, 1H), 6.70 (s, 1H), 6.50 (d, J=7.8 Hz, 1H), 6.42 (dd, J=16.8, 10.2 Hz, 1H), 6.23 (d, J=16.8 Hz, 1H), 5.73 (d, J=10.2 Hz, 1H), 4.48 (d, J=4.2 Hz, 2H), 3.85 (m, 2H), 3.81 (s, 3H), 3.52 (m, 2H), 3.15 (m, 2H), 2.95 (m, 2H), 2.86 (s, 3H). MS (ESI) m/z 508 (M+H)⁺.

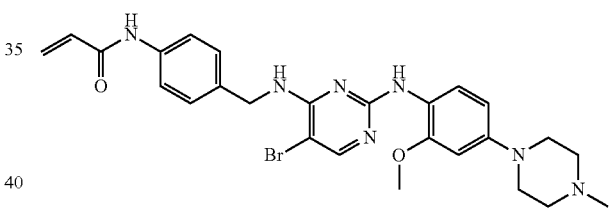

¹H NMR (400 MHz, TFA salt, DMSO-d₆) δ 10.07 (s, 1H), 9.89 (br, 1H), 8.46 (br, 1H), 8.03 (s, 1H), 7.52 (s, 1H), 7.50 (s, 1H), 7.40 (d, J=8.0 Hz, 1H), 7.10 (d, J=8.0 Hz, 1H), 6.64 (s, 1H), 6.43 (d, J=8.4 Hz, 1H), 6.36 (dd, J=16.8, 10.4 Hz, 1H), 6.19 (d, J=16.8 Hz, 1H), 5.67 (d, J=10.4 Hz, 1H), 4.41 (d, J=6.0 Hz, 2H), 3.80 (m, 2H), 3.73 (s, 3H), 3.36 (m, 2H), 3.09 (m, 2H), 2.89 (m, 2H), 2.80 (s, 3H). MS (ESI) m/z 552 (M+H)⁺.

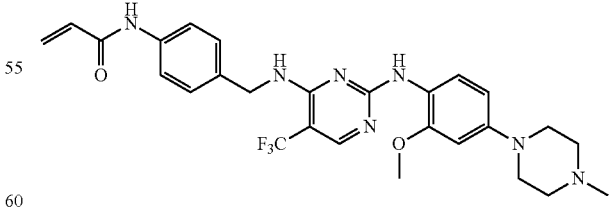

¹H NMR (400 MHz, DMSO-d₆) δ 10.06 (s, 1H), 8.09 (s, 1H), 8.00 (s, 1H), 7.59 (m, 1H), 7.55 (d, J=8.4 Hz, 1H), 7.41 (d, J=9.2 Hz, 1H), 7.13 (m, 1H), 6.60 (s, 1H), 6.41 (dd, J=16.8, 10.4 Hz, 1H), 6.23 (d, J=16.8 Hz, 1H), 5.73 (d, J=10.4 Hz, 1H), 4.46 (m, 2H), 3.76 (s, 3H), 3.12 (m, 4H), 2.45 (m, 4H), 2.22 (s, 3H). MS (ESI) m/z 542 (M+H)⁺.

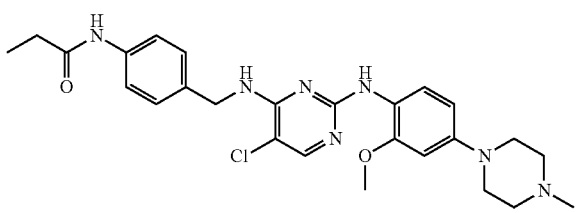 [SMILES: CCC(=O)Nc1ccc(CNc2nc(Nc3ccc(N4CCN(C)CC4)cc3OC)ncc2Cl)cc1]

¹H NMR (600 MHz, TFA salt, DMSO-d₆) δ 9.94 (br, 1H), 9.90 (s, 1H), 8.74 (br, 1H), 8.11 (s, 1H), 7.57 (s, 1H), 7.56 (s, 1H), 7.20 (m, 2H), 6.78 (s, 1H), 6.57 (d, J=8.4 Hz, 1H), 4.54 (m, 2H), 3.93 (m, 2H), 3.86 (s, 3H), 3.60 (m, 2H), 3.23 (m, 2H), 3.02 (m, 2H), 2.94 (s, 3H), 2.35 (q, J=7.2 Hz, 2H), 1.12 (t, J=7.2 Hz, 2H). MS (ESI) m/z 510 (M+H)⁺.

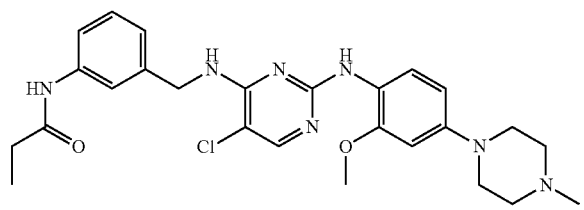 [SMILES: CCC(=O)Nc1cccc(CNc2nc(Nc3ccc(N4CCN(C)CC4)cc3OC)ncc2Cl)c1]

¹H NMR (600 MHz, TFA salt, DMSO-d₆) δ 9.91 (br, 1H), 9.89 (s, 1H), 8.76 (br, 1H), 8.09 (s, 1H), 7.52 (s, 1H), 7.48 (m, 1H), 7.45 (d, J=7.8 Hz, 1H), 7.22 (dd, J=7.8, 7.8 Hz, 1H), 6.88 (d, J=8.4 Hz, 1H), 6.69 (s, 1H), 6.47 (d, J=8.4 Hz, 1H), 4.55 (m, 2H), 3.85 (m, 2H), 3.80 (s, 3H), 3.53 (m, 2H), 3.15 (m, 2H), 2.94 (m, 2H), 2.88 (s, 3H), 2.30 (q, J=7.2 Hz, 2H), 1.07 (t, J=7.2 Hz, 2H). MS (ESI) m/z 510 (M+H)⁺.

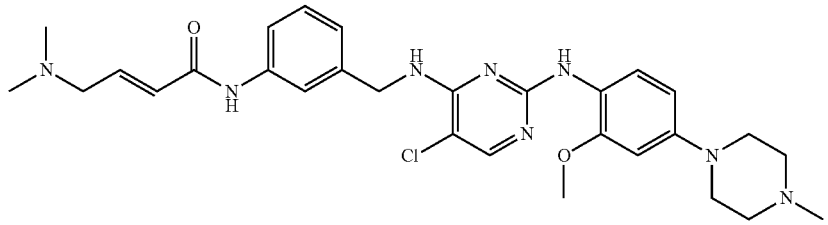

¹H NMR (600 MHz, DMSO-d₆) δ 10.06 (s, 1H), 7.90 (s, 1H), 7.80 (s, 1H), 7.67 (s, 1H), 7.59 (m, 1H), 7.52 (s, 1H), 7.36 (s, 1H), 7.24 (m, 1H), 6.95 (m, 1H), 6.72 (m, 1H), 6.55 (s, 1H), 6.31 (m, 1H), 6.27 (m, 1H), 4.55 (s, 2H), 3.78 (s, 3H), 3.35 (m, 2H), 3.06 (s, 6H), 2.45 (m, 4H), 2.23 (m, 4H), 2.19 (s, 3H). MS (ESI) m/z 565 (M+H)⁺.

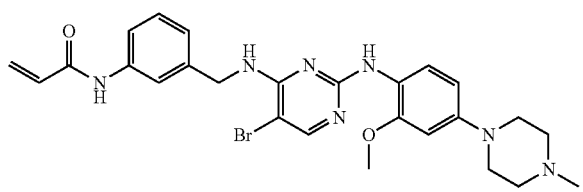

¹H NMR (600 MHz, TFA salt, DMSO-d₆) δ 10.18 (s, 1H), 9.88 (br, 1H), 8.49 (br, 1H), 8.13 (s, 1H), 7.67 (s, 1H), 7.53 (d, J=8.0 Hz, 1H), 7.47 (m, 1H), 7.27 (dd, J=7.8, 7.8 Hz, 1H), 6.92 (m, 1H), 6.68 (s, 1H), 6.45 (dd, J=16.8, 10.4 Hz, 1H), 6.44 (m, 1H), 6.26 (d, J=16.8 Hz, 1H), 5.77 (d, J=10.4 Hz, 1H), 4.56 (d, J=5.4 Hz, 2H), 3.82 (m, 2H), 3.79 (s, 3H), 3.52 (m, 2H), 3.15 (m, 2H), 2.92 (m, 2H), 2.87 (s, 3H). MS (ESI) m/z 552 (M+H)⁺.

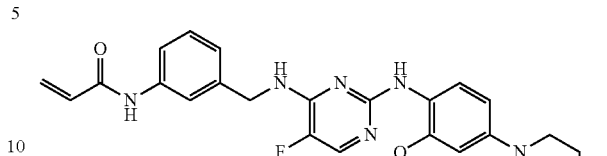

¹H NMR (600 MHz, TFA salt, DMSO-d₆) δ 10.19 (s, 1H), 9.92 (br, 1H), 8.04 (br, 1H), 7.70 (s, 1H), 7.52 (d, J=8.4 Hz, 1H), 7.46 (m, 1H), 7.28 (dd, J=7.8, 7.8 Hz, 1H), 6.97 (d, J=7.2 Hz, 1H), 6.69 (s, 1H), 6.47 (m, 1H), 6.42 (dd, J=16.8, 10.2 Hz, 1H), 6.25 (d, J=16.8 Hz, 1H), 5.76 (d, J=10.2 Hz, 1H), 4.56 (d, J=5.4 Hz, 2H), 3.83 (m, 2H), 3.79 (s, 3H), 3.51 (m, 2H), 3.13 (m, 2H), 2.93 (m, 2H), 2.86 (s, 3H). MS (ESI) m/z 492 (M+H)⁺.

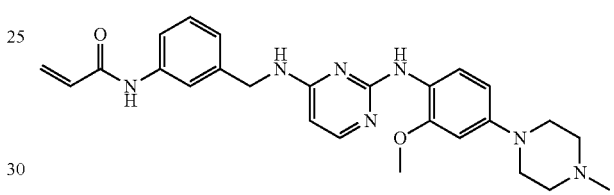

¹H NMR (600 MHz, DMSO-d₆) δ 10.08 (s, 1H), 7.82+D14 br, 1H), 7.69 (m, 1H), 7.59 (br, 1H), 7.49 (m, 1H), 7.20 (dd, J=7.8, 7.8 Hz, 1H), 7.10 (s, 1H), 6.95 (d, J=7.8 Hz, 1H), 6.51 (s, 1H), 6.47 (m, 1H), 6.36 (dd, J=16.8, 10.4 Hz, 1H), 6.29 (m, 1H), 6.18 (d, J=16.8 Hz, 1H), 5.91 (br, 1H), 5.67 (d, J=10.2 Hz, 1H), 4.42 (m, 2H), 3.83 (m, 2H), 3.74 (s, 3H), 2.99 (m, 4H), 2.41 (m, 4H), 2.18 (s, 3H). MS (ESI) m/z 474 (M+H)⁺.

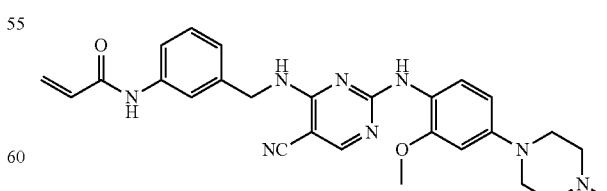

¹H NMR (600 MHz, TFA salt, DMSO) δ 10.15 (s, 1H), 9.80 (br, 1H), 8.42 (m, 1H), 8.32 (m, 1H), 8.20 (br, 1H), 7.61 (s, 1H), 7.52 (d, J=7.8 Hz, 1H), 7.47 (d, J=8.4 Hz, 1H), 7.22 (dd, J=8.4, 7.8 Hz, 1H), 6.84 (d, J=7.8 Hz, 1H), 6.68 (s, 1H), 6.45 (m, 1H), 6.44 (dd, J=16.8, 10.8 Hz, 1H), 6.25 (d, J=16.8 Hz, 1H), 5.76 (d, J=10.8 Hz, 1H), 4.35 (m, 2H), 3.85 (m, 2H), 3.78 (s, 3H), 3.53 (m, 2H), 3.16 (m, 2H), 2.93 (m, 2H), 2.88 (s, 3H). MS (ESI) m/z 499 (M+H)+.

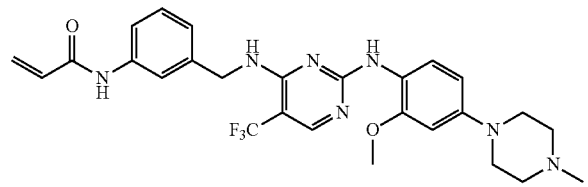 [SMILES: C=CC(=O)Nc1cccc(CNc2nc(Nc3ccc(N4CCN(C)CC4)cc3OC)ncc2Br)c1]

¹H NMR (600 MHz, TFA salt, DMSO-d₆) δ 10.17 (s, 1H), 9.82 (br, 1H), 8.47 (br, 1H), 8.24 (br, 1H), 7.71 (s, 1H), 7.49 (d, J=8.4 Hz, 1H), 7.46 (d, J=8.4 Hz, 1H), 7.25 (dd, J=8.4, 7.8 Hz, 1H), 6.88 (br, 1H), 6.67 (s, 1H), 6.45 (dd, J=16.8, 10.2 Hz, 1H), 6.42 (m, 1H), 6.26 (d, J=16.8 Hz, 1H), 5.77 (d, J=10.2 Hz, 1H), 4.58 (m, 2H), 3.82 (m, 2H), 3.79 (s, 3H), 3.52 (m, 2H), 3.15 (m, 2H), 2.92 (m, 2H), 2.88 (s, 3H). MS (ESI) m/z 542 (M+H)⁺.

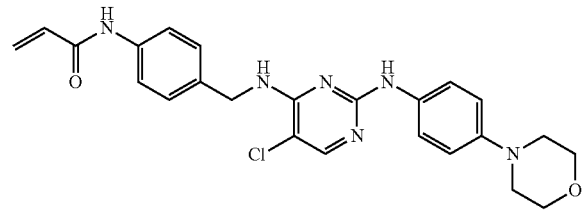 [SMILES: C=CC(=O)Nc1ccc(CNc2nc(Nc3ccc(N4CCOCC4)cc3)ncc2Cl)cc1]

¹H NMR (600 MHz, TFA salt, DMSO-d₆) δ 10.12 (s, 1H), 9.55 (br, 1H), 8.48 (br, 1H), 8.02 (s, 1H), 7.61 (d, J=8.4 Hz, 2H), 7.34 (d, J=7.8 Hz, 2H), 7.34 (d, J=8.4 Hz, 2H), 6.88 (d, J=7.8 Hz, 2H), 6.42 (dd, J=16.8, 10.2 Hz, 1H), 6.24 (d, J=16.8 Hz, 1H), 5.74 (d, J=10.2 Hz, 1H), 4.55 (d, J=6.0 Hz, 2H), 3.74 (m, 4H), 3.07 (m, 4H). MS (ESI) m/z 465 (M+H)⁺.

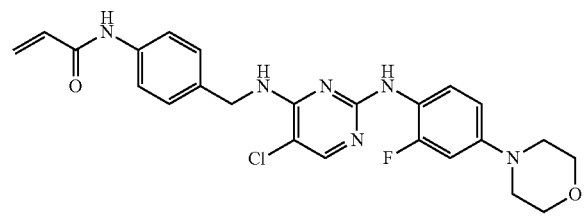 [SMILES: C=CC(=O)Nc1ccc(CNc2nc(Nc3ccc(N4CCOCC4)cc3F)ncc2Cl)cc1]

¹H NMR (600 MHz, TFA salt, DMSO-d₆) δ 10.10 (s, 1H), 9.50 (br, 1H), 8.22 (br, 1H), 8.03 (s, 1H), 7.60 (d, J=8.4 Hz, 2H), 7.52 (d, J=14.4 Hz, 1H), 7.26 (d, J=8.4 Hz, 2H), 7.21 (d, J=9.0 Hz, 1H), 6.91 (dd, J=10.4, 9.0 Hz, 1H), 6.41 (dd, J=16.8, 10.2 Hz, 1H), 6.23 (d, J=16.8 Hz, 1H), 5.73 (d, J=10.2 Hz, 1H), 4.58 (d, J=6.0 Hz, 2H), 3.73 (m, 4H), 2.93 (m, 4H). MS (ESI) nm/z 483 (M+H)⁺.

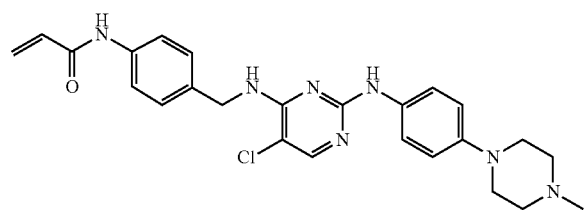 [SMILES: C=CC(=O)Nc1ccc(CNc2nc(Nc3ccc(N4CCN(C)CC4)cc3)ncc2Cl)cc1]

¹H NMR (600 MHz, TFA salt, DMSO-d₆) δ 10.13 (s, 1H), 9.74 (br, 1H), 9.46 (br, 1H), 8.26 (br, 1H), 8.02 (s, 1H), 7.51 (d, J=9.0 Hz, 2H), 7.40 (d, J=8.4 Hz, 2H), 7.25 (d, J=9.0 Hz, 2H), 6.89 (d, J=9.0 Hz, 2H), 6.42 (dd, J=16.8, 10.2 Hz, 1H), 6.24 (d, J=16.8 Hz, 1H), 5.74 (d, J=10.2 Hz, 1H), 4.56 (d, J=6.0 Hz, 2H), 3.74 (m, 2H), 3.52 (m, 2H), 3.16 (m, 2H), 2.89 (m, 2H), 2.87 (s, 3H). MS (ESI) m/z 478 (M+H)⁺.

¹H NMR (600 MHz, TFA salt, DMSO-d₆) δ 10.12 (s, 1H), 9.71 (br, 1H), 9.43 (br, 1H), 8.02 (s, 1H), 8.01 (br, 1H), 7.64 (d, J=15.0 Hz, 1H), 7.60 (d, J=8.4 Hz, 2H), 7.29 (d, J=8.4 Hz, 1H), 7.26 (d, J=9.0, 8.4 Hz, 1H), 6.98 (dd, J=9.0 Hz, 2H), 6.42 (dd, J=16.8, 10.2 Hz, 1H), 6.23 (d, J=16.8 Hz, 1H), 5.73 (d, J=10.2 Hz, 1H), 4.59 (d, J=6.0 Hz, 2H), 3.50 (m, 2H), 3.39 (m, 2H), 3.22 (m, 2H), 2.95 (m, 2H), 2.87 (s, 3H). MS (ESI) m/z 496 (M+H)⁺.

¹H NMR (600 MHz, TFA salt, DMSO-d6) δ 10.21 (s, 1H), 9.34 (br, 1H), 8.94 (s, 1H), 7.73 (s, 1H), 7.70 (m, 1H), 7.59 (s, 1H), 7.50 (d, J=7.8 Hz, 1H), 7.34 (m, 1H), 7.28 (dd, J=7.8, 7.8 Hz, 1H), 6.95 (m, 1H), 6.71 (d, J=7.8 Hz, 1H), 6.47 (m, 1H), 6.46 (dd, J=16.8, 10.2 Hz, 1H), 6.25 (d, J=16.8 Hz, 1H), 5.77 (d, J=10.2 Hz, 1H), 4.61 (br, 2H), 3.87 (m, 2H), 3.80 (s, 3H), 3.52 (m, 2H), 3.15 (m, 2H), 2.96 (m, 2H), 2.88 (s, 3H), 2.05 (s, 3H). MS (ESI) m/z 488 (M+H)+.

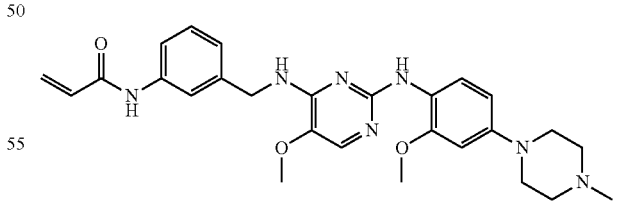

¹H NMR (600 MHz, TFA salt, DMSO-d₆) δ 10.20 (s, 1H), 10.02 (br, 1H), 9.32 (br, 1H), 9.22 (br, 1H), 7.67 (s, 1H), 7.52 (s, 1H), 7.51 (s, 1H), 7.27 (dd, J=7.8, 7.8 Hz, 1H), 6.92 (d, J=7.8 Hz, 1H), 6.71 (s, 1H), 6.49 (d, J=8.4 Hz, 1H), 6.44 (dd, J=16.8, 10.4 Hz, 1H), 6.25 (d, J=16.8 Hz, 1H), 5.77 (d, J=10.4 Hz, 1H), 4.56 (d, J=6.0 Hz, 2H), 3.87 (m, 2H), 3.84 (s, 3H), 3.80 (s, 3H), 3.73 (s, 3H), 3.53 (m, 2H), 3.15 (m, 2H), 2.95 (m, 2H), 2.88 (s, 3H). MS (ESI) m/z 504 (M+H)⁺.

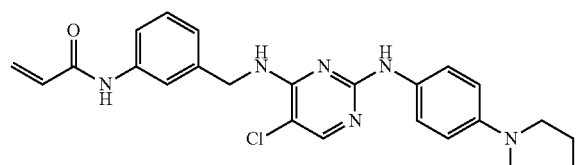

¹H NMR (600 MHz, DMSO-d₆) δ 10.17 (s, 1H), 8.93 (s, 1H), 7.92 (s, 1H), 7.79 (m, 1H), 7.72 (s, 1H), 7.53 (d, J=8.4 Hz, 1H), 7.34 (d, J=8.4 Hz, 2H), 7.28 (dd, J=8.4, 7.8 Hz, 1H), 7.01 (d, J=7.8 Hz, 1H), 6.73 d, J=8.4 Hz, 1H), 6.45 (dd, J=16.8, 10.2 Hz, 1H), 6.26 (d, J=16.8 Hz, 1H), 5.76 (d, J=10.2 Hz, 1H), 4.59 (d, J=6.0 Hz, 2H), 3.72 (t, J=4.8 Hz, 4H), 3.33 (s, 3H), 2.96 (t, J=4.8 Hz, 4H). MS (ESI) m/z 465 (M+H)⁺.

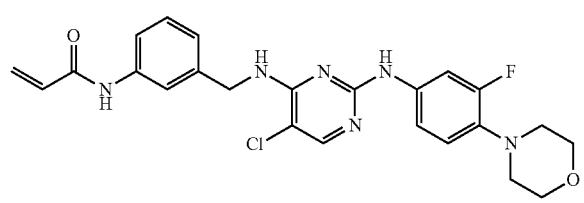 [SMILES: C=CC(=O)Nc1cccc(CNc2nc(Nc3ccc(N4CCOCC4)c(F)c3)ncc2Cl)c1]

¹H NMR (600 MHz, TFA salt, DMSO-d₆) δ 10.14 (s, 1H), 9.45 (br, 1H), 8.22 (br, 1H), 8.04 (s, 1H), 7.66 (s, 1H), 7.54 (d, J=7.8 Hz, 1H), 7.39 (d, J=15.6 Hz, 1H), 7.27 (dd, J=8.4, 7.8 Hz, 1H), 7.22 (d, J=8.4 Hz, 1H), 7.00 (d, J=7.8 Hz, 1H), 6.85 (dd, J=8.4, 8.4 Hz, 1H), 6.43 (dd, J=16.8, 10.4 Hz, 1H), 6.25 (d, J=16.8 Hz, 1H), 5.75 (d, J=10.4 Hz, 1H), 4.62 (d, J=5.4 Hz, 2H), 3.70 (t, J=4.8 Hz, 4H), 2.89 (t, J=4.8 Hz, 4H). MS (ESI) m/z 483 (M+H)⁺.

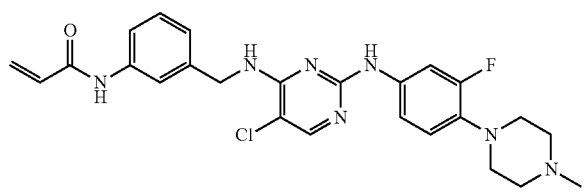 [SMILES: C=CC(=O)Nc1cccc(CNc2nc(Nc3ccc(N4CCN(C)CC4)c(F)c3)ncc2Cl)c1]

¹H NMR (600 MHz, TFA salt, DMSO-d₆) δ 10.14 (s, 1H), 9.75 (br, 1H), 9.39 (br, 1H), 8.02 (s, 1H), 8.01 (br, 1H), 7.62 (s, 1H), 7.56 (d, J=8.4 Hz, 1H), 7.52 (d, J=15.0 Hz, 1H), 7.27 (m, 2H), 7.02 (d, J=8.4 Hz, 1H), 6.93 (dd, J=9.6, 9.6 Hz, 1H), 6.43 (dd, J=16.8, 10.4 Hz, 1H), 6.24 (d, J=16.8 Hz, 1H), 5.74 (d, J=10.4 Hz, 1H), 4.63 (d, J=5.4 Hz, 2H), 3.48 (m, 2H), 3.36 (m, 2H), 3.19 (m, 2H), 2.93 (m, 2H), 2.86 (s, 3H). MS (ESI) m/z 496 (M+H)⁺.

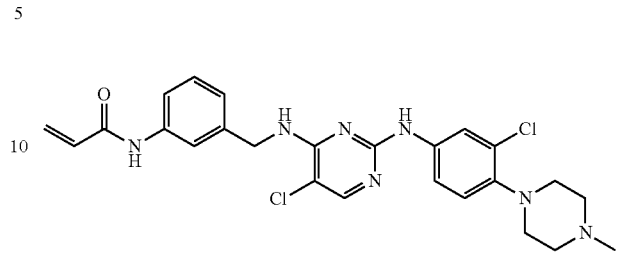

¹H NMR (600 MHz, TFA salt, DMSO-d₆) δ 10.06 (s, 1H), 9.64 (br, 1H), 9.31 (br, 1H), 7.96 (s, 1H), 7.92 (br, 1H), 7.73 (s, 1H), 7.55 (s, 1H), 7.50 (d, J=8.4 Hz, 1H), 7.42 (d, J=8.4 Hz, 1H), 7.19 (dd, J=8.4, 7.8 Hz, 1H), 6.98 (d, J=9.0 Hz, 1H), 6.96 (d, J=7.8 Hz, 1H), 6.36 (dd, J=16.8, 10.4 Hz, 1H), 6.18 (d, J=16.8 Hz, 1H), 5.68 (d, J=10.4 Hz, 1H), 4.57 (d, J=6.0 Hz, 2H), 3.43 (m, 2H), 3.23 (m, 2H), 3.11 (m, 2H), 2.85 (m, 2H), 2.81 (s, 3H). MS (ESI) m/z 512 (M+H)⁺.

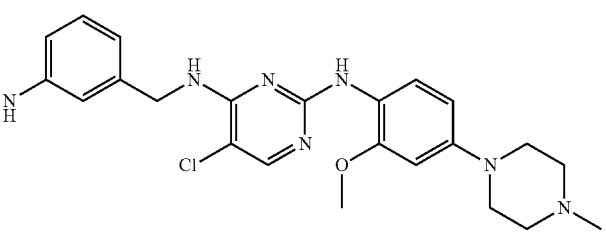

¹H NMR (600 MHz, DMSO-d6) δ 10.04 (s, 1H), 7.90 (s, 1H), 7.78 (m, 1H), 7.70 (d, J=9.0 Hz, 1H), 7.64 (s, 1H), 7.45 (s, 1H), 7.42 (d, J=8.4 Hz, 1H), 7.41 (s, 1H), 7.31 (dd, J=7.8, 7.8 Hz, 1H), 7.08 (d, J=7.8 Hz, 1H), 6.62 (s, 1H), 6.59 (s, 1H), 6.42 (d, J=9.0 Hz, 1H), 6.35 (m, 1H), 6.29 (d, J=8.4 Hz, 1H), 5.58 (m, 1H), 4.57 (d, J=6.0 Hz, 2H), 3.79 (s, 3H), 3.31 (m, 2H), 3.15 (m, 4H), 2.48 (m, 4H), 2.37 (m, 3H). MS (ESI) m/z 538 (M+H)+.

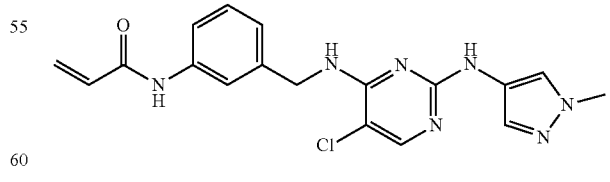

¹H NMR (600 MHz, DMSO-d₆) δ 10.13 (s, 1H), 9.39 (br, 1H), 7.99 (s, 1H), 7.60 (m, 1H), 7.58 (s, 1H), 7.31 (m, 1H), 7.29 (dd, J=8.4, 7.8 Hz, 1H), 7.04 (d, J=7.8 Hz, 1H), 6.42 (dd, J=16.8, 10.2 Hz, 1H), 6.24 (d, J=16.8 Hz, 1H), 5.74 (d, J=10.2 Hz, 1H), 4.65 (d, J=5.4 Hz, 2H), 3.68 (br, 3H). MS (ESI) m/z 384 (M+H)⁺.

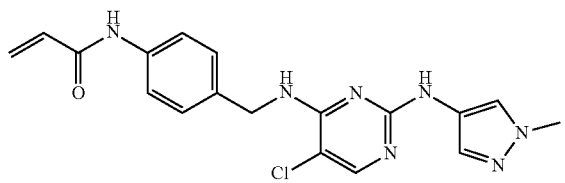 [SMILES: C=CC(=O)Nc1ccc(CNc2nc(Nc3cnn(C)c3)ncc2Cl)cc1]

¹H NMR (600 MHz, DMSO-d₆) δ 10.10 (s, 1H), 8.99 (br, 1H), 7.90 (s, 1H), 7.67 (m, 1H), 7.61 (d, J=8.4 Hz, 2H), 7.31 (m, 1H), 7.28 (d, J=9.0 Hz, 2H), 6.41 (dd, J=16.8, 10.2 Hz, 1H), 6.23 (d, J=16.8 Hz, 1H), 5.73 (d, J=10.2 Hz, 1H), 4.59 (d, J=5.4 Hz, 2H), 3.69 (br, 3H). MS (ESI) m/z 384 (M+H)⁺.

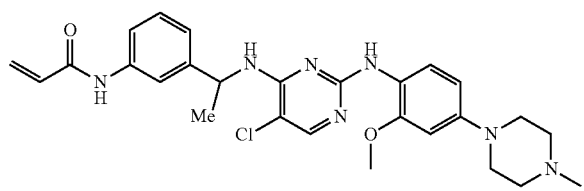 [SMILES: C=CC(=O)Nc1cccc(C(C)Nc2nc(Nc3ccc(N4CCN(C)CC4)cc3OC)ncc2Cl)c1]

¹H NMR (600 MHz, TFA salt, DMSO-d₆) δ 10.21 (s, 1H), 9.91 (br, 1H), 8.07 (s, 1H), 7.81 (s, 1H), 7.52 (m, 1H), 7.49 (d, J=7.8 Hz, 1H), 7.28 (dd, J=8.4, 7.8 Hz, 1H), 7.04 (m, 1H), 6.69 (s, 1H), 6.53 (d, J=9.0 Hz, 1H), 6.56 (dd, J=16.8, 10.4 Hz, 1H), 6.23 (d, J=16.8 Hz, 1H), 5.78 (d, J=10.4 Hz, 1H), 5.25 (br, 1H), 3.84 (m, 2H), 3.80 (s, 3H), 3.53 (m, 2H), 3.15 (m, 2H), 2.95 (m, 2H), 2.89 (s, 3H), 1.55 (d, J=7.2 Hz, 3H). MS (ESI) m/z 522 (M+H)⁺.

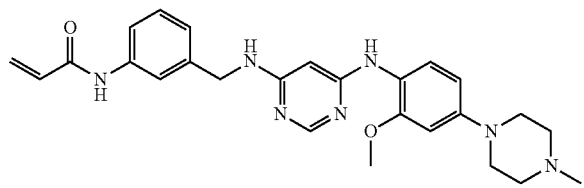 [SMILES: C=CC(=O)Nc1cccc(CNc2cc(Nc3ccc(N4CCN(C)CC4)cc3OC)ncn2)c1]

¹H NMR (600 MHz, TFA salt, DMSO) δ 10.20 (s, 1H), 10.00 (br, 1H), 8.69 (br, 1H), 8.27 (s, 1H), 7.65 (s, 1H), 7.56 (d, J=7.8 Hz, 1H), 7.31 (dd, J=8.4, 7.8 Hz, 1H), 6.97 (m, 1H), 6.73 (br, 1H), 6.58 (m, 1H), 6.44 (dd, J=16.8, 10.2 Hz, 1H), 6.26 (d, J=16.8 Hz, 1H), 5.77 (d, J=10.2 Hz, 1H), 4.48 (m, 2H), 3.92 (m, 2H), 3.76 (s, 3H), 3.55 (m, 2H), 3.16 (m, 2H), 2.99 (m, 2H), 2.89 (s, 3H). MS (ESI) m/z 474 (M+H)+.

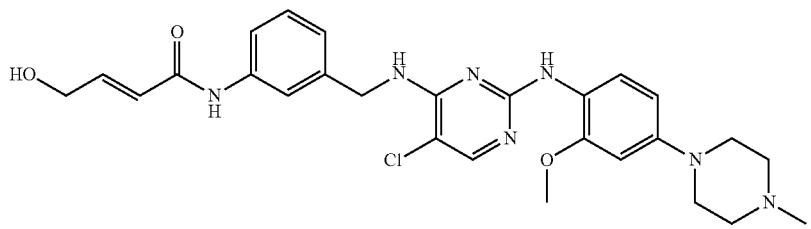 [SMILES: COc1cc(N2CCN(C)CC2)ccc1Nc1ncc(Cl)c(NCc2cccc(NC(=O)/C=C/CO)c2)n1]

¹H NMR (600 MHz, DMSO-d₆) δ 10.06 (s, 1H), 7.89 (s, 1H), 7.81 (m, 1H), 7.69 (s, 1H), 7.61 (d, J=9.0 Hz, 1H), 7.52 (d, J=8.4 Hz, 1H), 7.36 (s, 1H), 7.23 (dd, J=7.8, 7.8 Hz, 1H), 6.94 (d, J=7.8 Hz, 1H), 6.87 (m, 1H), 6.56 (s, 1H), 6.34 (m, 1H), 6.33 (s, 1H), 5.12 (br, 1H), 4.54 (d, J=6.0 Hz, 2H), 4.18 (s, 2H), 3.75 (s, 3H), 3.05 (m, 4H), 2.46 (m, 4H), 2.24 (s, 3H). MS (ESI) n/z 538 (M+H)⁺.

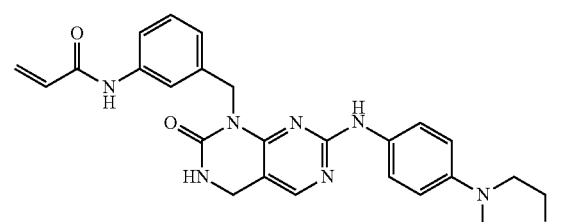

¹H NMR (600 MHz, TFA salt, DMSO) δ 10.17 (s, 1H), 9.76 (br, 1H), 9.33 (br, 1H), 8.08 (s, 1H), 7.62 (s, 1H), 7.59 (s, 1H), 7.55 (d, J=7.2 Hz, 1H), 7.36 (m, 1H), 7.25 (dd, J=8.4, 7.8 Hz, 1H), 6.92 (d, J=7.2 Hz, 1H), 6.82 (d, J=9.0 Hz, 2H), 6.43 (dd, J=16.8, 10.4 Hz, 1H), 6.26 (d, J=16.8 Hz, 1H), 5.76 (d, J=10.4 Hz, 1H), 5.01 (s, 2H), 4.31 (s, 2H), 3.67 (m, 2H), 3.49 (m, 2H), 3.13 (m, 2H), 2.87 (s, 3H), 2.86 (m, 2H). MS (ESI) m/z 499 (M+H)⁺.

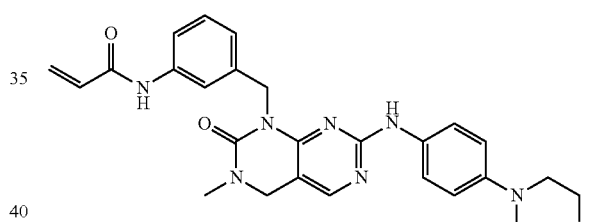

¹H NMR (600 MHz, TFA salt, DMSO) δ 10.16 (s, 1H), 9.71 (br, 1H), 9.34 (br, 1H), 8.10 (s, 1H), 7.60 (s, 1H), 7.56 (d, J=8.4 Hz, 1H), 7.38 (m, 1H), 7.25 (dd, J=8.4, 7.8 Hz, 1H), 6.92 (d, J=7.8 Hz, 1H), 6.82 (d, J=9.0 Hz, 2H), 6.44 (dd, J=16.8, 10.4 Hz, 1H), 6.26 (d, J=16.8 Hz, 1H), 5.77 (d, J=10.4 Hz, 1H), 5.13 (s, 2H), 4.40 (s, 3H), 3.68 (m, 2H), 3.49 (m, 2H), 3.14 (m, 2H), 2.97 (s, 3H), 2.86 (s, 3H), 2.84 (m, 2H). MS (ESI) n/z 513 (M+H)⁺.

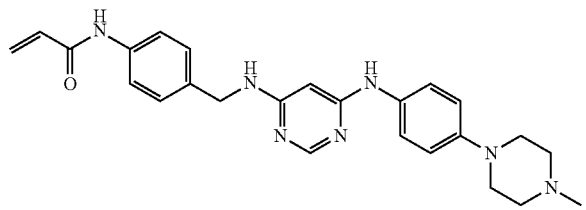 [SMILES: C=CC(=O)Nc1ccc(CNc2cc(Nc3ccc(N4CCN(C)CC4)cc3)ncn2)cc1]

$^1$H NMR (600 MHz, TFA salt, DMSO) δ 10.20 (s, 1H), 9.91 (br, 1H), 8.50 (br, 1H), 8.29 (s, 1H), 7.66 (d, J=8.4 Hz, 2H), 7.25 (d, J=8.4 Hz, 2H), 7.19 (m, 2H), 7.01 (m, 2H), 6.73 (br, 1H), 6.58 (m, 1H), 6.44 (dd, J=16.8, 10.2 Hz, 1H), 6.26 (d, J=16.8 Hz, 1H), 5.76 (d, J=10.2 Hz, 1H), 4.43 (m, 2H), 3.82 (m, 2H), 3.53 (m, 2H), 3.16 (m, 2H), 2.95 (m, 2H), 2.88 (s, 3H). MS (ESI) m/z 444 (M+H)+.

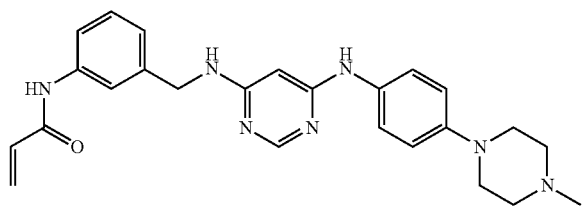 [SMILES: C=CC(=O)Nc1cccc(CNc2cc(Nc3ccc(N4CCN(C)CC4)cc3)ncn2)c1]

$^1$H NMR (600 MHz, TFA salt, DMSO) δ 10.20 (s, 1H), 9.92 (br, 1H), 8.47 (br, 1H), 8.28 (s, 1H), 7.65 (s, 1H), 7.56 (m, 1H), 7.32 (dd, J=8.4, 7.8 Hz, 1H), 7.20 (m, 1H), 7.00 (m, 3H), 6.44 (dd, J=16.8, 10.2 Hz, 1H), 6.25 (d, J=16.8 Hz, 1H), 5.76 (d, J=10.2 Hz, 1H), 4.46 (m, 2H), 3.79 (m, 2H), 3.53 (m, 2H), 3.15 (m, 2H), 2.94 (m, 2H), 2.87 (s, 3H). MS (ESI) m/z 444 (M+H)+.

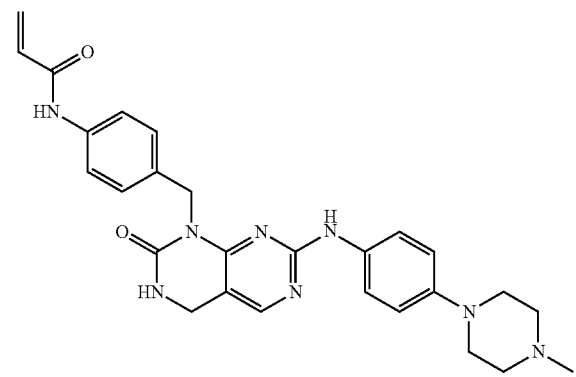 [SMILES: C=CC(=O)Nc1ccc(CN2C(=O)NCc3cnc(Nc4ccc(N5CCN(C)CC5)cc4)nc32)cc1]

$^1$H NMR (600 MHz, TFA salt, DMSO) δ 10.11 (s, 1H), 9.72 (br, 1H), 9.38 (br, 1H), 8.06 (s, 1H), 7.57 (d, J=9.0 Hz, 2H), 7.56 (s, 1H), 7.40 (d, J=8.4 Hz, 1H), 7.22 (d, J=8.4 Hz, 1H), 6.87 (d, J=9.0 Hz, 1H), 6.82 (d, J=9.0 Hz, 2H), 6.41 (dd, J=16.8, 10.4 Hz, 1H), 6.24 (d, J=16.8 Hz, 1H), 5.73 (d, J=10.4 Hz, 1H), 5.05 (s, 2H), 4.28 (s, 3H), 3.72 (m, 2H), 3.51 (m, 2H), 3.16 (m, 2H), 2.89 (m, 2H), 2.86 (s, 2H). MS (ESI) m/z 499 (M+H)+.

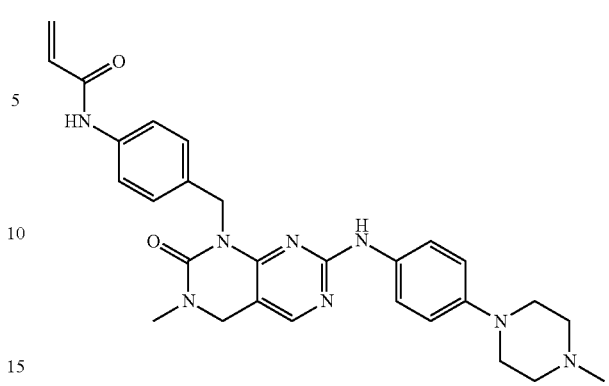

$^1$H NMR (600 MHz, TFA salt, DMSO) δ 10.09 (s, 1H), 9.70 (br, 1H), 9.37 (br, 1H), 8.06 (s, 1H), 7.55 (d, J=8.4 Hz, 2H), 7.39 (d, J=8.4 Hz, 2H), 7.20 (d, J=8.4 Hz, 2H), 6.85 (d, J=9.0 Hz, 1H). 6.82 (d, J=9.0 Hz, 2H), 6.39 (dd, J=16.8, 10.4 Hz, 1H), 6.21 (d, J=16.8 Hz, 1H), 5.71 (d, J=10.4 Hz, 1H), 5.07 (s, 2H), 4.36 (s, 3H), 3.70 (m, 2H), 3.49 (m, 2H), 3.15 (m, 2H), 2.93 (s, 3H), 2.87 (m, 2H). MS (ESI) m/z 512 (M+H)+.

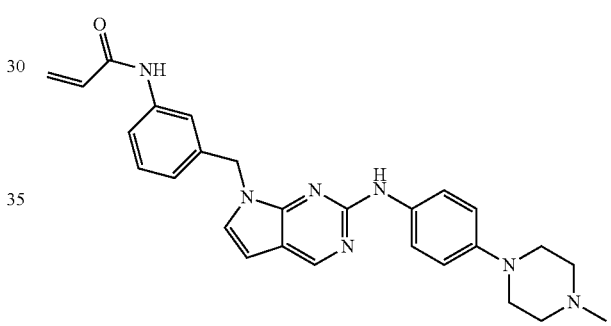

$^1$H NMR (600 MHz, DMSO) δ 10.15 (s, 1H), 9.12 (s, 1H), 8.65 (bs, 1H), 7.61 (d. J=9.0 Hz, 2H), 7.59 (m, 2H), 7.28 (s, 1H), 7.27 (m, 1H), 6.93 (d, J=8.4 Hz, 2H), 6.84 (m, 2H), 6.46 (d, J=3.6 Hz, 1H), 6.41 (dd, J=16.8, 10.4 Hz, 1H), 6.24 (d, J=16.8 Hz, 1H), 5.74 (d, J=10.4 Hz, 1H), 5.32 (s, 2H), 3.02 (m, 4H), 2.46 (m, 4H), 2.23 (s, 3H). MS (ESI) m/z 468 (M+H)$^+$.

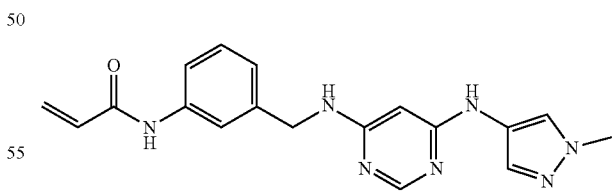

$^1$H NMR (600 MHz, TFA salt, DMSO) δ 10.14 (s, 1H), 9.45 (br, 1H), 8.22 (br, 1H), 8.04 (s, 1H), 7.66 (s, 1H), 7.54 (d, J=7.8 Hz, 1H), 7.27 (dd, J=8.4, 7.8 Hz, 1H), 7.22 (d, J=8.4 Hz, 1H), 7.00 (d, J=7.8 Hz, 1H), 6.85 (dd, J=8.4, 8.4 Hz, 1H), 6.43 (dd, J=16.8, 10.4 Hz, 1H), 6.25 (d, J=16.8 Hz, 1H), 5.75 (d, J=10.4 Hz, 1H), 4.62 (d, J=5.4 Hz, 2H), 3.70 (t, J=4.8 Hz, 4H), 2.89 (t, J=4.8 Hz, 4H). MS (ESI) m/z 483 (M+H)+.

171

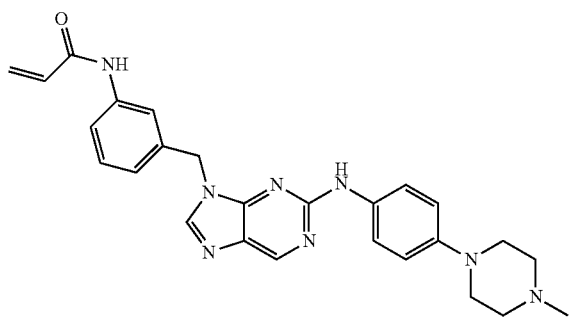 [SMILES: C=CC(=O)Nc1cccc(Cn2cnc3cnc(Nc4ccc(N5CCN(C)CC5)cc4)nc32)c1]

¹H NMR (600 MHz, MeOH) δ 8.51 (s, 1H), 8.42 (s, 1H), 7.66 (s, 1H), 7.62 (d, J=8.4 Hz, 2H), 7.61 (m, 1H), 7.37 (dd, J=8.4, 7.8 Hz, 2H), 7.12 (d, J=7.8 Hz, 2H), 6.95 (d, J=9.0 Hz, 2H), 6.37 (m, 2H), 5.75 (d, J=9.0 Hz, 1H), 5.48 (s, 2H), 3.15 (m, 4H), 2.64 (m, 4H), 2.36 (s, 3H). MS (ESI) m/z 469 (M+H)⁺.

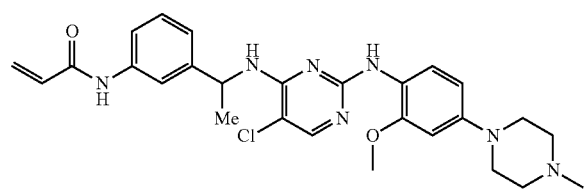 [SMILES: C=CC(=O)Nc1cccc(C(C)Nc2nc(Nc3ccc(N4CCN(C)CC4)cc3OC)ncc2Cl)c1]

¹H NMR (600 MHz, TFA salt, DMSO) δ 10.21 (s, 1H), 9.91 (br, 1H), 8.07 (s, 1H), 7.81 (s, 1H), 7.52 (m, 1H), 7.49 (d, J=7.8 Hz, 1H), 7.28 (dd, J=8.4, 7.8 Hz, 1H), 7.04 (m, 1H), 6.69 (s, 1H), 6.53 (d, J=9.0 Hz, 1H), 6.56 (dd, J=16.8, 10.4 Hz, 1H), 6.23 (d, J=16.8 Hz, 1H), 5.78 (d, J=10.4 Hz, 1H), 5.25 (br, 1H), 3.84 (m, 2H), 3.80 (s, 3H), 3.53 (m, 2H), 3.15 (m, 2H), 2.95 (m, 2H), 2.89 (s, 3H), 1.55 (d, J=7.2 Hz, 3H). MS (ESI) n/z 522 (M+H)⁺.

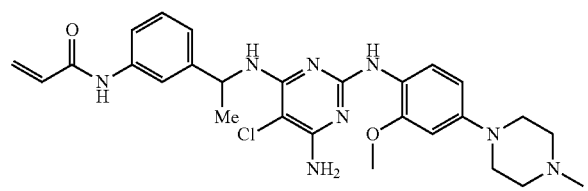 [SMILES: C=CC(=O)Nc1cccc(C(C)Nc2nc(Nc3ccc(N4CCN(C)CC4)cc3OC)nc(N)c2Cl)c1]

¹H NMR (600 MHz, DMSO) δ 10.10 (d, J=9.0 Hz, 1H), 8.11 (d, J=9.0 Hz, 1H), 7.62 (d, J=8.4 Hz, 1H), 7.49 (s, 1H), 7.25 (s, 1H), 7.24 (dd, J=8.4, 7.8 Hz, 1H), 7.00 (d, J=7.2 Hz, 1H), 6.95 (t, J=6.0 Hz, 1H), 6.64 (s, 1H), 6.43 (m, 2H), 6.24 (d, J=16.8 Hz, 1H), 5.91 (s, 2H), 5.73 (d, J=10.2 Hz, 1H), 4.55 (d, J=6.6 Hz, 2H), 3.86 (s, 3H), 3.11 (m, 4H), 2.49 (m, 4H), 2.25 (s, 3H). MS (ESI) n/z 523 (M+H)⁺.

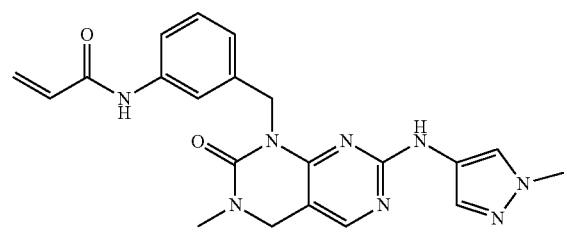 [SMILES: C=CC(=O)Nc1cccc(CN2C(=O)N(C)Cc3cnc(Nc4cnn(C)c4)nc32)c1]

172

¹H NMR (600 MHz, TFA salt, DMSO) δ 10.10 (s, 1H), 9.44 (br, 1H), 8.09 (s, 1H), 7.61 (d, J=8.4 Hz, 1H), 7.46 (br, 1H), 7.26 (dd, J=7.8, 7.2 Hz, 1H), 6.99 (m, 1H), 6.41 (dd, J=16.8, 10.2 Hz, 1H), 6.24 (d, J=16.8 Hz, 1H), 5.73 (d, J=10.2 Hz, 1H), 5.15 (br, 2H) 4.40 (br, 3H), 2.96 (s, 3H). MS (ESI) n/z 419 (M+H)⁺.

¹H NMR (600 MHz, DMSO-d6) δ 10.16 (s, 1H), 8.33 (d, J=9.0 Hz, 1H), 7.58 (d, J=8.4 Hz, 1H), 7.51 (s, 1H), 7.26 (dd, J=8.4, 7.8 Hz, 1H), 7.02 (m, 1H), 6.92 (d, J=7.8 Hz, 1H), 6.90 (s, 1H), 6.83 (m, 1H), 6.65 (s, 1H), 6.48 (d, J=7.8 Hz, 1H), 6.46 (m, 1H), 6.41 (dd, J=16.8, 10.2 Hz, 1H), 6.22 (d, J=16.8 Hz, 1H), 5.72 (d, J=10.2 Hz, 1H), 5.21 (s, 2H), 3.85 (s, 3H), 3.31 (m, 4H), 3.11 (m, 4H), 2.70 (m, 3H). MS (ESI) m/z 513 (M+H)+.

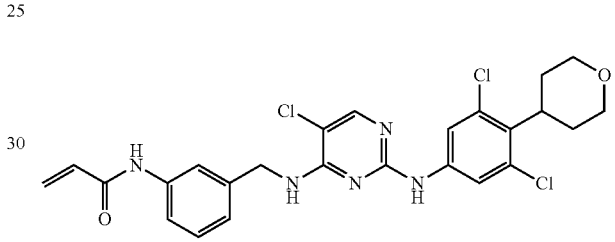

¹H NMR (600 MHz, TFA salt, DMSO) δ 10.02 (s, 1H), 9.39 (s, 1H), 7.99 (s, 1H), 7.94 (m, 1H), 7.77 (s, 2H), 7.58 (d, J=8.4 Hz, 1H), 7.57 (s, 1H), 7.25 (dd, J=8.4, 7.8 Hz, 1H), 7.03 (d, J=7.8 Hz, 1H), 6.42 (dd, J=16.8, 10.4 Hz, 1H), 6.23 (d, J=16.8 Hz, 1H), 5.73 (d, J=10.4 Hz, 1H), 4.66 (d, J=6.6 Hz, 2H), 3.66 (m, 4H), 3.04 (m, 4H). MS (ESI) n/z 532 (M+H)⁺.

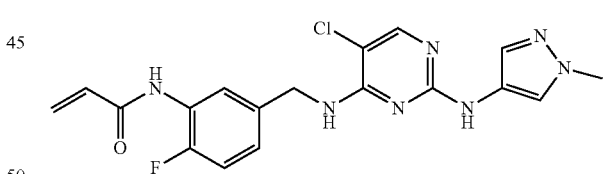

¹H NMR (600 MHz, TFA salt, DMSO) δ 9.93 (s, 1H), 8.02 (m, 1H), 7.98 (m, 1H), 7.36 (m, 1H), 7.24 (dd, J=8.4, 7.8 Hz, 1H), 7.12 (m, 1H), 6.60 (dd, J=16.8, 10.2 Hz, 1H), 6.26 (d, J=16.8 Hz, 1H), 5.77 (d, J=10.2 Hz, 1H), 4.63 (br, 2H) 3.73 (br, 3H). MS (ESI) m/z 402 (M+H)⁺.

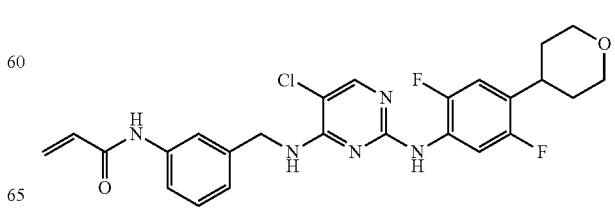

¹H NMR (600 MHz, DMSO) δ 10.09 (s, 1H), 8.52 (s, 1H), 7.95 (s, 1H), 7.82 (m, 1H), 7.57 (d, J=8.4 Hz, 1H), 7.54 (s, 1H), 7.52 (m, 1H), 7.23 (dd, J=7.8, 7.8 Hz, 1H), 6.94 (d, J=7.8 Hz, 1H), 6.86 (m, 1H), 6.43 (dd, J=16.8, 10.2 Hz, 1H), 6.24 (d, J=16.8 Hz, 1H), 5.74 (d, J=10.2 Hz, 1H), 4.55 (d, J=6.0 Hz, 2H), 3.72 (m, 4H), 2.94 (m, 4H). MS (ESI) n/z 500 (M+H)⁺.

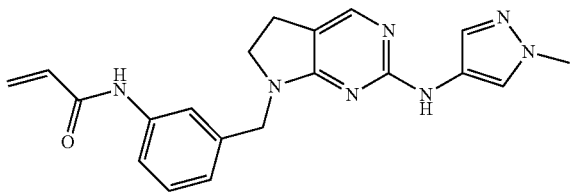 [SMILES: C=CC(=O)Nc1cccc(CN2CCc3cnc(Nc4cnn(C)c4)nc32)c1]

¹H NMR (600 MHz, TFA salt, DMSO) δ 10.24 (s, 1H), 9.72 (s, 1H), 9.42 (s, 1H), 7.88 (s, 1H), 7.68 (s, 1H), 7.65 (s, 1H), 7.60 (d, J=8.4 Hz, 1H), 7.59 (s, 1H), 7.37 (dd, J=8.4, 7.8 Hz, 1H), 6.96 (d, J=8.4 Hz, 1H), 6.43 (dd, J=16.8, 10.2 Hz, 1H), 6.26 (d, J=16.8 Hz, 1H), 5.77 (d, J=10.2 Hz, 1H), 5.29 (s, 2H), 3.76 (t, J=7.8 Hz, 1H), 3.02 (t, J=7.8 Hz, 1H). MS (ESI) m/z 376 (M+H)⁺.

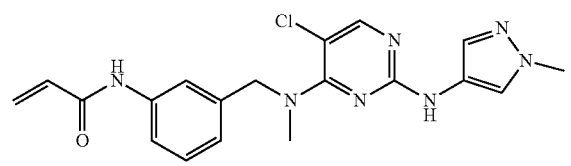 [SMILES: C=CC(=O)Nc1cccc(CN(C)c2nc(Nc3cnn(C)c3)ncc2Cl)c1]

¹H NMR (600 MHz, TFA salt, DMSO) δ 10.15 (s, 1H), 8.03 (s, 1H), 7.98 (m, 1H), 7.63 (d, J=7.8 Hz, 1H), 7.58 (br, 1H), 7.38 (br, 1H), 7.32 (dd, J=7.8, 7.8 Hz, 1H), 7.00 (d, J=7.8 Hz, 1H), 6.42 (dd, J=16.8, 10.2 Hz, 1H), 6.24 (d, J=16.8 Hz, 1H), 5.74 (d, J=10.2 Hz, 1H), 4.89 (br, 2H) 3.68 (br, 3H), 3.20 (br, 1H). MS (ESI) m/z 398 (M+H)⁺.

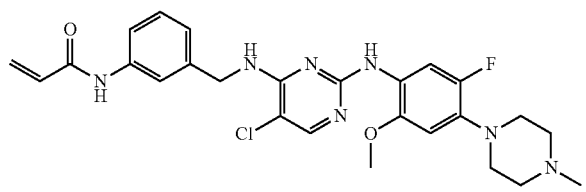 [SMILES: C=CC(=O)Nc1cccc(CNc2nc(Nc3cc(F)c(N4CCN(C)CC4)cc3OC)ncc2Cl)c1]

¹H NMR (600 MHz, DMSO-d₆) δ 10.10 (s, 1H), 7.98 (s, 1H), 7.88 (s, 1H), 7.86 (m, 1H), 7.59 (d, J=6.6 Hz, 1H), 7.54 (s, 1H), 7.49 (s, 1H), 7.24 (m, 1H), 6.99 (d, J=6.6 Hz, 1H), 6.62 (d, J=7.8 Hz, 1H), 6.42 (dd, J=16.8, 10.8 Hz, 1H), 6.22 (d, J=16.8 Hz, 1H), 5.72 (d, J=10.8 Hz, 1H), 4.59 (d, J=5.4 Hz, 2H), 3.80 (s, 3H), 2.98 (m, 4H), 2.53 (m, 4H), 2.28 (s, 3H). MS (ESI) n/z 526 (M+H)⁺.

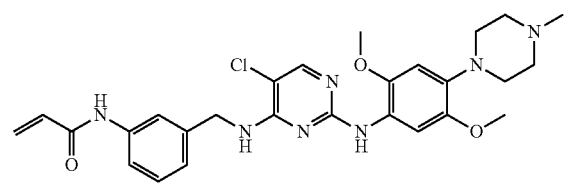 [SMILES: C=CC(=O)Nc1cccc(CNc2nc(Nc3cc(OC)c(N4CCN(C)CC4)cc3OC)ncc2Cl)c1]

¹H NMR (600 MHz, DMSO-d₆, TFA salt) δ 10.14 (s, 1H), 9.78 (br, 1H), 8.60 (br, 1H), 8.10 (s, 1H), 7.60 (m, 1H), 7.59 (s, 1H), 7.24 (m, 1H), 6.93 (s, 1H), 6.69 (s, 1H), 6.42 (dd, J=16.8, 10.8 Hz, 1H), 6.24 (d, J=16.8 Hz, 1H), 5.74 (d, J=10.8 Hz, 1H), 4.62 (d, J=5.4 Hz, 2H), 3.80 (s, 3H), 3.49 (m, 2H), 3.17 (m, 4H), 2.93 (m, 2H), 2.01 (s, 3H). MS (ESI) m/z 538 (M+H)⁺.

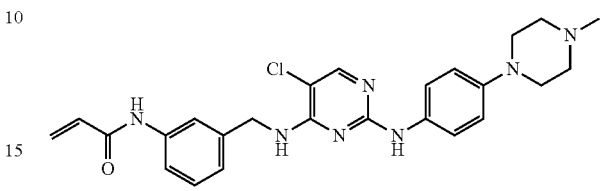

¹H NMR (600 MHz, DMSO-d₆) δ 10.16 (s, 1H), 8.90 (s, 1H), 7.91 (s, 1H), 7.77 (m, 1H), 7.70 (s, 1H), 7.53 (d, J=8.4 Hz, 1H), 7.32 (d, J=7.8 Hz, 2H), 7.29 (s, 1H), 7.27 (dd, J=7.8, 7.8 Hz, 1H), 7.00 (d, J=7.2 Hz, 1H), 6.71 (d, J=8.4 Hz, 2H), 6.43 (dd, J=16.8, 10.2 Hz, 1H), 6.25 (d, J=16.8 Hz, 1H), 5.75 (d, J=10.2 Hz, 1H), 4.58 (d, J=6.0 Hz, 2H), 2.98 (m, 4H), 2.42 (m, 4H), 2.21 (s, 3H). MS (ESI) m/z 478 (M+H)⁺.

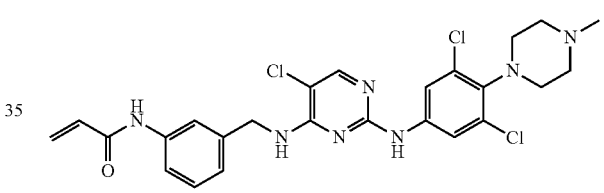

¹H NMR (600 MHz, TFA salt, DMSO-d₆) δ 10.11 (s, 1H), 9.64 (br, 1H), 9.52 (s, 1H), 8.07 (s, 1H), 7.98 (m, 1H), 7.82 (s, 1H), 7.75 (s, 1H), 7.58 (d, J=8.4 Hz, 1H), 7.57 (s, 1H), 7.42 (d, J=8.4 Hz, 1H), 7.25 (dd, J=8.4, 8.4 Hz, 1H), 7.03 (d, J=7.8 Hz, 1H), 6.42 (dd, J=16.8, 10.8 Hz, 1H), 6.24 (d, J=16.8 Hz, 1H), 5.73 (d, J=10.8 Hz, 1H), 4.66 (d, J=6.0 Hz, 2H), 3.54 (m, 2H), 3.43 (m, 2H), 3.10 (m, 2H), 3.04 (m, 2H), 2.87 (s, 3H). MS (ESI) m/z 546 (M+H)⁺.

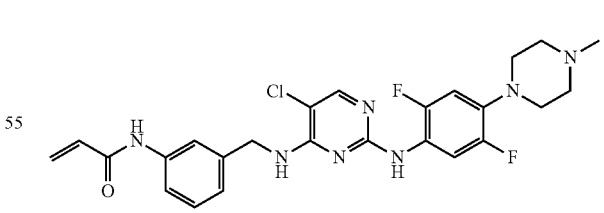

¹H NMR (600 MHz, DMSO-d6) δ 10.11 (s, 1H), 7.95 (br, 1H), 8.58 (s, 1H), 7.95 (s, 1H), 7.84 (t, J=6.0 Hz, 1H), 7.54 (s, 1H), 7.58 (m, 1H), 7.54 (s, 1H), 7.23 (dd, J=8.4, 7.8 Hz, 1H), 6.98 (t, J=10.2 Hz, 1H), 6.94 (d, J=8.4 Hz, 1H), 6.43 (dd, J=16.8, 10.8 Hz, 1H), 6.24 (d, J=16.8 Hz, 1H), 5.74 (d, J=10.8 Hz, 1H), 4.56 (d, J=6.6 Hz, 2H), 3.21 (m, 8H), 2.78 (s, 4H). MS (ESI) m/z 514 (M+H)+.

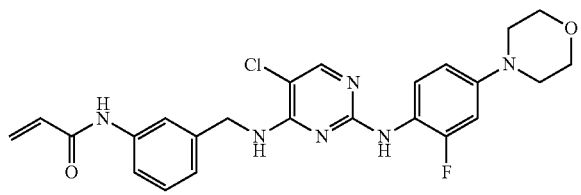 [SMILES: C=CC(=O)Nc1cccc(CNc2nc(Nc3ccc(N4CCOCC4)cc3F)ncc2Cl)c1]

¹H NMR (600 MHz, TFA salt, DMSO-d₆) δ 10.14 (s, 1H), 9.06 (br, 1H), 8.55 (br, 1H), 8.02 (s, 1H), 7.64 (s, 1H), 7.52 (d, J=8.4 Hz, 1H), 7.25 (m, 2H), 6.81 (d, J=13.8 Hz, 1H), 6.63 (d, J=7.8 Hz, 1H), 6.44 (dd, J=16.8, 10.4 Hz, 1H), 6.25 (d, J=16.8 Hz, 1H), 5.76 (d, J=10.2 Hz, 1H), 4.51 (d, J=5.4 Hz, 2H), 3.71 (m, 4H), 3.08 (m, 4H). MS (ESI) m/z 483 (M+H)⁺.

¹H NMR (600 MHz, TFA salt, DMSO-d₆) δ 10.10 (s, 1H), 9.48 (s, 1H), 8.06 (m, 1H), 8.05 (s, 1H), 7.58 (d, J=8.4 Hz, 1H), 7.56 (s, 1H), 7.28 (d, J=12.0 Hz, 2H), 7.26 (dd, J=7.8, 7.8 Hz, 1H), 7.02 (d, J=7.8 Hz, 1H), 6.42 (dd, J=16.8, 10.2 Hz, 1H), 6.23 (d, J=16.8 Hz, 1H), 5.73 (d, J=10.2 Hz, 1H), 4.64 (d, J=6.6 Hz, 2H), 3.55 (m, 1H), 3.05 (m, 2H), 2.89 (m, 2H), 1.77 (m, 2H), 1.46 (m, 2H). MS (ESI) m/z 515 (M+H)⁺.

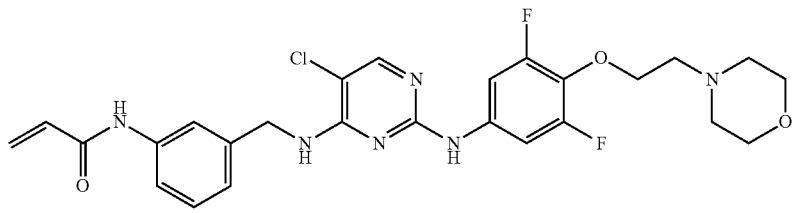

¹H NMR (600 MHz, TFA salt, DMSO-d₆) δ 10.12 (s, 1H), 9.53 (s, 1H), 8.06 (s, 1H), 7.99 (m, 1H), 7.59 (d, J=7.8 Hz, 1H), 7.56 (s, 1H), 7.46 (d, J=11.4 Hz, 2H), 7.26 (dd, J=8.4, 7.8 Hz, 1H), 7.03 (d, J=7.8 Hz, 1H), 6.42 (dd, J=16.8, 10.2 Hz, 1H), 6.23 (d, J=16.8 Hz, 1H), 5.74 (d, J=10.2 Hz, 1H), 4.65 (d, J=6.0 Hz, 2H), 4.33 (t, J=5.1 Hz, 2H), 4.00 (m, 2H), 3.73 (m, 2H), 3.55 (m, 2H), 3.48 (m, 2H), 3.22 (m, 2H). MS (ESI) m/z 545 (M+H)⁺.

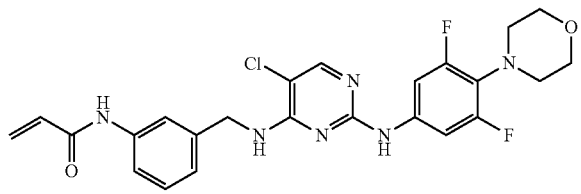 [SMILES: C=CC(=O)Nc1cccc(CNc2nc(Nc3cc(F)c(N4CCOCC4)c(F)c3)ncc2Cl)c1]

¹H NMR (600 MHz, TFA salt, DMSO-d₆) δ 10.09 (s, 1H), 9.45 (s, 1H), 8.04 (s, 1H), 7.97 (m, 1H), 7.58 (d, J=8.4 Hz, 1H), 7.55 (s, 1H), 7.34 (s, 1H), 7.32 (s, 1H), 7.26 (dd, J=8.4, 7.8 Hz, 1H), 7.02 (d, J=7.8 Hz, 1H), 6.42 (dd, J=16.8, 10.2 Hz, 1H), 6.23 (d, J=16.8 Hz, 1H), 5.73 (d, J=10.2 Hz, 1H), 4.64 (d, J=6.0 Hz, 2H), 3.64 (m, 4H), 2.98 (m, 3H). MS (ESI) m/z 501 (M+H)⁺.

¹H NMR (600 MHz, TFA salt, DMSO-d₆) δ 10.15 (s, 1H), 9.08 (br, 1H), 7.95 (br, 1H), 7.63 (br, 1H), 7.55 (d, J=7.8 Hz, 1H), 7.27 (dd, J=8.4, 7.8 Hz, 1H), 7.02 (d, J=7.8 Hz, 1H), 6.44 (dd, J=16.8, 10.2 Hz, 1H), 6.25 (d, J=16.8 Hz, 1H), 5.75 (d, J=10.2 Hz, 1H), 4.65 (d, J=5.4 Hz, 2H), 2.84-3.25 (m, 8H), 1.54 (m, 2H), 1.45 (m, 2H), 1.15 (t, J=7.2 Hz, 6H). MS (ESI) m/z 431 (M+H)⁺.

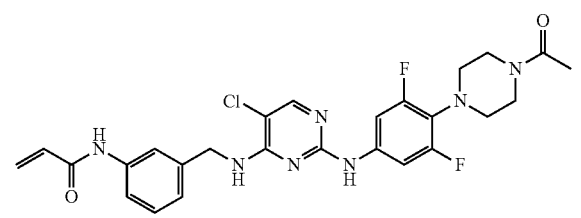 [SMILES: C=CC(=O)Nc1cccc(CNc2nc(Nc3cc(F)c(N4CCN(C(C)=O)CC4)c(F)c3)ncc2Cl)c1]

¹H NMR (600 MHz, TFA salt, DMSO) δ 10.20 (s, 1H), 9.92 (br, 1H), 8.47 (br, 1H), 8.28 (s, 1H), 7.65 (s, 1H), 7.56 (m, 1H), 7.32 (dd, J=8.4, 7.8 Hz, 1H), 7.20 (m, 1H), 7.00 (m, 3H), 6.44 (dd, J=16.8, 10.2 Hz, 1H), 6.25 (d, J=16.8 Hz, 1H), 5.76 (d, J=10.2 Hz, 1H), 4.46 (m, 2H), 3.79 (m, 2H), 3.53 (m, 2H), 3.15 (m, 2H), 2.94 (m, 2H), 2.87 (s, 3H). MS (ESI) m/z 444 (M+H)⁺.

¹H NMR (600 MHz, TFA salt, DMSO-d₆) δ 10.13 (s, 1H), 9.11 (br, 1H), 8.27 (br, 1H), 8.07 (d, J=7.8 Hz. 1H), 7.72 (br, 1H), 7.50 (d, J=7.8 Hz, 1H), 7.28 (d, J=8.4, 7.8 Hz, 1H), 7.05 (m, 1H), 6.42 (dd, J=16.8, 10.2 Hz, 1H), 6.24 (d, J=16.8 Hz, 1H), 5.74 (d, J=10.2 Hz, 1H), 4.54-4.70 (m, 1H), 4.32 (m, 1H), 3.20-3.58 (m, 4H), 1.93 (s, 3H), 1.73-1.90 (m, 2H). MS (ESI) nm/z 415 (M+H)⁺.

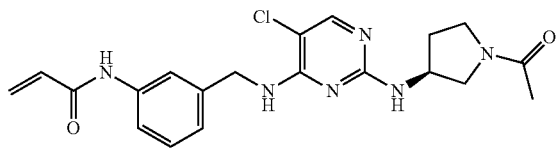 [SMILES: C=CC(=O)Nc1cccc(CNc2nc(N[C@H]3CCN(C(C)=O)C3)ncc2Cl)c1]

<sup>1</sup>H NMR (600 MHz, TFA salt, DMSO-d<sub>6</sub>) 10.13 (s, 1H), 9.14 (br, 1H), 8.32 (br, 1H), 8.09 (d, J=7.8 Hz, 1H), 7.73 (br, 1H), 7.50 (d, J=7.8 Hz, 1H), 7.28 (d, J=8.4, 7.8 Hz, 1H), 7.05 (m, 1H), 6.42 (dd, J=16.8, 10.2 Hz, 1H), 6.24 (d, J=16.8 Hz, 1H), 5.75 (d, J=10.2 Hz, 1H), 4.54-4.70 (m, 2H), 4.33 (m, 1H), 3.19-3.59 (m, 4H), 1.93 (s, 3H), 1.74-1.91 (m, 2H). MS (ESI) m/z 415 (M+H)$^+$.

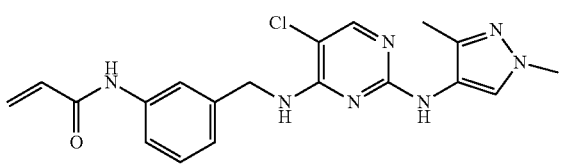 [SMILES: C=CC(=O)Nc1cccc(CNc2nc(Nc3cn(C)nc3C)ncc2Cl)c1]

<sup>1</sup>H NMR (600 MHz, TFA salt, DMSO-d<sub>6</sub>) δ 10.14 (s, 1H), 9.13 (br, 1H), 8.65 (br, 1H), 8.02 (m, 1H), 7.61 (s, 1H), 7.56 (d, J=8.4 Hz, 1H), 7.29 (dd, J=8.4, 7.8 Hz, 1H), 6.98 (m, 1H), 6.43 (dd, J=16.8, 10.2 Hz, 1H), 6.25 (d, J=16.8 Hz, 1H), 5.75 (d, J=10.8 Hz, 1H), 4.62 (m, 2H), 3.65 (br, 3H), 2.03 (s, 3H). MS (ESI) m/z 398 (M+H)$^+$.

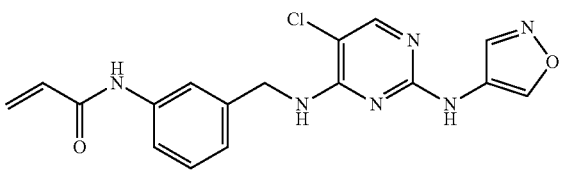 [SMILES: C=CC(=O)Nc1cccc(CNc2nc(Nc3cnoc3)ncc2Cl)c1]

<sup>1</sup>H NMR (600 MHz, TFA salt, DMSO-d6) δ 10.12 (s, 1H), 9.38 (br, 1H), 8.46 (s, 1H), 8.04 (s, 1H), 8.03 (m, 1H), 7.60 (d, J=8.4 Hz, 1H), 7.55 (s, 1H), 7.28 (dd, J=8.4, 7.8 Hz, 1H), 7.03 (d, J=8.4 Hz, 1H), 6.42 (dd, J=16.8, 10.2 Hz, 1H), 6.24 (d, J=16.8 Hz, 1H), 5.73 (d, J=10.8 Hz, 1H), 4.64 (d, J=6.0 Hz, 2H). MS (ESI) m/z 371 (M+H)$^+$.

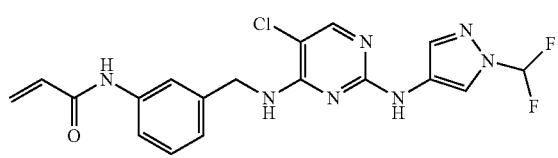 [SMILES: C=CC(=O)Nc1cccc(CNc2nc(Nc3cnn(C(F)F)c3)ncc2Cl)c1]

<sup>1</sup>H NMR (600 MHz, TFA salt, DMSO-d6) δ 10.11 (s, 1H), 9.52 (br, 1H), 8.05 (s, 1H), 7.69 (m, 1H), 7.58 (d, J=8.4 Hz, 1H), 7.57 (s, 1H), 7.26 (dd, J=8.4, 7.8 Hz, 1H), 7.03 (d, J=7.8 Hz, 1H), 6.42 (dd, J=16.8, 10.2 Hz, 1H), 6.24 (d, J=16.8 Hz, 1H), 5.73 (d, J=10.8 Hz, 1H), 4.66 (d, J=6.0 Hz, 2H). MS (ESI) m/z 420 (M+H)+.

<sup>1</sup>H NMR (600 MHz, TFA salt, DMSO-d6) δ 10.13 (s, 1H), 9.64 (br, 1H), 8.42 (br, 1H), 8.04 (s, 1H), 7.61 (s, 1H), 7.58 (d, J=7.8 Hz, 1H), 7.47 (s, 1H), 7.28 (dd, J=8.4, 7.8 Hz, 1H), 7.03 (d, J=7.8 Hz, 1H), 6.42 (dd, J=16.8, 10.2 Hz, 1H), 6.24 (d, J=16.8 Hz, 1H), 5.74 (d, J=10.8 Hz, 1H), 4.66 (d, J=6.0 Hz, 2H), 4.47 (m, 2H). MS (ESI) m/z 434 (M+H)+.

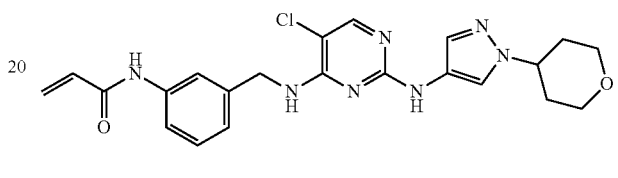

<sup>1</sup>H NMR (600 MHz, DMSO-d6) δ 10.12 (s, 1H), 9.07 (br, 1H), 7.93 (s, 1H), 7.73 (m, 1H), 7.61 (d, J=7.8 Hz, 1H), 7.56 (s, 1H), 7.28 (dd, J=7.8, 7.8 Hz, 1H), 7.02 (d, J=7.8 Hz, 1H), 6.42 (dd, J=16.8, 10.8 Hz, 1H), 6.24 (d, J=16.8 Hz, 1H), 5.73 (d, J=10.8 Hz, 1H), 4.66 (m, 2H), 4.01 (m, 1H), 3.88 (m, 2H), 3.38 (m, 2H), 1.57-1.88 (m, 4H). MS (ESI) m/z 454 (M+H)+.

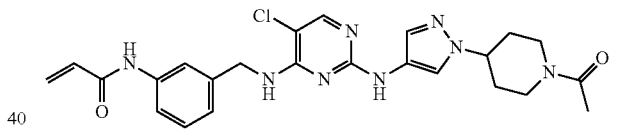

<sup>1</sup>H NMR (600 MHz, TFA salt, DMSO-d6) δ 10.14 (s, 1H), 9.72 (br, 1H), 8.54 (br, 1H), 8.06 (m, 1H), 7.59 (s, 1H), 7.59 (d, J=7.8 Hz, 1H), 7.38 (m, 1H), 7.29 (dd, J=8.4, 7.8 Hz, 1H), 7.01 (d, J=7.8 Hz, 1H), 6.42 (dd, J=16.8, 10.8 Hz, 1H), 6.24 (d, J=16.8 Hz, 1H), 5.74 (d, J=10.8 Hz, 1H), 4.68 (d, J=5.4 Hz, 1H), 4.40 (m, 1H), 4.12 (m, 1H), 3.84 (m, 1H), 3.12 (m, 1H), 2.64 (m, 1H), 2.02 (s, 3H), 1.42-1.92 (m, 4H). MS (ESI) m/z 495 (M+H)+.

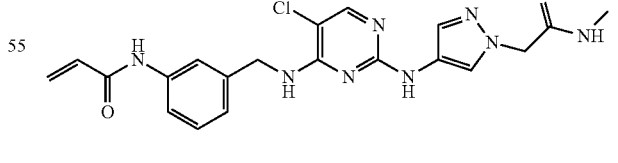

<sup>1</sup>H NMR (600 MHz, DMSO-d6) δ 10.10 (s, 1H), 9.06 (br, 1H), 7.93 (m, 1H), 7.81 (m, 1H), 7.72 (m, 1H), 7.63 (d, J=7.8 Hz, 1H), 7.53 (s, 1H), 7.37 (m, 1H), 7.27 (dd, J=8.4, 7.8 Hz, 1H), 7.05 (d, J=8.4 Hz, 1H), 6.43 (dd, J=16.8, 10.8 Hz, 1H), 6.24 (d, J=16.8 Hz, 1H), 5.73 (d, J=10.8 Hz, 1H), 4.64 (d, J=6.0 Hz, 2H), 4.58 (m, 2H), 2.60 (d, J=4.8 Hz, 3H). MS (ESI) m/z 441 (M+H)+.

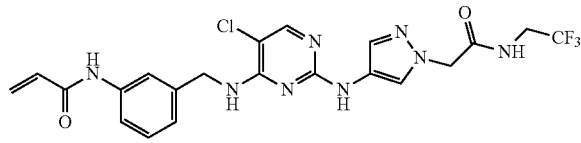 [SMILES: C=CC(=O)Nc1cccc(CNc2nc(Nc3cnn(CC(=O)NCC(F)(F)F)c3)ncc2Cl)c1]

¹H NMR (600 MHz, TFA salt, DMSO-d6) δ 10.10 (s, 1H), 9.63 (br, 1H), 8.74 (t. J=6.6 Hz, 1H), 8.46 (br, 1H), 8.03 (m, 1H), 7.60 (d, J=8.4 Hz, 1H), 7.56 (s, 1H), 7.42 (m, 1H), 7.27 (dd, J=8.4, 7.8 Hz, 1H), 7.03 (d, J=7.8 Hz, 1H), 6.42 (dd, J=16.8, 10.8 Hz, 1H), 6.23 (d, J=16.8 Hz, 1H), 5.73 (d, J=10.8 Hz, 1H), 4.77 (m, 2H), 4.64 (d, J=6.0 Hz, 2H), 3.95 (m, 2H). MS (ESI) m/z 509 (M+H)+.

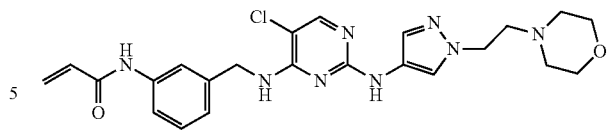

MS (ESI) m/z 483 (M+H)+.

¹H NMR (600 MHz, TFA salt, DMSO-d6) δ 10.13 (s, 1H), 9.65 (br, 1H), 8.48 (br, 1H), 8.04 (m, 1H), 7.59 (s, 2H), 7.37 (s, 1H), 7.38 (m, 1H), 7.28 (dd, J=8.4, 7.8 Hz, 1H), 7.03 (d, J=7.8 Hz, 1H), 6.42 (dd, J=16.8, 10.8 Hz, 1H), 6.24 (d, J=16.8 Hz, 1H), 5.74 (d, J=10.8 Hz, 1H), 4.66 (d, J=5.4 Hz, 2H), 4.09 (m, 2H), 3.54 (m, 2H), 3.16 (s, 3H). MS (ESI) m/z 428 (M+H)+.

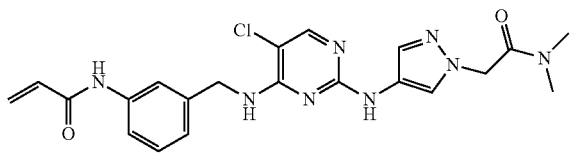 [SMILES: C=CC(=O)Nc1cccc(CNc2nc(Nc3cnn(CC(=O)N(C)C)c3)ncc2Cl)c1]

¹H NMR (600 MHz, DMSO-d6) δ 10.10 (s, 1H), 9.05 (br, 1H), 7.92 (m, 1H), 7.72 (m, 1H), 7.62 (d, J=8.4 Hz, 1H), 7.52 (s, 1H), 7.32 (m, 1H), 7.25 (dd, J=8.4, 7.8 Hz, 1H), 7.03 (d, J=7.8 Hz, 1H), 6.42 (dd, J=16.8, 10.8 Hz, 1H), 6.23 (d, J=16.8 Hz, 1H), 5.73 (d, J=10.8 Hz, 1H), 4.89 (m, 2H), 4.62 (d, J=5.4 Hz, 2H), 2.99 (s, 3H), 2.83 (s, 3H). MS (ESI) m/z 455 (M+H)+.

¹H NMR (600 MHz, DMSO-d6) δ 10.10 (s, 1H), 9.04 (br, 1H), 7.92 (s, 1H), 7.69 (m, 1H), 7.62 (d, J=8.4 Hz, 1H), 7.52 (s, 1H), 7.38 (m, 1H), 7.26 (dd, J=8.4, 7.8 Hz, 1H), 7.03 (d, J=7.8 Hz, 1H), 6.42 (dd, J=16.8, 10.8 Hz, 1H), 6.23 (d, J=16.8 Hz, 1H), 5.72 (d, J=10.8 Hz, 1H), 4.93 (m, 2H), 4.62 (d, J=5.4 Hz, 2H), 3.57 (m, 4H), 3.46 (m, 2H), 3.42 (m, 2H). MS (ESI) m/z 497 (M+H)+.

¹H NMR (600 MHz, TFA salt, DMSO-d6) δ 10.11 (s, 1H), 9.02 (br, 1H), 7.92 (s, 1H), 7.70 (m, 1H), 7.62 (d, J=8.4 Hz, 1H), 7.55 (s, 1H), 7.32 (m, 1H), 7.28 (dd, J=8.4, 7.8 Hz, 1H), 7.04 (d, J=7.8 Hz, 1H), 6.42 (dd, J=16.8, 10.8 Hz, 1H), 6.24 (d, J=16.8 Hz, 1H), 5.73 (d, J=10.8 Hz, 1H), 4.64 (d, J=5.4 Hz, 2H), 4.04 (m, 2H), 3.57 (m, 2H), 3.35 (m, 2H), 1.04 (t, J=7.2 Hz, 1H). MS (ESI) m/z 442 (M+H)+.

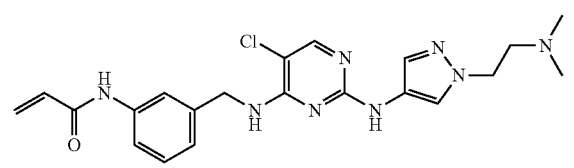 [SMILES: C=CC(=O)Nc1cccc(CNc2nc(Nc3cnn(CCN(C)C)c3)ncc2Cl)c1]

¹H NMR (600 MHz, TFA salt, DMSO-d6) δ 10.15 (s, 1H), 9.39 (br, 1H), 8.01 (br, 1H), 7.60 (m, 1H), 7.59 (s, 1H), 7.50 (m, 1H), 7.38 (m, 1H), 7.30 (dd, J=8.4, 7.8 Hz, 1H), 7.06 (d, J=7.8 Hz, 1H), 6.43 (dd, J=16.8, 10.8 Hz, 1H), 6.24 (d, J=16.8 Hz, 1H), 5.75 (d, J=10.8 Hz, 1H), 4.67 (m, 1H), 4.38 (m, 2H), 3.48 (m, 2H), 2.77 (s, 6H). MS (ESI) m/z 441 (M+H)+.

¹H NMR (600 MHz, TFA salt, DMSO-d6) δ 10.12 (s, 1H), 9.60 (br, 1H), 8.46 (br, 1H), 8.03 (m, 1H), 7.60 (d, J=8.4 Hz, 1H), 7.59 (s, 1H), 7.38 (m, 1H), 7.29 (dd, J=8.4, 7.8 Hz, 1H), 7.04 (d, J=7.8 Hz, 1H), 6.42 (dd, J=16.8, 10.8 Hz, 1H), 6.24 (d, J=16.8 Hz, 1H), 5.74 (d, J=10.8 Hz, 1H), 4.66 (d, J=6.0 Hz, 2H), 4.05 (m, 2H), 3.58 (m, 2H), 3.44 (m, 1H), 1.00 (d, J=6.0 Hz, 1H). MS (ESI) m/z 456 (M+H)+.

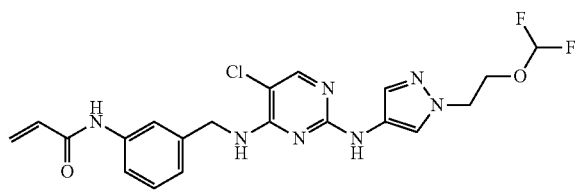 [SMILES: C=CC(=O)Nc1cccc(CNc2nc(Nc3cnn(CCOC(F)F)c3)ncc2Cl)c1]

¹H NMR (600 MHz, TFA salt, DMSO-d6) δ 10.13 (s, 1H), 9.63 (br, 1H), 8.47 (br, 1H), 8.04 (m, 1H), 7.59 (s, 1H), 7.58 (d, J=8.4 Hz, 1H), 7.42 (m, 1H), 7.28 (dd, J=8.4, 7.8 Hz, 1H), 7.04 (d, J=7.8 Hz, 1H), 6.42 (dd, J=16.8, 10.8 Hz, 1H), 6.24 (d, J=16.8 Hz, 1H), 5.74 (d, J=10.8 Hz, 1H), 4.66 (d, J=6.0 Hz, 2H), 4.21 (m, 2H), 4.08 (m, 2H), 3.44 (m, 1H), 1.00 (d, J=6.0 Hz, 1H). MS (ESI) m/z 464 (M+H)+.

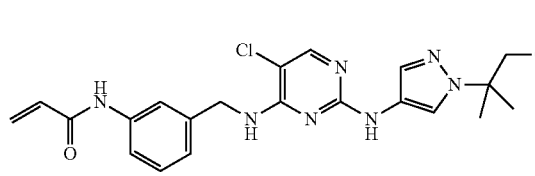

¹H NMR (600 MHz, TFA salt, DMSO-d6) δ 10.12 (s, 1H), 9.66 (br, 1H), 8.51 (br, 1H), 8.06 (s, 1H), 7.78 (s, 1H), 7.60 (d, J=7.8 Hz, 1H), 7.59 (s, 1H), 7.42 (s, 1H), 7.27 (dd, J=8.4, 7.8 Hz, 1H), 7.01 (d, J=7.8 Hz, 1H), 6.42 (dd, J=16.8, 10.8 Hz, 1H), 6.24 (d, J=16.8 Hz, 1H), 5.74 (d, J=10.8 Hz, 1H), 4.69 (m, 2H), 3.78 (m, 2H), 3.10 (s, 3H), 1.31 (m, 6H). MS (ESI) m/z 456 (M+H)+.

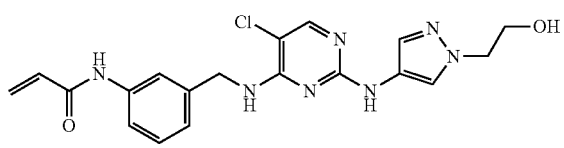 [SMILES: C=CC(=O)Nc1cccc(CNc2nc(Nc3cnn(CCO)c3)ncc2Cl)c1]

¹H NMR (600 MHz, TFA salt, DMSO-d6) 10.12 (s, 1H), 9.60 (br, 1H), 8.44 (br, 1H), 8.02 (s, 1H), 7.59 (d, J=7.8 Hz, 1H), 7.57 (s, 1H), 7.38 (s, 1H), 7.29 (dd, J=8.4, 7.8 Hz, 1H), 7.05 (d, J=7.8 Hz, 1H), 6.42 (dd, J=16.8, 10.8 Hz, 1H), 6.24 (d, J=16.8 Hz, 1H), 5.73 (d, J=10.8 Hz, 1H), 4.66 (d, J=5.9 Hz, 1H), 3.99 (m, 2H), 3.63 (m, 2H). MS (ESI) m/z 414 (M+H)+.

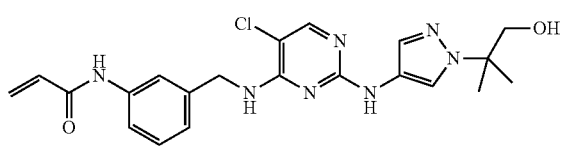 [SMILES: C=CC(=O)Nc1cccc(CNc2nc(Nc3cnn(C(C)(C)CO)c3)ncc2Cl)c1]

¹H NMR (600 MHz, DMSO-d6) δ 10.11 (s, 1H), 9.02 (br, 1H), 7.92 (s, 1H), 7.67 (m, 1H), 7.60 (d, J=7.8 Hz, 1H), 7.55 (s, 1H), 7.35 (m, 1H), 7.27 (dd, J=8.4, 7.8 Hz, 1H), 7.04 (d, J=7.8 Hz, 1H), 6.42 (dd, J=16.8, 10.8 Hz, 1H), 6.24 (d, J=16.8 Hz, 1H), 5.73 (d, J=10.8 Hz, 1H), 4.63 (d, J=5.4 Hz, 1H), 4.59 (s, 1H), 3.82 (m, 2H), 0.99 (s, 6H). MS (ESI) m/z 442 (M+H)+.

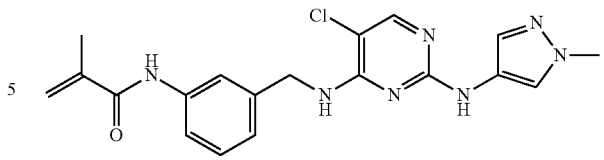

¹H NMR (600 MHz, TFA salt, DMSO-d6) δ 9.77 (s, 1H), 9.59 (br, 1H), 8.38 (br, 1H), 8.02 (s, 1H), 7.65 (s, 1H), 7.56 (d, J=8.4 Hz, 1H), 7.37 (m, 1H), 7.26 (dd, J=8.4, 7.8 Hz, 1H), 7.02 (d, J=7.8 Hz, 1H), 5.76 (s, 1H), 5.49 (s, 1H), 4.65 (d, J=5.4 Hz, 2H), 4.10 (br, 2H), 3.55 (br, 2H), 3.16 (s, 3H), 1.93 (s, 3H). MS (ESI) m/z 398 (M+H)+.

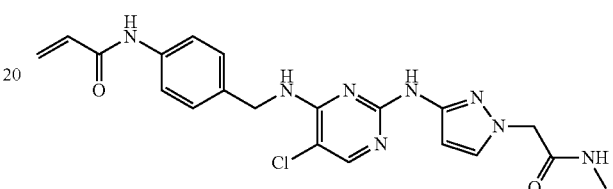

¹H NMR (600 MHz, DMSO-d6) δ 10.08 (s, 1H), 9.05 (br, 1H), 7.91 (s, 1H), 7.80 (m, 1H), 7.65 (m, 1H), 7.60 (d, J=7.8 Hz, 2H), 7.40 (m, 1H), 7.28 (d, J=8.4 Hz, 2H), 6.41 (dd, J=16.8, 10.8 Hz, 1H), 6.23 (d, J=16.8 Hz, 1H), 5.73 (d, J=10.8 Hz, 1H), 4.62 (s, 2H), 4.58 (d, J=5.4 Hz, 2H), 2.60 (d, J=4.8 Hz, 3H). MS (ESI) m/z 441 (M+H)+.

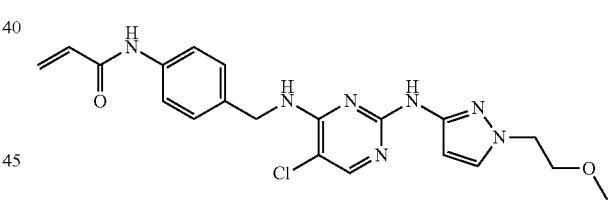

¹H NMR (600 MHz, DMSO-d6) δ 10.12 (s, 1H), 9.63 (br, 1H), 8.48 (br, 1H), 8.02 (m, 1H), 7.65 (m, 1H), 7.62 (d, J=8.4 Hz, 2H), 7.41 (m, 1H), 7.28 (d, J=7.8 Hz, 2H), 6.42 (dd, J=16.8, 10.8 Hz, 1H), 6.24 (d, J=16.8 Hz, 1H), 5.74 (d, J=10.8 Hz, 1H), 4.62 (m, 2H), 4.14 (m, 2H), 3.58 (m, 2H), 3.18 (s, 3H). MS (ESI) m/z 428 (M+H)+.

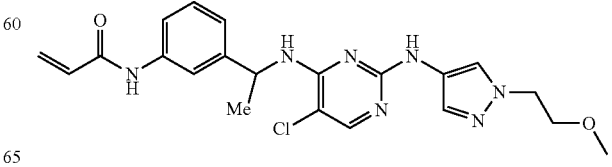

¹H NMR (600 MHz, TFA salt, DMSO-d6) δ 10.13 (s, 1H), 9.57 (br, 1H), 8.01 (m, 1H), 7.69 (s, 1H), 7.63 (m, 1H), 7.55 (d, J=8.4 Hz, 1H), 7.38 (m, 1H), 7.29 (dd, J=8.4, 7.8 Hz, 1H), 7.13 (d, J=7.8 Hz, 1H), 6.43 (dd, J=16.8, 10.8 Hz, 1H), 6.25 (d, J=16.8 Hz, 1H), 5.74 (d, J=10.8 Hz, 1H), 5.37 (m, 1H), 4.16 (m, 2H), 3.61 (m, 2H), 3.19 (s, 3H), 1.58 (d, J=7.8 Hz, 3H). MS (ESI) m/z 442 (M+H)+.

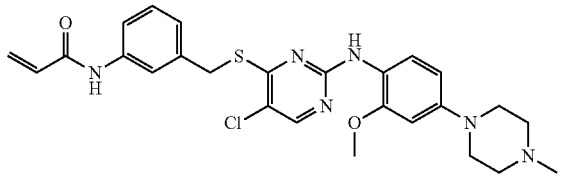 [SMILES: C=CC(=O)Nc1cccc(CSc2nc(Nc3ccc(N4CCN(C)CC4)cc3OC)ncc2Cl)c1]

¹H NMR (600 MHz, DMSO-d6) δ 10.16 (s, 1H), 8.42 (s, 1H), 8.14 (s, 1H), 7.70 (s, 1H), 7.54 (d, J=7.8 Hz, 1H), 7.38 (d, J=8.4 Hz, 1H), 7.20 (dd, J=7.8, 7.8 Hz, 1H), 6.89 (br, 1H), 6.62 (s, 1H), 6.43 (dd, J=16.8, 10.8 Hz, 1H), 6.42 (s, 1H), 6.24 (d, J=16.8 Hz, 1H), 5.75 (d, J=10.8 Hz, 1H), 4.34 (s, 2H), 3.77 (s, 3H), 3.10 (m, 4H), 2.42 (m, 4H), 2.21 (s, 3H). MS (ESI) m/z 525 (M+H)+.

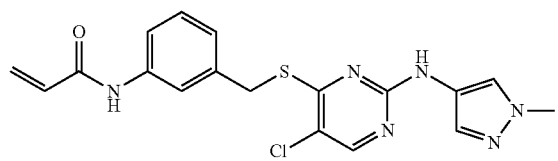 [SMILES: C=CC(=O)Nc1cccc(CSc2nc(Nc3cnn(C)c3)ncc2Cl)c1]

¹H NMR (600 MHz, TFA salt, DMSO-d6) δ 10.17 (s, 1H), 9.60 (s, 1H), 8.22 (s, 1H), 7.76 (m, 1H), 7.60 (m, 1H), 7.58 (m, 1H), 7.75 (s, 1H), 7.28 (dd, J=8.4, 7.8 Hz, 1H), 7.15 (m, 1H), 7.04 (d, J=7.8 Hz, 1H), 6.43 (dd, J=16.8, 10.8 Hz, 1H), 6.26 (d, J=16.8 Hz, 1H), 5.76 (d, J=10.8 Hz, 1H), 4.49 (s, 2H), 3.75 (br, 3H). MS (ESI) m/z 401 (M+H)+.

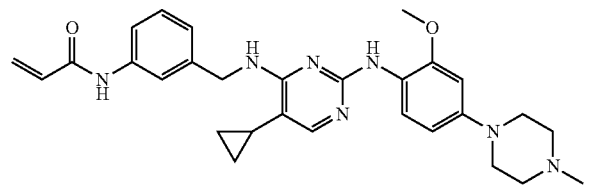 [SMILES: C=CC(=O)Nc1cccc(CNc2nc(Nc3ccc(N4CCN(C)CC4)cc3OC)ncc2C2CC2)c1]

MS (ESI) m/z 514 (M+H)+.

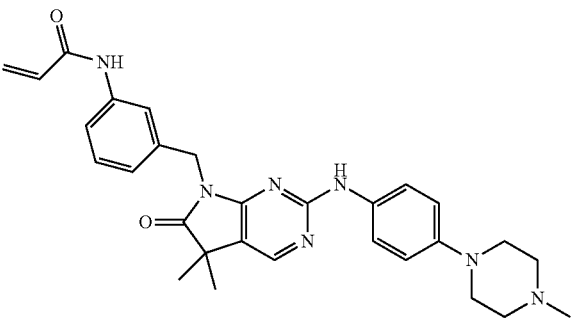 [SMILES: C=CC(=O)Nc1cccc(CN2C(=O)C(C)(C)c3cnc(Nc4ccc(N5CCN(C)CC5)cc4)nc32)c1]

¹H NMR (600 MHz, TFA salt, DMSO-d6) δ 10.18 (s, 1H), 9.72 (br, 1H), 9.55 (br, 1H), 8.21 (s, 1H), 7.65 (s, 1H), 7.54 (d, J=7.8 Hz, 1H), 7.51 (d, J=9.0 Hz, 2H), 7.31 (dd, J=8.4, 7.8 Hz, 2H), 6.99 (d, J=7.8 Hz, 1H), 6.91 (d, J=9.0 Hz, 2H), 6.41 (dd, J=16.8, 10.2 Hz, 1H), 6.24 (d, J=16.8 Hz, 1H), 5.76 (d, J=10.2 Hz, 1H), 4.84 (s, 2H), 3.72 (m, 2H), 3.51 (m, 2H), 3.16 (m, 2H), 2.89 (m, 2H), 2.86 (s, 3H). MS (ESI) m/z 512 (M+H)+.

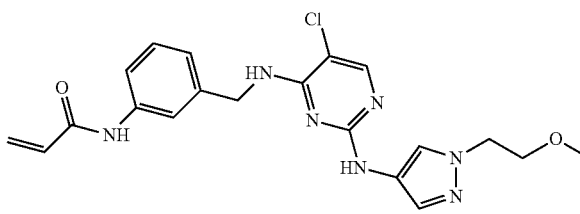

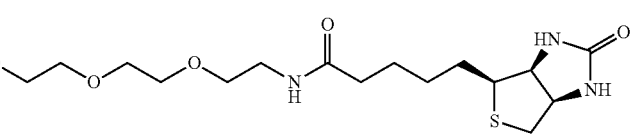

¹H NMR (600 MHz, TFA salt, DMSO-d6) δ 10.12 (s, 1H), 8.06 (br, 1H), 7.80 (m, 1H), 7.59 (s, 2H), 7.38 (m, 1H), 7.28 (dd, J=8.4, 7.8 Hz, 1H), 7.04 (d, J=7.8 Hz, 1H), 6.42 (dd, J=16.8, 10.2 Hz, 1H), 6.41 (m, 1H), 6.35 (br, 1H), 6.24 (d, J=16.8 Hz, 1H), 5.74 (d, J=10.2 Hz, 1H), 4.66 (d, J=5.4 Hz, 2H), 4.29 (m, 1H), 4.10 (m, 2H), 3.64 (m, 2H), 3.45 (m, 6H), 3.36 (d, J=6.0 Hz, 2H), 3.16 (m, 2H), 3.57 (m, 2H), 3.08 (m, 1H), 2.81 (dd, J=12.6, 4.8 Hz, 1H), 2.57 (d, J=12.6 Hz, 1H), 2.05 (t, J=7.5 Hz, 1H), 1.22-1.63 (m, 6H). MS (ESI) m/z 771 (M+H)+.

Example 2. Biological Assays

In Vitro Activity Assays

The in vitro activity of the compounds described herein in inhibiting JAK3 and other kinases were obtained using an INVITROGEN Select Screening assay as known in the art. The enzymatic IC$_{50}$ values determined from this assay are shown in Table 1.

Cell Proliferation Analysis

CellTiter-Glo® Luminescent cell viability assay (Promega) was used to assess cell survival following treatment with the compounds described herein. Cells were seeded into 384 well plates with the EL406 Combination Washer Dispenser (BioTek Instruments, Inc.), and the compounds were injected into the cells culture media with the JANUS Automated Workstation (PerkinElmer Inc.). Cells were treated with a series diluted inhibitors (20 to 0.04 µM) for 72 hours at 37° C. Luminescent measurement is performed using the 2104 Envision® Multilabel Reader (PerkinElmer Inc.). The cell lines employed include Ba/F3 (a murine interleukin-3 dependent pro-B cell line), NKL (a Natural Killer Cell Lymphoma (NKCL) cell line), CMK (an Acute Megakaryoblastic Leukemia (AMKL) cell line). The results are shown in Table 1.

TABLE 1

Exemplary biological assay results of exemplary compounds

| Compound | Enymatic IC$_{50}$ (nM) JAK3 | Ba/F3 IC$_{50}$ (nM) JAK3 | JAK1 | JAK2 | TYK2 | ABL | Cancer cell lines IC$_{50}$ (nM) NKL | CMK |
|---|---|---|---|---|---|---|---|---|
| 1 | 82.6 | | | | | | | |
| 2 | 4.81 | 60.4/ 62.6 | 2959/ 2941 | 3064/ 2650 | 2023/ 1944 | 2913/ 4166 | 19.7 | 8277 |
| 3 | 33.2 | | | | | | | |

TABLE 1-continued

Exemplary biological assay results of exemplary compounds

| Compound | Enzymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 4 | 57.2 | | | | | | | |
| 5 | 5420 | | | | | | | |
| 6 | 390 | | | | | | | |

TABLE 1-continued

Exemplary biological assay results of exemplary compounds

| Compound | Enzymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 7 (Cl-pyrimidine, dimethylamino crotonamide) | 258 | | | | | | | |
| 8 (Br-pyrimidine, acrylamide) | 2.33 | 107 | 2480 | 3005 | 2005 | 3022 | | |
| 9 (F-pyrimidine, acrylamide) | 30.5 | 755 | 11860 | 11870 | 5874 | 8890 | | |

TABLE 1-continued

Exemplary biological assay results of exemplary compounds

| Compound | Enymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 10 | 222 | | | | | | |
| 11 | 2570 | | | | | | |
| 12 | 18 | 307 | 3640 | 2426 | 1836 | 6036 | |

TABLE 1-continued

Exemplary biological assay results of exemplary compounds

| | Compound | Enzymatic IC$_{50}$ (nM) JAK3 | Ba/F3 IC$_{50}$ (nM) | | | | | Cancer cell lines IC$_{50}$ (nM) | |
|---|---|---|---|---|---|---|---|---|---|
| | | | JAK3 | JAK1 | JAK2 | TYK2 | ABL | NKL | CMK |
| 13 | | 0.866<br>AURKA 173 nM<br>AURKB 835 nM | 16.8 | 701 | 874 | 459 | 778 | | |
| 14 | | 3.5<br>AURKA 279 nM<br>AURKB 1310 nM | 30.5 | 1295 | 1866 | 607 | 2521 | | |
| 15 | | 0.689 | 10.6 | 172 | 200 | 144 | 158 | | |

TABLE 1-continued
Exemplary biological assay results of exemplary compounds
| Compound | | Enzymatic IC$_{50}$ (nM) | Ba/F3 IC$_{50}$ (nM) | | | | | Cancer cell lines IC$_{50}$ (nM) | |
|---|---|---|---|---|---|---|---|---|---|
| | | JAK3 | JAK3 | JAK1 | JAK2 | TYK2 | ABL | NKL | CMK |
| 16 | 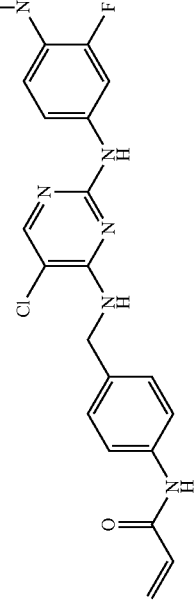 | 2.79 | 17.8 | 379 | 538 | 284 | 453 | | |
| 17 | 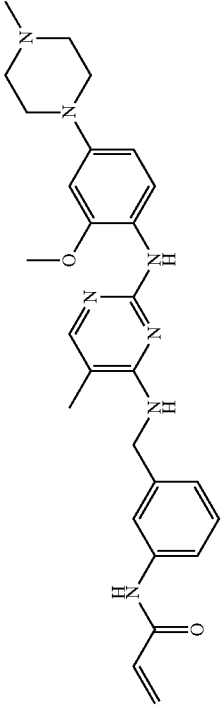 | 30.7 | 1089 | 3822 | 4094 | 3163 | 6185 | | |
| 18 | 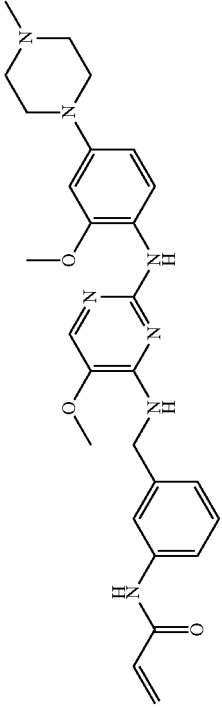 | 81.1 | | | | | | | |

TABLE 1-continued

Exemplary biological assay results of exemplary compounds

| Compound | | Enymatic IC$_{50}$ (nM) | Ba/F3 IC$_{50}$ (nM) | | | | | Cancer cell lines IC$_{50}$ (nM) | |
|---|---|---|---|---|---|---|---|---|---|
| | | JAK3 | JAK3 | JAK1 | JAK2 | TYK2 | ABL | NKL | CMK |
| 19 | (structure) | 1.32 | 6.7 | 2678 | 4284 | 2068 | 13430 | | |
| 20 | (structure) | 2.04 | 15.2 | 9438 | 16010 | 10360 | 17690 | | |
| 21 | (structure) | 0.897 | 14.8 | 821 | 993 | 599 | 1558 | | |

TABLE 1-continued

Exemplary biological assay results of exemplary compounds

| Compound | Enymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 22 | 2.01 | 196 | 378 | 692 | 894 | 1932 | | |
| 23 | 63.8 | 14650 | 18230 | 17240 | 12680 | 26660 | | |
| 24 | 245 | | | | | | | |

TABLE 1-continued

Exemplary biological assay results of exemplary compounds

| Compound | | Enzymatic IC$_{50}$ (nM) JAK3 | Ba/F3 IC$_{50}$ (nM) | | | | | Cancer cell lines IC$_{50}$ (nM) | |
|---|---|---|---|---|---|---|---|---|---|
| | | | JAK3 | JAK1 | JAK2 | TYK2 | ABL | NKL | CMK |
| 25 | [structure: N-methylpiperazine-phenyl (with methoxy) - NH - pyridine - NH - CH$_2$ - phenyl - NH - C(O) - CH=CH$_2$] | 15.3 | 246 | 2875 | 2304 | 1529 | 4555 | | |
| 26 | [structure: morpholine-phenyl - NH - chloropyrimidine - NH - CH$_2$ - phenyl - NH - C(O) - CH=CH$_2$] | 0.866 AURK A 173 nM AURK B 835 nM | 16.8 | 701 | 874 | 459 | 778 | | |
| 27 | [structure: morpholine-fluorophenyl - NH - chloropyrimidine - NH - CH$_2$ - phenyl - NH - C(O) - CH=CH$_2$] | 3.5 AURK A 279 nM AURK B 1310 nM | 30.5 | 1295 | 1866 | 607 | 2521 | | |

TABLE 1-continued

Exemplary biological assay results of exemplary compounds

| Compound | Enymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 28 [structure] | 0.689 | 10.6 | 172 | 200 | 144 | 158 | | |
| 29 [structure] | 2.79 | 17.8 | 379 | 538 | 284 | 453 | | |
| 30 [structure] | 0.94 | 144 | 11640 | 8398 | 3618 | 19170 | | |

TABLE 1-continued

Exemplary biological assay results of exemplary compounds

| Compound | Enymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 31 | 7.01 | 144 | 25120 | 8398 | 5948 | 4922 | | |
| 32 | 45.4 | 2618 | 12820 | 17050 | 11500 | 22410 | | |
| 33 | 9.88 | 1252 | 24250 | 30360 | 18500 | ~34090 | | |

TABLE 1-continued
Exemplary biological assay results of exemplary compounds
| Compound | Enzymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 34 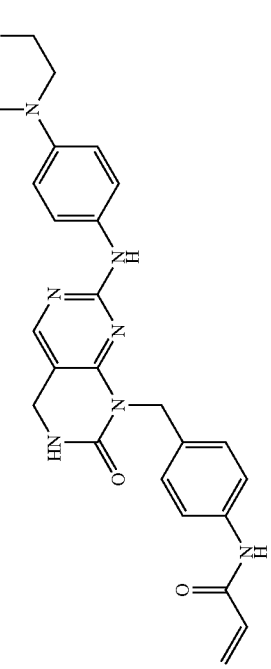 | 1.21 | 576 | >10000 | 30130 | 29550 | 29220 | | |
| 35 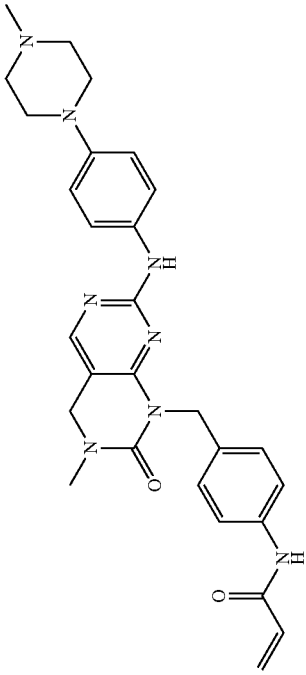 | 30.4 | 880 | 87570 | 14650 | 10130 | 8840 | | |

TABLE 1-continued

Exemplary biological assay results of exemplary compounds

| Compound | Enymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 36 | 0.7 | 8.1 | 1315 | 2733 | 4458 | 2989 | | |
| 37 | 0.6 | 10.4 | 2043 | 3878 | 1429 | 4055 | | |
| 38 | 27.9 | 3309 | 41910 | 719000 | 78050 | | | |
| 39 | 0.6 | 30.8 | 3103 | 8682 | 1574 | 3854 | | |

TABLE 1-continued
Exemplary biological assay results of exemplary compounds
| Compound | | Enzymatic IC$_{50}$ (nM) | Ba/F3 IC$_{50}$ (nM) | | | | | Cancer cell lines IC$_{50}$ (nM) | |
|---|---|---|---|---|---|---|---|---|---|
| | | JAK3 | JAK3 | JAK1 | JAK2 | TYK2 | ABL | NKL | CMK |
| 40 | 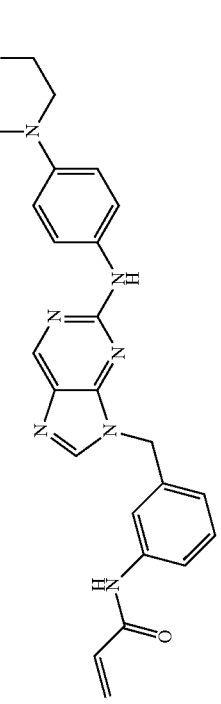 | 101 | 4749 | 26720 | 128000 | 24630 | | | |
| 41 | | 6.6 | 439 | 5034 | 6039 | 4215 | 6782 | | |
| 42 | | 499 | 2562 | 4268 | 5975 | 3212 | 5098 | | |

TABLE 1-continued

Exemplary biological assay results of exemplary compounds

| Compound | Enymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 43 | 20.9 | 400 | 13960 | >50000 | 50060 | >50000 | | |
| 44 | 2720 | 6232 | 7890 | 5306 | 4950 | 6671 | | |
| 45 | 100 | | | | | | | |

TABLE 1-continued

Exemplary biological assay results of exemplary compounds

| Compound | | Enzymatic IC$_{50}$ (nM) | Ba/F3 IC$_{50}$ (nM) | | | | | Cancer cell lines IC$_{50}$ (nM) | |
|---|---|---|---|---|---|---|---|---|---|
| | | JAK3 | JAK3 | JAK1 | JAK2 | TYK2 | ABL | NKL | CMK |
| 46 | *[structure]* | 4.4 | 102 | 3624 | 2326 | 1598 | 4123 | | |
| 47 | *[structure]* | 5.2 | 478 | >50000 | >50000 | >50000 | >50000 | | |
| 48 | *[structure]* | 8040 | >50000 | 56370 | 18070 | 8852 | >50000 | | |
| 49 | *[structure]* | 0.66 | 112 | 3490 | 4238 | 3943 | 5538 | | |

TABLE 1-continued

Exemplary biological assay results of exemplary compounds

| Compound | Enymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 50 | 20.5 | 100 | >50000 | >50000 | >50000 | >50000 | | |
| 51 | 1.25 | 33 | 2854 | 3870 | 1122 | 11040 | | |
| 52 | 20 | 75 | 1059 | 2685 | 992 | 3470 | | |
| 53 | 4.6 | 125 | 3182 | 5981 | 2569 | 7448 | | |

TABLE 1-continued

Exemplary biological assay results of exemplary compounds

| Compound | Enymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 54 | 12.4 | 433 | 2324 | 3101 | 1318 | 2848 | | |
| 55 | 170 | | | | | | | |
| 56 | 46 | 1305 | 3871 | 6175 | 3756 | 5257 | | |

TABLE 1-continued

Exemplary biological assay results of exemplary compounds

| Compound | Enzymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |

| 57 | 170 | | | | | | | |
| 58 | | 11 | 513 | 1013 | 1320 | 2077 | | |
| 59 | 1.4 | 29 | 3287 | 2910 | 1542 | 4494 | | |

TABLE 1-continued

Exemplary biological assay results of exemplary compounds

| Compound | | Enzymatic IC$_{50}$ (nM) | Ba/F3 IC$_{50}$ (nM) | | | | | Cancer cell lines IC$_{50}$ (nM) | |
|---|---|---|---|---|---|---|---|---|---|
| | | JAK3 | JAK3 | JAK1 | JAK2 | TYK2 | ABL | NKL | CMK |
| 60 | [structure] | 20 | 99 | >50000 | >50000 | >50000 | >50000 | | |
| 61 | [structure] | 3.6 | 23 | 2004 | 3290 | 4666 | 8769 | | |
| 62 | [structure] | 7.4 | 35 | 2484 | 4321 | 4702 | 2326 | | |

TABLE 1-continued

Exemplary biological assay results of exemplary compounds

| Compound | Enymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 63 | 6.2 | 54 | 2346 | 2916 | 4171 | 5477 | | |
| 64 | 24 | 5452 | 17440 | 30770 | 17300 | 27680 | | |
| 65 | 99 | 9802 | 20330 | 30780 | 24780 | 17270 | | |
| 66 | 1600 | 12430 | 6792 | 9695 | 8170 | 11150 | | |

TABLE 1-continued

Exemplary biological assay results of exemplary compounds

| Compound | | Enzymatic IC$_{50}$ (nM) JAK3 | Ba/F3 IC$_{50}$ (nM) | | | | | Cancer cell lines IC$_{50}$ (nM) | |
|---|---|---|---|---|---|---|---|---|---|
| | | | JAK3 | JAK1 | JAK2 | TYK2 | ABL | NKL | CMK |
| 67 | (structure) | 1.7 | 109 | 5198 | 8487 | 6502 | 11030 | | |
| 68 | (structure) | 2.9 | 114 | 2792 | 3993 | 2492 | 3998 | | |
| 69 | (structure) | 1.4 | 21 | 1686 | 3290 | 994 | 3136 | | |
| 70 | (structure) | <0.5 | 11 | 1780 | 3164 | 759 | 4374 | | |
| 71 | (structure) | 0.7 | 16 | 2143 | 2762 | 5581 | 11820 | | |

TABLE 1-continued

Exemplary biological assay results of exemplary compounds

| Compound | Enymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 72 | <0.5 | 110 | 3506 | 27680 | 17260 | 21820 | | |
| 73 | <0.5 | 143 | >50000 | >50000 | >50000 | | | |
| 74 | 0.5 | 110 | 3506 | 27680 | 17260 | 21820 | | |
| 75 | 1.1 | 67 | 4553 | 6223 | 3043 | 10610 | | |

TABLE 1-continued
Exemplary biological assay results of exemplary compounds
| Compound | Enymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 76 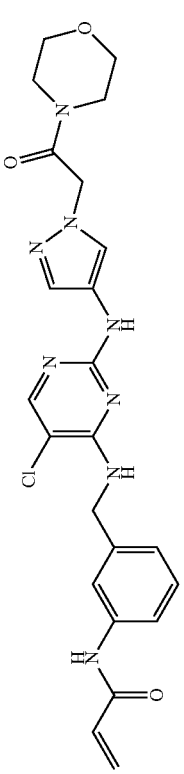 | 0.6 | 119 | 8223 | 19500 | 4998 | 18660 | | |
| 77 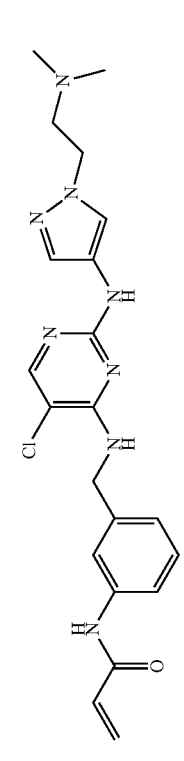 | <0.5 | 17 | 3129 | 6960 | 1887 | 5398 | | |
| 78 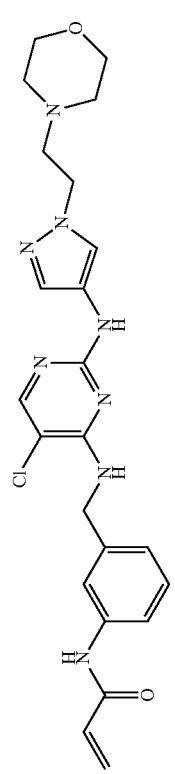 | <0.5 | 24 | 3462 | 6439 | 2227 | 6830 | | |
| 79 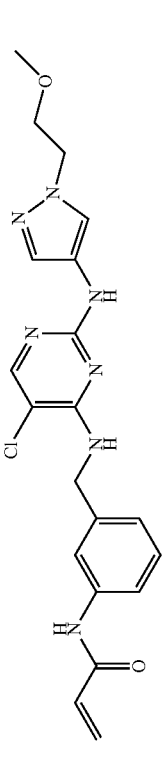 | <0.5 | 14 | 7346 | 32520 | 25680 | 25260 | | |
| 80 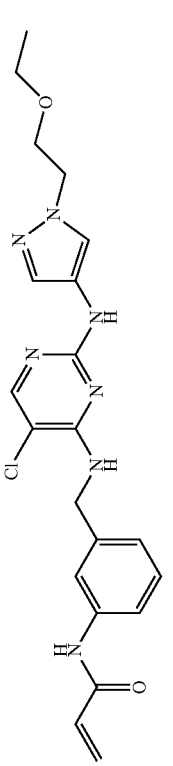 | <0.5 | 21 | 24680 | 6660 | 1342 | 13070 | | |

TABLE 1-continued

Exemplary biological assay results of exemplary compounds

| Compound | Enymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 81 | <0.5 | 36 | 2720 | 11580 | 1130 | 18070 | | |
| 82 | 0.7 | 68 | 32890 | >50000 | >50000 | >50000 | | |
| 83 | 0.6 | 124 | 3065 | 9098 | 3227 | 5973 | | |
| 84 | <0.5 | 29 | 2441 | 5164 | 4416 | 8718 | | |

TABLE 1-continued

Exemplary biological assay results of exemplary compounds

| | | Enymatic IC$_{50}$ (nM) | Ba/F3 IC$_{50}$ (nM) | | | | | Cancer cell lines IC$_{50}$ (nM) | |
|---|---|---|---|---|---|---|---|---|---|
| | Compound | JAK3 | JAK3 | JAK1 | JAK2 | TYK2 | ABL | NKL | CMK |
| 85 | | 0.6 | 92 | 5744 | 7287 | 4090 | 8369 | | |
| 86 | | 7.8 | 947 | 3825 | 9824 | 15090 | 23780 | | |
| 87 | | 2.0 | 465 | 7422 | 10120 | 6857 | 7811 | | |
| 88 | | 1.3 | 131 | 3117 | 5575 | 3549 | 3021 | | |

TABLE 1-continued

Exemplary biological assay results of exemplary compounds

| Compound | Enzymatic IC$_{50}$ (nM) | Ba/F3 IC$_{50}$ (nM) | | | | Cancer cell lines IC$_{50}$ (nM) | |
|---|---|---|---|---|---|---|---|
| | JAK3 | JAK3 | JAK1 | JAK2 | TYK2 | ABL | NKL | CMK |
| 89 | 1.6 | 57 | 3173 | 7731 | 5193 | 9942 | | |
| 90 | 12 | 433 | 2324 | 3101 | 1318 | 2848 | | |
| 91 | 220 | | | | | | | |

TABLE 1-continued

Exemplary biological assay results of exemplary compounds

| Compound | Enzymatic IC$_{50}$ (nM) | Ba/F3 IC$_{50}$ (nM) | | | | | Cancer cell lines IC$_{50}$ (nM) | |
|---|---|---|---|---|---|---|---|---|
| | JAK3 | JAK3 | JAK1 | JAK2 | TYK2 | ABL | NKL | CMK |
| 92 | 17 | 210 | 3457 | 4047 | 3327 | 2883 | | |
| 93 | 2.3 | 1266 | 18720 | >50000 | 15430 | >50000 | | |

The results show that compounds of the present disclosure, such as compound 2, are highly selective inhibitors of JAK3. For example, compound 2 showed a high degree of specificity for JAK3 relative to other JAK isoforms ($IC_{50}$ for JAK1=896 nM, JAK2=1050 nM, JAK3=4.8 nM). The selectivity of compound 2 is further confirmed on Ba/F3 proliferation assays ($IC_{50}$ for JAK1=2959 nm, JAK2=3064 nM, JAK3=60 nM). Compound 2 has a high aqueous solubility (>250 μM at 25° C.), good metabolic stability in vitro when incubated with human liver microsomes (clearance $Cl_i$=<0.5 mL/min/g), and reasonable pharmacokinetics in mouse (intravenous dose at 1 mg/kg: clearance was low ($Cl_b$=20 ml/min/kg), $V_{dss}$ was moderate (1.2 L/kg), and half-life was moderate (1.2 hours); PO dose at 10 mg/kg: $C_{max}$=294 ng/mL, $T_{max}$=2 hours, bioavailability=23%).

Profiling of compound 2 on primary immune cells has shown that it blocks IL-4 signaling (which is JAK3 dependent) but has no effect on signaling by cytokines that act via JAK2 or JAK1/Tyk2. Compound 2 also has shown strong anti-proliferative potency ($EC_{50}$=20 nM) on Natural Killer Cell Lymphoma (NKCL) cell line NKL which is IL-2 dependent (JAK3 is downstream to IL-2). Compound 2 doesn't shown anti-proliferative potency on Acute Megakaryoblastic Leukemia (AMKL) cell line CML, which was identified with activating mutation A572V of JAK3. JAK1/JAK3 heterodimer was reported to play imported roles in many cancer cells as in CMK, which was more likely to be dependent on both JAK1 and JAK3 kinase activities.

The results also show that compounds described herein have the ability to selectively inhibit the gatekeeper mutant (T790M) of EGFR. For example, compound 2 showed strong anti-proliferative potency on EGFR (T790M) dependent Ba/F3 (inhibition >90% at 200 nM).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

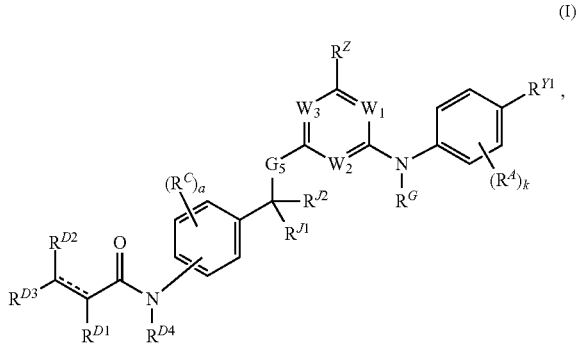

or a pharmaceutically acceptable salt thereof,
wherein:
$W_1$ is N, $W_2$ is N and $W_3$ is $CR^X$, or $W_1$ is N, $W_2$ is CH, and $W_3$ is N;
$R^{Y1}$ is a group of formula

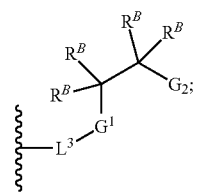

L³ is a bond or a linker selected from the group consisting of substituted and unsubstituted $C_{1-6}$alkylene, substituted and unsubstituted $C_{2-6}$alkenylene, substituted and unsubstituted $C_{2-6}$alkynylene, substituted and unsubstituted heteroC$_{1-6}$alkylene, substituted and unsubstituted heteroC$_{2-6}$alkenylene, and substituted and unsubstituted heteroC$_{2-6}$alkynylene;

$G_1$ is $NR^{G1a}$ and $G_2$ is $N(R^{G2a})_2$, $OR^{G2a}$, or $C(R^{G2a})_2$; or $G_1$ is $CHR^{G1a}$ and $G_2$ is $N(R^{G2a})_2$, $OR^{G2a}$;

each instance of $R^{G1a}$ and $R^{G2a}$ is independently hydrogen, substituted or unsubstituted alkyl, substituted or unsubstituted hydroxyl, a nitrogen protecting group when attached to a nitrogen atom, or an oxygen protecting group when attached to an oxygen atom, or $R^{G1a}$ and one instance of $R^{G2a}$ are joined to form the group —C(R$^B$)$_2$—C(R$^B$)$_2$—;

==== represents a single or double bond;

each instance of $R^{D1}$, $R^{D2}$, and $R^{D3}$ is independently hydrogen or substituted or unsubstituted alkyl;

$R^{D4}$ is hydrogen, substituted or unsubstituted alkyl, or a nitrogen protecting group;

$G_5$ is O, S, or $NR^E$;

each instance of $R^E$ and $R^G$ is independently hydrogen, substituted or unsubstituted alkyl, or a nitrogen protecting group;

each instance of $R^{J1}$ and $R^{J2}$ is independently hydrogen, halogen, or substituted or unsubstituted alkyl;

each instance of $R^A$ and $R^C$ is independently halogen, substituted or unsubstituted alkyl, substituted or unsubstituted alkenyl, substituted or unsubstituted alkynyl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$;

each instance of $R^B$ is independently hydrogen, halogen, substituted or unsubstituted alkyl, substituted or unsubstituted alkenyl, substituted or unsubstituted alkynyl, —OR$^{A1}$, —N(R$^{A1}$)$_2$, —SR$^{A1}$, —CN, —SCN, —C(=NR$^{A1}$)R$^{A1}$, —C(=NR$^{A1}$)OR$^{A1}$, —C(=NR$^{A1}$)N(R$^{A1}$)$_2$, —C(=O)R$^{A1}$, —C(=O)OR$^{A1}$, —C(=O)N(R$^{A1}$)$_2$, —NO$_2$, —NR$^{A1}$C(=O)R$^{A1}$, —NR$^{A1}$C(=O)OR$^{A1}$, —NR$^{A1}$C(=O)N(R$^{A1}$)$_2$, —OC(=O)R$^{A1}$, —OC(=O)OR$^{A1}$, or —OC(=O)N(R$^{A1}$)$_2$; or two R$^B$ groups attached to the same carbon atom are joined to form a =O group;

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^{A1}$ groups are joined to form a substituted or unsubstituted heterocyclic or substituted or unsubstituted heteroaryl ring;

a and k are each independently 0, 1, or 2, provided when k is 0, then $R^A$ is absent, and when a is 0, then $R^C$ is absent; and each instance of $R^X$ and $R^Z$ is independently hydrogen, halogen, substituted or unsubstituted alkyl, cyclopropyl, —CN, —OR$^{X1}$, or —NHR$^{X1}$, wherein R$^{X1}$ is hydrogen, substituted or unsubstituted alkyl, an oxygen protecting group when attached to an oxygen, or a nitrogen protecting group when attached to a nitrogen, or $R^X$ and $R^Z$ are joined to form a substituted or unsubstituted 5-membered heterocyclic ring, or a ring of formula:

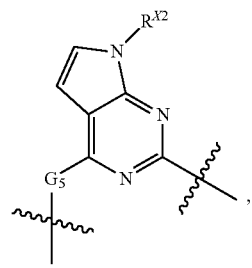

wherein $R^{X2}$ is hydrogen, substituted or unsubstituted alkyl, or a nitrogen protecting group;

or $R^X$ and $R^E$ are joined to form a substituted or unsubstituted 5- to 6-membered heterocyclic ring, or a ring of formula:

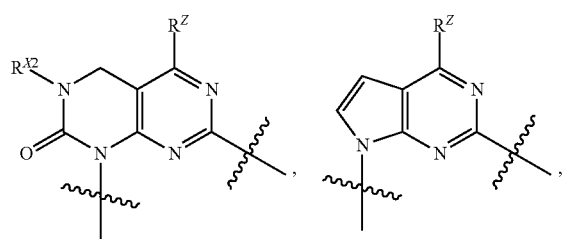

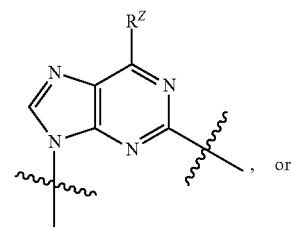, or

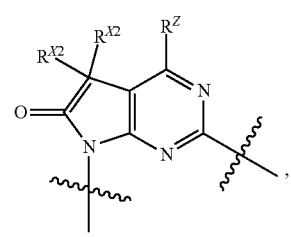, wherein $R^X$ is hydrogen, substituted or unsubstituted alkyl, or a nitrogen protecting group.

2. A compound of Formula (II):

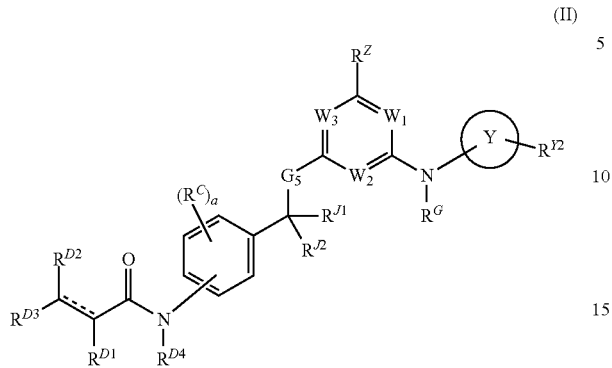

or a pharmaceutically acceptable salt thereof, wherein:

$W_1$ is N, $W_2$ is N and $W_3$ is $CR^X$, or $W_1$ is N, $W_2$ is CH, and $W_3$ is N;

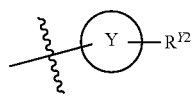

is selected from the group consisting of:

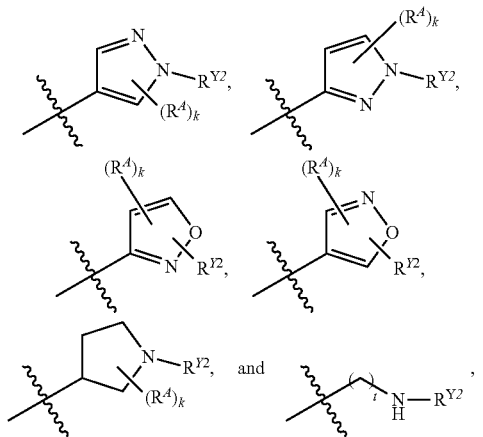

wherein t is 2, 3, 4, 5, or 6;

$R^{Y2}$ is hydrogen, substituted or unsubstituted alkyl, $-C(=O)R^{A2}$, a nitrogen protecting group if attached to a nitrogen atom, or a group of formula

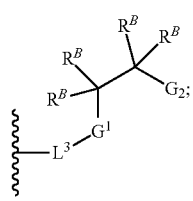

$R^{A2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$L^3$ is a bond or a linker selected from the group consisting of substituted and unsubstituted $C_{1-6}$alkylene, substituted and unsubstituted $C_{2-6}$alkenylene, substituted and unsubstituted $C_{2-6}$alkynylene, substituted and unsubstituted hetero$C_{1-6}$alkylene, substituted and unsubstituted hetero$C_{2-6}$alkenylene, and substituted and unsubstituted hetero$C_{2-6}$alkynylene;

$G_1$ is $NR^{G1a}$ and $G_2$ is $N(R^{G2a})_2$, $OR^{G2a}$, or $C(R^{G2a})_2$; or $G_1$ is $CHR^{G1a}$ and $G_2$ is $N(R^{G2a})_2$, $OR^{G2a}$;

each instance of $R^{G1a}$ and $R^{G2a}$ is independently hydrogen, substituted or unsubstituted alkyl, substituted or unsubstituted hydroxyl, a nitrogen protecting group when attached to a nitrogen atom, or an oxygen protecting group when attached to an oxygen atom, or $R^{G1a}$ and one instance of $R^{G2a}$ are joined to form the group $-C(R^B)_2-C(R^B)_2-$;

=== represents a single or double bond;

each instance of $R^{D1}$, $R^{D2}$, and $R^{D3}$ is independently hydrogen or substituted or unsubstituted alkyl;

$R^{D4}$ is hydrogen, substituted or unsubstituted alkyl, or a nitrogen protecting group;

$G_5$ is O, S, or $NR^E$;

each instance of $R^E$ and $R^G$ is independently hydrogen, substituted or unsubstituted alkyl, or a nitrogen protecting group;

each instance of $R^{J1}$ and $R^{J2}$ is independently hydrogen, halogen, or substituted or unsubstituted alkyl;

each instance of $R^A$ and $R^C$ is independently halogen, substituted or unsubstituted alkyl, substituted or unsubstituted alkenyl, substituted or unsubstituted alkynyl, $-OR^{A1}$, $-N(R^{A1})_2$, $-SR^{A1}$, $-CN$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, or $-OC(=O)N(R^{A1})_2$;

each instance of $R^B$ is independently halogen, substituted or unsubstituted alkyl, substituted or unsubstituted alkenyl, substituted or unsubstituted alkynyl, $-OR^{A1}$, $-N(R^{A1})_2$, $-SR^{A1}$, $-CN$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, or $-OC(=O)N(R^{A1})_2$; or two $R^B$ groups attached to the same carbon atom are joined to form a =O group;

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic or substituted or unsubstituted heteroaryl ring;

a and k are each independently 0, 1, or 2, provided when k is 0, then $R^A$ is absent, and when a is 0, then $R^C$ is absent; and each instance of $R^X$ and $R^Z$ is independently hydrogen, halogen, substituted or unsubstituted alkyl, cyclopropyl, —CN, —$OR^{X1}$, or —$NHR^{X1}$, wherein $R^{X1}$ is hydrogen, substituted or unsubstituted alkyl, an oxygen protecting group when attached to an oxygen, or a nitrogen protecting group when attached to a nitrogen, or $R^X$ and $R^Z$ are joined to form a substituted or unsubstituted 5-membered heterocyclic ring, or a ring of formula:

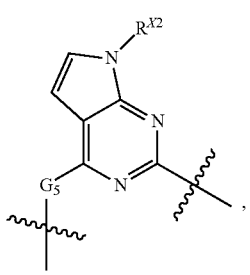

wherein $R^{X2}$ is hydrogen, substituted or unsubstituted alkyl, or a nitrogen protecting group;

or $R^X$ and $R^E$ are joined to form a substituted or unsubstituted 5- to 6-membered heterocyclic ring, or a ring of formula:

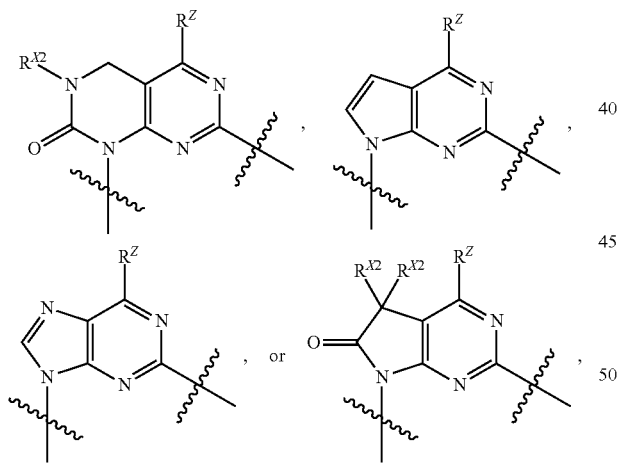

wherein $R^{X2}$ is hydrogen, substituted or unsubstituted alkyl, or a nitrogen protecting group.

3. The compound of claim 1, wherein the group

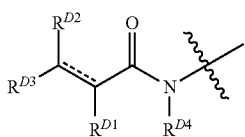

is attached meta to the point of attachment

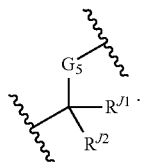

4. The compound of claim 1, wherein the group

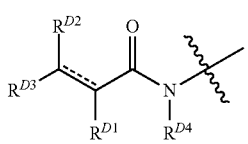

is attached para to the point of attachment

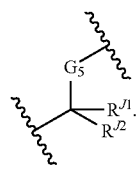

5. The compound of claim 1, wherein the ring system:

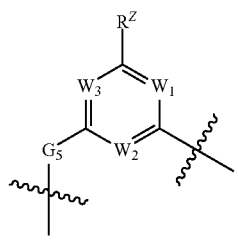

is a bicyclic ring system of formula:

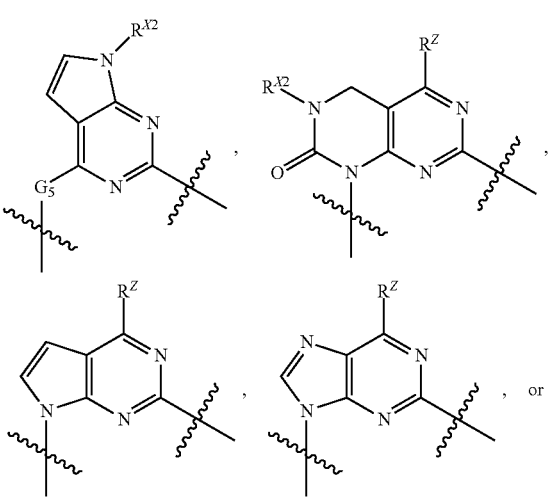

-continued

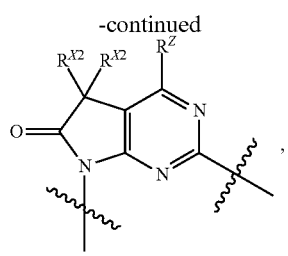

wherein $R^{X2}$ is hydrogen, substituted or unsubstituted alkyl, or a nitrogen protecting group.

6. The compound of claim 1, wherein the ring system:

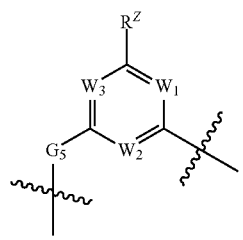

is of the formula:

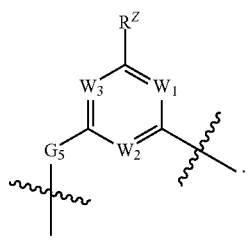

7. The compound of claim 1, wherein the ring system:

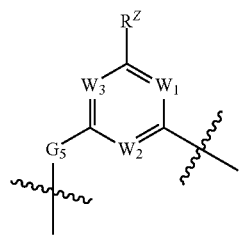

is of the formula:

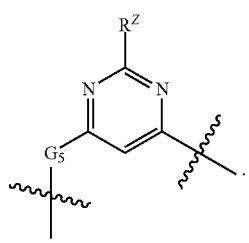

8. The compound of claim 1 of the Formula:

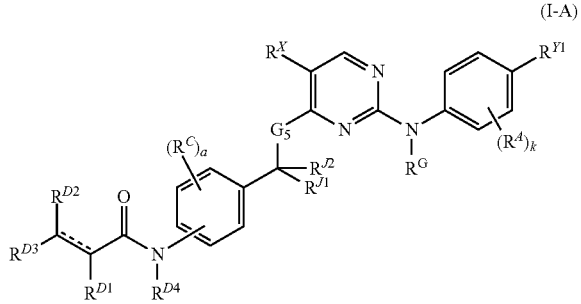

(I-A)

or a pharmaceutically acceptable salt thereof.

9. The compound of claim 1 of the Formula:

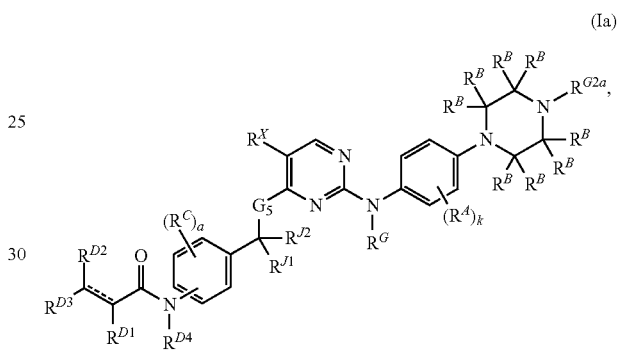

(Ia)

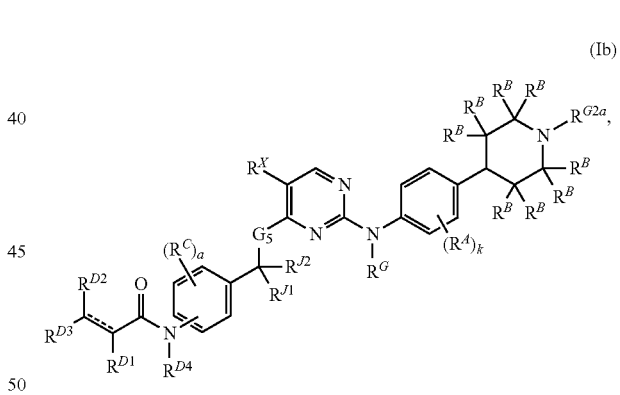

(Ib)

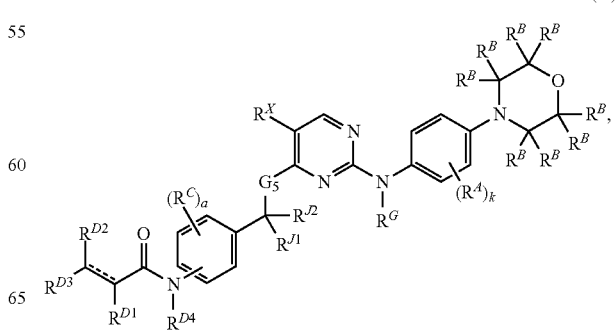

(Ic)

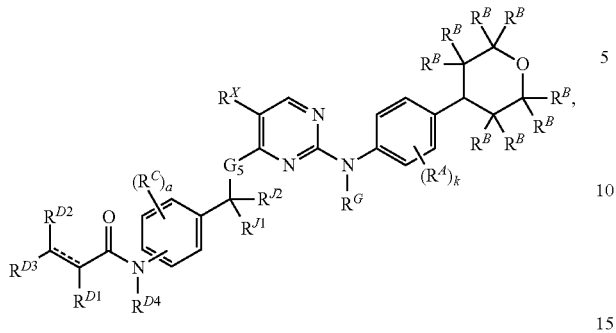
or a pharmaceutically acceptable salt thereof.
10. The compound of claim 1 selected from the group consisting of:
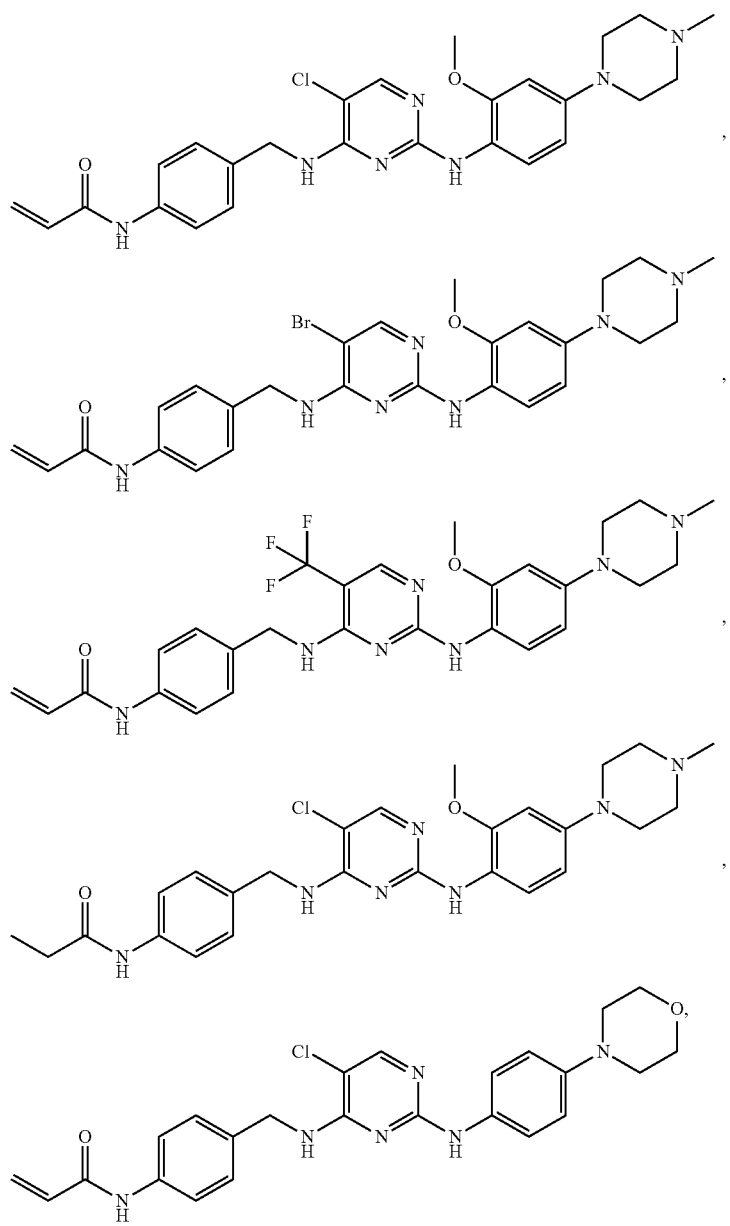

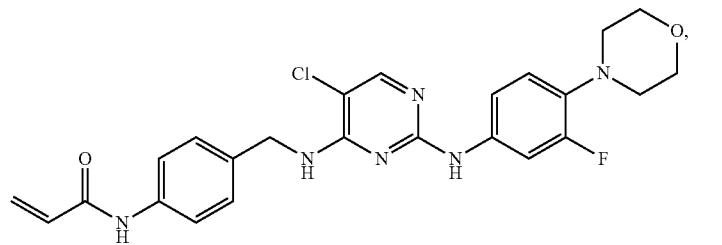
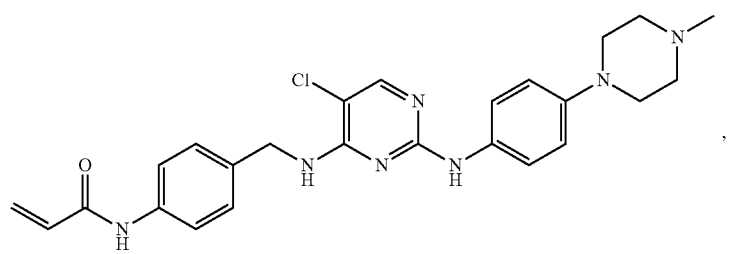
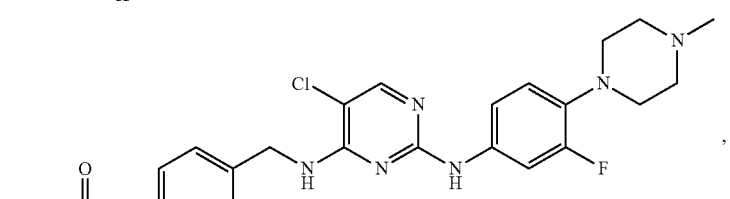
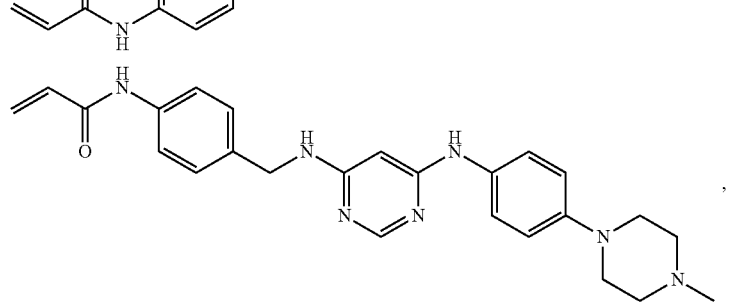
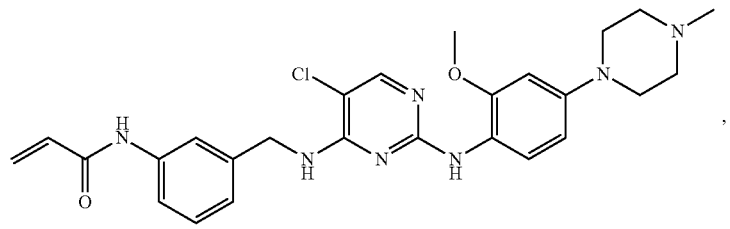
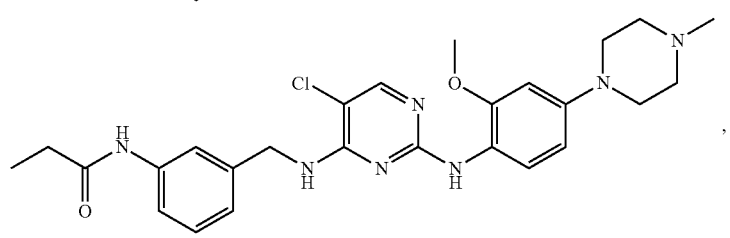
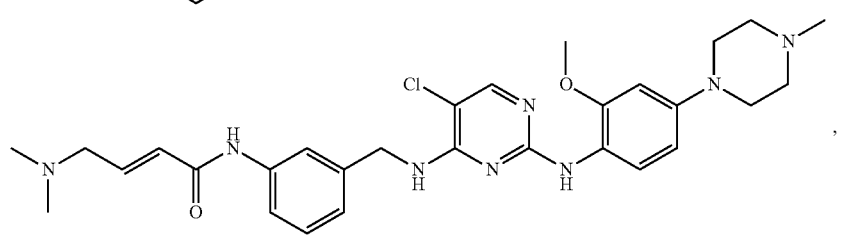

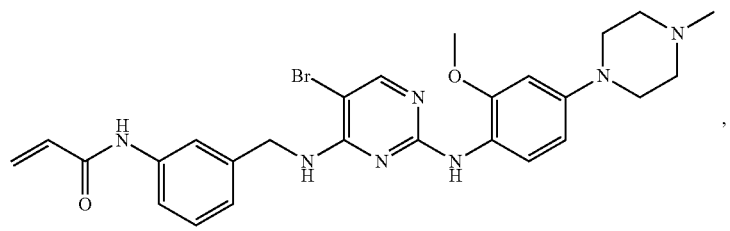,
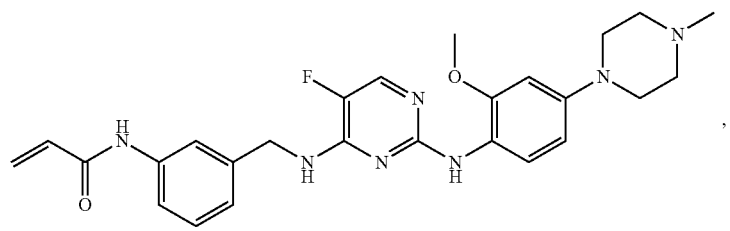,
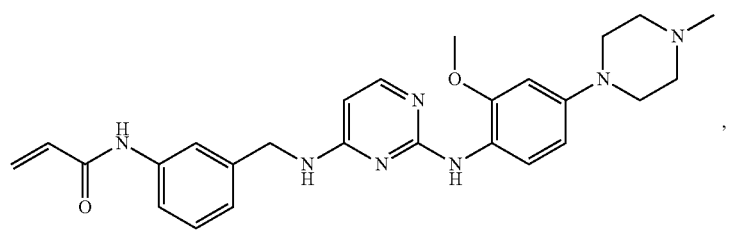,
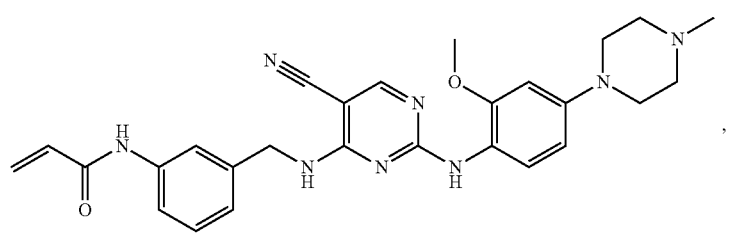,
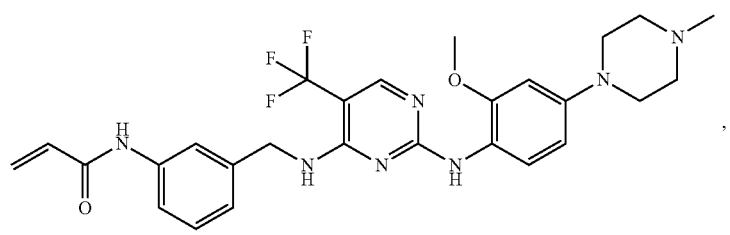,
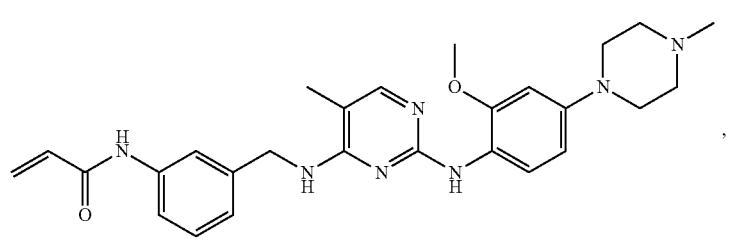,
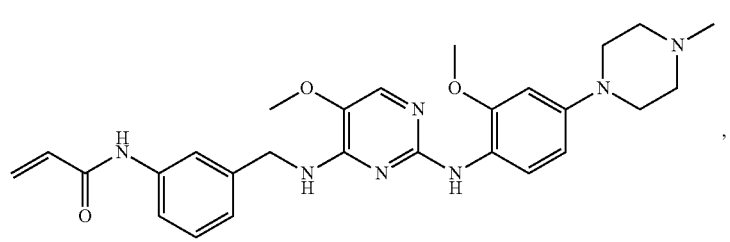,

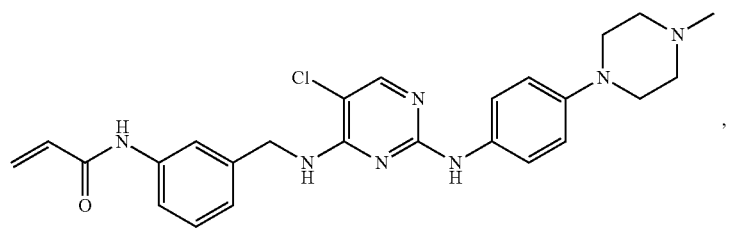,
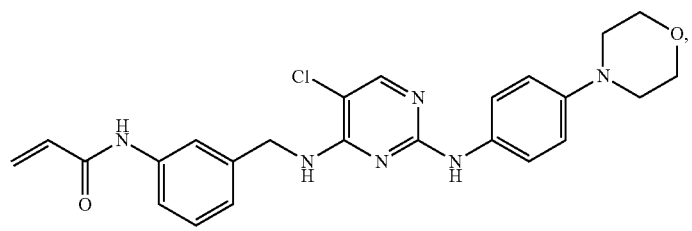,
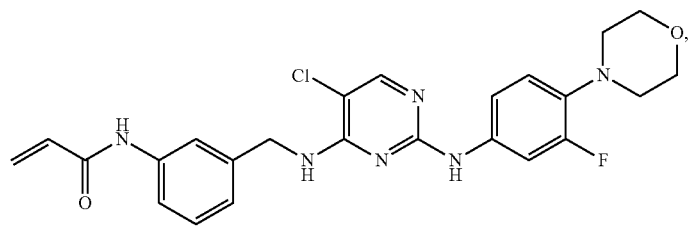,
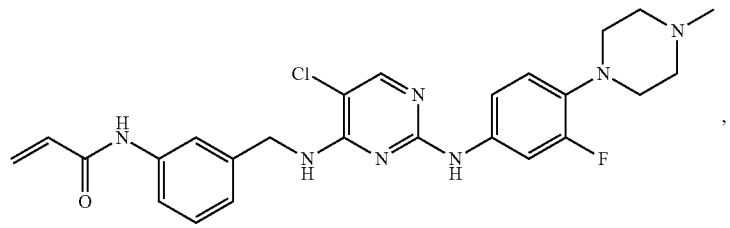,
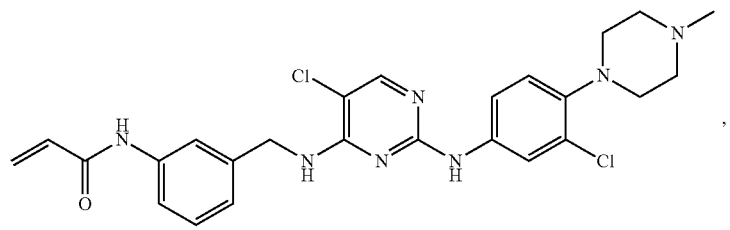,
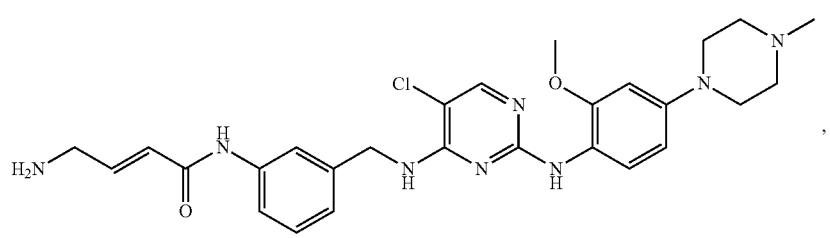,
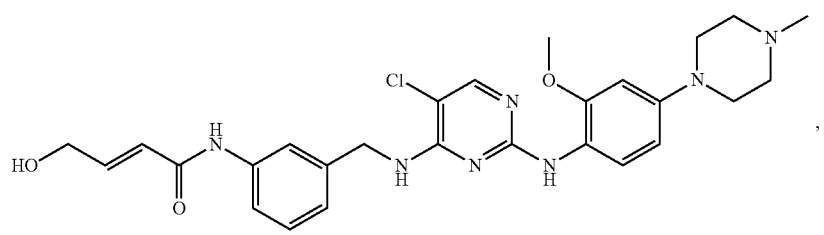,

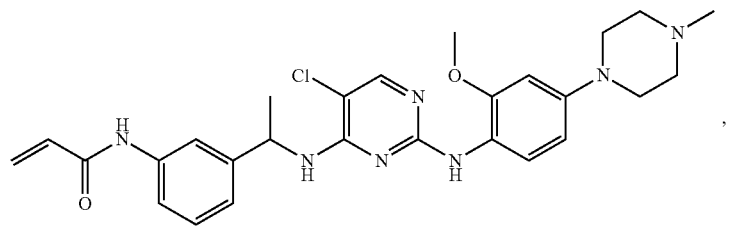,
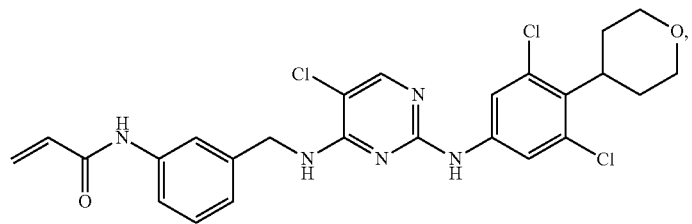,
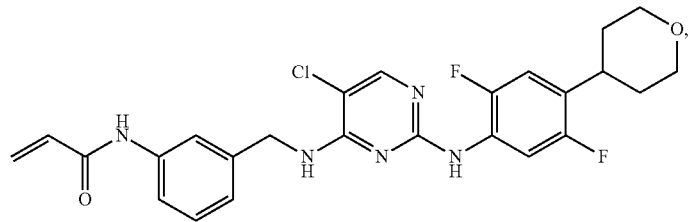,
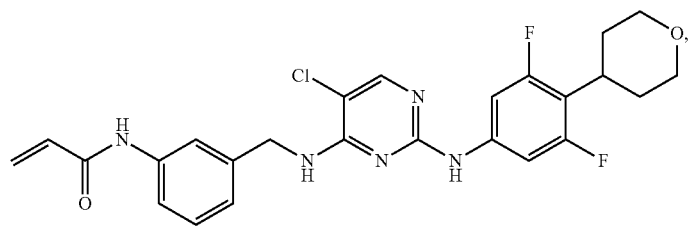,
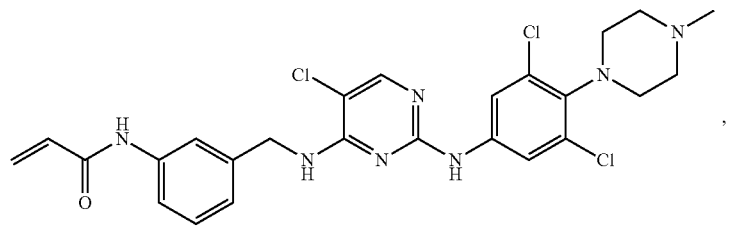,
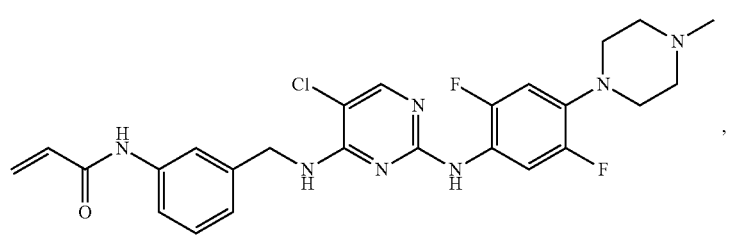,
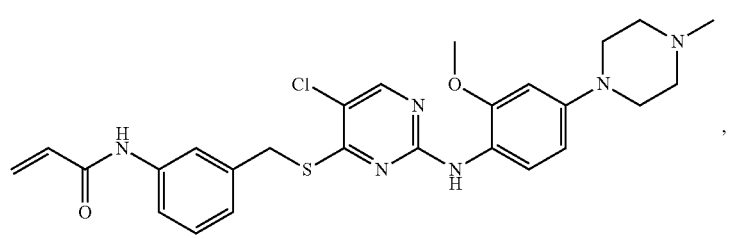,

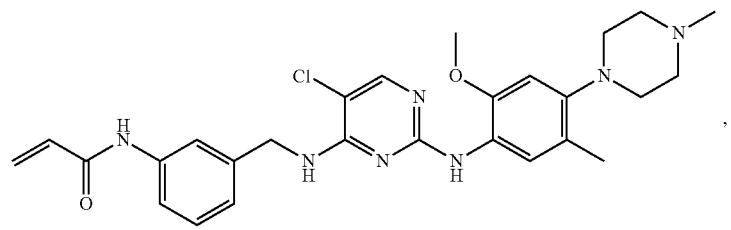,
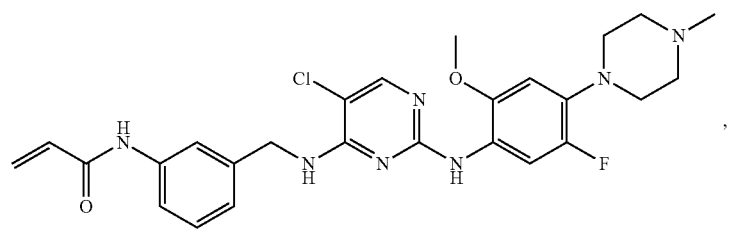,
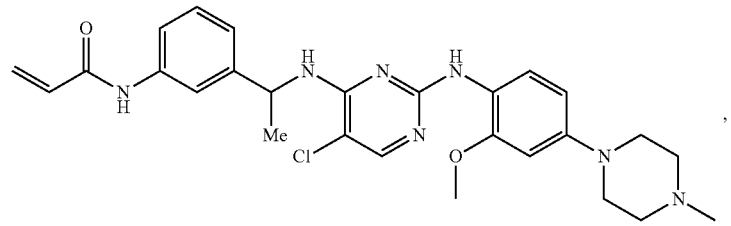,
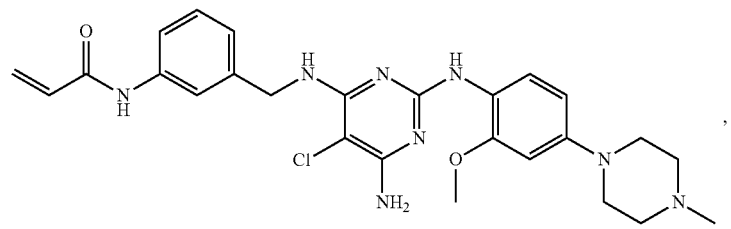,
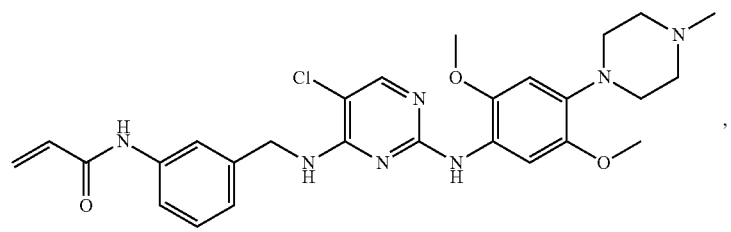,
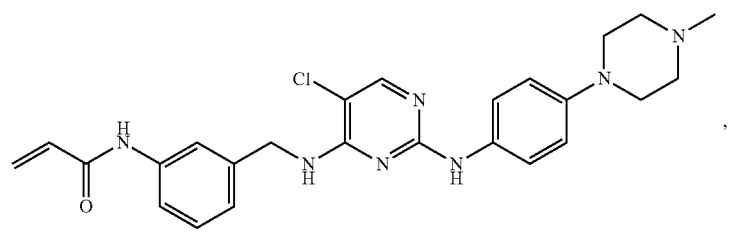,
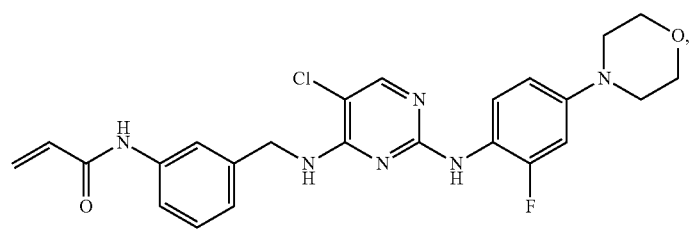

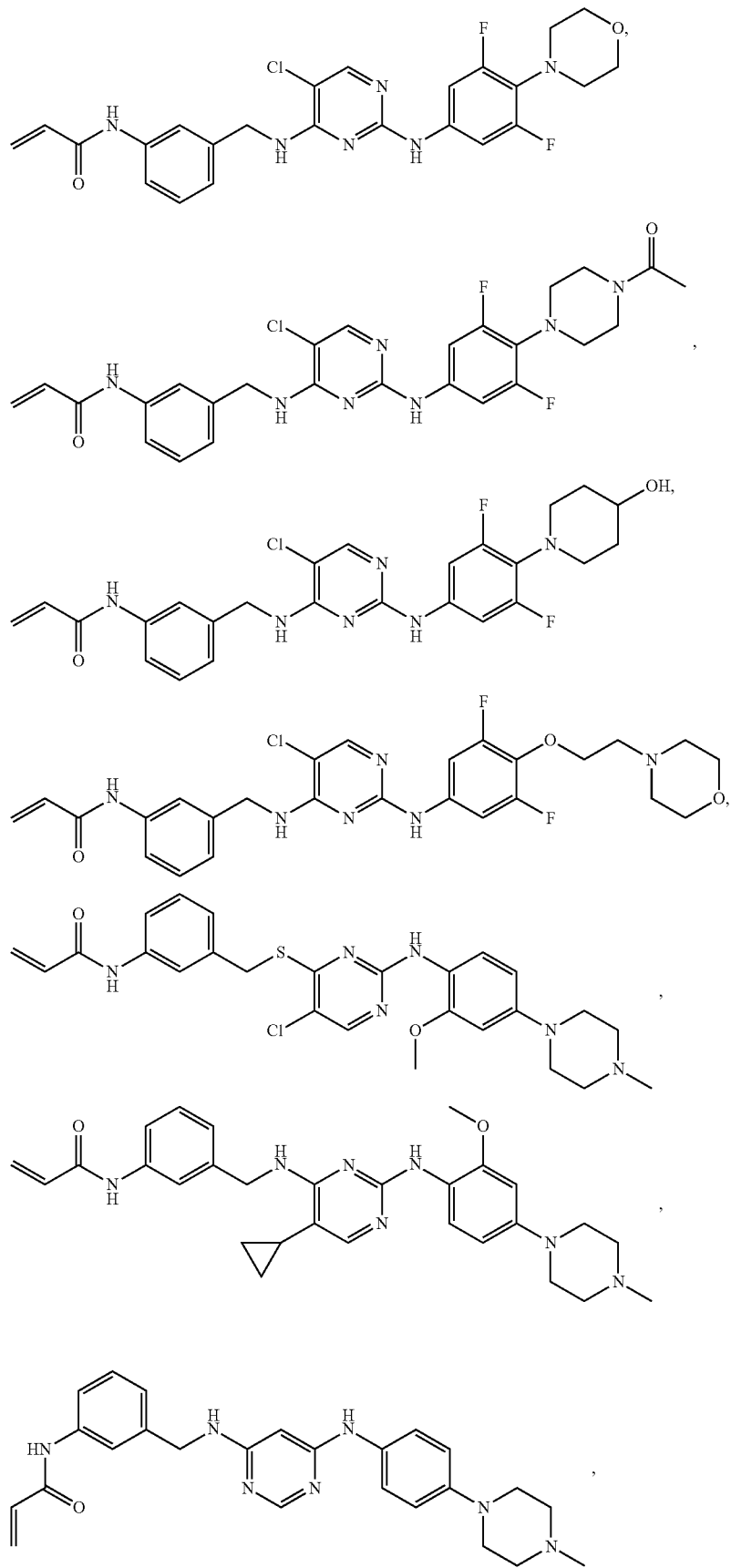

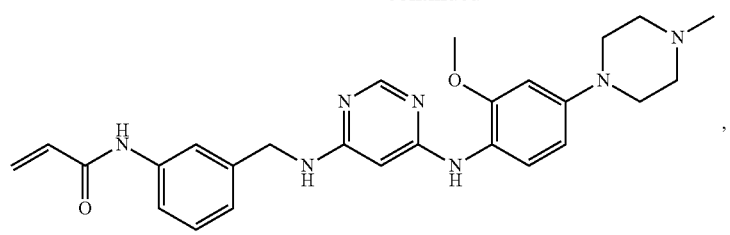,
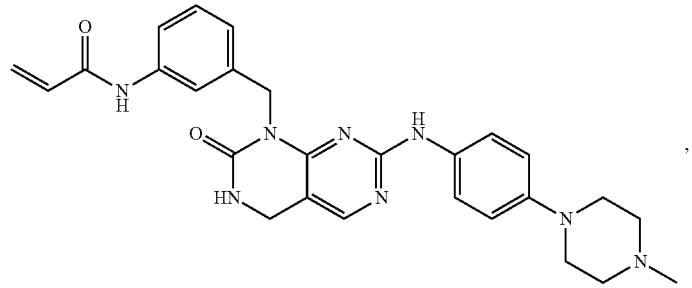,
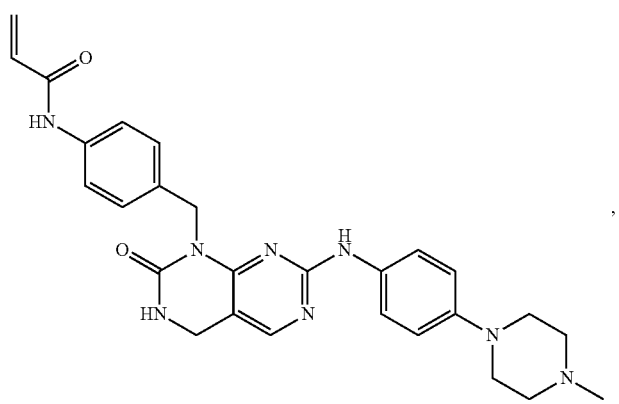,
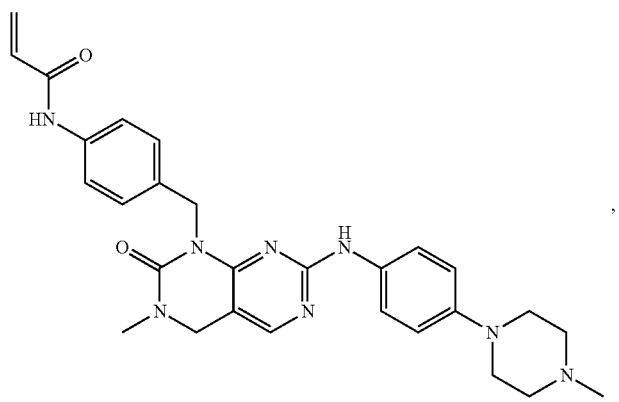,
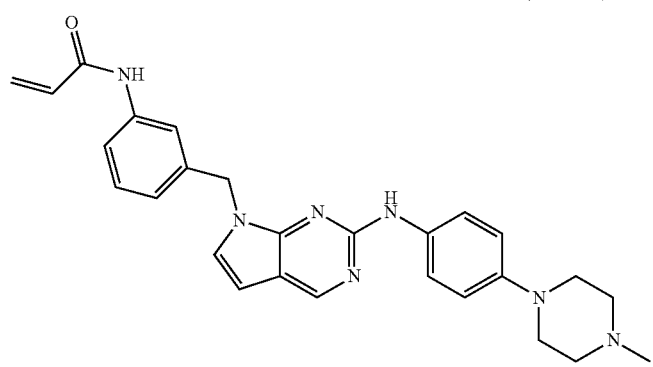

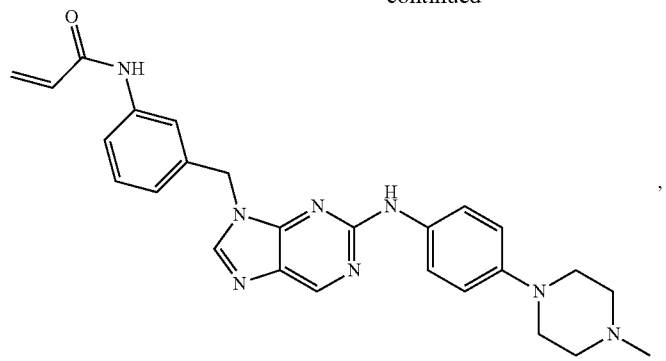
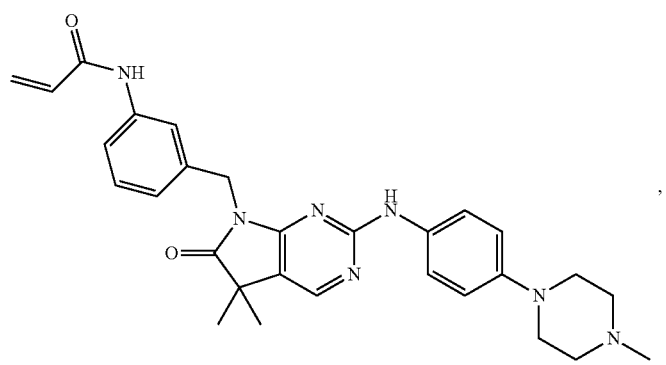
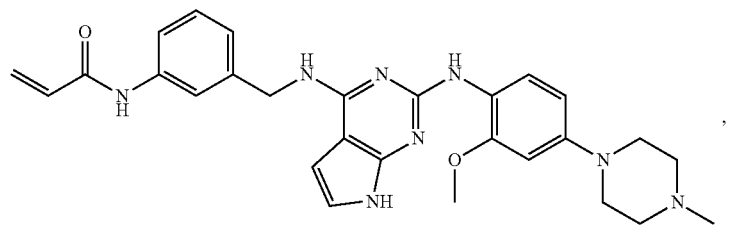
and pharmaceutically acceptable salts thereof.
11. The compound of claim 2 of the Formula:
12. The compound of claim 2 of the Formula:
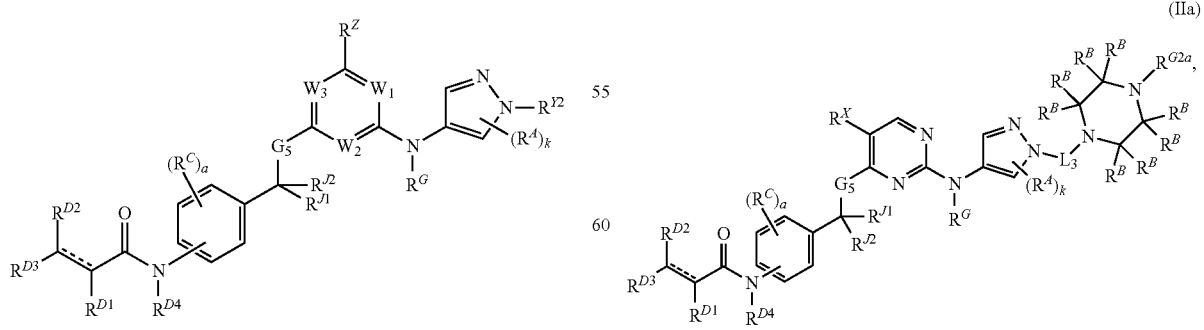
or a pharmaceutically acceptable salt thereof.

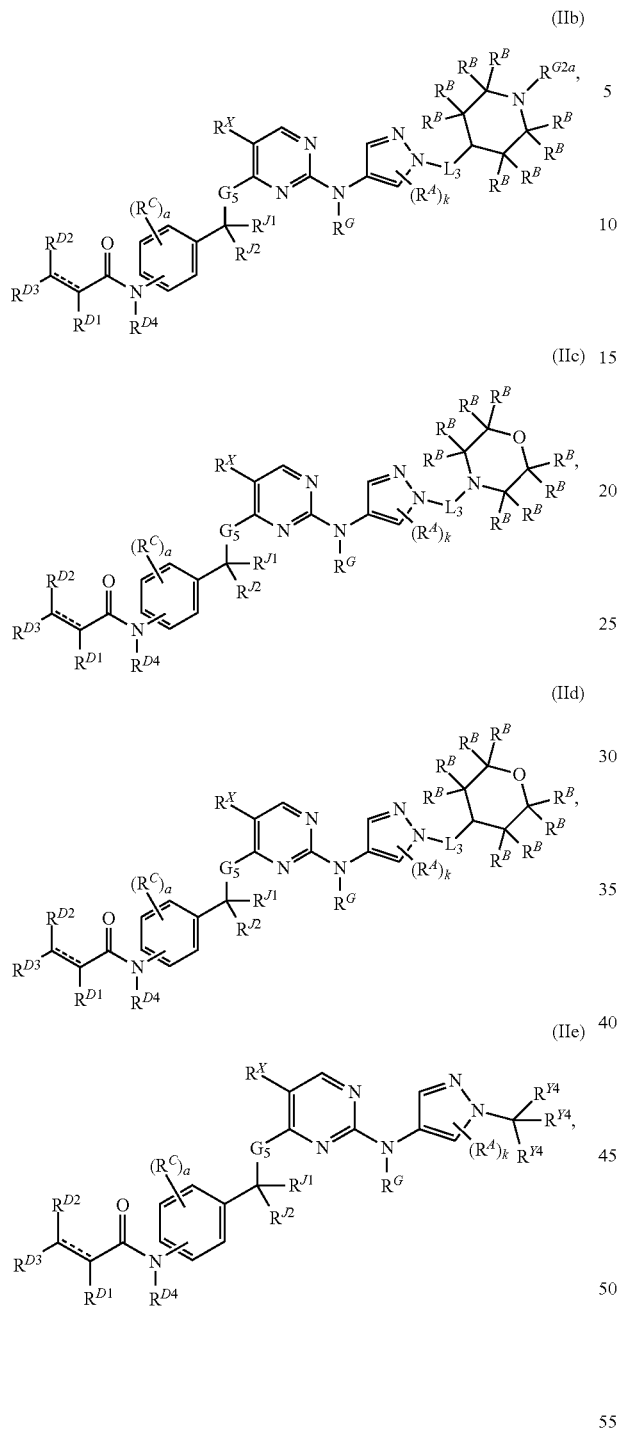

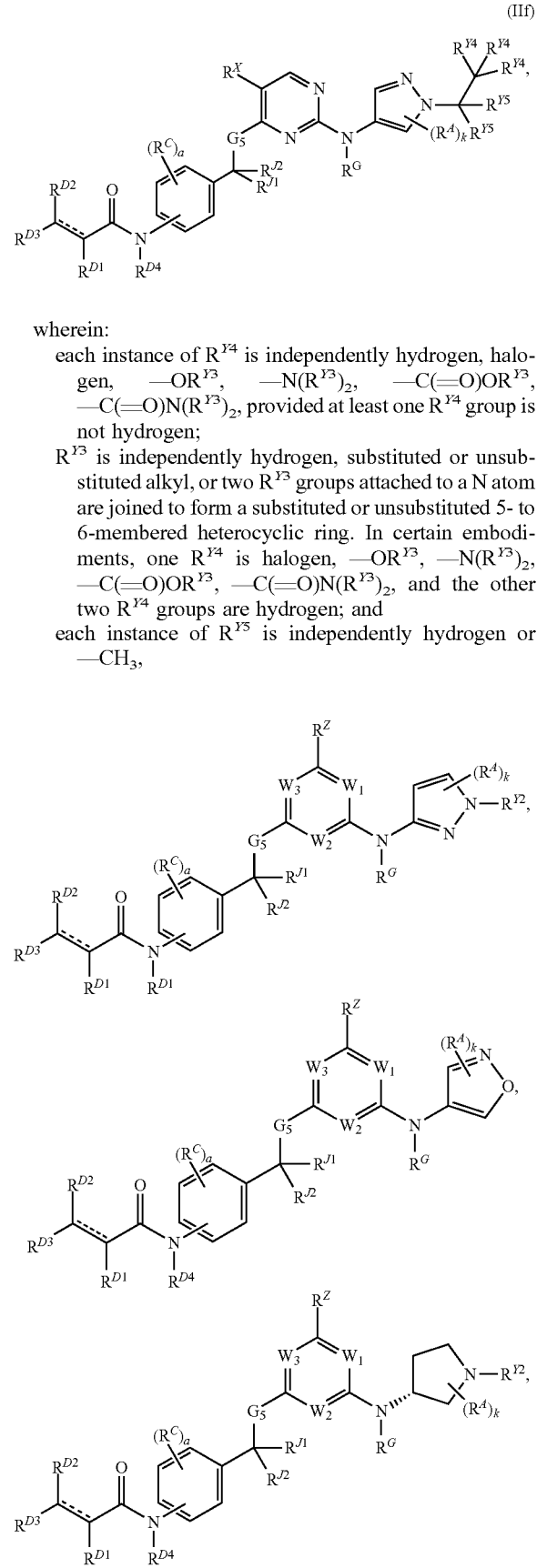

wherein:
each instance of $R^{Y4}$ is independently hydrogen, halogen, —$OR^{Y3}$, —$N(R^{Y3})_2$, —$C(=O)OR^{Y3}$, —$C(=O)N(R^{Y3})_2$, provided at least one $R^{Y4}$ group is not hydrogen; and
$R^{Y3}$ is independently hydrogen, substituted or unsubstituted alkyl, or two $R^{Y3}$ groups attached to a N atom are joined to form a substituted or unsubstituted 5- to 6-membered heterocyclic ring, wherein:
each instance of $R^{Y4}$ is independently hydrogen, halogen, —$OR^{Y3}$, —$N(R^{Y3})_2$, —$C(=O)OR^{Y3}$, —$C(=O)N(R^{Y3})_2$, provided at least one $R^{Y4}$ group is not hydrogen;
$R^{Y3}$ is independently hydrogen, substituted or unsubstituted alkyl, or two $R^{Y3}$ groups attached to a N atom are joined to form a substituted or unsubstituted 5- to 6-membered heterocyclic ring. In certain embodiments, one $R^{Y4}$ is halogen, —$OR^{Y3}$, —$N(R^{Y3})_2$, —$C(=O)OR^{Y3}$, —$C(=O)N(R^{Y3})_2$, and the other two $R^{Y4}$ groups are hydrogen; and
each instance of $R^{Y5}$ is independently hydrogen or —$CH_3$,

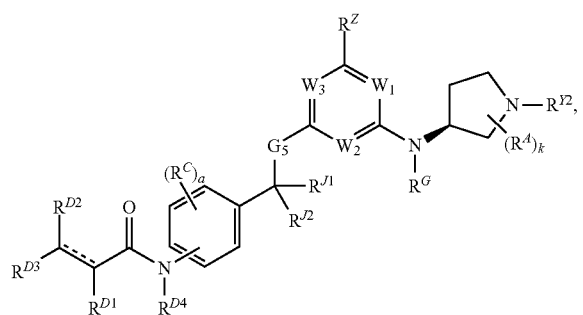
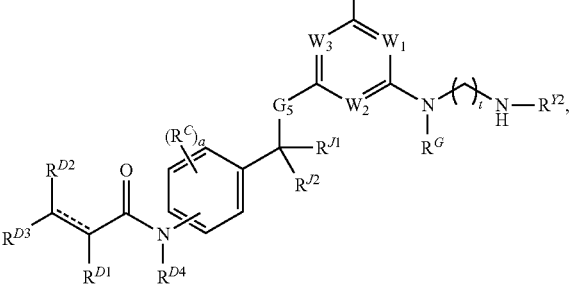
or a pharmaceutically acceptable salt thereof.
13. The compound of claim 2 selected from the group consisting of:
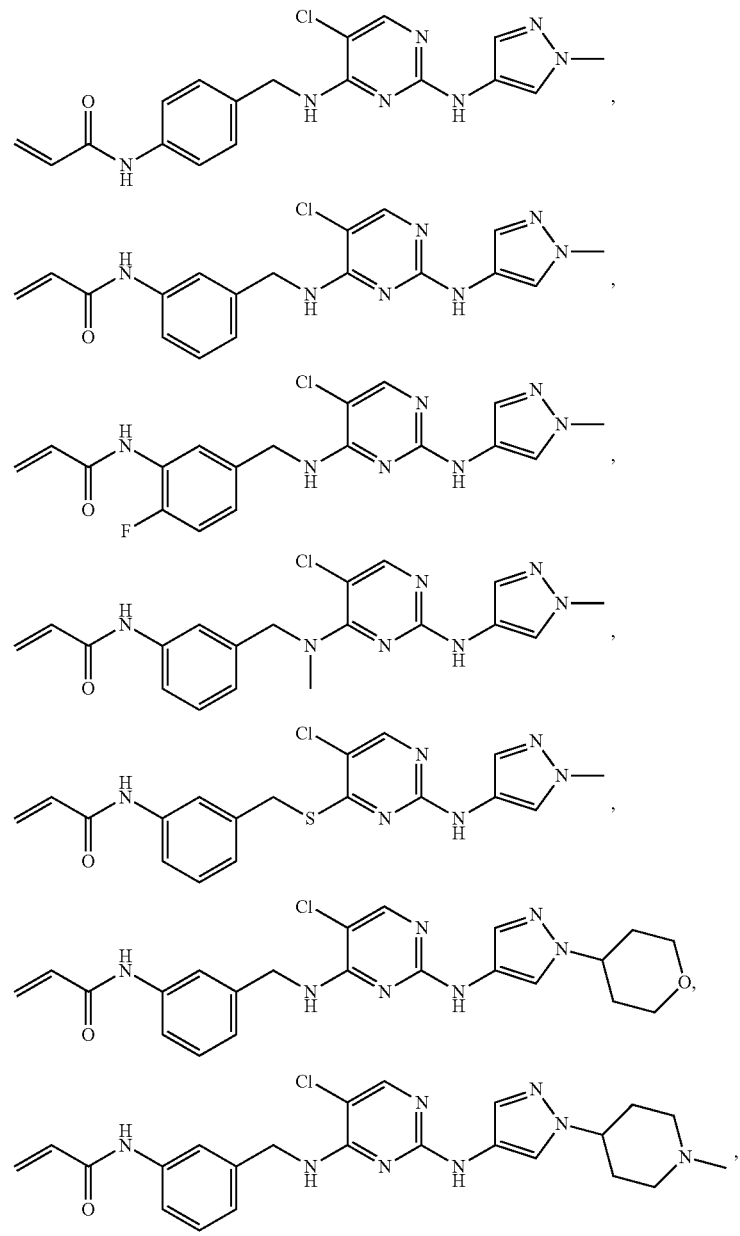

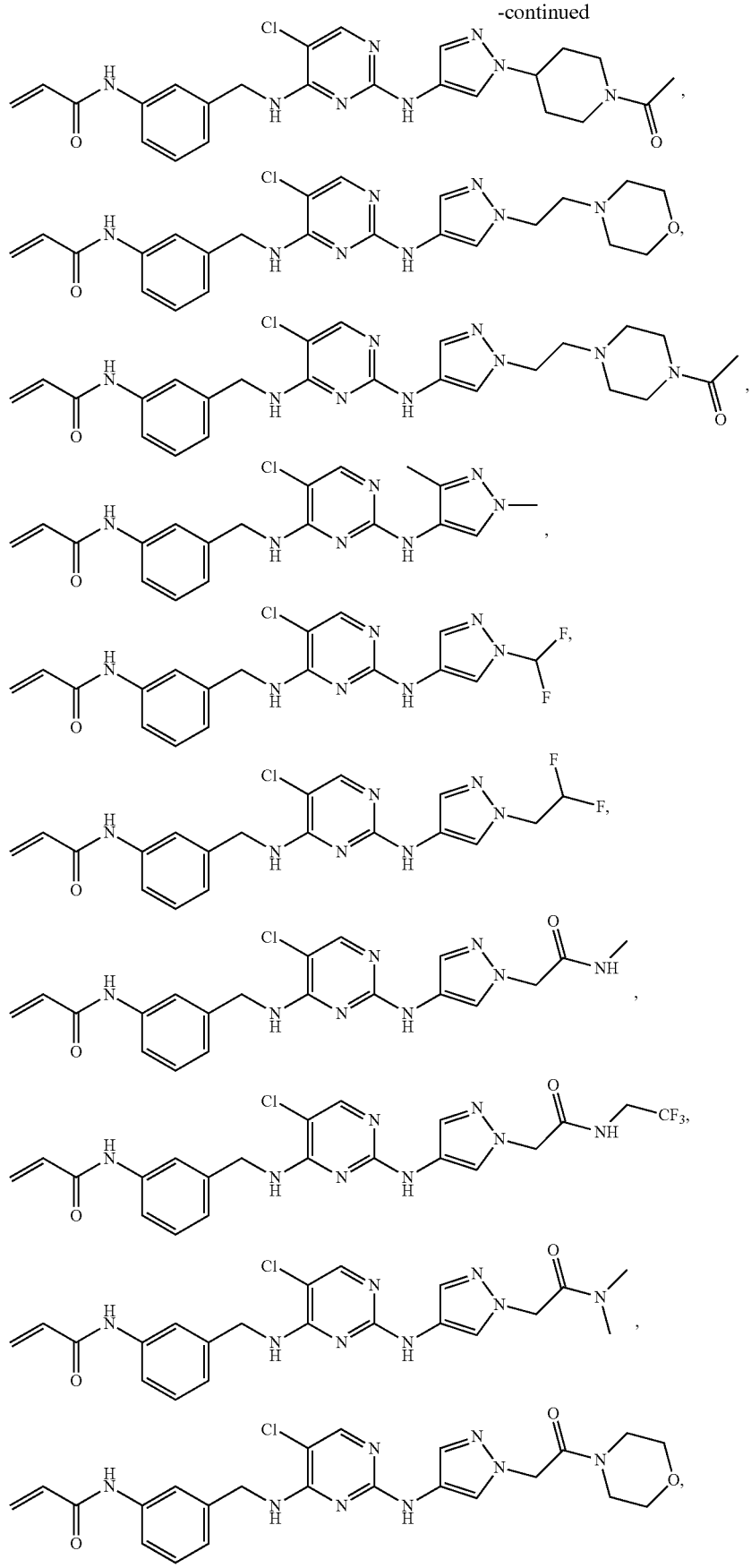

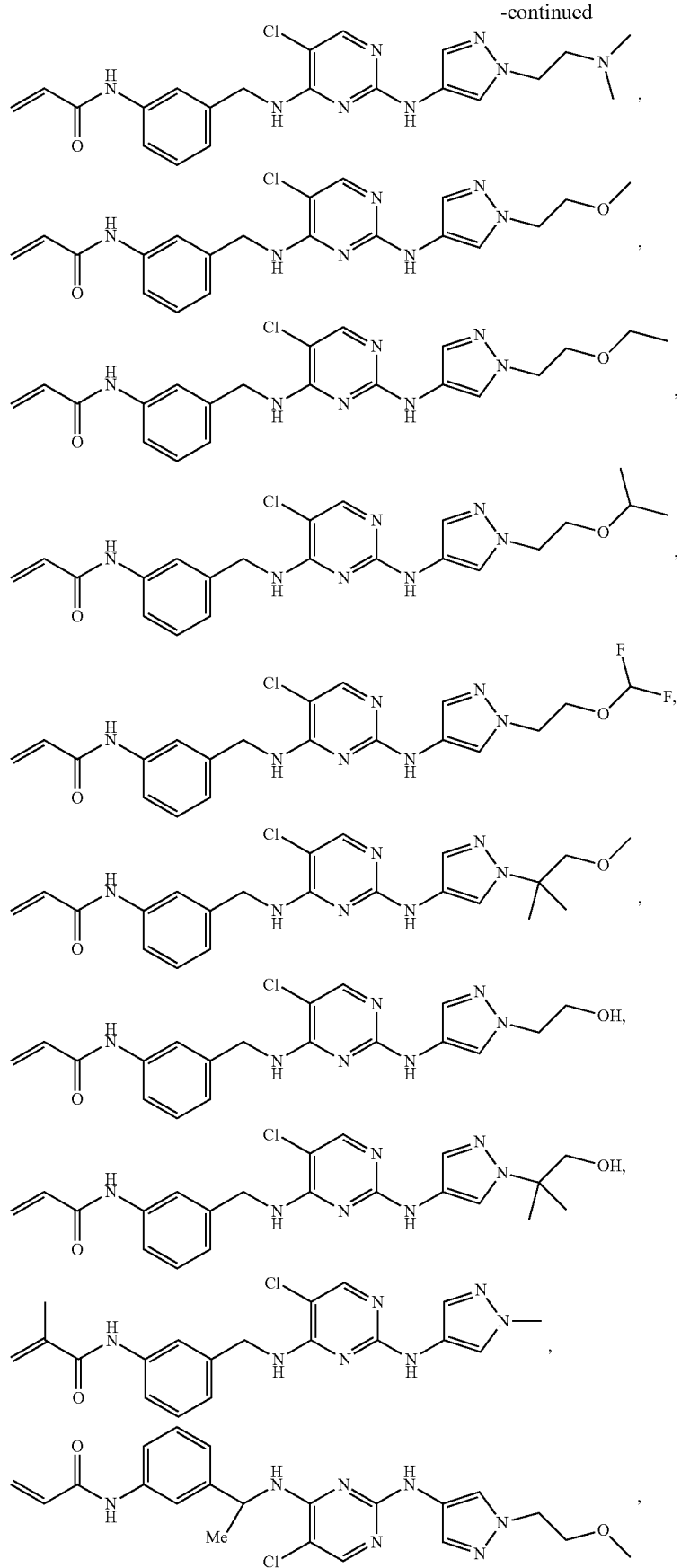

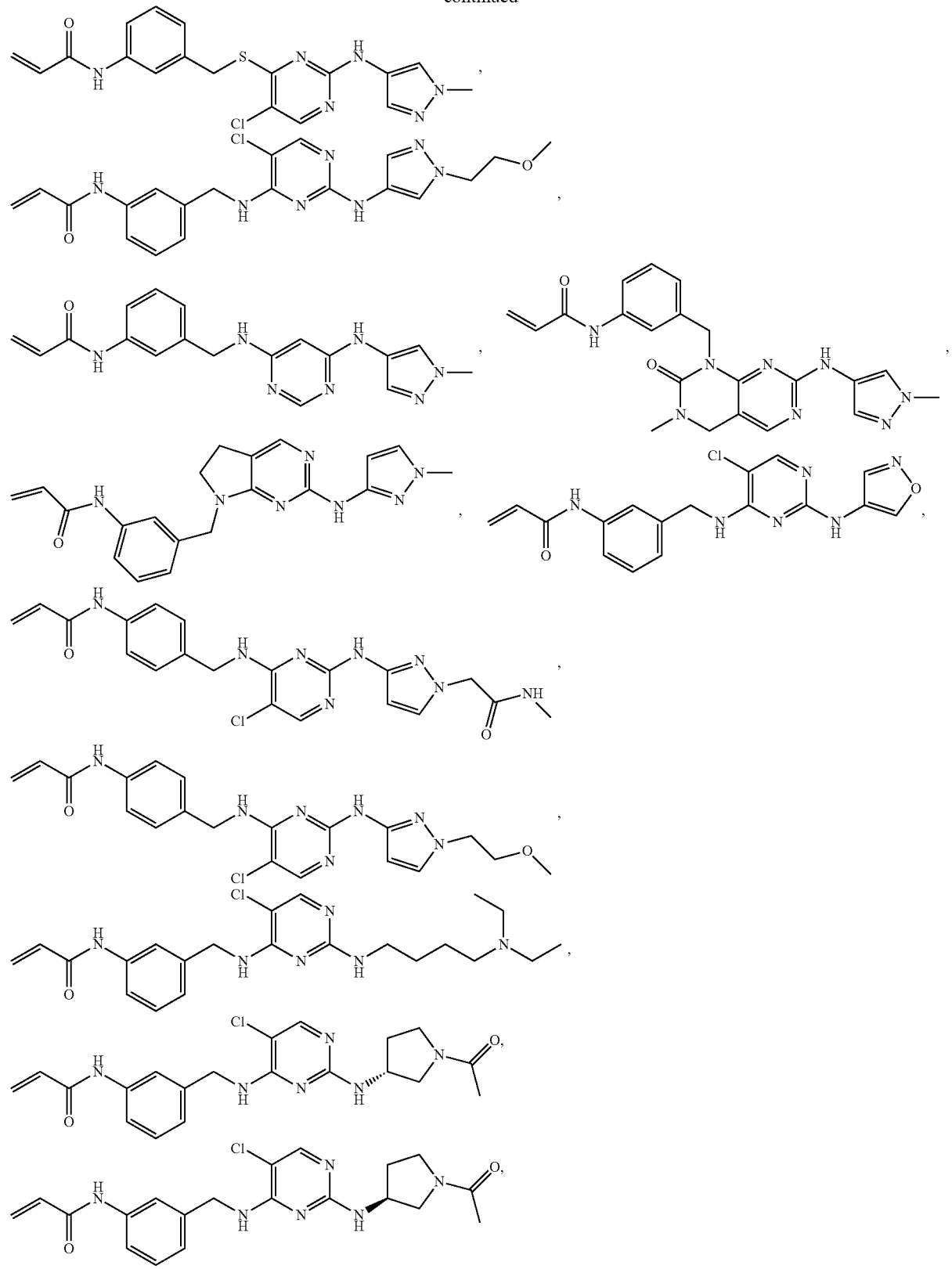
and pharmaceutically acceptable salts thereof.

14. A pharmaceutical composition comprising a compound of claim 1, or a pharmaceutically acceptable salt thereof, and a pharmaceutically acceptable excipient.

15. A method of reducing the activity of a Janus kinase (JAK) in a subject in need thereof, the method comprising administering to the subject a compound of claim 1, or a pharmaceutically acceptable salt thereof, in an amount sufficient to reduce the activity of the Janus kinase (JAK).

16. A method of treating a condition associated with aberrant activity of a Janus kinase in a subject in need thereof, the method comprising administering to the subject a compound of claim 1, or a pharmaceutically acceptable salt thereof, in an amount sufficient to treat the condition, wherein the condition is a hematological malignancy.

17. A kit comprising:
   a compound of claim 1, or a pharmaceutically acceptable salt thereof; and
   instructions for using the kit.

18. A labeled compound of Formula (I) or (II):

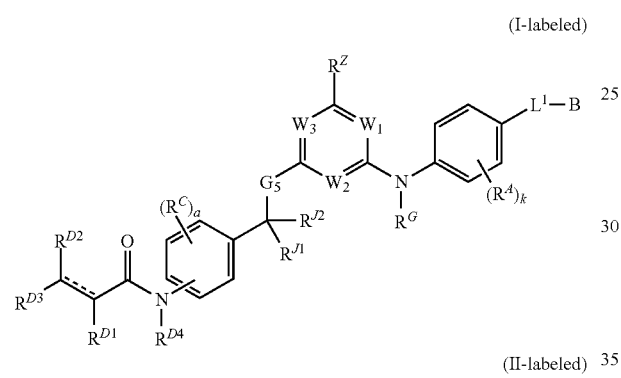

(I-labeled)

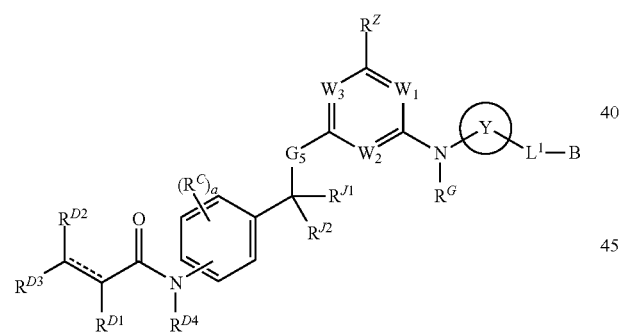

(II-labeled)

or a pharmaceutically acceptable salt thereof;
wherein:
Group

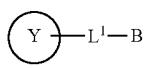

is selected from the group consisting of:

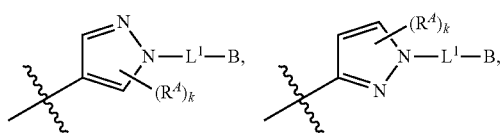

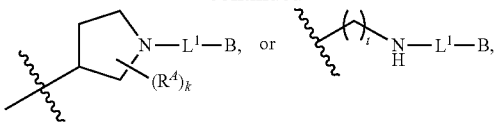

wherein t is 2, 3, 4, 5, or 6;

$L^1$ is a linking group selected from the group consisting of substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; and combinations thereof;

B is a label;

$W_1$ is N, $W_2$ is N and $W_3$ is $CR^X$, or $W_1$ is N, $W_2$ is CH, and $W_3$ is N;

═══ represents a single or double bond;

each instance of $R^{D1}$, $R^{D2}$, and $R^{D3}$ is independently hydrogen or substituted or unsubstituted alkyl;

$R^{D4}$ is hydrogen, substituted or unsubstituted alkyl, or a nitrogen protecting group;

$G_5$ is O, S, or $NR^E$;

each instance of $R^E$ and $R^G$ is independently hydrogen, substituted or unsubstituted alkyl, or a nitrogen protecting group;

each instance of $R^{J1}$ and $R^{J2}$ is independently hydrogen, halogen, or substituted or unsubstituted alkyl;

each instance of $R^A$ and $R^C$ is independently halogen, substituted or unsubstituted alkyl, substituted or unsubstituted alkenyl, substituted or unsubstituted alkynyl, —$OR^{A1}$, —$N(R^{A1})_2$, —$SR^{A1}$, —CN, —SCN, —C(=$NR^{A1}$)$R^{A1}$, —C(=$NR^{A1}$)$OR^{A1}$, —C(=$NR^{A1}$)N($R^{A1}$)$_2$, —C(=O)$R^{A1}$, —C(=O)$OR^{A1}$, —C(=O)N($R^{A1}$)$_2$, —NO$_2$, —$NR^{A1}$C(=O)$R^{A1}$, —$NR^{A1}$C(=O)$OR^{A1}$, —$NR^{A1}$C(=O)N($R^{A1}$)$_2$, —OC(=O)$R^{A1}$, —OC(=O)$OR^{A1}$, or —OC(=O)N($R^{A1}$)$_2$;

each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic or substituted or unsubstituted heteroaryl ring;

a and k are each independently 0, 1, or 2, provided when k is 0 then $R^A$ is absent, and when a is 0 then $R^C$ is absent; and each instance of $R^X$ and $R^Z$ is independently hydrogen, halogen, substituted or unsubstituted alkyl, cyclopropyl, —CN, —$OR^{X1}$, or —$NHR^{X1}$, wherein $R^{X1}$ is hydrogen, substituted or unsubstituted alkyl, an oxygen protecting group when attached to an oxygen, or a nitrogen protecting group when attached to a nitrogen, or R$^X$ and R$^Z$ are joined to form a substituted or unsubstituted 5-membered heterocyclic ring, or a ring of formula:

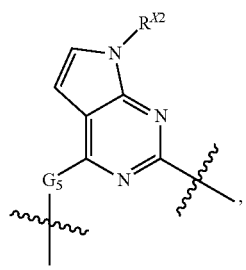

wherein R$^{X2}$ is hydrogen, substituted or unsubstituted alkyl, or a nitrogen protecting group;

or R$^X$ and R$^E$ are joined to form a substituted or unsubstituted 5- to 6-membered heterocyclic ring, or a ring of formula:

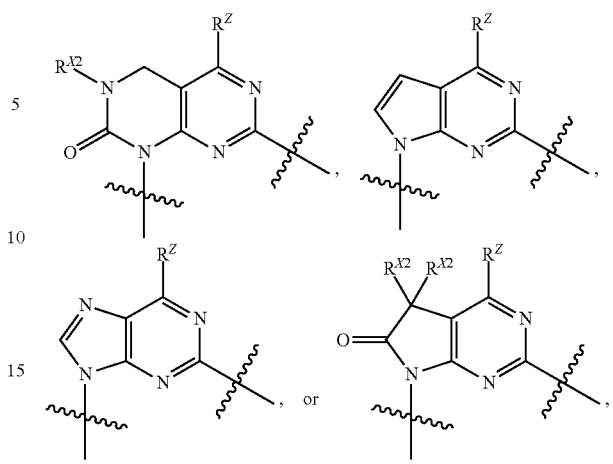

wherein R$^{X2}$ is hydrogen, substituted or unsubstituted alkyl, or a nitrogen protecting group.

19. The labeled compound of claim 18:

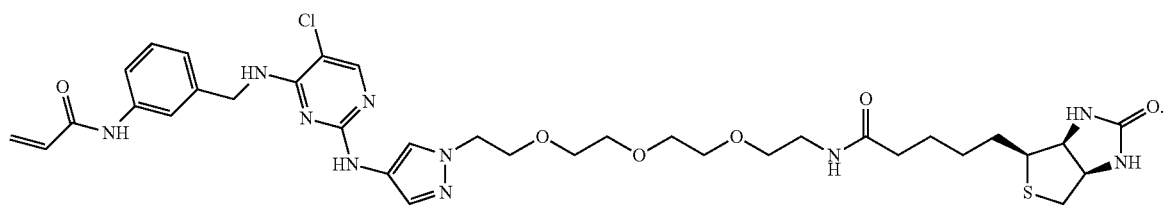 [SMILES: C=CC(=O)Nc1cccc(CNc2nc(Nc3cnn(CCOCCOCCOCCNC(=O)CCCC[C@@H]4SC[C@@H]5NC(=O)N[C@@H]54)c3)ncc2Cl)c1]

20. A pharmaceutical composition comprising a compound of claim 2, or a pharmaceutically acceptable salt thereof, and a pharmaceutically acceptable excipient.

21. A kit comprising:
a compound of claim 2, or a pharmaceutically acceptable salt thereof; and
instructions for using the kit.

22. A method of reducing the activity of a Janus kinase (JAK) in a subject in need thereof, the method comprising administering to the subject a compound of claim 2, or a pharmaceutically acceptable salt thereof, in an amount sufficient to reduce the activity of the Janus kinase (JAK).

23. A method of treating a condition associated with aberrant activity of a Janus kinase in a subject in need thereof, the method comprising administering to the subject a compound of claim 2, or a pharmaceutically acceptable salt thereof, in an amount sufficient to treat the condition, wherein the condition is a hematological malignancy.

24. The method of claim 16, wherein the hematological malignancy is leukemia or lymphoma.

25. The method of claim 16, wherein the Janus kinase is Janus kinase 3 (JAK3).

26. The method of claim 23, wherein the hematological malignancy is leukemia or lymphoma.

27. The method of claim 23, wherein the Janus kinase is Janus kinase 3 (JAK3).

* * * * *

UNITED STATES PATENT AND TRADEMARK OFFICE
CERTIFICATE OF CORRECTION

PATENT NO. : 10,017,477 B2
APPLICATION NO. : 15/305801
DATED : July 10, 2018
INVENTOR(S) : Nathanael S. Gray et al.

Page 1 of 2

It is certified that error appears in the above-identified patent and that said Letters Patent is hereby corrected as shown below:

In the Claims

In Claim 1, at Column 242, Lines 58-65, formula: " 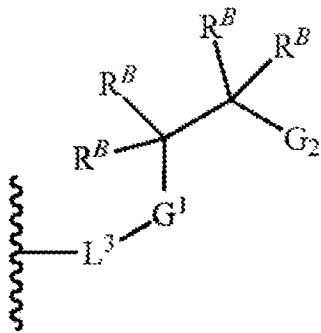 " should be replaced with the formula: -- 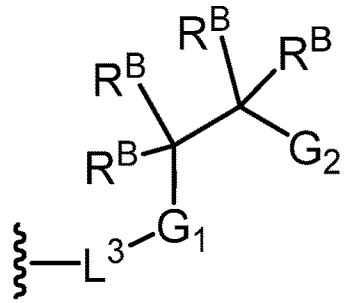 --.

Signed and Sealed this
Twenty-seventh Day of August, 2019

Andrei Iancu
*Director of the United States Patent and Trademark Office*

CERTIFICATE OF CORRECTION (continued)
U.S. Pat. No. 10,017,477 B2

In Claim 1, at Column 244, Lines 55-65, formula: " 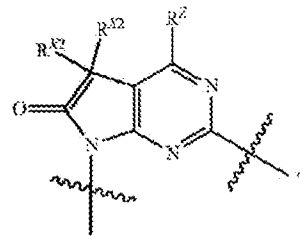 " should be replaced with the formula: -- 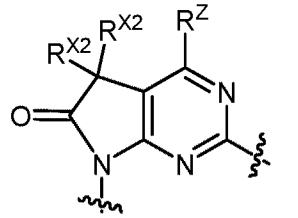 --.

In Claim 1, at Column 244, Line 66, the text: "wherein $R^X$ is hydrogen" should be replaced with the text: --wherein $R^{X2}$ is hydrogen--.

In Claim 6, at Column 249, Lines 30-40, formula: " 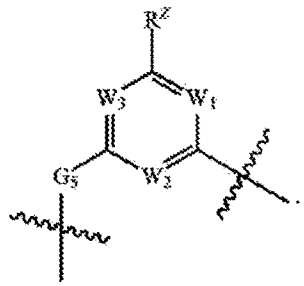 " should be replaced with the formula: -- 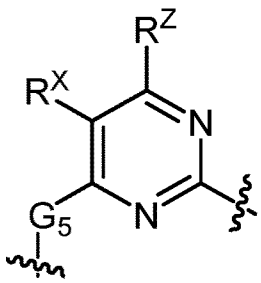 --.

In Claim 18, at Column 280, Line 21, the text: "B is a label;" should be replaced with the text: --B is a label.--.